(12) United States Patent
Wilson et al.

(10) Patent No.: US 11,555,059 B2
(45) Date of Patent: Jan. 17, 2023

(54) LDLR VARIANTS AND THEIR USE IN COMPOSITIONS FOR REDUCING CHOLESTEROL LEVELS

(71) Applicant: The Trustees of the University of Pennsylvania, Philadelphia, PA (US)

(72) Inventors: James M. Wilson, Philadelphia, PA (US); Daniel J. Rader, Philadelphia, PA (US); Suryanrayan Somanathan, Boston, MA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 15/306,419

(22) PCT Filed: Apr. 24, 2015

(86) PCT No.: PCT/US2015/027572
§ 371 (c)(1),
(2) Date: Oct. 24, 2016

(87) PCT Pub. No.: WO2015/164778
PCT Pub. Date: Oct. 29, 2015

(65) Prior Publication Data
US 2017/0101458 A1     Apr. 13, 2017

Related U.S. Application Data

(60) Provisional application No. 61/984,620, filed on Apr. 25, 2014, provisional application No. 62/022,627, filed on Jul. 9, 2014.

(51) Int. Cl.
| | |
|---|---|
| *C12N 7/00* | (2006.01) |
| *C12N 15/86* | (2006.01) |
| *A61P 3/06* | (2006.01) |
| *C07K 14/705* | (2006.01) |
| *A61K 48/00* | (2006.01) |
| *A61K 38/17* | (2006.01) |

(52) U.S. Cl.
CPC .......... *C07K 14/705* (2013.01); *A61K 38/177* (2013.01); *A61K 48/005* (2013.01); *C12N 7/00* (2013.01); *C12N 15/86* (2013.01); *C12N 2750/14143* (2013.01); *C12N 2830/008* (2013.01)

(58) Field of Classification Search
CPC ....... A61K 48/005; A61P 3/06; C07K 14/705; C12N 7/00; C12N 15/86; C12N 2750/14143; C12N 2830/008
See application file for complete search history.

(56) References Cited

U.S. PATENT DOCUMENTS

| | | | |
|---|---|---|---|
| 5,139,941 A | 8/1992 | Muzyczka et al. | |
| 5,478,745 A | 12/1995 | Samulski et al. | |
| 5,741,683 A | 4/1998 | Zhou et al. | |
| 5,817,789 A * | 10/1998 | Heartlein | C07K 14/79 435/320.1 |
| 6,057,152 A | 5/2000 | Samulski et al. | |
| 6,204,059 B1 | 3/2001 | Samulski et al. | |
| 6,268,213 B1 | 7/2001 | Samulski et al. | |
| 6,491,907 B1 | 12/2002 | Rabinowitz et al. | |
| 6,596,535 B1 | 7/2003 | Carter | |
| 6,660,514 B1 | 12/2003 | Zolotukhin et al. | |
| 6,951,753 B2 | 10/2005 | Shenk et al. | |
| 7,094,604 B2 | 8/2006 | Snyder et al. | |
| 7,125,717 B2 | 10/2006 | Carter | |
| 7,172,893 B2 | 2/2007 | Rabinowitz et al. | |
| 7,201,898 B2 | 4/2007 | Monahan et al. | |
| 7,229,823 B2 | 6/2007 | Samulski et al. | |
| 7,282,199 B2 | 10/2007 | Gao et al. | |
| 7,439,065 B2 | 10/2008 | Ferrari et al. | |
| 7,456,683 B2 | 11/2008 | Takano et al. | |
| 7,588,772 B2 | 9/2009 | Kay et al. | |
| 7,790,449 B2 | 9/2010 | Gao et al. | |
| 7,906,111 B2 | 3/2011 | Wilson et al. | |
| 7,943,374 B2 * | 5/2011 | Hildinger | C12N 15/86 435/325 |
| 8,319,480 B2 | 11/2012 | Ko et al. | |
| 8,962,330 B2 | 2/2015 | Gao et al. | |

(Continued)

FOREIGN PATENT DOCUMENTS

| | | |
|---|---|---|
| CN | 101018858 A | 8/2007 |
| CN | 102947453 A | 2/2013 |

(Continued)

OTHER PUBLICATIONS

Zhang et al, J. Biol. Chem. 282(25):18602-018612, 2007.*
Zelcer et al, Science 325:100-104, 2009.*
Al-Allafetal, Int. Arch. Med. 3: 36, 25 pages, 2010.*
Deng et al, J. Lipid Res. 60(3): 516-527, 2019.*
Nathwani et al, Gene Therapy 16: 60-69, 2009.*
Chandler et al, Gene Therapy 20: 1188-1191; Oct. 17, 2013, RE: PennVector P1015.*
Carillo-Carrasco et al, Human Gene Therapy 21: 1147-1154, 2010.*
GenBank BC014514.1, Homo sapiens low density lipoporotein receptor, 2008.*
Zelcer, N. et al., LXR Regulates Cholesterol Uptake Through Idol-Dependent Ubiquitination of the LDL Receptor, Science, Jul. 2009, 325(5936):100-104.

(Continued)

*Primary Examiner* — Kevin K Hill
(74) *Attorney, Agent, or Firm* — Howson & Howson LLP; Cathy A. Kodroff, Esq.

(57) ABSTRACT

A recombinant vector having an expression cassette is provided which comprises a modified human low density lipoprotein receptor (hLDLR) gene is provided, wherein said hLDLR gene encodes a modified hLDLR comprising (a) one or more of the following amino acid substitutions: L318H, N295D, H306D, V307D, N309A, D310N, L318H, and/or L318D; or (b) an amino acid substitution of any of (a) in combination with one or more of the following amino acid substitutions: K796, K809R and/or C818A. Also provided are pharmaceutical compositions containing this vector and uses therefor in lowering cholesterol and/or treating familial hypercholesterolemia.

13 Claims, 8 Drawing Sheets

Specification includes a Sequence Listing.

(56) References Cited

U.S. PATENT DOCUMENTS

| | | | |
|---|---|---|---|
| 8,962,332 B2 | 2/2015 | Gao et al. | |
| 9,719,106 B2 | 8/2017 | Tretiakova et al. | |
| 10,137,176 B2* | 11/2018 | Wilson | A61P 43/00 |
| 2002/0131956 A1* | 9/2002 | Walsh | C12N 15/86 |
| | | | 435/235.1 |
| 2007/0036760 A1 | 2/2007 | Wilson et al. | |
| 2009/0197338 A1 | 8/2009 | Vandenberghe et al. | |
| 2009/0227030 A1* | 9/2009 | Gao | A61K 9/0019 |
| | | | 435/455 |
| 2010/0047174 A1 | 2/2010 | Kay et al. | |
| 2012/0027726 A1 | 2/2012 | Bankiewicz et al. | |
| 2012/0252877 A1 | 4/2012 | Lo | |
| 2013/0045186 A1 | 2/2013 | Gao et al. | |
| 2013/0059732 A1 | 3/2013 | Lisowski et al. | |
| 2013/0072548 A1 | 3/2013 | Wright et al. | |
| 2013/0211380 A1* | 8/2013 | Cabrera Aquino | A61M 5/178 |
| | | | 604/508 |
| 2014/0155468 A1* | 6/2014 | Gregory | A61P 13/12 |
| | | | 514/44 R |
| 2014/0348876 A1 | 11/2014 | Jezek et al. | |
| 2015/0065556 A1* | 3/2015 | Birsoy | A01K 67/0276 |
| | | | 435/6.12 |
| 2016/0000887 A1* | 1/2016 | Wilson | A61K 38/47 |
| | | | 435/235.1 |
| 2016/0244501 A1* | 8/2016 | Ellsworth | C07K 14/705 |
| 2019/0002917 A1 | 1/2019 | Wilson et al. | |

FOREIGN PATENT DOCUMENTS

| | | |
|---|---|---|
| CN | 104520428 | 4/2015 |
| EP | 1310571 | 2/2006 |
| EP | 2529020 B1 | 4/2018 |
| JP | 2012-516357 | 7/2012 |
| WO | WO-2003/042397 | 5/2003 |
| WO | WO-2003052051 A2 | 6/2003 |
| WO | WO-2005/033321 | 4/2005 |
| WO | WO-2006/110689 | 10/2006 |
| WO | WO-2007/100682 | 9/2007 |
| WO | WO2011/094198 A1 | 8/2011 |
| WO | WO-2011/126808 | 10/2011 |
| WO | WO 2012/177741 | 12/2012 |
| WO | WO-2012/177741 | 12/2012 |
| WO | WO-2013/039969 | 3/2013 |
| WO | WO-2013/049493 | 4/2013 |
| WO | WO2013/123503 A1 | 8/2013 |
| WO | WO-2014/124282 | 8/2014 |
| WO | WO 2014/127196 A1 | 8/2014 |
| WO | WO 2015/051214 | 4/2015 |
| WO | WO-2015/051214 | 4/2015 |
| WO | WO 2015/164778 | 10/2015 |
| WO | WO-2017/100676 | 6/2017 |
| WO | WO-2017100682 A1 | 6/2017 |
| WO | WO-2018/152485 A1 | 8/2018 |

OTHER PUBLICATIONS

Gu, H. et al., Characterization of the role of EGF-A of low density lipoprotein receptor in PCSK9 binding, Journal of Lipid Research, Dec. 2013, 54(12):3345-3357.

Al-Allaf, F. A. et al., LDLR-Gene therapy for familial hypercholesterolaemia: problems, progress, and perspectives, International Archives of Medicine, Dec. 2010, 3(1):36.

Lagor, W. R. & Millar, J. S., Overview of the LDL receptor: relevance to cholesterol metabolism and future approaches for the treatment of coronary heart disease, Journal of Receptor, Ligand and Channel Research, Dec. 2009, 2010(3):1-14.

Zhang, D. et al., Binding of Proprotein Convertase Subtilisin/Kexin Type 9 to Epidermal Growth Factor-like Repeat A of Low Density Lipoprotein Receptor Decreases Receptor Recycling and Increases Degradation, The Journal of Biological Chemistry, Jun. 2007, 282(25):18602-16212.

Somanathan, S. et al., AAV Vectors Expressing LDLR Gain-of-Function Variants Demonstrate Increased Efficacy in Mouse Models of Familial Hypercholesterolemia, Circulation Research, Aug. 2014, 115(6):591-599.

Written Opinion dated Jul. 16, 2015 in corresponding International Patent Application No. PCT/US2015/027572, filed Apr. 24, 2015.

International Search Report dated Jul. 16, 2015 in corresponding International Patent Application No. PCT/US2015/027572, filed Apr. 24, 2015.

International Preliminary Report on Patentability dated Oct. 25, 2016 in corresponding International Patent Application No. PCT/US2015/027572, filed Apr. 24, 2015.

A Communication pursuant to Article 94(3) EPC dated Oct. 30, 2017 issued in the European patent application counterpart with Application No. 15721097.2.

Abifadel M, et al., Mutations in PCSK9 cause autosomal dominant hypercholesterolemia. Nat Genet. Jun. 2003;34(2):154-156. (Published online: May 2003).

Blumenthal RS, Statins: effective antiatherosclerotic therapy. Am Heart J. Apr. 2000;139(4):577-83. (Apr. 2000).

Brantly ML, et al., Sustained transgene expression despite T lymphocyte responses in a clinical trial of rAAV1-AAT gene therapy. Proc Natl Acad Sci U S A. Sep. 22, 2009;106(38):16363-8. doi: 10.1073/pnas.0904514106. (Epub Aug. 12, 2009).

Buning et al., Recent developments in adeno-associated virus vector technology. J Gene Med. Jul. 2008;10(7):717-733. doi: 10.1002/jgm.1205. (First published: May 2008).

Cohen J, et al., Low LDL cholesterol in individuals of African descent resulting from frequent nonsense mutations in PCSK9. Nat Genet. Feb. 2005;37(2):161-5. (Epub Jan. 16, 2005).

Fisher K et al, Transduction with recombinant adeno-associated virus for gene therapy is limited by leading-strand synthesis. J Virol. Jan. 1996;70(1):520-32. (Jan. 1996).

Fitzgerald K, et al, Effect of an RNA interference drug on the synthesis of proprotein convertase subtilisin/kexin type 9 (PCSK9) and the concentration of serum LDL cholesterol in healthy volunteers: a randomised, single-blind, placebo-controlled, phase 1 trial. Lancet. Jan. 4, 2014;383(9911):60-68. doi: 10.1016/S0140-6736(13)61914-5. (Epub Oct. 3, 2013).

Giugliano RP, et al., Efficacy, safety, and tolerability of a monoclonal antibody to proprotein convertase subtilisin/kexin type 9 in combination with a statin in patients with hypercholesterolaemia (LAPLACE-TIMI 57): a randomised, placebo-controlled, dose-ranging, phase 2 study. Lancet. Dec. 8, 2012;380(9858):2007-2017. doi: 10.1016/S0140-6736(12)61770-X. (Epub Nov. 6, 2012).

Grieger JC, et al, Adeno-associated virus as a gene therapy vector: vector development, production and clinical applications. Adv Biochem Eng Biotechnol. 2005;99:119-45. (Published online: Oct. 25, 2005).

Hovingh GK, et al., Diagnosis and treatment of familial hypercholesterolaemia. Apr. 2013;34(13):962-71. doi: 10.1093/eurheartj/eht015. (Epub Feb. 2013).

Hussain MM, et al, The mammalian low-density lipoprotein receptor family. Annu Rev Nutr. 1999;19:141-172. (Jul. 1999).

Kassim SH, et al., Gene therapy in a humanized mouse model of familial hypercholesterolemia leads to marked regression of atherosclerosis. PLoS One. Oct. 19, 2010;5(10):e13424. doi: 10.1371/journal.pone.0013424. (Oct. 2010).

Marais AD, Familial hypercholesterolaemia. Clin Biochem Rev. 2004;25(1):49-68, (Feb. 2004).

McCarty DM et al, Self-complementary recombinant adeno-associated virus (scAAV) vectors promote efficient transduction independently of DNA synthesis, Gene Ther. Aug. 2001;8(16):1248-1254. (Aug. 2001).

McGowan MP. Emerging low-density lipoprotein (LDL) therapies: Management of severely elevated LDL cholesterol—the role of LDL-apheresis. J Clin Lipidol. May-Jun. 2013;7(3 Suppl):S21-6. doi: 10.1016/j.jacl.2013.03.002. (Epub Mar. 26, 2013).

Miyatake et al., Transcriptional targeting of herpes simplex virus for cell-specific replication. J Virol. Jul. 1997;71(7):5124-5132. (Jul. 1997).

Nathwani AC, et al, Adenovirus-associated virus vector-mediated gene transfer in hemophilia B. N Engl J Med. Dec. 22, 2011;365(25):2357-65. doi: 10.1056/NEJMoa1108046. (Epub Dec. 10, 2011).

(56) References Cited

OTHER PUBLICATIONS

Raal F, et al., Elevated PCSK9 levels in untreated patients with heterozygous or homozygous familial hypercholesterolemia and the response to high-dose statin therapy. J Am Heart Assoc. Apr. 24, 2013;2(2):e000028. doi: 10.1161/JAHA.112.000028. (Published online Apr. 24, 2013).
Raal FJ, Homozygous familial hypercholesterolemia: current perspectives on diagnosis and treatment. Atherosclerosis. Aug. 2012;223(2):262-268. doi: 10.1016/j.atherosclerosis.2012.02.019. (Epub Feb. 16, 2012).
Sandig et al., HBV-derived promoters direct liver-specific expression of an adenovirally transduced LDL receptor gene. Gene Ther. Nov. 1996;3(11):1002-1009. (Nov. 1996).
Sorrentino V, et al., Identification of a loss-of-function inducible degrader of the low-density lipoprotein receptor variant in individuals with low circulating low-density lipoprotein. Eur Heart J. May 2013;34(17):1292-1297. doi: 10.1093/eurheartj/ehs472. (Epub Jan. 16, 2013).
Thomson JD, et al, A comprehensive comparison of multiple sequence alignments, Nucleic Acids Res. Jul. 1, 1999;27(13):2682-90. (Jul. 1999).
Wang L, et al., Preclinical evaluation of a clinical candidate AAV8 vector for ornithine transcarbamylase (OTC) deficiency reveals functional enzyme from each persisting vector genome. Mol Genet Metab. Feb. 2012; 105(2):203-111. doi: 10.1016/j.ymgme.2011.10.020. (Epub Nov. 7, 2011.).
Wang Y, et al., Molecular characterization of proprotein convertase subtilisin/kexin type 9-mediated degradation of the LDLR. J Lipid Res. Sep. 2012;53(9):1932-1943, doi: 10.1194/jlr.M028563. (Epub Jul. 4, 2012).
Ward NJ, et al, Codon optimization of human factor VIII cDNAs leads to high-level expression. Blood. Jan. 20, 2011;117(3):798-807. doi: 10.1182/blood-2010-05-282707, (Epub Nov. 1, 2010).
Zelcern, et al., LXR regulates cholesterol uptake through Idol-dependent ubiquitination of the LDL receptor. Science. Jul. 3, 2009;325(5936):100-104. doi: 10.1126/science.1168974, (Epub Jun. 11, 2009).
Zhang H, et al., Adenovirus-adeno-associated virus hybrid for large-scale recombinant adeno-associated virus production. Hum Gene Ther. Sep. 2009;20(9):922-9. doi: 10.1089/hum.2009.125. (Online Ahead of Editing: Jul. 20, 2009).
Zhang L, et al, Feedback regulation of cholesterol uptake by the LXR-IDOL-LDLR axis. Arterioscler Thromb Vasc Biol. Nov. 2012;32(11):2541-6. doi: 10.1161/ATVBAHA.112.250571. (Epub Aug. 30, 2012).
Kwon HJ, et al., Molecular basis for LDL receptor recognition by PCSK9. Proc Natl Acad Sci U S A. Feb. 12, 2008;105(6):1820-5. doi: 10.1073/pnas.0712064105. (Epub Feb. 4, 2008).
Zhang DW, et al., Binding of proprotein convertase subtilisin/kexin type 9 to epidermal growth factor-like repeat A of low density lipoprotein receptor decreases receptor recycling and increases degradation. J Biol Chem. Jun. 22, 2007;282(25):18602-12. (Epub Apr. 23, 2007).
Anna Tretiakova and James M. Wilson. U.S. Appl. No. 61/817,110, filed Apr. 29, 2013.
Zelcern, et al., Supplemental Material, LXR regulates cholesterol uptake through Idol-dependent ubiquitination of the LDL receptor. Science. Jul. 3, 2009;325(5936):100-104. Retrieved from https://www.ncbi.nlm.nih.gov/pmc/articles/PMC2777523/bin/NIHMS151722-supplement-1.pdf (Epub Jun. 11, 2009).
Kassim, et al., Adeno-associated virus serotype 8 gene therapy leads to significant lowering of plasma cholesterol levels in humanized mouse models of homozygous and heterozygous familial hypercholesterolemia. Hum Gene Ther. Jan. 2013;24(1):19-26. doi: 10.1089/hum.2012.108. Epub Nov. 14, 2012.
Chen, et al., Biodistribution of AAV8 vectors expressing human low-density lipoprotein receptor in a mouse model of homozygous familial hypercholesterolemia. Hum Gene Ther Clin Dev. Dec. 2013;24(4):154-60. doi: 10.1089/humc.2013.082. Epub Nov. 9, 2013.

Greig Ja, et al., Nonclinical Pharmacology/Toxicology Study of AAVS.TBG.mLDLR and AAVS.TBG.hLDLR in a Mouse Model of Homozygous Familial Hypercholesterolemia. Hum Gene Ther Clin Dev. Mar. 2017;28(1):28-38. doi: 10.1089/humc.2017.007. Published online Mar. 1, 2017.
A Communication pursuant to Article 94(3) EPC dated Jun. 28, 2018 issued in the European patent application counterpart with Application No. 15721097.2.
"Apolipoprotein B; APOB", MIM 107730, 20 pages, accessed on Jan. 4, 2019 from https://omim.org/entry/107730, last update on Aug. 18, 2015.
"Baxalta Reports Continued Progress on Phase 1/2 Clinical Trial of BAX335, Investigational Gene Therapy Treatment for Hemophilia B", Jun. 24, 2015, accessed on Jan. 8, 2019 from http://www.baxalta.com/newsroom/press-releases/clinical-trial-bax335.page.
"Common Terminology Criteria for Adverse Events (CTCAE) Version 4.0", Published: May 28, 2009 (v4.03: Jun. 14, 2010) accessed on Jan. 11, 2019 from https://evs.nci.nih.gov/ftp1/CTCAE/CTCAE_4.03_2010-06-14 QuickReference 5x7.pdf.
"Kynamro", 2 pages, accessed on Jan. 9, 2018 from http://www.goodrx.com/kynamro.
"Lomitapide", 2 pages, accessed on Jan. 9, 2018 from http://www.goodrx.com/lomitapide.
"Low Density Lipoprotein Receptor Adaptor Protein 1; LDLRAP1", MIM 605747, 6 pages, accessed on January 4, 2019 from http://omim.org/entry/605747, last update on Apr. 16, 2018.
"Low Density Lipoprotein Receptor; LDLR", MTM 606945, 25 pages, accessed on Jan. 4, 2019 from http://omim.org/entry/606945, last update on Nov. 28, 2017.
"LSPD, The Liver Specific Gene Promoter Database", Cold Spring Harbor, accessed on Jan. 4, 2019 from http://rulai.cshl.edu/LSPD/, 2 pages.
"Prednisone Prescribing Information", 29 pages, revised Nov. 2017, accessed on Jan. 11, 2019 from https://www.drugs.com/cdi/prednisone-tablets.html. Revised Nov. 2017.
"Procedure: LDL-Apheresis", 1 page, accessed on Jan. 4, 2019 from https://cdn.ymaws.com/www.apheresis.org/resource/resmgr/fact_sheets_file/ldl_apheresis.pdf.
"Proprotein Convertase, Subtilisin/Kexin-Type, 9; PCSK9", MIM 607786, 7 pages, accessed on Jan. 4, 2019 from https://omim.org/entry/607786, last update on Jul. 24, 2013.
"UniProtKB—P01130 (LDLR_Human)", 21 pages accessed on Jan. 4, 2019 from http://www.uniprot.org/uniprot/P01130, last update on Dec. 5, 2018.
"Audentes Announces Positive Interim Data from First Dose Cohort of ASPIRO, a Phase 1/2 Clinical Trial of AT132 in Patients With X-Linked Myotubular Myopathy." Jan. 4, 2018, 7 pages, accessed on Jan. 8, 2019 from http://investors.audentestx.com/news-releases/news-release-details/audentes-announces-positive-interim-data-first-dose-cohort-0.
25 Percent LDL-C Reduction in Very High-Risk Patient Population.
"Genzyme and Isis Announce that Mipomersen Phase 3 Study in Patients with Homozygous Familial Hypercholesterolemia Met Primary Endpoint", May 20, 2009, 6 pages, accessed on Jan. 8, 2019 from https://news.genzyme.com/press-release/genzyme-and-isis-announce-mipomersen-phase-3-study-patients-homozygous-familial-hyperc.
Ajufo, et al., Recent Developments in Gene Therapy for Homozygous Familial Hypercholesterolemia. Curr Atheroscler Rep. May 2016;18(5):22. doi: 10.1007/s11883-016-0579-0. First Online: Mar. 15, 2016.
Akacele, et al., A two-hybrid screen identifies cathepsins B and L as uncoating factors for adeno-associated virus 2 and 8. Mol Ther. Feb. 2007;15(2):330-9.
Alexander, et al., Macrophage reverse cholesterol transport in mice expressing ApoA-I Milano. Arterioscler Thromb Vasc Biol. Oct. 2009;29(10):1496-501. doi: 10.1161/ATVBAHA. 109.191379, Epub Aug. 6, 2009.
Allay, et al., Good manufacturing practice production of self-complementary serotype 8 adeno-associated viral vector for a hemophilia B clinical trial. Hum Gene Ther, 2011. 22(5): p. 595-604, Published online Mar. 17, 2011.

(56) References Cited

OTHER PUBLICATIONS

Alwaili, et al., High-density lipoproteins and cardiovascular disease: 2010 update. Expert Rev Cardiovasc Ther. Mar. 2010;8(3):413-23. doi: 10.1586/erc.10.4.
Backes and Moriarty, Effect of atorvastatin and bezafibrate on plasma levels of C-reactive protein in combined (mixed) hyperlipidemia. Atherosclerosis. Jun. 2002;162(2):245-51.
Backes, et al., Role of C-Reactive Protein in Cardiovascular Disease. Ann Pharmacother, Jan. 2004;38(1):110-8, First Published Jan. 1, 2004.
Backes, et al., The effect of micronized fenofibrate on lipid profiles of patients converted from gemfibrozil. Hospital Pharmacy, 37(9), 953-956. First Published Sep. 1, 2002.
Badellino, et al., Endothelial lipase is increased in vivo by inflammation in humans. Circulation. Feb. 5, 2008;117(5):678-85. doi: 10.1161/Circulationaha. 107.707349. Epub Jan. 22, 2008.
Bell, et al., Analysis of tumors arising in male B6C3F1 mice with and without AAV vector delivery to liver. Mol Ther. Jul. 2006;14(1):34-44. Epub May 6, 2006.
Bell, et al., Evaluation of adeno-associated viral vectors for liver-directed gene transfer in dogs. Hum Gene Ther. Aug. 2011;22(8):985-97. doi: 10.1089/hum.2010.194. Published Online:Jan. 4, 2011.
Bell, et al., No evidence for tumorigenesis of AAV vectors in a large-scale study in mice. Mol Ther. Aug. 2005;12(2):299-306.
Benitec Biopharma Limited, "Fifth patient dosed in Benitec's TT-034 Phase I/IIa clinical trial for prevention of HCV infection", 1 page, accessed on Jan. 8, 2019 from https://www.news-medical.net/news/20150429/Fifth-patient-dosed-in-Benitecs-TT-034-Phase-IIIa-clinical-trial-for-prevention-of-HCV-infection.aspx.
Bertolini, et al., 2013, Spectrum of mutations and phenotypic expression in patients with autosomal dominant hypercholesterolemia identified in Italy. Atherosclerosis. Apr. 2013;227(2):342-8. doi: 10.1016/j.atherosclerosis.2013.01.007. Epub Jan. 19, 2013.
Bilheimer, et al., Liver transplantation to provide low-density-lipoprotein receptors and lower plasma cholesterol in a child with homozygous familial hypercholesterolemia. N Engl J Med. Dec. 27, 1984;311(26): 1658-64.
Boutin, et al., Prevalence of serum IgG and neutralizing factors against adeno-associated virus (AAV) types 1, 2, 5, 6, 8, and 9 in the healthy population: implications for gene therapy using AAV vectors. Hum Gene Ther. Jun. 2010;21(6):704-12, doi: 10,1089/hum.2009.182. Published Online:Apr. 28, 2010.
Bowles, et al., Phase 1 gene therapy for Duchenne muscular dystrophy using a translational optimized AAV vector. Mol Ther. Feb. 2012;20(2):443-55. doi: 10.1038/mt.2011.237. Epub Nov. 8, 2011.
Brousseau, et al., LCAT modulates atherogenic plasma lipoproteins and the extent of atherosclerosis only in the presence of normal LDL receptors in transgenic rabbits. Arterioscler Thromb Vasc Biol. Feb. 2000;20(2):450-8.
Brown, et al. A receptor-mediated pathway for cholesterol homeostasis. Science. Apr. 4, 1986;232(4746):34-47.
Brunt, et al., Histopathology of nonalcoholic fatty liver disease. World J Gastroenterol. Nov. 14, 2010;16(42):5286-96. (Published online Nov. 14, 2010).
Brunt. Pathology of nonalcoholic fatty liver disease. Nat Rev Gastroenterol Hepatol. Apr. 2010;7(4):195-203, doi: 10.1038/nrgastro.2010.21. Epub Mar. 2, 2010.
Buning, et al., Engineering the AAV capsid to optimize vector-host-interactions. Curr Opin Pharmacol. Oct. 2015;24:94-104. doi: 10.1016/j.coph.2015.08.002. Epub Aug. 25, 2015.
Burkhardt, et al., Trib 1, a novel lipid and myocardial infarction associated gene, regulates hepatic lipogenesis and VLDL production in mice. J Clin Invest. Dec. 2010;120(12):4410-4, doi: 10.1172/JCI44213, Epub Nov. 15, 2010.
Calcedo, et al., Worldwide Epidemiology of Neutralizing Antibodies to Adeno-Associated Viruses. Journal of Infectious Diseases, 2009. 199(3): p. 381-390, Published: Feb. 1, 2009.

Cantz, et al., Concise review: cell therapies for hereditary metabolic liver diseases-concepts, clinical results, and future developments. Stem Cells. Apr. 2015;33(4):1055-62, doi: 10.1002/stem.1920. First published: Dec. 19, 2014.
Cayo, et al., JD induced pluripotent stem cell-derived hepatocytes faithfully recapitulate the pathophysiology of familial hypercholesterolemia. Hepatology. Dec. 2012;56(6):2163-71. doi: 10.1002/hep.25871. First published: May 31, 2012.
Chen, et al., Determination of specific CD4 and CD8 T cell epitopes after AAV2-and AAV8-hF.IX gene therapy. Mol Ther. Feb. 2006;13(2):260-9. (Available online Nov. 29, 2005).
Chen, et al., Prolonged correction of hyperlipidemia in mice with familial hypercholesterolemia using an adeno-associated viral vector expressing very-low-density lipoprotein receptor. Mol Ther. Sep. 2000;2(3):256-61.
Chowdhury, et al., Long-term improvement of hypercholesterolemia after ex vivo gene therapy in LDLR-deficient rabbits. Science. Dec. 20, 1991;254(5039):1802-5.
Clement, et al., Large-scale adeno-associated viral vector production using a herpesvirus-based system enables manufacturing for clinical studies. Hum Gene Ther. Aug. 2009;20(8):796-806. doi: 10.1089/hum.2009.094. Online Ahead of Editing: Jul. 1, 2009.
Couto, et al., Direct exposure of mouse spermatozoa to very high concentrations of a serotype-2 adeno-associated virus gene therapy vector fails to lead to germ cell transduction. Hum Gene Ther. Mar. 2004;15(3):287-91.
Cuchel, et al., Inhibition of microsomal triglyceride transfer protein in familial hypercholesterolemia. N Engl J Med. Jan. 11, 2007;356(2):148-56.
Cuchel, et al., Efficacy and safety of a microsomal triglyceride transfer protein inhibitor in patients with homozygous familial hypercholesterolaemia: a single-arm, open-label, phase 3 study. Lancet. Jan. 5, 2013;381(9860):40-6. doi: 10.1016/S0140-6736(12)61731-0, Epub Nov. 2, 2012.
Cuchel, et al., Homozygous familial hypercholesterolaemia: new insights and guidance for clinicians to improve detection and clinical management. A position paper from the Consensus Panel on Familial Hypercholesterolaemia of the European Atherosclerosis Society. Eur Heart J. Aug. 21, 2014;35(32):2146-57. doi: 10.1093/eurheartj/ehu274, Epub Jul. 22, 2014.
Cuchel, et al., Lovastatin decreases de novo cholesterol synthesis and LDL Apo B-100 production rates in combined-hyperlipidemic males. Arterioscler Thromb Vasc Biol. Oct. 1997; 17(10):1910-7.
Cuchel, et al., Pathways by which reconstituted high-density lipoprotein mobilizes free cholesterol from whole body and from macrophages. Arterioscler Thromb Vasc Biol. Mar. 2010;30(3):526-32. doi: 10.1161/ATVBAHA.109.196105. Epub Dec. 17, 2009.
Daskalopoulou and Mikhailidis, Reaching goal in hypercholesterolaemia: dual inhibition of cholesterol synthesis and absorption with simvastatin plus ezetimibe. Curr Med Res Opin. Mar. 2006;22(3):511-28. Published online: Feb. 1, 2006.
Daugherty, Mouse models of atherosclerosis. American Journal of the Medical Sciences, Jan. 2002;323(1):3-10.
Davidoff Am, et al., Comparison of the ability of adeno-associated viral vectors pseudotyped with serotype 2, 5, and 8 capsid proteins to mediate efficient transduction of the liver in murine and nonhuman primate models. Mol Ther. Jun. 2005;11(6):875-88.
Deckelbaum, et al., Failure of complete bile diversion and oral bile acid therapy in the treatment of homozygous familial hypercholesterolemia. N Engl J Med. Mar. 3, 1977;296(9):465-70.
Donsante, et al. Observed incidence of tumorigenesis in long-term rodent studies of rAAV vectors. Gene Ther. Sep. 2001;8(17):1343-6, Published: Aug. 28, 2001.
Edmondson, et al., Loss-of-function variants in endothelial lipase are a cause of elevated HDL cholesterol in humans. J Clin Invest. Apr. 2009; 119(4):1042-50. doi: 10.1172/JCI37176. Epub Mar. 16, 2009.
Espejel, et al., Induced pluripotent stem cell-derived hepatocytes have the functional and proliferative capabilities needed for liver regeneration in mice.J Clin Invest. Sep. 2010;120(9):3120-6, doi: 10.1172/JCI43267. Epub Aug. 25, 2010.

(56) References Cited

OTHER PUBLICATIONS

Fattahi, et al., Disease-corrected hepatocyte-like cells from familial hypercholesterolemia-induced pluripotent stem cells. Mol Biotechnol. Jul. 2013;54(3):863-73. doi: 10.1007/s12033-012-9635-3. First Online: Dec. 18, 2012.
Favaro, et al., Host and vector-dependent effects on the risk of germline transmission of AAV vectors. Mol Ther. Jun. 2009;17(6):1022-30. doi: 10.1038/mt.2009.56. Epub Mar. 17, 2009.
Favaro, et al., Safety of liver gene transfer following peripheral intravascular delivery of adeno-associated virus (AAV)-5 and AAV-6 in a large animal model. Hum Gene Ther. Jul. 2011;22(7):843-52. doi: 10.1089/hum.2010.155. Epub Mar. 8, 2011.
Finn, et al., The efficacy and the risk of immunogenicity of FIX Padua (R338L) in hemophilia B dogs treated by AAV muscle gene therapy. Blood. Nov. 29, 2012;120(23):4521-3, doi: 10.1182/blood-2012-06-440123. Epub Aug. 23, 2012.
Forman, et al., Treatment of homozygous familial hypercholesterolaemia with portacaval shunt. Atherosclerosis. Feb. 1982;41(2-3):349-61.
Gagne, et al., Efficacy and safety of ezetimibe coadministered with atorvastatin or simvastatin in patients with homozygous familial hypercholesterolemia. Circulation. May 28, 2002;105(21):2469-75, (Article online May 6, 2002).
Gao, et al., Adeno-associated viruses undergo substantial evolution in primates during natural infections. Proc Natl Acad Sci U S A. May 13, 2003;100(10):6081-6. Epub Apr. 25, 2003.
Gao, et al., Adeno-associated virus-mediated gene transfer to non-human primate liver can elicit destructive transgene-specific T cell responses. Hum Gene Ther. Sep. 2009;20(9):930-42. doi: 10.1089/hum.2009.060. (Published Online: Aug. 17, 2009).
Gao, et al., Clades of Adeno-associated viruses are widely disseminated in human tissues. J Virol. Jun. 2004;78(12):63 81-8, (Published online May 26, 2004.).
Gao, et al., New recombinant serotypes of AAV vectors. Current Gene Therapy, Jun. 2005;5(3):285-97.
Gao, et al., Novel adeno-associated viruses from rhesus monkeys as vectors for human gene therapy. Proc Natl Acad Sci U S A. Sep. 3, 2002;99(18):11854-9. Epub Aug. 21, 2002.
Gaudet, et al. Efficacy and long-term safety of alipogene tiparvovec (AAV1-LPLS447X) gene therapy for lipoprotein lipase deficiency: an open-label trial. Gene Ther. Apr. 2013;20(4):361-9. doi: 10.1038/gt.2012.43. Epub Jun. 21, 2012.
Gaudet, et al., Gene therapy for lipoprotein lipase deficiency. Curr Opin Lipidol. Aug. 2012;23(4):310-20. doi: 10.1097/MOL.0b013e3283555a7e.
GenBank Accession No. AF513852, 2 pages, accessed on Jan. 4, 2019 from https://www.ncbi.nlm.nih.gov/nuccore/AF513852, last update on Sep. 5, 2002.
GenBank Accession No. NC001401, 5 pages, accessed on Jan. 4, 2019 from https://www.ncbi.nlm.nih.gov/nuccore/NC_001401, last update on Aug. 13, 2018.
GenBank Accession No. NM000527, 7 pages, accessed on Jan. 4, 2019 from https://www.ncbi.nlm.nih.gov/nuccore/NM_000527, last update on Dec. 2, 2018.
GenBank Accession No. U47121, 2 pages, accessed on Jan. 4, 2019 from https://www.ncbi.nlm.nih.gov/nuccore/U47121, last update on Sep. 13, 1999.
GenBank Accession No. V00882.1, 2 pages, accessed on Jan. 4, 2019 from https://www.ncbi.nlm.nih.gov/nuccore/V00882.1, last update on Nov. 14, 2006.
GenBank Accession No. YP_077180, 2 pages, accessed on Jan. 4, 2019 from https://www.ncbi.nlm.nih.gov/protein/YP_077180, last update on Aug. 13, 2018.
George, et al., Hemophilia B gene therapy with a high-specific-activity factor IX variant. N Engl J Med. Dec. 7, 2017;377(23):2215-2227. doi: 10.1056/NEJMoa1708538.
Gil-Farina, et al., Recombinant AAV Integration is Not Associated With Hepatic Genotoxicity in Nonhuman Primates and Patients. Mol Ther. Jun. 2016;24(6):1100-1105. Mol Ther. Jun. 2016;24(6):1100-1105. doi: 10.1038/mt.2016.52. Epub Mar. 7, 2016.
Glynera® (alipogene tiparvovec) Summary of Product Characteristics. Amsterdam, The Netherlands: uniQure biopharma BV, retrieved from https://www.ema.europa.eu/en/medicines/human/EPAR/glybera#product-information-section on Jan. 11, 2019. Frist published Nov. 29, 2012, last update Jul. 10, 2017.
Goldstein and Brown. The LDL receptor defect in familial hypercholesterolemia. Implications for pathogenesis and therapy. Med Clin North Am. Mar. 1982;66(2):335-62.
Goldstein, et al., Esterification of low density lipoprotein cholesterol in human fibroblasts and its absence in homozygous familial hypercholesterolemia. Proc Natl Acad Sci U S A. Nov. 1974;71(11):4288-92.
Graham, et al., Characteristics of a human cell line transformed by DNA from human adenovirus type 5. J Gen Virol. Jul. 1977;36(1):59-74, (Jul. 1, 1977).
Greig, et al., Non-Clinical Study Examining AAVS.TBG.hLDLR Vector-Associated Toxicity in Chow-Fed Wild-Type and LDLR+/− Rhesus Macaques. Hum Gene Ther Clin Dev. Mar. 2017;28(1):39-50, doi: 10.1089/humc.2017.014.
Griffon, et al., Identification of the active form of endothelial lipase, a homodimer in a head-to-tail conformation. J Biol Chem. Aug. 28, 2009;284(35):23322-30. doi: 10.1074/jbc.M109.037002. Epub Jun. 30, 2009.
Grimm, et al., Titration of AAV-2 particles via a novel capsid Elisa: packaging of genomes can limit production of recombinant AAV-2. Gene Ther. Jul. 1999;6(7):1322-30.
Grossman, et al., A pilot study of ex vivo gene therapy for homozygous familial hypercholesterolaemia. Nat Med. Nov. 1995;1(11):1148-54. (Published: Nov. 1, 1995).
Grossman, et al., Successful ex vivo gene therapy directed to liver in a patient with familial hypercholesterolaemia. Nat Genet. Apr. 1994;6(4):335-41.
Grossman, et al., Transplantation of genetically modified autologous hepatocytes into nonhuman primates: feasibility and short-term toxicity. Hum Gene Ther. Oct. 1992;3(5):501-10.
Haitas, et al. Natural history and cardiac manifestations of homozygous familial hypercholesterolaemia. Q J Med. Jul. 1990;76(279):731-40.
Hastie and Samulski. AAV at 50: A golden anniversary of discovery, research, and gene therapy success, a personal perspective. Hum Gene Ther. May 2015;26(5):257-65, doi: 10.1089/hum.2015.025. Epub Apr. 20, 2015.
Hauck, et al., Undetectable transcription of cap in a clinical AAV vector: implications for preformed capsid in immune responses. Mol Ther. Jan. 2009;17(1):144-52. doi: 10.1038/mt.2008.227. Epub Oct. 21, 2008.
Haurigot, et al., Safety of AAV factor IX peripheral transvenular gene delivery to muscle in hemophilia B dogs. Mol Ther. Jul. 2010;18(7):1318-29. doi: 10.1038/mt.2010.73. Epub Apr. 27, 2010.
Hermonat and Muzyczka. Use of adeno-associated virus as a mammalian DNA cloning vector: transduction of neomycin resistance into mammalian tissue culture cells. Proc Natl Acad Sci U S A, Oct. 1984;81(20):6466-70.
Herzog RW. Immune Responses to AAV Capsid: Are Mice Not Humans After All? Mol Ther. Apr. 2007;15(4):649-50.
Hibbitt, et al., Long-term physiologically regulated expression of the low-density lipoprotein receptor in vivo using genomic DNA mini-gene constructs. Mol Ther. Feb. 2010;18(2):317-26, doi: 10.1038/mt.2009.249. Epub Oct. 27, 2009.
Hibbitt, et al., RNAi-mediated knockdown of HMG CoA reductase enhances gene expression from physiologically regulated low-density lipoprotein receptor therapeutic vectors in vivo. Gene Ther. Apr. 2012; 19(4):463-7. doi: 10.1038/gt.2011.103, Epub Jul. 28, 2011.
Hiles and Moriarty. Pulse Pressure and Risk of Cardiovascular Disease, Journal of American Medical Association, JAMA. Jan. 8, 2003;289(2):174-5; author reply 175. Jan. 8, 2003.
Hirano, et al., Targeted Disruption of the Mouse apobec-1 Gene Abolishes Apolipoprotein B mRNA Editing and Eliminates Apolipoprotein B48. Journal of Biological Chemistry, Apr. 25, 1996;271(17):9887-90, Apr. 26, 1996.

(56) References Cited

OTHER PUBLICATIONS

Hoeg, et al., Liver transplantation for treatment of cardiovascular disease: comparison with medication and plasma exchange in homozygous familial hypercholesterolemia. Am J Cardiol. Mar. 1, 1987;59(6):705-7.

Hui, et al., Modulation of CD8+ T cell responses to AAV vectors with IgG-derived MHC class II epitopes. Mol Ther. Sep. 2013;21(9):1727-37. doi: 10,103 8/mt.2013.166. Epub Jul. 16, 2013.

Huijgen, et al., Familial hypercholesterolemia: current treatment and advances in management. Expert Review of Cardiovascular Therapy, 2008. 6(4): p. 567-581. Expert Rev Cardiovasc Ther. Apr. 2008;6(4):567-81. doi: 10.1586/14779072.6.4.567.

Hummel, et al., Familial hypercholesterolemia in a rhesus monkey pedigree: molecular basis of low density lipoprotein receptor deficiency. Proc Natl Acad Sci U S A. Apr. 1990;87(8):3122-6, (Apr. 1, 1990.).

Ibrahim, et al., Translational lessons from a case of combined heart and liver transplantation for familial hypercholesterolemia 20 years post-operatively. J Cardiovasc Transl Res. Jun. 2012;5(3):351-8. doi: 10.1007/s12265-011-9311-1. Epub Sep. 1, 2011

Ishibashi, et al., Hypercholesterolemia in low density lipoprotein receptor knockout mice and its reversal by adenovirus-mediated gene delivery. J Clin Invest. Aug. 1993;92(2):883-93, First published Aug. 1, 1993.

Jiang, et al., Effects of transient immunosuppression on adenoas-sociated, virus-mediated, liver-directed gene transfer in rhesus macaques and implications for human gene therapy. Blood. Nov. 15, 2006;108(10):3321-8, Epub Jul. 25, 2006.

Jin, et al., Hepatic Proprotein Convertases Modulate HDL Metabolism. Cell Metab. Aug. 2007;6(2):129-36, Published: Aug. 7, 2007.

Joshi-Barve, et al., Palmitic acid induced production of proinflammatory cytokine interleukin-8 from hepatocytes. Hepatology. Sep. 2007;46(3):823-30. First published: Aug. 24, 2007.

Kanda, et al., MCP-1 contributes to macrophage infiltration into adipose tissue, insulin resistance, and hepatic steatosis in obesity. J Clin Invest. Jun. 2006;116(6):1494-505, Epub May 11, 2006.

Kassim, et al., Identification and functional characterization in vivo of a novel splice variant of LDLR in rhesus macaques. Physiol Genomics. Aug. 16, 2011;43(15):911-6. doi: 10.1152/physiolgenomics. 00006.2011. Epub May 31, 2011.

Keller, et al., Regression of valvular aortic stenosis due to homozygous familial hypercholesterolemia following plasmapheresis. Klin Wochenschr. Apr. 1, 1986;64(7):338-41.

Khachadurian, et al., Cholestyramine therapy in patients homozygous for familial hypercholesterolemia (familial hypercholesterolemic xanthomatosis). J Atheroscler Res. Jan.-Feb. 1968;8(1):177-88.

Khachadurian, et al., Experiences with the homozygous cases of familial hypercholesterolemia. A report of 52 patients. Nutr Metab. 1973; 15(1):132-40.

Khera, et al., Cholesterol efflux capacity, high-density lipoprotein function, and atherosclerosis. N Engl J Med. Jan. 13, 2011;364(2):127-35. doi: 10.1056/NEJMoa1001689.

King, et al., Plasma-exchange therapy of homozygous familial hypercholesterolemia. N Engl J Med. Jun. 26, 1980;302(26): 1457-9.

Kolansky, et al., Longitudinal evaluation and assessment of cardiovascular disease in patients with homozygous familial hypercholesterolemia. Am J Cardiol. Dec. 1, 2008;102(11):1438-43. doi: 10.1016/j.amjcard.2008.07.035. Epub Sep. 11, 2008.

Kotin, Large-scale recombinant adeno-associated virus production. Hum Mol Genet. Apr. 15, 2011;20(R1):R2-6. doi: 10.1093/hmg/ddr141. Epub Apr. 29, 2011.

Kotterman, et al., Engineering adeno-associated viruses for clinical gene therapy. Nat Rev Genet. Jul. 2014;15(7):445-51. doi: 10.1038/nrg3742. Epub May 20, 2014.

Kozarsky, et al., Effective treatment of familial hypercholesterolaemia in the mouse model using adenovirus-mediated transfer of the VLDL receptor gene. Nat Genet. May 1996;13(1):54-62.

Kozarsky, et al., In vivo correction of low density lipoprotein receptor deficiency in the Watanabe heritable hyperlipidemic rabbit with recombinant adenoviruses. J Biol Chem. May 6, 1994;269(18):13695-702.

Kucukkartallar, et al., Liver transplantation as a treatment option for three siblings with homozygous familial hypercholesterolemia. Pediatr Transplant. May 2011;15(3):281-4, doi: 10.1111/j.1399-3046.2010. 01469.x. Epub Jan. 17, 2011.

Leonard, et al., Progression of atheroma in homozygous familial hypercholesterolaemia during regular plasma exchange. Lancet. Oct. 10, 1981;2(8250):811.

Levy, et al., Cholestyramine in type II hyperlipoproteinemia. A double-blind trial. Ann Intern Med. Jul. 1973;79(1):51-8.

Li, et al., A preclinical animal model to assess the effect of pre-existing immunity on AAV-mediated gene transfer. Mol Ther. Jul. 2009;17(7):1215-24. doi: 10,1038/mt.2009.79. Epub Apr. 14, 2009.

Li, et al., Adeno-associated virus type 2 (AAV2) capsid-specific cytotoxic T lymphocytes eliminate only vector-transduced cells coexpressing the AAV2 capsid in vivo, J Virol. Jul. 2007;81(14):7540-7. Epub May 2, 2007.

Li, et al., Assessing the potential for AAV vector genotoxicity in a murine model. Blood. Mar. 24, 2011;117(12):3311-9. doi: 10.1182/blood-2010-08-302729. Epub Nov. 24, 2010.

Li, et al., Cellular immune response to cryptic epitopes during therapeutic gene transfer. Proc Natl Acad Sci U S A. Jun. 30, 2009;106(26):10770-4. doi: 10.1073/pnas.0902269106, Epub Jun. 16, 2009.

Li, et al., Pre-existing AAV capsid-specific CD8+ T cells are unable to eliminate AAV-transduced hepatocytes. Mol Ther. Apr. 2007;15(4):792-800. Epub Jan. 23, 2007.

Linton, et al., Transgenic mice expressing high plasma concentrations of human apolipoprotein B100 and lipoprotein(a). J Clin Invest. Dec. 1993;92(6):3029-37. (First published Dec. 1, 1993).

Lisowski, et al., Adeno-associated virus serotypes for gene therapeutics. Curr Opin Pharmacol. Oct. 2015;24:59-67. doi: 10.1016/j.coph.2015.07.006. Epub Aug. 25, 2015.

Lisowski, et al., Selection and evaluation of clinically relevant AAV variants in a xenograft liver model. Nature. Feb. 20, 2014;506(7488):382-6. doi: 10.1038/nature12875. Epub Dec. 25, 2013.

Liu, et al., Neutralizing antibodies against AAV2, AAV5 and AAV8 in healthy and HIV-1-infected subjects in China: implications for gene therapy using AAV vectors. Gene Ther. Aug. 2014;21(8):732-8. doi: 10.1038/gt.2014.47. Epub May 22, 2014.

Lock, et al., Absolute determination of single-stranded and self-complementary adeno-associated viral vector genome titers by droplet digital PCR. Hum Gene Ther Methods. Apr. 2014;25(2):115-25. doi: 10.1089/hgtb.2013.131. Epub Dec. 12, 2013.

Lock, et al., Rapid, simple, and versatile manufacturing of recombinant adeno-associated viral vectors at scale. Hum Gene Ther. Oct. 2010;21(10):1259-71. doi: 10.1089/hum.2010.055. (Published Online:Sep. 24, 2010).

Luo, et al., Adeno-associated virus-mediated cancer gene therapy: current status. Cancer Lett. Jan. 28, 2015;356(2Pt B):347-56. doi: 10.1016/j.canlet.2014.10.045. Epub Nov. 10, 2014.

Luxturna™ (voretigene neparvovec-rzyl) Prescribing Information, 2017, acessed on Jan. 9, 2018 from https://www.fda.gov/downloads/BiologicsBloodVaccines/CellularGeneTherapyProducts/ApprovedProducts/UCM589541.pdf.

Mabuchi, et al., Development of coronary heart disease in familial hypercholesterolemia. Circulation. Feb. 1989;79(2):225-32.

Mabuchi, et al., Homozygous familial hypercholesterolemia in Japan. Am J Med. Aug. 1978;65(2):290-7.

Maclaren, et al. Retinal gene therapy in patients with choroideremia: initial findings from a phase 1/2 clinical trial. Lancet. Mar. 29, 2014;383(9923):1129-37. doi: 10.1016/S0140-6736(13)62117-0, Epub Jan. 16, 2014.

Maguire AM et al. Safety and efficacy of gene transfer for Leber's congenital amaurosis. N Engl J Med. May 22, 2008;358(21):2240-8. doi: 10.1056/NEJMoa0802315. Epub Apr. 27, 2008.

(56) References Cited

OTHER PUBLICATIONS

Maheshri, et al., Directed evolution of adeno-associated virus yields enhanced gene delivery vectors. Nat Biotechnol, Feb. 2006;24(2):198-204, Epub Jan. 22, 2006.
Malatack, Liver transplantation as treatment for familial homozygous hypercholesterolemia: too early or too late. Pediatr Transplant. Mar. 2011;15(2):123-5. doi: 10.1111/j.1399-3046.2010.01458.x. Epub Jan. 10, 2011.
Malloy, et al., Complementarity of colestipol, niacin, and lovastatin in treatment of severe familial hypercholesterolemia. Ann Intern Med. Nov. 1987;107(5):616-23.
Manno, et al., AAV-mediated factor IX gene transfer to skeletal muscle in patients with severe hemophilia B. Blood. Apr. 15, 2003;101(8):2963-72. Epub Dec. 19, 2002.
Manno, et al., Successful transduction of liver in hemophilia by AAV-Factor IX and limitations imposed by the host immune response. Nat Med. Mar. 2006;12(3):342-7, Epub Feb. 12, 2006.
Marais, et al., A dose-titration and comparative study of rosuvastatin and atorvastatin in patients with homozygous familial hypercholesterolaemia. Atherosclerosis. Mar. 2008;197(1):400-6, Epub Aug. 28, 2007.
Martino, et al., Engineered AAV vector minimizes in vivo targeting of transduced hepatocytes by capsid-specific CD8+ T cells. Blood. Mar. 21, 2013;121(12):2224-3 3, doi: 10.1182/blood-2012-10-460733. Epub Jan. 16, 2013.
McCaffrey, et al., The host response to adenovirus, helper-dependent adenovirus, and adeno-associated virus in mouse liver. Mol Ther. May 2008;16(5):931-41. doi: 10.1038/mt.2008.37. Epub Mar. 18, 2008.
McCarty, et al., Integration of adeno-associated virus (AAV) and recombinant AAV vectors. Annu Rev Genet. 2004;38:819-45. First published online as a Review in Advance on Aug. 30, 2004.
Mendell, et al., Dystrophin immunity in Duchenne's muscular dystrophy. N Engl J Med. Oct. 7, 2010;363(15):1429-37, doi: 10.1056/NEJMoa1000228.
Mietzsch, et al., OneBac: platform for scalable and high-titer production of adeno-associated virus serotype 1-12 vectors for gene therapy. Hum Gene Ther. Mar. 2014;25(3):212-22, doi: 10.1089/hum.2013.184. Published online Dec. 3, 2013.
Mimuro J et al. Minimizing the inhibitory effect of neutralizing antibody for efficient gene expression in the liver with adeno-associated virus 8 vectors. Mol Ther. Feb. 2013;21(2):318-23. doi: 10.1038/mt.2012.258. Epub Dec. 18, 2012.
Mingozzi, et al., AAV-1-mediated gene transfer to skeletal muscle in humans results in dose-dependent activation of capsid-specific T cells. Blood. Sep. 3, 2009;114(10):2077-86, doi: 10.1182/blood-2008-07-167510, Epub Jun. 8, 2009.
Mingozzi, et al., CD8(+) T-cell responses to adeno-associated virus capsid in humans. Nat Med. Apr. 2007;13(4):419-22, Epub Mar. 18, 2007.
Mingozzi, et al., Therapeutic in vivo gene transfer for genetic disease using AAV: progress and challenges. Nat Rev Genet. May 2011;12(5):341-55. doi: 10.1038/nrg2988. Published: Apr. 18, 2011.
Moorjani, et al., Homozygous familial hypercholesterolemia among French Canadians in Quebec Province. Arteriosclerosis. Mar.-Apr. 1989;9(2):211-6.
Moorjani, et al., Mutations of low-density-lipoprotein-receptor gene, variation in plasma cholesterol, and expression of coronary heart disease in homozygous familial hypercholesterolaemia. Lancet. May 22, 1993;341(8856):1303-6. (Published: May 22, 1993).
Moriarty PM, et al., A Study to Demonstrate the Utility of Help LDL Apheresis Treatment for Patients with Non-ST Elevation Acute Coronary Syndrome. Atherosclerosis, Supplements, vol. 3, No. 2, June (2002) 166-167.
Moriarty, et al., C-reactive protein and other markers of inflammation among patients undergoing Help LDL apheresis. Atherosclerosis. Oct. 2001;158(2):495-8.
Musunuru, et al., From noncoding variant to phenotype via SORT1 at the lp13 cholesterol locus. Nature. Aug. 5, 2010;466(7307):714-9. doi: 10.103 8/nature09266. Published: Aug. 5, 2010.
Nakai, et al., Unrestricted hepatocyte transduction with adeno-associated virus serotype 8 vectors in mice. J Virol. Jan. 2005;79(1):214-24. Published online Dec. 13, 2004.
Nathwani, et al. Self-complementary adeno-associated virus vectors containing a novel liver-specific human factor IX expression cassette enable highly efficient transduction of murine and nonhuman primate liver. Blood. Apr. 1, 2006;107(7):2653-61. Epub Dec. 1, 2005.
Nathwani, et al., Long-term safety and efficacy following systemic administration of a self-complementary AAV vector encoding human FIX pseudotyped with serotype 5 and 8 capsid proteins. Mol Ther. May 2011;19(5):876-85. doi: 10.1038/mt.2010.274. Epub Jan. 18, 2011.
Nathwani, et al., Long-term safety and efficacy of factor IX gene therapy in hemophilia B. N Engl J Med. Nov. 20, 2014;371(21):1994-2004. doi: 10.1056/NEJMoa1407309. Nov. 20, 2014.
Nathwani, et al., Safe and efficient transduction of the liver after peripheral vein infusion of self-complementary AAV vector results in stable therapeutic expression of human FIX in nonhuman primates. Blood. Feb. 15, 2007;109(4):1414-21. Epub Nov. 7, 2006.
National Eye Institute, "NEI Human Gene Therapy Trial for Retinoschisis Underway", 3 pages, accessed on Jan. 8, 2019 from https://nei.nih.gov/news/briefs/nei-human-gene-therapy-trial-retinoschisis-underway.
Nomura, et al., Low-density lipoprotein receptor gene therapy using helperdependent adenovirus produces long-term protection against atherosclerosis in a mouse model of familial hypercholesterolemia. Gene Ther. Oct. 2004;11(20):1540-8. (Published: Jul. 22, 2004).
Nordestgaard, et al., Familial hypercholesterolaemia is underdiagnosed and undertreated in the general population: guidance for clinicians to prevent coronary heart disease: consensus statement of the European Atherosclerosis Society. Eur Heart J. Dec. 2013;34(45):3478-90a. doi: 10.1093/eurheartj/eht273. Epub Aug. 15, 2013.
Ordonez, et al., Using human-induced pluripotent stem cells to model monogenic metabolic disorders of the liver. Semin Liver Dis. Nov. 2012;32(4):298-306. doi: 10.1055/S-0032-1329898.
Passini, et al., CNS-targeted gene therapy improves survival and motor function in a mouse model of spinal muscular atrophy. J Clin Invest. Apr. 2010; 120(4):1253-64. doi: 10.1172/JCI41615, Epub Mar. 15, 2010.
Patrick M. Moriarty and Daniel J. Rader, PowerPoint slides titled "Human Gene Protocol #1201-1144: AAV8-mediated Low Density Lipoprotein Receptor Gene Replacement in Subjects with Homozygous Familial Hypercholesterolemia" presented on Mar. 7, 2012 before Recombinant DNA Advisory Committee (RAC), accessed on Jan. 8, 2019 from https://osp.od.nih.gov/wp-content/uploads/2013/12/1144_Rader.pdf.
Paulk, et al., Adeno-associated virus gene repair corrects a mouse model of hereditary tyrosinemia in vivo. Hepatology. Apr. 2010;51(4):1200-8. doi: 10.1002/hep.23481. (First published: Mar. 26, 2010).
Powell-Braxton, et al., A mouse model of human familial hypercholesterolemia: markedly elevated low density lipoprotein cholesterol levels and severe atherosclerosis on a low-fat chow diet. Nat Med. Aug. 1998;4(8):934-8.
Raal, et al., Inhibition of cholesterol synthesis by atorvastatin in homozygous familial hypercholesterolaemia. Atherosclerosis. Jun. 2000;150(2):421-8.
Raal, et al., Inhibition of PCSK9 with evolocumab in homozygous familial hypercholesterolaemia (TESLA Part B): a randomised, double-blind, placebo-controlled trial. Lancet. Jan. 24, 2015;385(9965):341-50. doi: 10.1016/S0140-6736(14)61374-X. Epub Oct. 1, 2014.
Raal, et al., Low-density lipoprotein cholesterol-lowering effects of AMG 145, a monoclonal antibody to proprotein convertase subtilisin/kexin type 9 serine protease in patients with heterozygous familial hypercholesterolemia: the Reduction of LDL-C with PCSK9 Inhibition in Heterozygous Familial Hypercholesterolemia Disorder (Rutherford) randomized trial. Circulation. Nov. 13, 2012;126(20):2408-17. doi: 10.1161/Circulationaha. 112.144055. Epub Nov. 5, 2012.
Raal, et al., Mipomersen, an apolipoprotein B synthesis inhibitor, for lowering of LDL cholesterol concentrations in patients with

(56) References Cited

OTHER PUBLICATIONS homozygous familial hypercholesterolaemia: a randomised, double-blind, placebo-controlled trial. Lancet. Mar. 20, 2010;375(9719):998-1006. doi: 10.1016/S0140-6736(10)60284-X. Published:Mar. 14, 2010.

Raal, et al., PCSK9 inhibition with evolocumab (AMG 145) in heterozygous familial hypercholesterolaemia (Rutherford-2): a randomised, double-blind, placebo-controlled trial. Lancet. Jan. 24, 2015;385(9965):331-40. doi: 10.1016/S0140-6736(14)61399-4, Epub Oct. 1, 2014.

Raal, et al., Reduction in mortality in subjects with homozygous familial hypercholesterolemia associated with advances in lipid-lowering therapy. Circulation. Nov. 15, 2011;124(20):2202-7. doi: 10.1161/Circulationaha.111.042523. Epub Oct. 10, 2011.

Rader, et al., State of the art: atherosclerosis in a limited edition. Nat Med. Aug. 1998;4(8):899-900, (Aug. 1998).

Ramakrishnan, et al. Restoration of Physiologically Responsive Low-Density Lipoprotein Receptor-Mediated Endocytosis in Genetically Deficient Induced Pluripotent Stem Cells. Sci Rep. Aug. 26, 2015;5:13231. doi: 10.1038/srep13231. Published: Aug. 26, 2015.

Rangarajan, et al. AAV5-Factor VIII Gene Transfer in Severe Hemophilia A. N Engl J Med. Dec. 28, 2017;377(26):2519-2530. doi: 10.1056/NEJMoa1708483. Epub Dec. 9, 2017.

Rashid, et al., Modeling inherited metabolic disorders of the liver using human induced pluripotent stem cells. J Clin Invest. Sep. 2010;120(9):3127-36. doi: 10.1172/JCI43122, Epub Aug. 25, 2010.

Reilly, et al., Identification of ADAMTS7 as a novel locus for coronary atherosclerosis and association of ABO with myocardial infarction in the presence of coronary atherosclerosis: two genome-wide association studies. Lancet. Jan. 29, 2011;377(9763):383-92, doi: 10.1016/S0140-6736(10)61996-4, Epub Jan. 14, 2011.

Robins, et al., Evidence for separate pathways of transport of newly synthesized and preformed cholesterol into bile. J Biol Chem. Jun. 10, 1985;260(11):6511-3.

Rohlmann, et al., Inducible inactivation of hepatic LRP gene by cre-mediated recombination confirms role of LRP in clearance of chylomicron remnants. J Clin Invest. Feb. 1, 1998; 101(3): 689-695.

Rosas, et al., Patterns of scAAV vector insertion associated with oncogenic events in a mouse model for genotoxicity. Mol Ther. Nov. 2012;20(11):2098-110. doi: 10.1038/mt.2012.197. Epub Sep. 18, 2012.

Samuel, et al., Phylogenetic and pathotypic characterization of newcastle disease viruses circulating in west Africa and efficacy of a current vaccine. J Clin Microbiol. Mar. 2013;51(3):771-81. doi: 10.1128/JCM.02750-12. Epub Dec. 19, 2012.

Sanan, et al., Low density lipoprotein receptor-negative mice expressing human apolipoprotein B-100 develop complex atherosclerotic lesions on a chow diet: No accentuation by apolipoprotein(a). Proc Natl Acad Sci U S A. Apr. 14, 1998;95(8):4544-9, Published Apr. 14, 1998.

Scanu, et al., Genetically determined hypercholesterolemia in a rhesus monkey family due to a deficiency of the LDL receptor. J Lipid Res. Dec. 1988;29(12):1671-81.

Schuettrumpf, et al., Inadvertent germline transmission of AAV2 vector: findings in a rabbit model correlate with those in a human clinical trial. Mol Ther. Jun. 2006;13(6):1064-73, Epub May 2, 2006.

Schunkert, et al., Large-scale association analysis identifies 13 new susceptibility loci for coronary artery disease. Nat Genet. Mar. 6, 2011;43(4):333-8. doi: 10.1038/ng.784. Published: Mar. 6, 2011.

Shaw, et al., Combined transplantation of the heart and liver. Ann Surg. Dec. 1985;202(6):667-72, (Publication Date: Dec. 1, 1985).

Siders, et al., Cytotoxic T lymphocyte responses to transgene product, not adeno-associated viral capsid protein, limit transgene expression in mice. Hum Gene Ther. Jan. 2009;20(1):11-20, doi: 10.1089/hum.2008.055, Published Online: Jan. 14, 2009.

Sjouke, et al., Homozygous autosomal dominant hypercholesterolaemia in the Netherlands: prevalence, genotype-phenotype relationship, and clinical outcome. Eur Heart J. Mar. 1, 2015;36(9):560-5. doi: 10.1093/eurheartj/ehu058. Epub Feb. 28, 2014.

Sommer, et al., Quantification of adeno-associated virus particles and empty capsids by optical density measurement. Mol Ther. Jan. 2003;7(1): 122-8.

Spark Therapeutics, 2015 Annual Report. 124 pages, accessed on Jan. 8, 2019 from http://www.annualreports.com/HostedData/AnnualReportArchive/s//NASDAQ_ONCE_2015.pdf, (Mar. 2016).

Starzl, et al., Heart-liver transplantation in a patient with familial hypercholesterolaemia. Lancet. Jun. 23, 1984;1(8391):1382-3.

Starzl, et al., Portacaval shunt in patients with familial hypercholesterolemia. Ann Surg. Sep. 1983; 198(3): 273-283.

Stein, et al., Effect of a monoclonal antibody to PCSK9, REGN727/SAR236553, to reduce low-density lipoprotein cholesterol in patients with heterozygous familial hypercholesterolaemia on stable statin dose with or without ezetimibe therapy: a phase 2 randomised controlled trial. Lancet. Jul. 7, 2012;380(9836):29-36. doi: 10.1016/S0140-6736(12)60771-S. Epub May 26, 2012.

Stein, et al., Effect of the proprotein convertase subtilisin/kexin 9 monoclonal antibody, AMG 145, in homozygous familial hypercholesterolemia. Circulation. Nov. 5, 2013;128(19):2113-20. doi: 10.1161/Circulationaha. 113.004678. Epub Sep. 6, 2013.

Stein, et al., Nonprogression of coronary artery atherosclerosis in homozygous familial hypercholesterolemia after 31 months of repetitive plasma exchange. Clin Cardiol. Mar. 1986;9(3):115-9, First published: Mar. 1986.

Stoffel, et al., Selective removal of apolipoprotein B-containing serum lipoproteins from blood plasma. Proc Natl Acad Sci U S A, Jan. 1981;78(1):611-5.

Sun, et al., Efficacy of an adeno-associated virus 8-pseudotyped vector in glycogen storage disease type II. Mol Ther, Jan. 2005;11(1):57-65.

Sun, et al., Molecular analysis of vector genome structures after liver transduction by conventional and self-complementary adeno-associated viral serotype vectors in murine and nonhuman primate models. Hum Gene Ther. Jun. 2010;21(6):750-61. doi: 10.1089/hum.2009.214.Published Online:May 5, 2010.

Tanigawa, et al., Expression of cholesteryl ester transfer protein in mice promotes macrophage reverse cholesterol transport. Circulation. Sep. 11, 2007;116(11):1267-73. Epub Aug. 20, 2007 .

Tanigawa, et al., Lecithin: cholesterol acyltransferase expression has minimal effects on macrophage reverse cholesterol transport in vivo. Circulation. Jul. 14, 2009;120(2):160-9. doi: 10.1161/Circulationaha. 108.825109. Epub Jun. 29, 2009.

Tateya, et al., An Increase in the Circulating Concentration of Monocyte Chemoattractant Protein-1 Elicits Systemic Insulin Resistance Irrespective of Adipose Tissue Inflammation in Mice. Endocrinology. Mar. 2010;151(3):971-9. doi: 10.1210/en.2009-0926. Epub Jan. 7, 2010.

Teslovich, et al., Biological, Clinical, and Population Relevance of 95 Loci Mapped for Serum Lipid Concentrations. Nature. Aug. 5, 2010;466(7307):707-13. doi: 10.1038/nature09270. Published: Aug. 5, 2010.

Thomas, et al., Rapid uncoating of vector genomes is the key to efficient liver transduction with pseudotyped adeno-associated virus vectors. J Virol. Mar. 2004;78(6):3110-22, Published online Feb. 27, 2004.

Thomas, et al., Scalable recombinant adeno-associated virus production using recombinant herpes simplex virus type 1 coinfection of suspension-adapted mammalian cells. Hum Gene Ther. Aug. 2009;2(08):861-70. doi: 10.1089/hum.2009.004. Online Ahead of Editing: May 6, 2009.

Thompson, et al., Familial Hypercholesterolaemia Regression Study: a randomised trial of low-density-lipoprotein apheresis. Lancet. Apr. 1, 1995;345(8953):811-6. (Apr. 1995).

Thompson, et al., Improved survival of patients with homozygous familial hypercholesterolaemia treated with plasma exchange. Br Med J (Clin Res Ed). Dec. 14, 1985;291(6510):1671-3.

Thompson, LDL apheresis. Atherosclerosis, Atherosclerosis. Mar. 2003;167(1):1-13, (Mar. 2003).

Tiniakos, et al., Nonalcoholic Fatty Liver Disease: Pathology and Pathogenesis. Annu Rev Pathol. 2010;5:145-71. doi: 10.1146/annurev-pathol-121808-102132. First published online as a Review in Advance on Sep. 30, 2009.

(56) References Cited

OTHER PUBLICATIONS

Uauy, et al., Lovastatin therapy in receptor-negative homozygous familial hypercholesterolemia: lack of effect on low-density lipoprotein concentrations or turnover, J Pediatr, 1988. 113(2): p. 387-392, Aug. 1988.
Vaessen, et al., Gene therapy in disorders of lipoprotein metabolism. Curr Gene Ther. Feb. 2007;7(1):35-47.
Valdivtelso, et al., Lipids and lipoprotein changes after heart and liver transplantation in a patient with homozygous familial hypercholesterolemia. Ann Intern Med. Feb. 1988;108(2):204-6.
Van Craeyveld, et al., Gene therapy for familial hypercholesterolemia. Curr. Pharm. Des. 2011;17:2575-91.
Vandenberghe, et al., Heparin binding directs activation of T cells against adeno-associated virus serotype 2 capsid. Nat Med. Aug. 2006;12(8):967-71. Epub Jul. 16, 2006.
Vandenberghe, et al., Tailoring the AAV vector capsid for gene therapy. Gene Ther. Mar. 2009;16(3):311-9. doi: 10.1038/gt.2008.170. Epub Dec. 4, 2008.
Vella, et al., Low-density lipoprotein apheresis for the treatment of refractory hyperlipidemia. Mayo Clin Proc. Oct. 2001;76(10):1039-46.
Virag, et al., Producing recombinant adeno-associated virus in foster cells: overcoming production limitations using a baculovirus-insect cell expression strategy. Hum Gene Ther. Aug. 2009;20(8):807-17. doi: 10.1089/hum.2009.092.
Vuorio, et al., Hypolipidemic treatment of heterozygous familial hypercholesterolemia: a lifelong challenge. Expert Rev Cardiovasc Ther. May 2004;2(3):405-15.
Wang, et al., Adeno-associated virus serotype 8 efficiently delivers genes to muscle and heart. Nat Biotechnol. Mar. 2005;23(3):321-8. Epub Feb. 27, 2005.
Wang, et al., Assessment of toxicity and biodistribution of recombinant AAV8 vector-mediated immunomodulatory gene therapy in mice with Pompe disease. Mol Ther Methods Clin Dev. Jun. 11, 2014;1:14018. doi: 10.1038/mtm.2014.18. eCollection 2014. Jan. 1, 2014.
Wang, et al., Cross-presentation of adeno-associated virus serotype 2 capsids activates cytotoxic T cells but does not render hepatocytes effective cytolytic targets. Hum Gene Ther. Mar. 2007;18(3):185-94. Online Ahead of Print: Feb. 26, 2007.
Wang, et al., Impact of pre-existing immunity on gene transfer to nonhuman primate liver with adeno-associated virus 8 vectors. Hum Gene Ther. 2011 ov;22(11):1389-401. doi: 10.1089/hum.2011.031. Published Online:Apr. 8, 2011.
Wang, et al., Sustained correction of disease in naive and AAV2-pretreated hemophilia B dogs: AAV2/8-mediated, liver-directed gene therapy. Blood. Apr. 15, 2005;105(8):3079-86. Epub Jan. 6, 2005.
Wang, et al., Sustained expression of therapeutic level of factor IX in hemophilia B dogs by AAV-mediated gene therapy in liver. Mol Ther. Feb. 2000;1(2):154-8.
Wang, et al., Systematic evaluation of AAV vectors for liver directed gene transfer in murine models. Mol Ther. Jan. 2010;18(1):118-25. doi: 10.1038/mt.2009.246. Epub Oct. 27, 2009.
Wang, et al., The pleiotropic effects of natural AAV infections on liver-directed gene transfer in macaques. Mol Ther. Jan. 2010;18(1):126-34. doi: 10.1038/mt.2009.245. Epub Nov. 3, 2009.
Watanabe, Serial inbreeding of rabbits with hereditary hyperlipidemia (WHHL-rabbit). Atherosclerosis. Jun. 1980;36(2):261-8.
Wilson, et al., Temporary amelioration of hyperlipidemia in low density lipoprotein receptor-deficient rabbits transplanted with genetically modified hepatocytes. Proc Natl Acad Sci U S A. Nov. 1990;87(21):8437-41. Published Nov. 1, 1990.
Wobus, et al., J. Virol. Monoclonal antibodies against the adeno-associated virus type 2 (AAV-2) capsid: epitope mapping and identification of capsid domains involved in AAV-2-cell interaction and neutralization of AAV-2 infection. J Virol. Oct. 2000;74(19):9281-93. (Oct. 2000).
Wright, et al., Identification of factors that contribute to recombinant AAV2 particle aggregation and methods to prevent its occurrence during vector purification and formulation. Mol Ther. Jul. 2005;12(1):171-8. Available online Apr. 9, 2005.
Wu, et al., Adeno-associated virus serotypes: vector toolkit for human gene therapy. Mol Ther. Sep. 2006;14(3):316-27. Epub Jul. 7, 2006.
Yasuda, et al., Tissue-specific liver X receptor activation promotes macrophage reverse cholesterol transport in vivo. Arterioscler Thromb Vasc Biol. Apr. 2010;30(4):781-6, doi: 10.1161/ATVBAHA. 109.195693. Epub Jan. 28, 2010.
Ye, et al., Herpes simplex virus clearance during purification of a recombinant adeno-associated virus serotype 1 vector. Hum Gene Ther Clin Dev. Dec. 2014;25(4):212-7. doi: 10.1089/humc.2014.060. (Dec. 2014).
Yokoyama, et al., Selective removal of low density lipoprotein by plasmapheresis in familial hypercholesterolemia. Arteriosclerosis. Nov.-Dec. 1985;5(6):613-22.
International Preliminary Report on Patentability dated Jun. 12, 2018 in International Patent Application No. PCT/US2016/065984, filed Dec. 9, 2016.
Martin Lock and Mauricio Alvira. U.S. Appl. No. 62/266,341, filed Dec. 11, 2015.
Martin Lock and Mauricio Alvira. U.S. Appl. No. 62/322,098, filed Apr. 13, 2016.
Written Opinion and International Search Report dated Jun. 22, 2018 in International Patent Application No. PCT/US2018/018678, filed Feb. 20, 2018.
Office Action issued in the corresponding Japanese Patent Application No. 2016-564200, dispatched Feb. 27, 2019, with an unofficial translation provided by the Japanese Agent.
Deng et al., Identification of amino acid residues in the ligand binding repeats of LDL receptor important for PCSK9 binding. J Lipid Res. Mar. 2019;60(3):516-527 (Epub Jan. 7, 2019.).
Ellsworth et al., U.S. Appl. No. 62/052,139, filed Sep. 18, 2014.
Ellsworth et al., U.S. Appl. No. 61/952,906, filed Mar. 14, 2014.
Ellsworth et al., U.S. Appl. No. 61/903,485, filed Nov. 13, 2013.
Ellsworth et al., U.S. Appl. No. 61/886,137, filed Oct. 3, 2013.
Response filed on Oct. 24, 2019 in reply to the Apr. 17, 2019 Office Action in the corresponding European Patent Application No. 15721097.2.
Response filed on Jan. 8, 2019 in reply to the Jun. 28, 2018 Office Action in the corresponding European Patent Application No. 15721097.2.
Response filed on May 9, 2018 in reply to the Oct. 30, 2017 Office Action in the corresponding European Patent Application No. 15721097.2.
Response filed on Jun. 6, 2017 in the corresponding European Patent , Application No. 15721097.2 in reply to a Communication inviting the Applicant to respond to the objections raised in the International Search Report and Written Opinion.
Office Action issued in the corresponding European Patent Application No. 15721097.2, dated Apr. 17, 2019.
Non-Final Office Action dated Apr. 2, 2020 issued in corresponding U.S. Appl. No. 16/060,409, and Response filed Jul. 2, 2020.
Notice of Allowance dated Aug. 19, 2020 issued in corresponding U.S. Appl. No. 16/060,409.
Communication dated May 20, 2020 issued in corresponding European Patent Application No. 16825936.4.
Office Action dated Jun. 2, 2020 issued in corresponding Brazilian Patent Application No. BR112016024379-0, with unofficial translation provided by local Agent.
Office Action dated Aug. 31, 2020 issued in corresponding Colombian Patent Application No. NC2018/0007165.
Ezim et al., Recent Developments in Gene Therapy for Homozygous Familial Hypercholesterolemia, Current Atherosclerosis Reports, vol. 18(5):22, May 2016.
Somanathan et al., AAV Vectors Expressing LDLR Gain-of-Function Variants Demonstrate Increased Efficacy in Mouse Models of Familial Hypercholesterolemia, Clinical Track, vol. 115(6):591-9, Aug. 2014.
Urabe et al., Removal of Empty Capsids from Type 1 Adeno-Associated Virus Vector Stocks by Anion-Exchange Chromatography Potentiates Transgene Expression, Molecular Therapy, vol. 13(4):823-828, Apr. 2006.

(56) References Cited

OTHER PUBLICATIONS

Office Action dated Dec. 16, 2020 issued in corresponding Japanese Patent Application No. 2018-530566, with translation provided by local Agent.

Extended European Search Reported dated Dec. 1, 2020 issued in corresponding European Patent application No. 18754347.5.

Restriction Requirement dated Jul. 23, 2021 issued in corresponding U.S. Appl. No. 16/486,981.

Wang L., et al., Developing a Second-Generation Clinical Candidate AAV Vector for Gene Therapy of Familial Hypercholesterolemia, Molecular Therapy: Methods & Clinical Development, Sep. 10, 2021, 22:1-10; epub May 5, 2021.

BioQuest (https://www.aatbio.com/resources/buffer-preparations-and-recipes/pbs-phosphate-buffered-saline; last visited Oct. 6, 2021.

Scripps Laboratories (https://scrippslabs.com/phosphate-buffer-formulations; last visited Oct. 6, 2021.

Harrington, E.A., et al., Neutralizing Antibodies Against Adeno-Associated Viral Capsids in Patients with mut Methylmalonic Acidemia, May 2016, Human Gene Therapy, 27(5):345-353, Epub Mar. 22, 2016.

Office Action dated May 8, 2021 issued in related Chinese Patent Application No. 201680081580.9, with translation provided by local Agent.

Office Action dated Mar. 10, 2021 issued in related Colombian Patent Application No. NC2018/0007165.

Communication, which is an Extended European Search Report, dated 182. Oct. 18, 2021 issued in European Patent Application No. 21166865.2.

Office Action dated Jan. 19, 2022 issued in a related Japanese Patent Application No. 2019-545363.

Office Action dated Nov. 26, 2021 issued in a related U.S. Appl. No. 16/486,981.

Office Action dated May 12, 2022 issued in a related U.S. Appl. No. 16/486,981.

\* cited by examiner

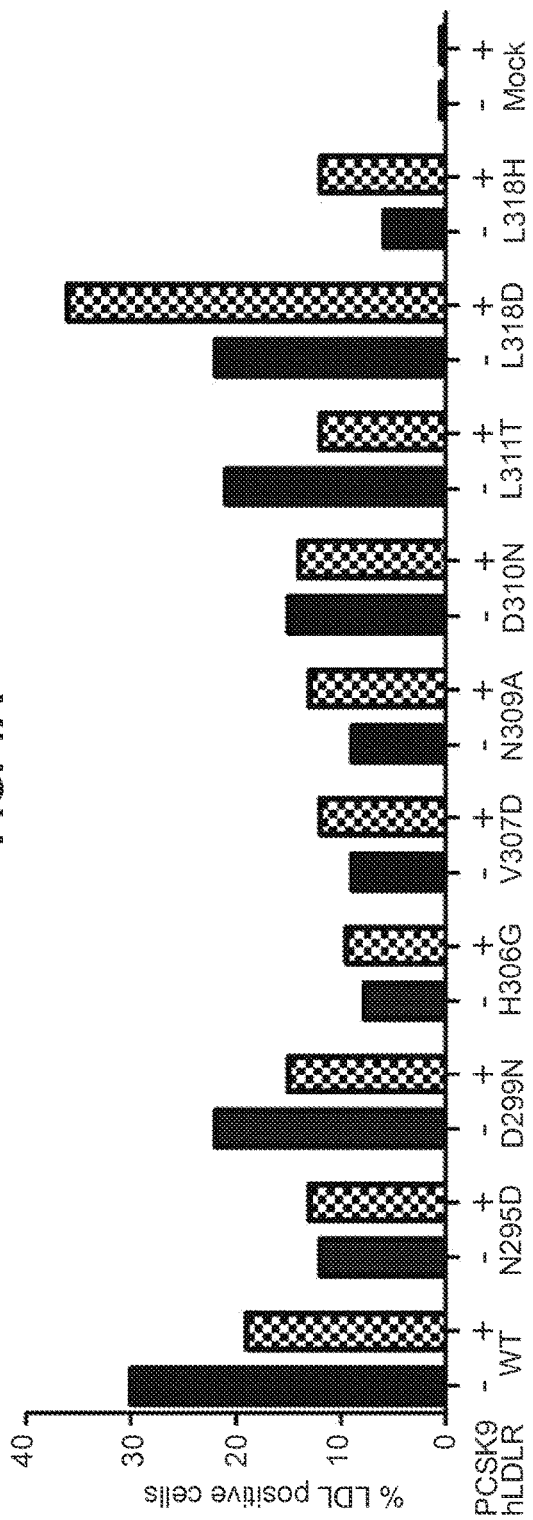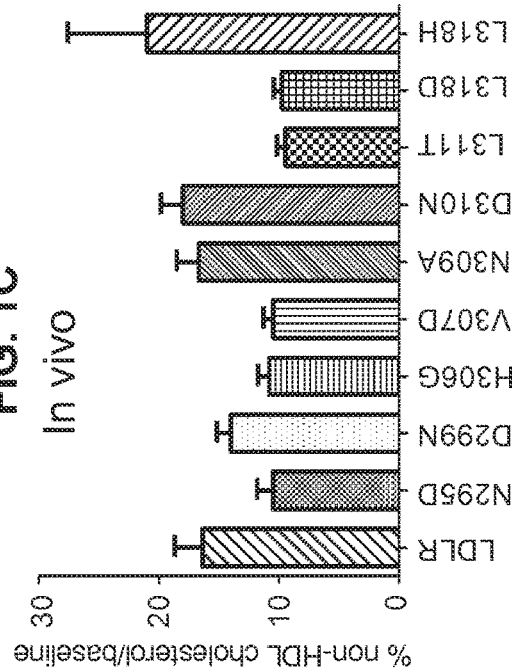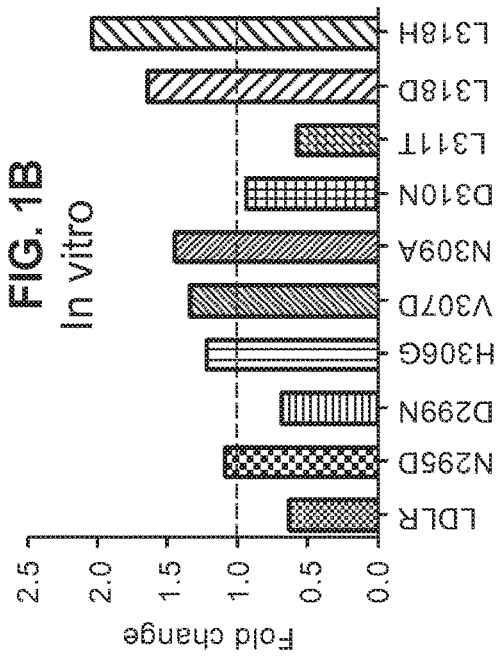

SEQUENCE LISTING

<160> NUMBER OF SEQ ID NOS: 40

<210> SEQ ID NO 1

```
<211> LENGTH: 839
<212> TYPE: PRT
<213> ORGANISM: Homo sapiens

<400> SEQUENCE: 1

Ala Val Gly Asp Arg Cys Glu Arg Asn Glu Phe Gln Cys Gln Asp Gly
 1               5                  10                  15

Lys Cys Ile Ser Tyr Lys Trp Val Cys Asp Gly Ser Ala Glu Cys Gln
                20                  25                  30

Asp Gly Ser Asp Glu Ser Gln Glu Thr Cys Leu Ser Val Thr Cys Lys
            35                  40                  45

Ser Gly Asp Phe Ser Cys Gly Gly Arg Val Asn Arg Cys Ile Pro Gln
        50                  55                  60

Phe Trp Arg Cys Asp Gly Gln Val Asp Cys Asp Asn Gly Ser Asp Glu
65                  70                  75                  80

Gln Gly Cys Pro Pro Lys Thr Cys Ser Gln Asp Glu Phe Arg Cys His
                85                  90                  95

Asp Gly Lys Cys Ile Ser Arg Gln Phe Val Cys Asp Ser Asp Arg Asp
            100                 105                 110

Cys Leu Asp Gly Ser Asp Glu Ala Ser Cys Pro Val Leu Thr Cys Gly
        115                 120                 125

Pro Ala Ser Phe Gln Cys Asn Ser Ser Thr Cys Ile Pro Gln Leu Trp
130                 135                 140

Ala Cys Asp Asn Asp Pro Asp Cys Glu Asp Gly Ser Asp Glu Trp Pro
145                 150                 155                 160

Gln Arg Cys Arg Gly Leu Tyr Val Phe Gln Gly Asp Ser Ser Pro Cys
                165                 170                 175

Ser Ala Phe Glu Phe His Cys Leu Ser Gly Glu Cys Ile His Ser Ser
            180                 185                 190

Trp Arg Cys Asp Gly Gly Pro Asp Cys Lys Asp Lys Ser Asp Glu Glu
        195                 200                 205

Asn Cys Ala Val Ala Thr Cys Arg Pro Asp Glu Phe Gln Cys Ser Asp
210                 215                 220

Gly Asn Cys Ile His Gly Ser Arg Gln Cys Asp Arg Glu Tyr Asp Cys
225                 230                 235                 240

Lys Asp Met Ser Asp Glu Val Gly Cys Val Asn Val Thr Leu Cys Glu
                245                 250                 255

Gly Pro Asn Lys Phe Lys Cys His Ser Gly Glu Cys Ile Thr Leu Asp
            260                 265                 270

Lys Val Cys Asn Met Ala Arg Asp Cys Arg Asp Trp Ser Asp Glu Pro
        275                 280                 285

Ile Lys Glu Cys Gly Thr Asn Glu Cys Leu Asp Asn Asn Gly Gly Cys
290                 295                 300

Ser His Val Cys Asn Asp Leu Lys Ile Gly Tyr Glu Cys Leu Cys Pro
305                 310                 315                 320

Asp Gly Phe Gln Leu Val Ala Gln Arg Arg Cys Glu Asp Ile Asp Glu
                325                 330                 335

Cys Gln Asp Pro Asp Thr Cys Ser Gln Leu Cys Val Asn Leu Glu Gly
            340                 345                 350

Gly Tyr Lys Cys Gln Cys Glu Glu Gly Phe Gln Leu Asp Pro His Thr
        355                 360                 365

Lys Ala Cys Lys Ala Val Gly Ser Ile Ala Tyr Leu Phe Phe Thr Asn
370                 375                 380

Arg His Glu Val Arg Lys Met Thr Leu Asp Arg Ser Glu Tyr Thr Ser
```

-continued

```
              385                 390                 395                 400
        Leu Ile Pro Asn Leu Arg Asn Val Val Ala Leu Asp Thr Glu Val Ala
                        405                 410                 415

Ser Asn Arg Ile Tyr Trp Ser Asp Leu Ser Gln Arg Met Ile Cys Ser
                        420                 425                 430

Thr Gln Leu Asp Arg Ala His Gly Val Ser Ser Tyr Asp Thr Val Ile
                        435                 440                 445

Ser Arg Asp Ile Gln Ala Pro Asp Gly Leu Ala Val Asp Trp Ile His
                    450                 455                 460

Ser Asn Ile Tyr Trp Thr Asp Ser Val Leu Gly Thr Val Ser Val Ala
        465                 470                 475                 480

Asp Thr Lys Gly Val Lys Arg Lys Thr Leu Phe Arg Glu Asn Gly Ser
                            485                 490                 495

Lys Pro Arg Ala Ile Val Val Asp Pro Val His Gly Phe Met Tyr Trp
                            500                 505                 510

Thr Asp Trp Gly Thr Pro Ala Lys Ile Lys Lys Gly Gly Leu Asn Gly
                        515                 520                 525

Val Asp Ile Tyr Ser Leu Val Thr Glu Asn Ile Gln Trp Pro Asn Gly
                    530                 535                 540

Ile Thr Leu Asp Leu Leu Ser Gly Arg Leu Tyr Trp Val Asp Ser Lys
        545                 550                 555                 560

Leu His Ser Ile Ser Ser Ile Asp Val Asn Gly Gly Asn Arg Lys Thr
                            565                 570                 575

Ile Leu Glu Asp Glu Lys Arg Leu Ala His Pro Phe Ser Leu Ala Val
                        580                 585                 590

Phe Glu Asp Lys Val Phe Trp Thr Asp Ile Ile Asn Glu Ala Ile Phe
                    595                 600                 605

Ser Ala Asn Arg Leu Thr Gly Ser Asp Val Asn Leu Leu Ala Glu Asn
                        610                 615                 620

Leu Leu Ser Pro Glu Asp Met Val Leu Phe His Asn Leu Thr Gln Pro
        625                 630                 635                 640

Arg Gly Val Asn Trp Cys Glu Arg Thr Thr Leu Ser Asn Gly Gly Cys
                            645                 650                 655

Gln Tyr Leu Cys Leu Pro Ala Pro Gln Ile Asn Pro His Ser Pro Lys
                        660                 665                 670

Phe Thr Cys Ala Cys Pro Asp Gly Met Leu Leu Ala Arg Asp Met Arg
                    675                 680                 685

Ser Cys Leu Thr Glu Ala Glu Ala Ala Val Ala Thr Gln Glu Thr Ser
        690                 695                 700

Thr Val Arg Leu Lys Val Ser Ser Thr Ala Val Arg Thr Gln His Thr
        705                 710                 715                 720

Thr Thr Arg Pro Val Pro Asp Thr Ser Arg Leu Pro Gly Ala Thr Pro
                            725                 730                 735

Gly Leu Thr Thr Val Glu Ile Val Thr Met Ser His Gln Ala Leu Gly
                        740                 745                 750

Asp Val Ala Gly Arg Gly Asn Glu Lys Lys Pro Ser Ser Val Arg Ala
                    755                 760                 765

Leu Ser Ile Val Leu Pro Ile Val Leu Leu Val Phe Leu Cys Leu Gly
                    770                 775                 780

Val Phe Leu Leu Trp Lys Asn Trp Arg Leu Lys Asn Ile Asn Ser Ile
        785                 790                 795                 800

Asn Phe Asp Asn Pro Val Tyr Gln Lys Thr Thr Glu Asp Glu Val His
                            805                 810                 815
```

-continued

```
Ile Cys His Asn Gln Asp Gly Tyr Ser Tyr Pro Ser Arg Gln Met Val
            820                 825                 830
Ser Leu Glu Asp Asp Val Ala
        835

<210> SEQ ID NO 2
<211> LENGTH: 21
<212> TYPE: PRT
<213> ORGANISM: Homo sapiens

<400> SEQUENCE: 2

Met Gly Pro Trp Gly Trp Lys Leu Arg Trp Thr Val Ala Leu Leu Leu
1               5                   10                  15
Ala Ala Ala Gly Thr
            20

<210> SEQ ID NO 3
<211> LENGTH: 682
<212> TYPE: PRT
<213> ORGANISM: Homo sapiens
<220> FEATURE:
<221> NAME/KEY: MISC_FEATURE
<222> LOCATION: (1)..(682)
<223> OTHER INFORMATION: LDLR Isoform 2

<400> SEQUENCE: 3

Met Gly Pro Trp Gly Trp Lys Leu Arg Trp Thr Val Ala Leu Leu Leu
1               5                   10                  15
Ala Ala Ala Gly Thr Ala Val Gly Asp Arg Cys Glu Arg Asn Glu Phe
            20                  25                  30
Gln Cys Gln Asp Gly Lys Cys Ile Ser Tyr Lys Trp Val Cys Asp Gly
        35                  40                  45
Ser Ala Glu Cys Gln Asp Gly Ser Asp Glu Ser Gln Glu Thr Cys Leu
    50                  55                  60
Ser Val Thr Cys Lys Ser Gly Asp Phe Ser Cys Gly Gly Arg Val Asn
65                  70                  75                  80
Arg Cys Ile Pro Gln Phe Trp Arg Cys Asp Gly Gln Val Asp Cys Asp
                85                  90                  95
Asn Gly Ser Asp Glu Gln Gly Cys Pro Val Ala Thr Cys Arg Pro Asp
            100                 105                 110
Glu Phe Gln Cys Ser Asp Gly Asn Cys Ile His Gly Ser Arg Gln Cys
        115                 120                 125
Asp Arg Glu Tyr Asp Cys Lys Asp Met Ser Asp Glu Val Gly Cys Val
    130                 135                 140
Asn Val Thr Leu Cys Glu Gly Pro Asn Lys Phe Lys Cys His Ser Gly
145                 150                 155                 160
Glu Cys Ile Thr Leu Asp Lys Val Cys Asn Met Ala Arg Asp Cys Arg
                165                 170                 175
Asp Trp Ser Asp Glu Pro Ile Lys Glu Cys Gly Thr Asn Glu Cys Leu
            180                 185                 190
Asp Asn Asn Gly Gly Cys Ser His Val Cys Asn Asp Leu Lys Ile Gly
        195                 200                 205
Tyr Glu Cys Leu Cys Pro Asp Gly Phe Gln Leu Val Ala Gln Arg Arg
    210                 215                 220
Cys Glu Asp Ile Asp Glu Cys Gln Asp Pro Asp Thr Cys Ser Gln Leu
225                 230                 235                 240
Cys Val Asn Leu Glu Gly Gly Tyr Lys Cys Gln Cys Glu Glu Gly Phe
```

```
                245                 250                 255
Gln Leu Asp Pro His Thr Lys Ala Cys Lys Ala Val Gly Ser Ile Ala
            260                 265                 270
Tyr Leu Phe Phe Thr Asn Arg His Glu Val Arg Lys Met Thr Leu Asp
        275                 280                 285
Arg Ser Glu Tyr Thr Ser Leu Ile Pro Asn Leu Arg Asn Val Val Ala
    290                 295                 300
Leu Asp Thr Glu Val Ala Ser Asn Arg Ile Tyr Trp Ser Asp Leu Ser
305                 310                 315                 320
Gln Arg Met Ile Cys Ser Thr Gln Leu Asp Arg Ala His Gly Val Ser
            325                 330                 335
Ser Tyr Asp Thr Val Ile Ser Arg Asp Ile Gln Ala Pro Asp Gly Leu
        340                 345                 350
Ala Val Asp Trp Ile His Ser Asn Ile Tyr Trp Thr Asp Ser Val Leu
    355                 360                 365
Gly Thr Val Ser Val Ala Asp Thr Lys Gly Val Lys Arg Lys Thr Leu
370                 375                 380
Phe Arg Glu Asn Gly Ser Lys Pro Arg Ala Ile Val Val Asp Pro Val
385                 390                 395                 400
His Gly Phe Met Tyr Trp Thr Asp Trp Gly Thr Pro Ala Lys Ile Lys
            405                 410                 415
Lys Gly Gly Leu Asn Gly Val Asp Ile Tyr Ser Leu Val Thr Glu Asn
        420                 425                 430
Ile Gln Trp Pro Asn Gly Ile Thr Leu Asp Leu Leu Ser Gly Arg Leu
    435                 440                 445
Tyr Trp Val Asp Ser Lys Leu His Ser Ile Ser Ser Ile Asp Val Asn
    450                 455                 460
Gly Gly Asn Arg Lys Thr Ile Leu Glu Asp Glu Lys Arg Leu Ala His
465                 470                 475                 480
Pro Phe Ser Leu Ala Val Phe Glu Asp Lys Val Phe Trp Thr Asp Ile
            485                 490                 495
Ile Asn Glu Ala Ile Phe Ser Ala Asn Arg Leu Thr Gly Ser Asp Val
        500                 505                 510
Asn Leu Leu Ala Glu Asn Leu Leu Ser Pro Glu Asp Met Val Leu Phe
    515                 520                 525
His Asn Leu Thr Gln Pro Arg Glu Ala Glu Ala Val Ala Thr Gln
    530                 535                 540
Glu Thr Ser Thr Val Arg Leu Lys Val Ser Ser Thr Ala Val Arg Thr
545                 550                 555                 560
Gln His Thr Thr Thr Arg Pro Val Pro Asp Thr Ser Arg Leu Pro Gly
            565                 570                 575
Ala Thr Pro Gly Leu Thr Thr Val Glu Ile Val Thr Met Ser His Gln
        580                 585                 590
Ala Leu Gly Asp Val Ala Gly Arg Gly Asn Glu Lys Lys Pro Ser Ser
        595                 600                 605
Val Arg Ala Leu Ser Ile Val Leu Pro Ile Val Leu Leu Val Phe Leu
    610                 615                 620
Cys Leu Gly Val Phe Leu Leu Trp Lys Asn Trp Arg Leu Lys Asn Ile
625                 630                 635                 640
Asn Ser Ile Asn Phe Asp Asn Pro Val Tyr Gln Lys Thr Thr Glu Asp
            645                 650                 655
Glu Val His Ile Cys His Asn Gln Asp Gly Tyr Ser Tyr Pro Ser Arg
        660                 665                 670
```

```
Gln Met Val Ser Leu Glu Asp Val Ala
        675                 680
```

<210> SEQ ID NO 4
<211> LENGTH: 693
<212> TYPE: PRT
<213> ORGANISM: Homo sapiens
<220> FEATURE:
<221> NAME/KEY: MISC_FEATURE
<222> LOCATION: (1)..(693)
<223> OTHER INFORMATION: LDLR Isoform 3

<400> SEQUENCE: 4

```
Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Leu Thr Leu Cys Glu Gly Pro
            100                 105                 110

Asn Lys Phe Lys Cys His Ser Gly Glu Cys Ile Thr Leu Asp Lys Val
        115                 120                 125

Cys Asn Met Ala Arg Asp Cys Arg Asp Trp Ser Asp Glu Pro Ile Lys
    130                 135                 140

Glu Cys Gly Thr Asn Glu Cys Leu Asp Asn Asn Gly Gly Cys Ser His
145                 150                 155                 160

Val Cys Asn Asp Leu Lys Ile Gly Tyr Glu Cys Leu Cys Pro Asp Gly
                165                 170                 175

Phe Gln Leu Val Ala Gln Arg Arg Cys Glu Asp Ile Asp Glu Cys Gln
            180                 185                 190

Asp Pro Asp Thr Cys Ser Gln Leu Cys Val Asn Leu Glu Gly Gly Tyr
        195                 200                 205

Lys Cys Gln Cys Glu Glu Gly Phe Gln Leu Asp Pro His Thr Lys Ala
    210                 215                 220

Cys Lys Ala Val Gly Ser Ile Ala Tyr Leu Phe Phe Thr Asn Arg His
225                 230                 235                 240

Glu Val Arg Lys Met Thr Leu Asp Arg Ser Glu Tyr Thr Ser Leu Ile
                245                 250                 255

Pro Asn Leu Arg Asn Val Val Ala Leu Asp Thr Glu Val Ala Ser Asn
            260                 265                 270

Arg Ile Tyr Trp Ser Asp Leu Ser Gln Arg Met Ile Cys Ser Thr Gln
        275                 280                 285

Leu Asp Arg Ala His Gly Val Ser Ser Tyr Asp Thr Val Ile Ser Arg
    290                 295                 300

Asp Ile Gln Ala Pro Asp Gly Leu Ala Val Asp Trp Ile His Ser Asn
305                 310                 315                 320

Ile Tyr Trp Thr Asp Ser Val Leu Gly Thr Val Ser Val Ala Asp Thr
                325                 330                 335
```

```
Lys Gly Val Lys Arg Lys Thr Leu Phe Arg Glu Asn Gly Ser Lys Pro
            340                 345                 350

Arg Ala Ile Val Val Asp Pro Val His Gly Phe Met Tyr Trp Thr Asp
        355                 360                 365

Trp Gly Thr Pro Ala Lys Ile Lys Lys Gly Gly Leu Asn Gly Val Asp
    370                 375                 380

Ile Tyr Ser Leu Val Thr Glu Asn Ile Gln Trp Pro Asn Gly Ile Thr
385                 390                 395                 400

Leu Asp Leu Leu Ser Gly Arg Leu Tyr Trp Val Asp Ser Lys Leu His
                405                 410                 415

Ser Ile Ser Ser Ile Asp Val Asn Gly Gly Asn Arg Lys Thr Ile Leu
            420                 425                 430

Glu Asp Glu Lys Arg Leu Ala His Pro Phe Ser Leu Ala Val Phe Glu
        435                 440                 445

Asp Lys Val Phe Trp Thr Asp Ile Ile Asn Glu Ala Ile Phe Ser Ala
    450                 455                 460

Asn Arg Leu Thr Gly Ser Asp Val Asn Leu Leu Ala Glu Asn Leu Leu
465                 470                 475                 480

Ser Pro Glu Asp Met Val Leu Phe His Asn Leu Thr Gln Pro Arg Gly
                485                 490                 495

Val Asn Trp Cys Glu Arg Thr Thr Leu Ser Asn Gly Gly Cys Gln Tyr
            500                 505                 510

Leu Cys Leu Pro Ala Pro Gln Ile Asn Pro His Ser Pro Lys Phe Thr
        515                 520                 525

Cys Ala Cys Pro Asp Gly Met Leu Leu Ala Arg Asp Met Arg Ser Cys
    530                 535                 540

Leu Thr Glu Ala Glu Ala Ala Val Ala Thr Gln Glu Thr Ser Thr Val
545                 550                 555                 560

Arg Leu Lys Val Ser Ser Thr Ala Val Arg Thr Gln His Thr Thr Thr
                565                 570                 575

Arg Pro Val Pro Asp Thr Ser Arg Leu Pro Gly Ala Thr Pro Gly Leu
            580                 585                 590

Thr Thr Val Glu Ile Val Thr Met Ser His Gln Ala Leu Gly Asp Val
        595                 600                 605

Ala Gly Arg Gly Asn Glu Lys Lys Pro Ser Ser Val Arg Ala Leu Ser
    610                 615                 620

Ile Val Leu Pro Ile Val Leu Leu Val Phe Leu Cys Leu Gly Val Phe
625                 630                 635                 640

Leu Leu Trp Lys Asn Trp Arg Leu Lys Asn Ile Asn Ser Ile Asn Phe
                645                 650                 655

Asp Asn Pro Val Tyr Gln Lys Thr Thr Glu Asp Glu Val His Ile Cys
            660                 665                 670

His Asn Gln Asp Gly Tyr Ser Tyr Pro Ser Arg Gln Met Val Ser Leu
        675                 680                 685

Glu Asp Asp Val Ala
    690

<210> SEQ ID NO 5
<211> LENGTH: 819
<212> TYPE: PRT
<213> ORGANISM: Homo sapiens
<220> FEATURE:
<221> NAME/KEY: MISC_FEATURE
<222> LOCATION: (1)..(819)
<223> OTHER INFORMATION: LDLR Isoform 4
```

<400> SEQUENCE: 5

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Ser
    50                  55                  60

Pro Lys Thr Cys Ser Gln Asp Glu Phe Arg Cys His Asp Gly Lys Cys
65                  70                  75                  80

Ile Ser Arg Gln Phe Val Cys Asp Ser Asp Arg Asp Cys Leu Asp Gly
                85                  90                  95

Ser Asp Glu Ala Ser Cys Pro Val Leu Thr Cys Gly Pro Ala Ser Phe
            100                 105                 110

Gln Cys Asn Ser Ser Thr Cys Ile Pro Gln Leu Trp Ala Cys Asp Asn
        115                 120                 125

Asp Pro Asp Cys Glu Asp Gly Ser Asp Glu Trp Pro Gln Arg Cys Arg
    130                 135                 140

Gly Leu Tyr Val Phe Gln Gly Asp Ser Ser Pro Cys Ser Ala Phe Glu
145                 150                 155                 160

Phe His Cys Leu Ser Gly Glu Cys Ile His Ser Ser Trp Arg Cys Asp
                165                 170                 175

Gly Gly Pro Asp Cys Lys Asp Lys Ser Asp Glu Glu Asn Cys Ala Val
            180                 185                 190

Ala Thr Cys Arg Pro Asp Glu Phe Gln Cys Ser Asp Gly Asn Cys Ile
        195                 200                 205

His Gly Ser Arg Gln Cys Asp Arg Glu Tyr Asp Cys Lys Asp Met Ser
    210                 215                 220

Asp Glu Val Gly Cys Val Asn Val Thr Leu Cys Glu Gly Pro Asn Lys
225                 230                 235                 240

Phe Lys Cys His Ser Gly Glu Cys Ile Thr Leu Asp Lys Val Cys Asn
                245                 250                 255

Met Ala Arg Asp Cys Arg Asp Trp Ser Asp Glu Pro Ile Lys Glu Cys
            260                 265                 270

Gly Thr Asn Glu Cys Leu Asp Asn Asn Gly Gly Cys Ser His Val Cys
        275                 280                 285

Asn Asp Leu Lys Ile Gly Tyr Glu Cys Leu Cys Pro Asp Gly Phe Gln
    290                 295                 300

Leu Val Ala Gln Arg Arg Cys Glu Asp Ile Asp Glu Cys Gln Asp Pro
305                 310                 315                 320

Asp Thr Cys Ser Gln Leu Cys Val Asn Leu Glu Gly Gly Tyr Lys Cys
                325                 330                 335

Gln Cys Glu Glu Gly Phe Gln Leu Asp Pro His Thr Lys Ala Cys Lys
            340                 345                 350

Ala Val Gly Ser Ile Ala Tyr Leu Phe Phe Thr Asn Arg His Glu Val
        355                 360                 365

Arg Lys Met Thr Leu Asp Arg Ser Glu Tyr Thr Ser Leu Ile Pro Asn
    370                 375                 380

Leu Arg Asn Val Val Ala Leu Asp Thr Glu Val Ala Ser Asn Arg Ile
385                 390                 395                 400

Tyr Trp Ser Asp Leu Ser Gln Arg Met Ile Cys Ser Thr Gln Leu Asp
                405                 410                 415

Arg Ala His Gly Val Ser Ser Tyr Asp Thr Val Ile Ser Arg Asp Ile
             420                 425                 430

Gln Ala Pro Asp Gly Leu Ala Val Asp Trp Ile His Ser Asn Ile Tyr
             435                 440                 445

Trp Thr Asp Ser Val Leu Gly Thr Val Ser Val Ala Asp Thr Lys Gly
             450                 455                 460

Val Lys Arg Lys Thr Leu Phe Arg Glu Asn Gly Ser Lys Pro Arg Ala
465                 470                 475                 480

Ile Val Val Asp Pro Val His Gly Phe Met Tyr Trp Thr Asp Trp Gly
                 485                 490                 495

Thr Pro Ala Lys Ile Lys Lys Gly Gly Leu Asn Gly Val Asp Ile Tyr
             500                 505                 510

Ser Leu Val Thr Glu Asn Ile Gln Trp Pro Asn Gly Ile Thr Leu Asp
             515                 520                 525

Leu Leu Ser Gly Arg Leu Tyr Trp Val Asp Ser Lys Leu His Ser Ile
530                 535                 540

Ser Ser Ile Asp Val Asn Gly Gly Asn Arg Lys Thr Ile Leu Glu Asp
545                 550                 555                 560

Glu Lys Arg Leu Ala His Pro Phe Ser Leu Ala Val Phe Glu Asp Lys
                 565                 570                 575

Val Phe Trp Thr Asp Ile Ile Asn Glu Ala Ile Phe Ser Ala Asn Arg
             580                 585                 590

Leu Thr Gly Ser Asp Val Asn Leu Leu Ala Glu Asn Leu Leu Ser Pro
             595                 600                 605

Glu Asp Met Val Leu Phe His Asn Leu Thr Gln Pro Arg Gly Val Asn
610                 615                 620

Trp Cys Glu Arg Thr Thr Leu Ser Asn Gly Gly Cys Gln Tyr Leu Cys
625                 630                 635                 640

Leu Pro Ala Pro Gln Ile Asn Pro His Ser Pro Lys Phe Thr Cys Ala
                 645                 650                 655

Cys Pro Asp Gly Met Leu Leu Ala Arg Asp Met Arg Ser Cys Leu Thr
             660                 665                 670

Glu Ala Glu Ala Ala Val Ala Thr Gln Glu Thr Ser Thr Val Arg Leu
             675                 680                 685

Lys Val Ser Ser Thr Ala Val Arg Thr Gln His Thr Thr Thr Arg Pro
690                 695                 700

Val Pro Asp Thr Ser Arg Leu Pro Gly Ala Thr Pro Gly Leu Thr Thr
705                 710                 715                 720

Val Glu Ile Val Thr Met Ser His Gln Ala Leu Gly Asp Val Ala Gly
                 725                 730                 735

Arg Gly Asn Glu Lys Lys Pro Ser Ser Val Arg Ala Leu Ser Ile Val
             740                 745                 750

Leu Pro Ile Val Leu Leu Val Phe Leu Cys Leu Gly Val Phe Leu Leu
             755                 760                 765

Trp Lys Asn Trp Arg Leu Lys Asn Ile Asn Ser Ile Asn Phe Asp Asn
             770                 775                 780

Pro Val Tyr Gln Lys Thr Thr Glu Asp Glu Val His Ile Cys His Asn
785                 790                 795                 800

Gln Asp Gly Tyr Ser Tyr Pro Ser Arg Gln Met Val Ser Leu Glu Asp
                 805                 810                 815

Asp Val Ala

```
<210> SEQ ID NO 6
<211> LENGTH: 858
<212> TYPE: PRT
<213> ORGANISM: Homo sapiens
<220> FEATURE:
<221> NAME/KEY: MISC_FEATURE
<222> LOCATION: (1)..(858)
<223> OTHER INFORMATION: LDLR Isoform 5

<400> SEQUENCE: 6
```

| Met | Gly | Pro | Trp | Gly | Trp | Lys | Leu | Arg | Trp | Thr | Val | Ala | Leu | Leu | Leu |
|-----|-----|-----|-----|-----|-----|-----|-----|-----|-----|-----|-----|-----|-----|-----|-----|
| 1 | | | | 5 | | | | | 10 | | | | | 15 | |

| Ala | Ala | Ala | Gly | Thr | Ala | Val | Gly | Asp | Arg | Cys | Glu | Arg | Asn | Glu | Phe |
| | | | 20 | | | | | 25 | | | | | 30 | | |

| Gln | Cys | Gln | Asp | Gly | Lys | Cys | Ile | Ser | Tyr | Lys | Trp | Val | Cys | Asp | Gly |
| | | 35 | | | | | 40 | | | | | 45 | | | |

| Ser | Ala | Glu | Cys | Gln | Asp | Gly | Ser | Asp | Glu | Ser | Gln | Glu | Thr | Cys | Leu |
| | 50 | | | | | 55 | | | | | 60 | | | | |

| Ser | Val | Thr | Cys | Lys | Ser | Gly | Asp | Phe | Ser | Cys | Gly | Gly | Arg | Val | Asn |
| 65 | | | | | 70 | | | | | 75 | | | | | 80 |

| Arg | Cys | Ile | Pro | Gln | Phe | Trp | Arg | Cys | Asp | Gly | Gln | Val | Asp | Cys | Asp |
| | | | | 85 | | | | | 90 | | | | | 95 | |

| Asn | Gly | Ser | Asp | Glu | Gln | Gly | Cys | Pro | Pro | Lys | Thr | Cys | Ser | Gln | Asp |
| | | | 100 | | | | | 105 | | | | | 110 | | |

| Glu | Phe | Arg | Cys | His | Asp | Gly | Lys | Cys | Ile | Ser | Arg | Gln | Phe | Val | Cys |
| | | 115 | | | | | 120 | | | | | 125 | | | |

| Asp | Ser | Asp | Arg | Asp | Cys | Leu | Asp | Gly | Ser | Asp | Glu | Ala | Ser | Cys | Pro |
| | 130 | | | | | 135 | | | | | 140 | | | | |

| Val | Leu | Thr | Cys | Gly | Pro | Ala | Ser | Phe | Gln | Cys | Asn | Ser | Ser | Thr | Cys |
| 145 | | | | | 150 | | | | | 155 | | | | | 160 |

| Ile | Pro | Gln | Leu | Trp | Ala | Cys | Asp | Asn | Asp | Pro | Asp | Cys | Glu | Asp | Gly |
| | | | | 165 | | | | | 170 | | | | | 175 | |

| Ser | Asp | Glu | Trp | Pro | Gln | Arg | Cys | Arg | Gly | Leu | Tyr | Val | Phe | Gln | Gly |
| | | | 180 | | | | | 185 | | | | | 190 | | |

| Asp | Ser | Ser | Pro | Cys | Ser | Ala | Phe | Glu | Phe | His | Cys | Leu | Ser | Gly | Glu |
| | 195 | | | | | 200 | | | | | 205 | | | | |

| Cys | Ile | His | Ser | Ser | Trp | Arg | Cys | Asp | Gly | Gly | Pro | Asp | Cys | Lys | Asp |
| 210 | | | | | 215 | | | | | 220 | | | | | |

| Lys | Ser | Asp | Glu | Glu | Asn | Cys | Ala | Val | Ala | Thr | Cys | Arg | Pro | Asp | Glu |
| 225 | | | | | 230 | | | | | 235 | | | | | 240 |

| Phe | Gln | Cys | Ser | Asp | Gly | Asn | Cys | Ile | His | Gly | Ser | Arg | Gln | Cys | Asp |
| | | | 245 | | | | | 250 | | | | | 255 | | |

| Arg | Glu | Tyr | Asp | Cys | Lys | Asp | Met | Ser | Asp | Glu | Val | Gly | Cys | Val | Asn |
| | | | 260 | | | | | 265 | | | | | 270 | | |

| Val | Thr | Leu | Cys | Glu | Gly | Pro | Asn | Lys | Phe | Lys | Cys | His | Ser | Gly | Glu |
| | | 275 | | | | | 280 | | | | | 285 | | | |

| Cys | Ile | Thr | Leu | Asp | Lys | Val | Cys | Asn | Met | Ala | Arg | Asp | Cys | Arg | Asp |
| | | 290 | | | | | 295 | | | | | 300 | | | |

| Trp | Ser | Asp | Glu | Pro | Ile | Lys | Glu | Cys | Gly | Thr | Asn | Glu | Cys | Leu | Asp |
| 305 | | | | | 310 | | | | | 315 | | | | | 320 |

| Asn | Asn | Gly | Gly | Cys | Ser | His | Val | Cys | Asn | Asp | Leu | Lys | Ile | Gly | Tyr |
| | | | | 325 | | | | | 330 | | | | | 335 | |

| Glu | Cys | Leu | Cys | Pro | Asp | Gly | Phe | Gln | Leu | Val | Ala | Gln | Arg | Arg | Cys |
| | | | 340 | | | | | 345 | | | | | 350 | | |

| Glu | Asp | Ile | Asp | Glu | Cys | Gln | Asp | Pro | Asp | Thr | Cys | Ser | Gln | Leu | Cys |
| | | 355 | | | | | 360 | | | | | 365 | | | |

```
Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780
```

```
Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
            805                 810                 815

Asn Ile Asn Ser Ile Asn Phe Asp Asn Pro Val Tyr Gln Lys Thr Thr
        820                 825                 830

Glu Asp Glu Val His Ile Cys His Asn Gln Asp Gly Tyr Ser Tyr Pro
    835                 840                 845

Ser Met Val Ser Leu Glu Asp Asp Val Ala
    850                 855
```

<210> SEQ ID NO 7
<211> LENGTH: 739
<212> TYPE: PRT
<213> ORGANISM: Homo sapiens
<220> FEATURE:
<221> NAME/KEY: MISC_FEATURE
<222> LOCATION: (1)..(739)
<223> OTHER INFORMATION: LDLR isoform 6

<400> SEQUENCE: 7

```
Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Asn Ser Ser Thr Cys Ile Pro Gln Leu Trp Ala Cys Asp Asn
        35                  40                  45

Asp Pro Asp Cys Glu Asp Gly Ser Asp Glu Trp Pro Gln Arg Cys Arg
50                  55                  60

Gly Leu Tyr Val Phe Gln Gly Asp Ser Ser Pro Cys Ser Ala Phe Glu
65                  70                  75                  80

Phe His Cys Leu Ser Gly Glu Cys Ile His Ser Ser Trp Arg Cys Asp
                85                  90                  95

Gly Gly Pro Asp Cys Lys Asp Lys Ser Asp Glu Glu Asn Cys Ala Val
            100                 105                 110

Ala Thr Cys Arg Pro Asp Glu Phe Gln Cys Ser Asp Gly Asn Cys Ile
        115                 120                 125

His Gly Ser Arg Gln Cys Asp Arg Glu Tyr Asp Cys Lys Asp Met Ser
    130                 135                 140

Asp Glu Val Gly Cys Val Asn Val Thr Leu Cys Glu Gly Pro Asn Lys
145                 150                 155                 160

Phe Lys Cys His Ser Gly Glu Cys Ile Thr Leu Asp Lys Val Cys Asn
                165                 170                 175

Met Ala Arg Asp Cys Arg Asp Trp Ser Asp Glu Pro Ile Lys Glu Cys
            180                 185                 190

Gly Thr Asn Glu Cys Leu Asp Asn Asn Gly Gly Cys Ser His Val Cys
        195                 200                 205

Asn Asp Leu Lys Ile Gly Tyr Glu Cys Leu Cys Pro Asp Gly Phe Gln
    210                 215                 220

Leu Val Ala Gln Arg Arg Cys Glu Asp Ile Asp Glu Cys Gln Asp Pro
225                 230                 235                 240

Asp Thr Cys Ser Gln Leu Cys Val Asn Leu Glu Gly Gly Tyr Lys Cys
                245                 250                 255

Gln Cys Glu Glu Gly Phe Gln Leu Asp Pro His Thr Lys Ala Cys Lys
            260                 265                 270

Ala Val Gly Ser Ile Ala Tyr Leu Phe Phe Thr Asn Arg His Glu Val
```

```
            275                 280                 285
Arg Lys Met Thr Leu Asp Arg Ser Glu Tyr Thr Ser Leu Ile Pro Asn
290                 295                 300

Leu Arg Asn Val Val Ala Leu Asp Thr Glu Val Ala Ser Asn Arg Ile
305                 310                 315                 320

Tyr Trp Ser Asp Leu Ser Gln Arg Met Ile Cys Ser Thr Gln Leu Asp
                    325                 330                 335

Arg Ala His Gly Val Ser Ser Tyr Asp Thr Val Ile Ser Arg Asp Ile
                340                 345                 350

Gln Ala Pro Asp Gly Leu Ala Val Asp Trp Ile His Ser Asn Ile Tyr
            355                 360                 365

Trp Thr Asp Ser Val Leu Gly Thr Val Ser Val Ala Asp Thr Lys Gly
        370                 375                 380

Val Lys Arg Lys Thr Leu Phe Arg Glu Asn Gly Ser Lys Pro Arg Ala
385                 390                 395                 400

Ile Val Val Asp Pro Val His Gly Phe Met Tyr Trp Thr Asp Trp Gly
                    405                 410                 415

Thr Pro Ala Lys Ile Lys Lys Gly Gly Leu Asn Gly Val Asp Ile Tyr
                420                 425                 430

Ser Leu Val Thr Glu Asn Ile Gln Trp Pro Asn Gly Ile Thr Leu Asp
            435                 440                 445

Leu Leu Ser Gly Arg Leu Tyr Trp Val Asp Ser Lys Leu His Ser Ile
        450                 455                 460

Ser Ser Ile Asp Val Asn Gly Gly Asn Arg Lys Thr Ile Leu Glu Asp
465                 470                 475                 480

Glu Lys Arg Leu Ala His Pro Phe Ser Leu Ala Val Phe Glu Asp Lys
                    485                 490                 495

Val Phe Trp Thr Asp Ile Ile Asn Glu Ala Ile Phe Ser Ala Asn Arg
                500                 505                 510

Leu Thr Gly Ser Asp Val Asn Leu Leu Ala Glu Asn Leu Leu Ser Pro
            515                 520                 525

Glu Asp Met Val Leu Phe His Asn Leu Thr Gln Pro Arg Gly Val Asn
        530                 535                 540

Trp Cys Glu Arg Thr Thr Leu Ser Asn Gly Gly Cys Gln Tyr Leu Cys
545                 550                 555                 560

Leu Pro Ala Pro Gln Ile Asn Pro His Ser Pro Lys Phe Thr Cys Ala
                    565                 570                 575

Cys Pro Asp Gly Met Leu Leu Ala Arg Asp Met Arg Ser Cys Leu Thr
                580                 585                 590

Glu Ala Glu Ala Ala Val Ala Thr Gln Glu Thr Ser Thr Val Arg Leu
            595                 600                 605

Lys Val Ser Ser Thr Ala Val Arg Thr Gln His Thr Thr Thr Arg Pro
        610                 615                 620

Val Pro Asp Thr Ser Arg Leu Pro Gly Ala Thr Pro Gly Leu Thr Thr
625                 630                 635                 640

Val Glu Ile Val Thr Met Ser His Gln Ala Leu Gly Asp Val Ala Gly
                    645                 650                 655

Arg Gly Asn Glu Lys Lys Pro Ser Ser Val Arg Ala Leu Ser Ile Val
                660                 665                 670

Leu Pro Ile Val Leu Leu Val Phe Leu Cys Leu Gly Val Phe Leu Leu
            675                 680                 685

Trp Lys Asn Trp Arg Leu Lys Asn Ile Asn Ser Ile Asn Phe Asp Asn
        690                 695                 700
```

Pro Val Tyr Gln Lys Thr Thr Glu Asp Glu Val His Ile Cys His Asn
705                 710                 715                 720

Gln Asp Gly Tyr Ser Tyr Pro Ser Arg Gln Met Val Ser Leu Glu Asp
                725                 730                 735

Asp Val Ala

<210> SEQ ID NO 8
<211> LENGTH: 7756
<212> TYPE: DNA
<213> ORGANISM: Artificial Sequence
<220> FEATURE:
<223> OTHER INFORMATION: Synthetic pAAV-CB-hLDLR
<220> FEATURE:
<221> NAME/KEY: CDS
<222> LOCATION: (6)..(2588)
<223> OTHER INFORMATION: hLDLR
<220> FEATURE:
<221> NAME/KEY: misc_feature
<222> LOCATION: (2188)..(2207)
<223> OTHER INFORMATION: Y828F seq primer
<220> FEATURE:
<221> NAME/KEY: misc_feature
<222> LOCATION: (2434)..(2471)
<223> OTHER INFORMATION: K6 R primer
<220> FEATURE:
<221> NAME/KEY: misc_feature
<222> LOCATION: (2436)..(2534)
<223> OTHER INFORMATION: IDOL mutations
<220> FEATURE:
<221> NAME/KEY: misc_feature
<222> LOCATION: (2436)..(2588)
<223> OTHER INFORMATION: cytoplasmic tail
<220> FEATURE:
<221> NAME/KEY: misc_feature
<222> LOCATION: (2451)..(2453)
<223> OTHER INFORMATION: K5 mutation
<220> FEATURE:
<221> NAME/KEY: misc_feature
<222> LOCATION: (2477)..(2510)
<223> OTHER INFORMATION: K20 R primter
<220> FEATURE:
<221> NAME/KEY: misc_feature
<222> LOCATION: (2493)..(2495)
<223> OTHER INFORMATION: K20 mutation
<220> FEATURE:
<221> NAME/KEY: misc_feature
<222> LOCATION: (2505)..(2537)
<223> OTHER INFORMATION: C29 A primer
<220> FEATURE:
<221> NAME/KEY: misc_feature
<222> LOCATION: (2505)..(2537)
<223> OTHER INFORMATION: C29 A primer
<220> FEATURE:
<221> NAME/KEY: misc_feature
<222> LOCATION: (2520)..(2522)
<223> OTHER INFORMATION: C29 mutation
<220> FEATURE:
<221> NAME/KEY: polyA_signal
<222> LOCATION: (2655)..(2781)
<223> OTHER INFORMATION: rabbit globulin polyA
<220> FEATURE:
<221> NAME/KEY: repeat_region
<222> LOCATION: (2870)..(2999)
<223> OTHER INFORMATION: 3' ITR (complement)
<220> FEATURE:
<221> NAME/KEY: rep_origin
<222> LOCATION: (3176)..(3631)
<223> OTHER INFORMATION: complementary strand f1 ori
<220> FEATURE:
<221> NAME/KEY: misc_feature
<222> LOCATION: (3762)..(4619)
<223> OTHER INFORMATION: AP(R) marker
<220> FEATURE:
<221> NAME/KEY: rep_origin
<222> LOCATION: (4793)..(5381)

```
<223> OTHER INFORMATION: origin of replication
<220> FEATURE:
<221> NAME/KEY: repeat_region
<222> LOCATION: (5821)..(5950)
<223> OTHER INFORMATION: 5' ITR
<220> FEATURE:
<221> NAME/KEY: promoter
<222> LOCATION: (6018)..(6399)
<223> OTHER INFORMATION: CMV IE promoter
<220> FEATURE:
<221> NAME/KEY: promoter
<222> LOCATION: (6402)..(6688)
<223> OTHER INFORMATION: CB promoter
<220> FEATURE:
<221> NAME/KEY: TATA_signal
<222> LOCATION: (6656)..(6659)
<220> FEATURE:
<221> NAME/KEY: Intron
<222> LOCATION: (6778)..(7750)
<223> OTHER INFORMATION: chicken beta actin intron

<400> SEQUENCE: 8 cgcgt atg ggg ccc tgg ggc tgg aaa ttg cgc tgg acc gtc gcc ttg ctc       50
      Met Gly Pro Trp Gly Trp Lys Leu Arg Trp Thr Val Ala Leu Leu
      1               5                  10                  15 ctc gcc gcg gcg ggg act gca gtg ggc gac aga tgt gaa aga aac gag         98
Leu Ala Ala Ala Gly Thr Ala Val Gly Asp Arg Cys Glu Arg Asn Glu
                20                  25                  30 ttc cag tgc caa gac ggg aaa tgc atc tcc tac aag tgg gtc tgc gat        146
Phe Gln Cys Gln Asp Gly Lys Cys Ile Ser Tyr Lys Trp Val Cys Asp
        35                  40                  45 ggc agc gct gag tgc cag gat ggc tct gat gag tcc cag gag acg tgc        194
Gly Ser Ala Glu Cys Gln Asp Gly Ser Asp Glu Ser Gln Glu Thr Cys
    50                  55                  60 ttg tct gtc acc tgc aaa tcc ggg gac ttc agc tgt ggg ggc cgt gtc        242
Leu Ser Val Thr Cys Lys Ser Gly Asp Phe Ser Cys Gly Gly Arg Val
65                  70                  75 aac cgc tgc att cct cag ttc tgg agg tgc gat ggc caa gtg gac tgc        290
Asn Arg Cys Ile Pro Gln Phe Trp Arg Cys Asp Gly Gln Val Asp Cys
                85                  90                  95
80 gac aac ggc tca gac gag caa ggc tgt ccc ccc aag acg tgc tcc cag        338
Asp Asn Gly Ser Asp Glu Gln Gly Cys Pro Pro Lys Thr Cys Ser Gln
                100                 105                 110 gac gag ttt cgc tgc cac gat ggg aag tgc atc tct cgg cag ttc gtc        386
Asp Glu Phe Arg Cys His Asp Gly Lys Cys Ile Ser Arg Gln Phe Val
        115                 120                 125 tgt gac tca gac cgg gac tgc ttg gac ggc tca gac gag gcc tcc tgc        434
Cys Asp Ser Asp Arg Asp Cys Leu Asp Gly Ser Asp Glu Ala Ser Cys
    130                 135                 140 ccg gtg ctc acc tgt ggt ccc gcc agc ttc cag tgc aac agc tcc acc        482
Pro Val Leu Thr Cys Gly Pro Ala Ser Phe Gln Cys Asn Ser Ser Thr
145                 150                 155 tgc atc ccc cag ctg tgg gcc tgc gac aac gac ccc gac tgc gaa gat        530
Cys Ile Pro Gln Leu Trp Ala Cys Asp Asn Asp Pro Asp Cys Glu Asp
160                 165                 170                 175 ggc tcg gat gag tgg ccg cag cgc tgt agg ggt ctt tac gtg ttc caa        578
Gly Ser Asp Glu Trp Pro Gln Arg Cys Arg Gly Leu Tyr Val Phe Gln
                180                 185                 190 ggg gac agt agc ccc tgc tcg gcc ttc gag ttc cac tgc cta agt ggc        626
Gly Asp Ser Ser Pro Cys Ser Ala Phe Glu Phe His Cys Leu Ser Gly
        195                 200                 205 gag tgc atc cac tcc agc tgg cgc tgt gat ggt ggc ccc gac tgc aag        674
Glu Cys Ile His Ser Ser Trp Arg Cys Asp Gly Gly Pro Asp Cys Lys
    210                 215                 220
```

```
                                   -continued gac aaa tct gac gag gaa aac tgc gct gtg gcc acc tgt cgc cct gac      722
Asp Lys Ser Asp Glu Glu Asn Cys Ala Val Ala Thr Cys Arg Pro Asp
    225                 230                 235 gaa ttc cag tgc tct gat gga aac tgc atc cat ggc agc cgg cag tgt      770
Glu Phe Gln Cys Ser Asp Gly Asn Cys Ile His Gly Ser Arg Gln Cys
240                 245                 250                 255 gac cgg gaa tat gac tgc aag gac atg agc gat gaa gtt ggc tgc gtt      818
Asp Arg Glu Tyr Asp Cys Lys Asp Met Ser Asp Glu Val Gly Cys Val
                260                 265                 270 aat gtg aca ctc tgc gag gga ccc aac aag ttc aag tgt cac agc ggc      866
Asn Val Thr Leu Cys Glu Gly Pro Asn Lys Phe Lys Cys His Ser Gly
            275                 280                 285 gaa tgc atc acc ctg gac aaa gtc tgc aac atg gct aga gac tgc cgg      914
Glu Cys Ile Thr Leu Asp Lys Val Cys Asn Met Ala Arg Asp Cys Arg
        290                 295                 300 gac tgg tca gat gaa ccc atc aaa gag tgc ggg acc aac gaa tgc ttg      962
Asp Trp Ser Asp Glu Pro Ile Lys Glu Cys Gly Thr Asn Glu Cys Leu
    305                 310                 315 gac aac aac ggc ggc tgt tcc cac gtc tgc aat gac ctt aag atc ggc     1010
Asp Asn Asn Gly Gly Cys Ser His Val Cys Asn Asp Leu Lys Ile Gly
320                 325                 330                 335 tac gag tgc ctg tgc ccc gac ggc ttc cag ctg gtg gcc cag cga aga     1058
Tyr Glu Cys Leu Cys Pro Asp Gly Phe Gln Leu Val Ala Gln Arg Arg
                340                 345                 350 tgc gaa gat atc gat gag tgt cag gat ccc gac acc tgc agc cag ctc     1106
Cys Glu Asp Ile Asp Glu Cys Gln Asp Pro Asp Thr Cys Ser Gln Leu
            355                 360                 365 tgc gtg aac ctg gag ggt ggc tac aag tgc cag tgt gag gaa ggc ttc     1154
Cys Val Asn Leu Glu Gly Gly Tyr Lys Cys Gln Cys Glu Glu Gly Phe
        370                 375                 380 cag ctg gac ccc cac acg aag gcc tgc aag gct gtg ggc tcc atc gcc     1202
Gln Leu Asp Pro His Thr Lys Ala Cys Lys Ala Val Gly Ser Ile Ala
    385                 390                 395 tac ctc ttc ttc acc aac cgg cac gag gtc agg aag atg acg ctg gac     1250
Tyr Leu Phe Phe Thr Asn Arg His Glu Val Arg Lys Met Thr Leu Asp
400                 405                 410                 415 cgg agc gag tac acc agc ctc atc ccc aac ctg agg aac gtg gtc gct     1298
Arg Ser Glu Tyr Thr Ser Leu Ile Pro Asn Leu Arg Asn Val Val Ala
                420                 425                 430 ctg gac acg gag gtg gcc agc aat aga atc tac tgg tct gac ctg tcc     1346
Leu Asp Thr Glu Val Ala Ser Asn Arg Ile Tyr Trp Ser Asp Leu Ser
            435                 440                 445 cag aga atg atc tgc agc acc cag ctt gac aga gcc cac ggc gtc tct     1394
Gln Arg Met Ile Cys Ser Thr Gln Leu Asp Arg Ala His Gly Val Ser
        450                 455                 460 tcc tat gac acc gtc atc agc agg gac atc cag gcc ccc gac ggg ctg     1442
Ser Tyr Asp Thr Val Ile Ser Arg Asp Ile Gln Ala Pro Asp Gly Leu
    465                 470                 475 gct gtg gac tgg atc cac agc aac atc tac tgg acc gac tct gtc ctg     1490
Ala Val Asp Trp Ile His Ser Asn Ile Tyr Trp Thr Asp Ser Val Leu
480                 485                 490                 495 ggc act gtc tct gtt gcg gat acc aag ggc gtg aag agg aaa acg tta     1538
Gly Thr Val Ser Val Ala Asp Thr Lys Gly Val Lys Arg Lys Thr Leu
                500                 505                 510 ttc agg gag aac ggc tcc aag cca agg gcc atc gtg gtg gat cct gtt     1586
Phe Arg Glu Asn Gly Ser Lys Pro Arg Ala Ile Val Val Asp Pro Val
            515                 520                 525 cat ggc ttc atg tac tgg act gac tgg gga act ccc gcc aag atc aag     1634
His Gly Phe Met Tyr Trp Thr Asp Trp Gly Thr Pro Ala Lys Ile Lys
        530                 535                 540
```

```
aaa ggg ggc ctg aat ggt gtg gac atc tac tcg ctg gtg act gaa aac    1682
Lys Gly Gly Leu Asn Gly Val Asp Ile Tyr Ser Leu Val Thr Glu Asn
        545                 550                 555 att cag tgg ccc aat ggc atc acc cta gat ctc ctc agt ggc cgc ctc    1730
Ile Gln Trp Pro Asn Gly Ile Thr Leu Asp Leu Leu Ser Gly Arg Leu
560                 565                 570                 575 tac tgg gtt gac tcc aaa ctt cac tcc atc tca agc atc gat gtc aat    1778
Tyr Trp Val Asp Ser Lys Leu His Ser Ile Ser Ser Ile Asp Val Asn
                580                 585                 590 ggg ggc aac cgg aag acc atc ttg gag gat gaa aag agg ctg gcc cac    1826
Gly Gly Asn Arg Lys Thr Ile Leu Glu Asp Glu Lys Arg Leu Ala His
            595                 600                 605 ccc ttc tcc ttg gcc gtc ttt gag gac aaa gta ttt tgg aca gat atc    1874
Pro Phe Ser Leu Ala Val Phe Glu Asp Lys Val Phe Trp Thr Asp Ile
        610                 615                 620 atc aac gaa gcc att ttc agt gcc aac cgc ctc aca ggt tcc gat gtc    1922
Ile Asn Glu Ala Ile Phe Ser Ala Asn Arg Leu Thr Gly Ser Asp Val
625                 630                 635 aac ttg ttg gct gaa aac cta ctg tcc cca gag gat atg gtc ctc ttc    1970
Asn Leu Leu Ala Glu Asn Leu Leu Ser Pro Glu Asp Met Val Leu Phe
640                 645                 650                 655 cac aac ctc acc cag cca aga gga gtg aac tgg tgt gag agg acc acc    2018
His Asn Leu Thr Gln Pro Arg Gly Val Asn Trp Cys Glu Arg Thr Thr
                660                 665                 670 ctg agc aat ggc ggc tgc cag tat ctg tgc ctc cct gcc ccg cag atc    2066
Leu Ser Asn Gly Gly Cys Gln Tyr Leu Cys Leu Pro Ala Pro Gln Ile
            675                 680                 685 aac ccc cac tcg ccc aag ttt acc tgc gcc tgc ccg gac ggc atg ctg    2114
Asn Pro His Ser Pro Lys Phe Thr Cys Ala Cys Pro Asp Gly Met Leu
        690                 695                 700 ctg gcc agg gac atg agg agc tgc ctc aca gag gct gag gct gca gtg    2162
Leu Ala Arg Asp Met Arg Ser Cys Leu Thr Glu Ala Glu Ala Ala Val
705                 710                 715 gcc acc cag gag aca tcc acc gtc agg cta aag gtc agc tcc aca gcc    2210
Ala Thr Gln Glu Thr Ser Thr Val Arg Leu Lys Val Ser Ser Thr Ala
720                 725                 730                 735 gta agg aca cag cac aca acc acc cgg cct gtt ccc gac acc tcc cgg    2258
Val Arg Thr Gln His Thr Thr Thr Arg Pro Val Pro Asp Thr Ser Arg
                740                 745                 750 ctg cct ggg gcc acc cct ggg ctc acc acg gtg gag ata gtg aca atg    2306
Leu Pro Gly Ala Thr Pro Gly Leu Thr Thr Val Glu Ile Val Thr Met
            755                 760                 765 tct cac caa gct ctg ggc gac gtt gct ggc aga gga aat gag aag aag    2354
Ser His Gln Ala Leu Gly Asp Val Ala Gly Arg Gly Asn Glu Lys Lys
        770                 775                 780 ccc agt agc gtg agg gct ctg tcc att gtc ctc ccc atc gtg ctc ctc    2402
Pro Ser Ser Val Arg Ala Leu Ser Ile Val Leu Pro Ile Val Leu Leu
785                 790                 795 gtc ttc ctt tgc ctg ggg gtc ttc ctt ctg tgg aag aac tgg cgg ctt    2450
Val Phe Leu Cys Leu Gly Val Phe Leu Leu Trp Lys Asn Trp Arg Leu
800                 805                 810                 815 aag aac atc aac agc atc aac ttt gac aac ccc gtc tat cag aag acc    2498
Lys Asn Ile Asn Ser Ile Asn Phe Asp Asn Pro Val Tyr Gln Lys Thr
                820                 825                 830 aca gag gat gag gtc cac att tgc cac aac cag gac ggc tac agc tac    2546
Thr Glu Asp Glu Val His Ile Cys His Asn Gln Asp Gly Tyr Ser Tyr
            835                 840                 845 ccc tcg aga cag atg gtc agt ctg gag gat gac gtg gcg tga            2588
Pro Ser Arg Gln Met Val Ser Leu Glu Asp Asp Val Ala
```

```
                850         855         860
acgcgtggta cctctagagt cgacccgggc ggcctcgagg acggggtgaa ctacgcctga   2648
ggatccgatc tttttccctc tgccaaaaat tatggggaca tcatgaagcc ccttgagcat   2708
ctgacttctg gctaataaag gaaatttatt ttcattgcaa tagtgtgttg aatttttttg   2768
tgtctctcac tcggaagcaa ttcgttgatc tgaatttcga ccacccataa tacccattac   2828
cctggtagat aagtagcatg gcgggttaat cattaactac aaggaacccc tagtgatgga   2888
gttggccact ccctctctgc gcgctcgctc gctcactgag gccgggcgac caaaggtcgc   2948
ccgacgcccg ggctttgccc gggcggcctc agtgagcgag cgagcgcgca gccttaatta   3008
acctaattca ctggccgtcg ttttacaacg tcgtgactgg gaaaaccctg gcgttaccca   3068
acttaatcgc cttgcagcac atccccctttt cgccagctgg cgtaatagcg aagaggcccg   3128
caccgatcgc ccttcccaac agttgcgcag cctgaatggc gaatgggacg cgccctgtag   3188
cggcgcatta agcgcggcgg gtgtggtggt tacgcgcagc gtgaccgcta cacttgccag   3248
cgccctagcg cccgctcctt tcgctttctt cccttccttt ctcgccacgt tcgccggctt   3308
tccccgtcaa gctctaaatc gggggctccc tttagggttc cgatttagtg ctttacggca   3368
cctcgacccc aaaaaacttg attagggtga tggttcacgt agtgggccat cgccctgata   3428
gacggttttt cgccctttga cgttggagtc acgttctttt aatagtggac tcttgttcca   3488
aactggaaca cactcaacc ctatctcggt ctattctttt gatttataag ggattttgcc   3548
gatttcggcc tattggttaa aaaatgagct gatttaacaa aaatttaacg cgaattttaa   3608
caaaatatta acgcttacaa tttaggtggc acttttcggg gaaatgtgcg cggaacccct   3668
atttgtttat ttttctaaat acattcaaat atgtatccgc tcatgagaca ataaccctga   3728
taaatgcttc aataatattg aaaaaggaag agtatgagta ttcaacattt ccgtgtcgcc   3788
cttattccct tttttgcggc attttgcctt cctgttttg ctcacccaga aacgctggtg   3848
aaagtaaaag atgctgaaga tcagttgggt gcacgagtgg gttacatcga actggatctc   3908
aacagcggta agatccttga gttttcgc cccgaagaac gttttccaat gatgagcact   3968
tttaaagttc tgctatgtgg cgcggtatta tcccgtattg acgccgggca agagcaactc   4028
ggtcgccgca tacactattc tcagaatgac ttggttgagt actcaccagt cacagaaaag   4088
catcttacgg atggcatgac agtaagagaa ttatgcagtg ctgccataac catgagtgat   4148
aacactgcgg ccaacttact tctgacaacg atcggaggac cgaaggagct aaccgctttt   4208
ttgcacaaca tgggggatca tgtaactcgc cttgatcgtt gggaaccgga gctgaatgaa   4268
gccataccaa acgacgagcg tgacaccacg atgcctgtag caatggcaac aacgttgcgc   4328
aaactattaa ctggcgaact acttactcta gcttcccggc aacaattaat agactggatg   4388
gaggcggata aagttgcagg accacttctg cgctcggccc ttccggctgg ctggtttatt   4448
gctgataaat ctggagccgg tgagcgtggg tctcgcggta tcattgcagc actggggcca   4508
gatggtaagc cctcccgtat cgtagttatc tacacgacgg ggagtcaggc aactatggat   4568
gaacgaaata gacagatcgc tgagataggt gcctcactga ttaagcattg gtaactgtca   4628
gaccaagttt actcatatat actttagatt gatttaaaac ttcatttta atttaaaagg   4688 atctaggtga agatcctttt tgataatctc atgaccaaaa tcccttaacg tgagttttcg   4748
ttccactgag cgtcagaccc cgtagaaaag atcaaaggat cttcttgaga tcctttttt   4808 ctgcgcgtaa tctgctgctt gcaaacaaaa aaaccaccgc taccagcggt ggtttgtttg   4868
ccggatcaag agctaccaac tctttttccg aaggtaactg gcttcagcag agcgcagata   4928
```

```
ccaaatactg ttcttctagt gtagccgtag ttaggccacc acttcaagaa ctctgtagca    4988
ccgcctacat acctcgctct gctaatcctg ttaccagtgg ctgctgccag tggcgataag    5048
tcgtgtctta ccgggttgga ctcaagacga tagttaccgg ataaggcgca gcggtcgggc    5108
tgaacggggg gttcgtgcac acagcccagc ttggagcgaa cgacctacac cgaactgaga    5168
tacctacagc gtgagctatg agaaagcgcc acgcttcccg aagggagaaa ggcggacagg    5228
tatccggtaa gcggcagggt cggaacagga gagcgcacga gggagcttcc agggggaaac    5288
gcctggtatc tttatagtcc tgtcgggttt cgccacctct gacttgagcg tcgatttttg    5348
tgatgctcgt caggggggcg gagcctatgg aaaaacgcca gcaacgcggc ctttttacgg    5408
ttcctggcct tttgctggcc ttttgctcac atgttctttc ctgcgttatc ccctgattct    5468
gtggataacc gtattaccgc ctttgagtga gctgataccg ctcgccgcag ccgaacgacc    5528
gagcgcagcg agtcagtgag cgaggaagcg gaagagcgcc caatacgcaa accgcctctc    5588
cccgcgcgtt ggccgattca ttaatgcagc tggcacgaca ggtttcccga ctggaaagcg    5648
ggcagtgagc gcaacgcaat taatgtgagt tagctcactc attaggcacc ccaggcttta    5708
cactttatgc ttccggctcg tatgttgtgt ggaattgtga gcggataaca atttcacaca    5768
ggaaacagct atgaccatga ttacgccaga tttaattaag gccttaatta ggctgcgcgc    5828
tcgctcgctc actgaggccg cccgggcaaa gcccgggcgt cgggcgacct ttggtcgccc    5888
ggcctcagtg agcgagcgag cgcgcagaga gggagtggcc aactccatca ctaggggttc    5948
cttgtagtta atgattaacc cgccatgcta cttatctacc agggtaatgg ggatcctcta    6008
gaactatagc tagtcgacat tgattattga ctagttatta atagtaatca attacggggt    6068
cattagttca tagcccatat atggagttcc gcgttacata acttacggta aatggcccgc    6128
ctggctgacc gcccaacgac ccccgcccat tgacgtcaat aatgacgtat gttcccatag    6188
taacgccaat agggactttc cattgacgtc aatgggtgga gtatttacgg taaactgccc    6248
acttggcagt acatcaagtg tatcatatgc caagtacgcc ccctattgac gtcaatgacg    6308
gtaaatggcc cgcctggcat tatgcccagt acatgacctt atgggacttt cctacttggc    6368
agtacatcta cgtattagtc atcgctatta ccatggtcga ggtgagcccc acgttctgct    6428
tcactctccc catctccccc ccctccccac cccaattttg tatttatttt attttttaat    6488
tattttgtgc agcgatgggg gcggggggg gggggggcg cgcgccaggc ggggcggggc    6548
ggggcgaggg gcgggcggg gcgaggcgga gaggtgcggc ggcagccaat cagagcggcg    6608
cgctccgaaa gtttcctttt atggcgaggc ggcggcggcg gcggccctat aaaaagcgaa    6668
gcgcgcggcg ggcggggagt cgctgcgacg ctgccttcgc cccgtgcccc gctccgccgc    6728
cgcctcgcgc cgcccgcccc ggctctgact daccgcgtta ctcccacagg tgagcgggcg    6788
ggacggccct tctcctccgg gctgtaatta gcgcttggtt taatgacggc ttgtttcttt    6848
tctgtggctg cgtgaaagcc ttgagggget ccggagggc ctttgtgcg ggggagcgg    6908
ctcgggggt gcgtgcgtgt gtgtgtgcgt ggggagcgcc gcgtgcggct ccgcgctgcc    6968
cggcggctgt gagcgctgcg ggcgcggcgc ggggctttgt gcgctccgca gtgtgcgcga    7028
ggggagcgcg gccgggggcg gtgccccgcg gtgcgggggg ggctgcgagg ggaacaaagg    7088
ctgcgtgcgg ggtgtgtgcg tggggggggtg agcagggggt gtgggcgcgt cggtcgggct    7148
gcaaccccc ctgcacccc ctccccgagt tgctgagcac ggcccggctt cgggtgcggg    7208
gctccgtacg gggcgtggcg cggggctcgc cgtgccgggc ggggggtggc ggcaggtggg    7268
```

-continued

```
ggtgccgggc ggggcggggc cgcctcgggc cggggagggc tcggggagg ggcgcggcgg      7328 cccccggagc gccggcggct gtcgaggcgc ggcgagccgc agccattgcc ttttatggta      7388
atcgtgcgag agggcgcagg gacttccttt gtcccaaatc tgtgcggagc cgaaatctgg      7448
gaggcgccgc cgcacccct ctagcgggcg cggggcgaag cggtgcggcg ccggcaggaa       7508
ggaaatgggc ggggagggcc ttcgtgcgtc gccgcgccgc cgtccccttc tccctctcca      7568
gcctcggggc tgtccgcggg gggacggctg ccttcggggg ggacggggca gggcggggtt      7628
cggcttctgg cgtgtgaccg gcggctctag agcctctgct aaccatgttc atgccttctt      7688
ctttttccta cagctcctgg gcaacgtgct ggttattgtg ctgtctcatc attttggcaa      7748
agaattca                                                               7756
```

<210> SEQ ID NO 9
<211> LENGTH: 860
<212> TYPE: PRT
<213> ORGANISM: Artificial Sequence
<220> FEATURE:
<223> OTHER INFORMATION: Synthetic Construct

<400> SEQUENCE: 9

```
Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270
```

```
Val Thr Leu Cys Glu Gly Pro Asn Lys Phe Lys Cys His Ser Gly Glu
            275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
```

```
                690             695             700
Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
                820                 825                 830

Glu Asp Glu Val His Ile Cys His Asn Gln Asp Gly Tyr Ser Tyr Pro
            835                 840                 845

Ser Arg Gln Met Val Ser Leu Glu Asp Asp Val Ala
        850                 855                 860

<210> SEQ ID NO 10
<211> LENGTH: 7756
<212> TYPE: DNA
<213> ORGANISM: Artificial Sequence
<220> FEATURE:
<223> OTHER INFORMATION: Synthetic CB7.hLDLR (K25R-C29A) - IDOL
<220> FEATURE:
<221> NAME/KEY: polyA_signal
<222> LOCATION: (66)..(192)
<223> OTHER INFORMATION: rabbit globulin polyA
<220> FEATURE:
<221> NAME/KEY: repeat_region
<222> LOCATION: (281)..(410)
<223> OTHER INFORMATION: 3' ITR, located on complement
<220> FEATURE:
<221> NAME/KEY: rep_origin
<222> LOCATION: (587)..(1042)
<223> OTHER INFORMATION: f1/ori, located on complement
<220> FEATURE:
<221> NAME/KEY: misc_feature
<222> LOCATION: (1173)..(2030)
<223> OTHER INFORMATION: maker AP(R)
<220> FEATURE:
<221> NAME/KEY: rep_origin
<222> LOCATION: (2204)..(2792)
<223> OTHER INFORMATION: origin of replication
<220> FEATURE:
<221> NAME/KEY: repeat_region
<222> LOCATION: (3232)..(3361)
<223> OTHER INFORMATION: 5' ITR
<220> FEATURE:
<221> NAME/KEY: repeat_region
<222> LOCATION: (3429)..(3810)
<223> OTHER INFORMATION: CMV IE promoter
<220> FEATURE:
<221> NAME/KEY: promoter
<222> LOCATION: (3813)..(4094)
<220> FEATURE:
<221> NAME/KEY: TATA_signal
<222> LOCATION: (4067)..(4070)
<220> FEATURE:
<221> NAME/KEY: Intron
<222> LOCATION: (4189)..(5161)
<220> FEATURE:
<221> NAME/KEY: CDS
<222> LOCATION: (5173)..(7755)
```

```
<223> OTHER INFORMATION: hLDLR
<220> FEATURE:
<221> NAME/KEY: misc_feature
<222> LOCATION: (6187)..(6189)
<223> OTHER INFORMATION: site of L318D mutation affecting PCSK9 binding
<220> FEATURE:
<221> NAME/KEY: misc_feature
<222> LOCATION: (7601)..(7638)
<223> OTHER INFORMATION: K6 ®¶rimer
<220> FEATURE:
<221> NAME/KEY: misc_feature
<222> LOCATION: (7603)..(7701)
<223> OTHER INFORMATION: IDOL mutations
<220> FEATURE:
<221> NAME/KEY: misc_feature
<222> LOCATION: (7618)..(7620)
<223> OTHER INFORMATION: K6-mutation
<220> FEATURE:
<221> NAME/KEY: misc_feature
<222> LOCATION: (7644)..(7677)
<223> OTHER INFORMATION: K20 R primer
<220> FEATURE:
<221> NAME/KEY: misc_feature
<222> LOCATION: (7660)..(7662)
<223> OTHER INFORMATION: K20 mutation
<220> FEATURE:
<221> NAME/KEY: misc_structure
<222> LOCATION: (7672)..(7704)
<223> OTHER INFORMATION: C29 primer
<220> FEATURE:
<221> NAME/KEY: misc_feature
<222> LOCATION: (7689)..(7689)
<223> OTHER INFORMATION: C29 mutation

<400> SEQUENCE: 10
cgcgtggtac ctctagagtc gacccgggcg gcctcgagga cggggtgaac tacgcctgag      60
gatccgatct ttttccctct gccaaaaatt atggggacat catgaagccc cttgagcatc     120
tgacttctgg ctaataaagg aaatttattt tcattgcaat agtgtgttgg aattttttgt     180
gtctctcact cggaagcaat tcgttgatct gaatttcgac cacccataat acccattacc     240
ctggtagata gtagcatgg cgggttaatc attaactaca aggaacccct agtgatggag      300
ttggccactc cctctctgcg cgctcgctcg ctcactgagg ccgggcgacc aaaggtcgcc     360
cgacgcccgg gctttgcccg gcggcctca gtgagcgagc gagcgcgcag ccttaattaa      420
cctaattcac tggccgtcgt tttacaacgt cgtgactggg aaaaccctgg cgttacccaa     480
cttaatcgcc ttgcagcaca tccccctttc gccagctggc gtaatagcga agaggcccgc     540
accgatcgcc cttcccaaca gttgcgcagc ctgaatggcg aatgggacgc gccctgtagc     600
ggcgcattaa gcgcggcggg tgtggtggtt acgcgcagcg tgaccgctac acttgccagc     660
gccctagcgc ccgctccttt cgctttcttc ccttcctttc tcgccacgtt cgccggcttt     720
ccccgtcaag ctctaaatcg ggggctccct ttagggttcc gatttagtgc tttacggcac     780
ctcgacccca aaaaacttga ttagggtgat ggttcacgta gtgggccatc gccctgatag     840
acggtttttc gccctttgac gttggagtcc acgttcttta atagtggact cttgttccaa     900
actggaacaa cactcaaccc tatctcggtc tattcttttg atttataagg gattttgccg     960
atttcggcct attggttaaa aaatgagctg atttaacaaa aatttaacgc gaattttaac    1020
aaaatattaa cgcttacaat ttaggtggca ctttttcgggg aaatgtgcgc ggaacccta    1080 tttgtttatt tttctaaata cattcaaata tgtatccgct catgagacaa taaccctgat    1140
aaatgcttca ataatattga aaaggaaga gtatgagtat tcaacatttc cgtgtcgccc    1200
ttattcccct ttttgcggca ttttgccttc ctgtttttgc tcacccagaa acgctggtga    1260
aagtaaaaga tgctgaagat cagttgggtg cacgagtggg ttacatcgaa ctggatctca    1320
```

```
acagcggtaa gatccttgag agttttcgcc ccgaagaacg ttttccaatg atgagcactt   1380
ttaaagttct gctatgtggc gcggtattat cccgtattga cgccgggcaa gagcaactcg   1440
gtcgccgcat acactattct cagaatgact tggttgagta ctcaccagtc acagaaaagc   1500
atcttacgga tggcatgaca gtaagagaat tatgcagtgc tgccataacc atgagtgata   1560
acactgcggc caacttactt ctgacaacga tcggaggacc gaaggagcta accgcttttt   1620
tgcacaacat gggggatcat gtaactcgcc ttgatcgttg ggaaccggag ctgaatgaag   1680
ccataccaaa cgacgagcgt gacaccacga tgcctgtagc aatggcaaca cgttgcgca   1740 aactattaac tggcgaacta cttactctag cttcccggca acaattaata gactggatgg   1800
aggcggataa agttgcagga ccacttctgc gctcggccct tccggctggc tggtttattg   1860
ctgataaatc tggagccggt gagcgtgggt ctcgcggtat cattgcagca ctggggccag   1920
atggtaagcc ctcccgtatc gtagttatct acacgacggg gagtcaggca actatggatg   1980
aacgaaatag acagatcgct gagataggtg cctcactgat taagcattgg taactgtcag   2040
accaagttta ctcatatata ctttagattg atttaaaact tcattttta tttaaaagga   2100 tctaggtgaa gatccttttt gataatctca tgaccaaaat cccttaacgt gagttttcgt   2160
tccactgagc gtcagacccc gtagaaaaga tcaaaggatc ttcttgagat ccttttttc   2220 tgcgcgtaat ctgctgcttg caaacaaaaa aaccaccgct accagcggtg tttgtttgc   2280 cggatcaaga gctaccaact ctttttccga aggtaactgg cttcagcaga gcgcagatac   2340
caaatactgt tcttctagtg tagccgtagt taggccacca cttcaagaac tctgtagcac   2400
cgcctacata cctcgctctg ctaatcctgt taccagtggc tgctgccagt ggcgataagt   2460
cgtgtcttac cgggttggac tcaagacgat agttaccgga taaggcgcag cggtcgggct   2520 gaacggggg ttcgtgcaca cagcccagct tggagcgaac gacctacacc gaactgagat   2580
acctacagcg tgagctatga aaagcgcca cgcttcccga agggagaaag gcggacaggt   2640
atccggtaag cggcagggtc ggaacaggag agcgcacgag ggagcttcca ggggaaacg   2700 cctggtatct ttatagtcct gtcgggtttc gccacctctg acttgagcgt cgatttttgt   2760
gatgctcgtc agggggggcgg agcctatgga aaaacgccag caacgcggcc tttttacggt   2820
tcctggcctt ttgctggcct tttgctcaca tgttctttcc tgcgttatcc cctgattctg   2880
tggataaccg tattaccgcc tttgagtgag ctgataccgc tcgccgcagc cgaacgaccg   2940
agcgcagcga gtcagtgagc gaggaagcgg aagagcgccc aatacgcaaa ccgcctctcc   3000
ccgcgcgttg gccgattcat taatgcagct ggcacgacag gtttcccgac tggaaagcgg   3060
gcagtgagcg caacgcaatt aatgtgagtt agctcactca ttaggcaccc caggctttac   3120
actttatgct tccggctcgt atgttgtgtg gaattgtgag cggataacaa tttcacacag   3180
gaaacagcta tgaccatgat tacgccagat ttaattaagg ccttaattag ctgcgcgct   3240 cgctcgctca ctgaggccgc ccgggcaaag cccgggcgtc gggcgacctt tggtcgcccg   3300
gcctcagtga gcgagcgagc gcgcagagag ggagtggcca actccatcac tagggttcc   3360 ttgtagttaa tgattaaccc gccatgctac ttatctacca gggtaatggg gatcctctag   3420
aactatagct agtcgacatt gattattgac tagttattaa tagtaatcaa ttacggggtc   3480
attagttcat agcccatata tggagttccg cgttacataa cttacggtaa atggcccgcc   3540
tggctgaccg cccaacgacc cccgcccatt gacgtcaata atgacgtatg ttcccatagt   3600
aacgccaata gggactttcc attgacgtca atgggtggag tatttacggt aaactgccca   3660
```

```
cttggcagta catcaagtgt atcatatgcc aagtacgccc cctattgacg tcaatgacgg    3720
taaatggccc gcctggcatt atgcccagta catgacctta tgggactttc ctacttggca    3780
gtacatctac gtattagtca tcgctattac catggtcgag gtgagcccca cgttctgctt    3840
cactctcccc atctccccccc cctcccacc cccaattttg tatttattta ttttttaatt    3900
attttgtgca gcgatggggg cggggggggg gggggggcgc gcgccaggcg gggcggggcg    3960
gggcgagggg cggggcgggg cgaggcgag aggtgcggcg gcagccaatc agagcggcgc    4020
gctccgaaag tttccttta tggcgaggcg gcggcggcgg cggccctata aaaagcgaag    4080
cgcgcggcgg gcggggagtc gctgcgacgc tgccttcgcc ccgtgccccg ctccgccgcc    4140
gcctcgcgcc gcccgccccg gctctgactg accgcgttac tcccacaggt gagcgggcgg    4200
gacggcccct tcctccgggg ctgtaattag cgcttggttt aatgacggct tgtttctttt    4260
ctgtggctgc gtgaaagcct tgaggggctc cgggagggcc ctttgtgcgg ggggagcggg    4320
tcggggggtg cgtgcgtgt tgtgtgcgtg gggagcgccg cgtgcggctc cgcgctgccc    4380
ggcggctgtg agcgctgcgg gcgcggcgcg gggctttgtg cgctccgcag tgtgcgcgag    4440
gggagcgcgg ccgggggcgg tgccccgcgg tgcggggggg gctgcgaggg aacaaaggc    4500 tgcgtgcggg gtgtgtgcgt gggggggtga gcaggggtg tgggcgcgtc ggtcgggctg    4560 caacccccc tgcacccccc tccccgagtt gctgagcacg gcccggcttc gggtgcgggg    4620
ctccgtacgg ggcgtggcgc ggggctcgcc gtgccgggcg ggggtggcg gcaggtgggg    4680 gtgccgggcg gggcggggcc gcctcgggcc ggggagggct cggggaggg gcgcggcggc    4740 ccccggagcg ccggcggctg tcgaggcgcg gcgagccgca gccattgcct tttatggtaa    4800
tcgtgcgaga gggcgcaggg acttcctttg tcccaaatct gtgcggagcc gaaatctggg    4860
aggcgccgcc gcaccccctc tagcgggcgc ggggcgaagc ggtgcggcgc cggcaggaag    4920
gaaatgggcg gggagggcct tcgtgcgtcg ccgcgccgcc gtccccttct ccctctccag    4980
cctcggggct gtccgcgggg ggacggctgc cttcggggg gacggggcag ggcggggttc    5040
ggcttctggc gtgtgaccgg cggctctaga gcctctgcta accatgttca tgccttcttc    5100
tttttcctac agctcctggg caacgtgctg gttattgtgc tgtctcatca ttttggcaaa    5160
gaattcacgc gt atg ggg ccc tgg ggc tgg aaa ttg cgc tgg acc gtc gcc    5211
             Met Gly Pro Trp Gly Trp Lys Leu Arg Trp Thr Val Ala
              1               5                  10 ttg ctc ctc gcc gcg gcg ggg act gca gtg ggc gac aga tgt gaa aga       5259
Leu Leu Leu Ala Ala Ala Gly Thr Ala Val Gly Asp Arg Cys Glu Arg
     15                  20                  25 aac gag ttc cag tgc caa gac ggg aaa tgc atc tcc tac aag tgg gtc       5307
Asn Glu Phe Gln Cys Gln Asp Gly Lys Cys Ile Ser Tyr Lys Trp Val
30                  35                  40                  45 tgc gat ggc agc gct gag tgc cag gat ggc tct gat gag tcc cag gag       5355
Cys Asp Gly Ser Ala Glu Cys Gln Asp Gly Ser Asp Glu Ser Gln Glu
                 50                  55                  60 acg tgc ttg tct gtc acc tgc aaa tcc ggg gac ttc agc tgt ggg ggc       5403
Thr Cys Leu Ser Val Thr Cys Lys Ser Gly Asp Phe Ser Cys Gly Gly
             65                  70                  75 cgt gtc aac cgc tgc att cct cag ttc tgg agg tgc gat ggc caa gtg       5451
Arg Val Asn Arg Cys Ile Pro Gln Phe Trp Arg Cys Asp Gly Gln Val
         80                  85                  90 gac tgc gac aac ggc tca gac gag caa ggc tgt ccc ccc aag acg tgc       5499
Asp Cys Asp Asn Gly Ser Asp Glu Gln Gly Cys Pro Pro Lys Thr Cys
     95                  100                 105 tcc cag gac gag ttt cgc tgc cac gat ggg aag tgc atc tct cgg cag       5547
```

```
                Ser Gln Asp Glu Phe Arg Cys His Asp Gly Lys Cys Ile Ser Arg Gln
                110                 115                 120                 125 ttc gtc tgt gac tca gac cgg gac tgc ttg gac ggc tca gac gag gcc           5595
Phe Val Cys Asp Ser Asp Arg Asp Cys Leu Asp Gly Ser Asp Glu Ala
                130                 135                 140 tcc tgc ccg gtg ctc acc tgt ggt ccc gcc agc ttc cag tgc aac agc           5643
Ser Cys Pro Val Leu Thr Cys Gly Pro Ala Ser Phe Gln Cys Asn Ser
            145                 150                 155 tcc acc tgc atc ccc cag ctg tgg gcc tgc gac aac gac ccc gac tgc           5691
Ser Thr Cys Ile Pro Gln Leu Trp Ala Cys Asp Asn Asp Pro Asp Cys
        160                 165                 170 gaa gat ggc tcg gat gag tgg ccg cag cgc tgt agg ggt ctt tac gtg           5739
Glu Asp Gly Ser Asp Glu Trp Pro Gln Arg Cys Arg Gly Leu Tyr Val
    175                 180                 185 ttc caa ggg gac agt agc ccc tgc tcg gcc ttc gag ttc cac tgc cta           5787
Phe Gln Gly Asp Ser Ser Pro Cys Ser Ala Phe Glu Phe His Cys Leu
190                 195                 200                 205 agt ggc gag tgc atc cac tcc agc tgg cgc tgt gat ggt ggc ccc gac           5835
Ser Gly Glu Cys Ile His Ser Ser Trp Arg Cys Asp Gly Gly Pro Asp
                210                 215                 220 tgc aag gac aaa tct gac gag gaa aac tgc gct gtg gcc acc tgt cgc           5883
Cys Lys Asp Lys Ser Asp Glu Glu Asn Cys Ala Val Ala Thr Cys Arg
            225                 230                 235 cct gac gaa ttc cag tgc tct gat gga aac tgc atc cat ggc agc cgg           5931
Pro Asp Glu Phe Gln Cys Ser Asp Gly Asn Cys Ile His Gly Ser Arg
        240                 245                 250 cag tgt gac cgg gaa tat gac tgc aag gac atg agc gat gaa gtt ggc           5979
Gln Cys Asp Arg Glu Tyr Asp Cys Lys Asp Met Ser Asp Glu Val Gly
    255                 260                 265 tgc gtt aat gtg aca ctc tgc gag gga ccc aac aag ttc aag tgt cac           6027
Cys Val Asn Val Thr Leu Cys Glu Gly Pro Asn Lys Phe Lys Cys His
270                 275                 280                 285 agc ggc gaa tgc atc acc ctg gac aaa gtc tgc aac atg gct aga gac           6075
Ser Gly Glu Cys Ile Thr Leu Asp Lys Val Cys Asn Met Ala Arg Asp
                290                 295                 300 tgc cgg gac tgg tca gat gaa ccc atc aaa gag tgc ggg acc aac gaa           6123
Cys Arg Asp Trp Ser Asp Glu Pro Ile Lys Glu Cys Gly Thr Asn Glu
            305                 310                 315 tgc ttg gac aac aac ggc ggt tgt tcc cac gtc tgc aat gac ctt aag           6171
Cys Leu Asp Asn Asn Gly Gly Cys Ser His Val Cys Asn Asp Leu Lys
        320                 325                 330 atc ggc tac gag tgc ctg tgc ccc gac ggc ttc cag ctg gtg gcc cag           6219
Ile Gly Tyr Glu Cys Leu Cys Pro Asp Gly Phe Gln Leu Val Ala Gln
    335                 340                 345 cga aga tgc gaa gat atc gat gag tgt cag gat ccc gac acc tgc agc           6267
Arg Arg Cys Glu Asp Ile Asp Glu Cys Gln Asp Pro Asp Thr Cys Ser
350                 355                 360                 365 cag ctc tgc gtg aac ctg gag ggt ggc tac aag tgc cag tgt gag gaa           6315
Gln Leu Cys Val Asn Leu Glu Gly Gly Tyr Lys Cys Gln Cys Glu Glu
                370                 375                 380 ggc ttc cag ctg gac ccc cac acg aag gcc tgc aag gct gtg ggc tcc           6363
Gly Phe Gln Leu Asp Pro His Thr Lys Ala Cys Lys Ala Val Gly Ser
            385                 390                 395 atc gcc tac ctc ttc ttc acc aac cgg cac gag gtc agg aag atg acg           6411
Ile Ala Tyr Leu Phe Phe Thr Asn Arg His Glu Val Arg Lys Met Thr
        400                 405                 410 ctg gac cgg agc gag tac acc agc ctc atc ccc aac ctg agg aac gtg           6459
Leu Asp Arg Ser Glu Tyr Thr Ser Leu Ile Pro Asn Leu Arg Asn Val
    415                 420                 425
```

```
gtc gct ctg gac acg gag gtg gcc agc aat aga atc tac tgg tct gac    6507
Val Ala Leu Asp Thr Glu Val Ala Ser Asn Arg Ile Tyr Trp Ser Asp
430             435                 440                 445 ctg tcc cag aga atg atc tgc agc acc cag ctt gac aga gcc cac ggc    6555
Leu Ser Gln Arg Met Ile Cys Ser Thr Gln Leu Asp Arg Ala His Gly
        450                 455                 460 gtc tct tcc tat gac acc gtc atc agc agg gac atc cag gcc ccc gac    6603
Val Ser Ser Tyr Asp Thr Val Ile Ser Arg Asp Ile Gln Ala Pro Asp
            465                 470                 475 ggg ctg gct gtg gac tgg atc cac agc aac atc tac tgg acc gac tct    6651
Gly Leu Ala Val Asp Trp Ile His Ser Asn Ile Tyr Trp Thr Asp Ser
                480                 485                 490 gtc ctg ggc act gtc tct gtt gcg gat acc aag ggc gtg aag agg aaa    6699
Val Leu Gly Thr Val Ser Val Ala Asp Thr Lys Gly Val Lys Arg Lys
495                 500                 505 acg tta ttc agg gag aac ggc tcc aag cca agg gcc atc gtg gtg gat    6747
Thr Leu Phe Arg Glu Asn Gly Ser Lys Pro Arg Ala Ile Val Val Asp
510             515                 520                 525 cct gtt cat ggc ttc atg tac tgg act gac tgg gga act ccc gcc aag    6795
Pro Val His Gly Phe Met Tyr Trp Thr Asp Trp Gly Thr Pro Ala Lys
        530                 535                 540 atc aag aaa ggg ggc ctg aat ggt gtg gac atc tac tcg ctg gtg act    6843
Ile Lys Lys Gly Gly Leu Asn Gly Val Asp Ile Tyr Ser Leu Val Thr
            545                 550                 555 gaa aac att cag tgg ccc aat ggc atc acc cta gat ctc ctc agt ggc    6891
Glu Asn Ile Gln Trp Pro Asn Gly Ile Thr Leu Asp Leu Leu Ser Gly
                560                 565                 570 cgc ctc tac tgg gtt gac tcc aaa ctt cac tcc atc tca agc atc gat    6939
Arg Leu Tyr Trp Val Asp Ser Lys Leu His Ser Ile Ser Ser Ile Asp
575                 580                 585 gtc aat ggg ggc aac cgg aag acc atc ttg gag gat gaa aag agg ctg    6987
Val Asn Gly Gly Asn Arg Lys Thr Ile Leu Glu Asp Glu Lys Arg Leu
590             595                 600                 605 gcc cac ccc ttc tcc ttg gcc gtc ttt gag gac aaa gta ttt tgg aca    7035
Ala His Pro Phe Ser Leu Ala Val Phe Glu Asp Lys Val Phe Trp Thr
        610                 615                 620 gat atc atc aac gaa gcc att ttc agt gcc aac cgc ctc aca ggt tcc    7083
Asp Ile Ile Asn Glu Ala Ile Phe Ser Ala Asn Arg Leu Thr Gly Ser
            625                 630                 635 gat gtc aac ttg ttg gct gaa aac cta ctg tcc cca gag gat atg gtc    7131
Asp Val Asn Leu Leu Ala Glu Asn Leu Leu Ser Pro Glu Asp Met Val
                640                 645                 650 ctc ttc cac aac ctc acc cag cca aga gga gtg aac tgg tgt gag agg    7179
Leu Phe His Asn Leu Thr Gln Pro Arg Gly Val Asn Trp Cys Glu Arg
655                 660                 665 acc acc ctg agc aat ggc ggc tgc cag tat ctg tgc ctc cct gcc ccg    7227
Thr Thr Leu Ser Asn Gly Gly Cys Gln Tyr Leu Cys Leu Pro Ala Pro
670             675                 680                 685 cag atc aac ccc cac tcg ccc aag ttt acc tgc gcc tgc ccg gac ggc    7275
Gln Ile Asn Pro His Ser Pro Lys Phe Thr Cys Ala Cys Pro Asp Gly
        690                 695                 700 atg ctg ctg gcc agg gac atg agg agc tgc ctc aca gag gct gag gct    7323
Met Leu Leu Ala Arg Asp Met Arg Ser Cys Leu Thr Glu Ala Glu Ala
            705                 710                 715 gca gtg gcc acc cag gag aca tcc acc gtc agg cta aag gtc agc tcc    7371
Ala Val Ala Thr Gln Glu Thr Ser Thr Val Arg Leu Lys Val Ser Ser
                720                 725                 730 aca gcc gta agg aca cag cac aca acc acc cgg cct gtt ccc gac acc    7419
Thr Ala Val Arg Thr Gln His Thr Thr Thr Arg Pro Val Pro Asp Thr
735                 740                 745
```

```
tcc cgg ctg cct ggg gcc acc cct ggg ctc acc acg gtg gag ata gtg    7467
Ser Arg Leu Pro Gly Ala Thr Pro Gly Leu Thr Thr Val Glu Ile Val
750             755                 760                 765 aca atg tct cac caa gct ctg ggc gac gtt gct ggc aga gga aat gag    7515
Thr Met Ser His Gln Ala Leu Gly Asp Val Ala Gly Arg Gly Asn Glu
                770                 775                 780 aag aag ccc agt agc gtg agg gct ctg tcc att gtc ctc ccc atc gtg    7563
Lys Lys Pro Ser Ser Val Arg Ala Leu Ser Ile Val Leu Pro Ile Val
            785                 790                 795 ctc ctc gtc ttc ctt tgc ctg ggg gtc ttc ctt cta tgg aag aac tgg    7611
Leu Leu Val Phe Leu Cys Leu Gly Val Phe Leu Leu Trp Lys Asn Trp
        800                 805                 810 cgg ctt aag aac atc aac agc atc aac ttt gac aac ccc gtc tat cag    7659
Arg Leu Lys Asn Ile Asn Ser Ile Asn Phe Asp Asn Pro Val Tyr Gln
    815                 820                 825 agg acc aca gag gat gag gtc cac att gcc cac aac cag gac ggc tac    7707
Arg Thr Thr Glu Asp Glu Val His Ile Ala His Asn Gln Asp Gly Tyr
830                 835                 840                 845 agc tac ccc tcg aga cag atg gtc agt ctg gag gat gac gtg gcg tga a  7756
Ser Tyr Pro Ser Arg Gln Met Val Ser Leu Glu Asp Asp Val Ala
                850                 855                 860

<210> SEQ ID NO 11
<211> LENGTH: 860
<212> TYPE: PRT
<213> ORGANISM: Artificial Sequence
<220> FEATURE:
<223> OTHER INFORMATION: Synthetic Construct

<400> SEQUENCE: 11

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
                20                  25                  30

Gln Cys Gln Asp Gly Lys Cys Ile Ser Tyr Lys Trp Val Cys Asp Gly
            35                  40                  45

Ser Ala Glu Cys Gln Asp Gly Ser Asp Glu Ser Gln Glu Thr Cys Leu
        50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
```

```
                210                 215                 220
Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
                260                 265                 270

Val Thr Leu Cys Glu Gly Pro Asn Lys Phe Lys Cys His Ser Gly Glu
                275                 280                 285

Cys Ile Thr Leu Asp Lys Val Cys Asn Met Ala Arg Asp Cys Arg Asp
                290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
                340                 345                 350

Glu Asp Ile Asp Glu Cys Gln Asp Pro Asp Thr Cys Ser Gln Leu Cys
                355                 360                 365

Val Asn Leu Glu Gly Gly Tyr Lys Cys Gln Cys Glu Glu Gly Phe Gln
                370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
                420                 425                 430

Asp Thr Glu Val Ala Ser Asn Arg Ile Tyr Trp Ser Asp Leu Ser Gln
                435                 440                 445

Arg Met Ile Cys Ser Thr Gln Leu Asp Arg Ala His Gly Val Ser Ser
                450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
                500                 505                 510

Arg Glu Asn Gly Ser Lys Pro Arg Ala Ile Val Val Asp Pro Val His
                515                 520                 525

Gly Phe Met Tyr Trp Thr Asp Trp Gly Thr Pro Ala Lys Ile Lys Lys
                530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
                580                 585                 590

Gly Asn Arg Lys Thr Ile Leu Glu Asp Glu Lys Arg Leu Ala His Pro
                595                 600                 605

Phe Ser Leu Ala Val Phe Glu Asp Lys Val Phe Trp Thr Asp Ile Ile
                610                 615                 620

Asn Glu Ala Ile Phe Ser Ala Asn Arg Leu Thr Gly Ser Asp Val Asn
625                 630                 635                 640
```

Leu Leu Ala Glu Asn Leu Leu Ser Pro Glu Asp Met Val Leu Phe His
              645                 650                 655

Asn Leu Thr Gln Pro Arg Gly Val Asn Trp Cys Glu Arg Thr Thr Leu
          660                 665                 670

Ser Asn Gly Gly Cys Gln Tyr Leu Cys Leu Pro Ala Pro Gln Ile Asn
      675                 680                 685

Pro His Ser Pro Lys Phe Thr Cys Ala Cys Pro Asp Gly Met Leu Leu
  690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Thr Ala Val
              725                 730                 735

Arg Thr Gln His Thr Thr Thr Arg Pro Val Pro Asp Thr Ser Arg Leu
          740                 745                 750

Pro Gly Ala Thr Pro Gly Leu Thr Thr Val Glu Ile Val Thr Met Ser
      755                 760                 765

His Gln Ala Leu Gly Asp Val Ala Gly Arg Gly Asn Glu Lys Lys Pro
  770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
              805                 810                 815

Asn Ile Asn Ser Ile Asn Phe Asp Asn Pro Val Tyr Gln Arg Thr Thr
          820                 825                 830

Glu Asp Glu Val His Ile Ala His Asn Gln Asp Gly Tyr Ser Tyr Pro
      835                 840                 845

Ser Arg Gln Met Val Ser Leu Glu Asp Asp Val Ala
  850                 855                 860

<210> SEQ ID NO 12
<211> LENGTH: 7059
<212> TYPE: DNA
<213> ORGANISM: Artificial Sequence
<220> FEATURE:
<223> OTHER INFORMATION: Synthetic pAAV.TBG.PI.hLDLR
<220> FEATURE:
<221> NAME/KEY: repeat_region
<222> LOCATION: (1)..(130)
<223> OTHER INFORMATION: 5' ITR
<220> FEATURE:
<221> NAME/KEY: enhancer
<222> LOCATION: (221)..(320)
<223> OTHER INFORMATION: alpha mic/bik
<220> FEATURE:
<221> NAME/KEY: enhancer
<222> LOCATION: (327)..(426)
<223> OTHER INFORMATION: alpha mic/bik
<220> FEATURE:
<221> NAME/KEY: promoter
<222> LOCATION: (442)..(901)
<223> OTHER INFORMATION: TBG
<220> FEATURE:
<221> NAME/KEY: TATA_signal
<222> LOCATION: (885)..(888)
<220> FEATURE:
<221> NAME/KEY: Intron
<222> LOCATION: (1027)..(1159)
<223> OTHER INFORMATION: intron 1
<220> FEATURE:
<221> NAME/KEY: CDS
<222> LOCATION: (1245)..(3827)
<223> OTHER INFORMATION: hLDLR variant
<220> FEATURE:
<221> NAME/KEY: misc_feature

```
<222> LOCATION: (2256)..(2258)
<223> OTHER INFORMATION: C before L318D
<220> FEATURE:
<221> NAME/KEY: misc_feature
<222> LOCATION: (2259)..(2261)
<223> OTHER INFORMATION: L318D mutation
<220> FEATURE:
<221> NAME/KEY: misc_feature
<222> LOCATION: (3673)..(3710)
<223> OTHER INFORMATION: K6 R primter
<220> FEATURE:
<221> NAME/KEY: misc_feature
<222> LOCATION: (3675)..(3773)
<223> OTHER INFORMATION: IDOL mutations
<220> FEATURE:
<221> NAME/KEY: misc_feature
<222> LOCATION: (3690)..(3692)
<223> OTHER INFORMATION: K6-mutation
<220> FEATURE:
<221> NAME/KEY: misc_feature
<222> LOCATION: (3716)..(3749)
<223> OTHER INFORMATION: K20 R primter
<220> FEATURE:
<221> NAME/KEY: misc_feature
<222> LOCATION: (3732)..(3734)
<223> OTHER INFORMATION: K20 mutations
<220> FEATURE:
<221> NAME/KEY: misc_feature
<222> LOCATION: (3744)..(3776)
<223> OTHER INFORMATION: C29 A Primer
<220> FEATURE:
<221> NAME/KEY: misc_feature
<222> LOCATION: (3761)..(3761)
<223> OTHER INFORMATION: C29 mutation
<220> FEATURE:
<221> NAME/KEY: polyA_signal
<222> LOCATION: (3894)..(4020)
<223> OTHER INFORMATION: rabbit globulin polyA
<220> FEATURE:
<221> NAME/KEY: repeat_region
<222> LOCATION: (4109)..(4238)
<223> OTHER INFORMATION: 3' ITR (complementary strand)
<220> FEATURE:
<221> NAME/KEY: rep_origin
<222> LOCATION: (4415)..(4870)
<223> OTHER INFORMATION: (located on complementary strand)
<220> FEATURE:
<221> NAME/KEY: rep_origin
<222> LOCATION: (6032)..(6620)

<400> SEQUENCE: 12
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct tgtagttaat gattaacccg ccatgctact tatctaccag ggtaatgggg     180
atcctctaga actatagcta gaattcgccc ttaagctagc aggttaattt ttaaaaagca     240
gtcaaaagtc caagtggccc ttggcagcat ttactctctc tgtttgctct ggttaataat     300
ctcaggagca caaacattcc agatccaggt taatttttaa aaagcagtca aaagtccaag     360
tggcccttgg cagcatttac tctctctgtt tgctctggtt aataatctca ggagcacaaa     420
cattccagat ccggcgcgcc agggctggaa gctacctttg acatcatttc ctctgcgaat     480
gcatgtataa tttctacaga acctattaga aaggatcacc cagcctctgc ttttgtacaa     540
ctttccctta aaaaactgcc aattccactg ctgtttggcc caatagtgag aactttttcc     600
tgctgcctct tggtgctttt gcctatggcc cctattctgc ctgctgaaga cactcttgcc     660
agcatggact taaacccctc cagctctgac aatcctcttt ctcttttgtt ttacatgaag     720
ggtctggcag ccaaagcaat cactcaaagt tcaaacctta tcatttttg ctttgttcct     780 cttggccttg gttttgtaca tcagctttga aaataccatc ccagggttaa tgctgggtt     840
```

```
aatttataac taagagtgct ctagttttgc aatacaggac atgctataaa aatggaaaga    900
tgttgctttc tgagagacag ctttattgcg gtagtttatc acagttaaat tgctaacgca    960
gtcagtgctt ctgacacaac agtctcgaac ttaagctgca gaagttggtc gtgaggcact   1020
gggcaggtaa gtatcaaggt tacaagacag gtttaaggag accaatagaa actgggcttg   1080
tcgagacaga gaagactctt gcgtttctga taggcaccta ttggtcttac tgacatccac   1140
tttgcctttc tctccacagg tgtccactcc cagttcaatt acagctctta aggctagagt   1200
acttaatacg actcactata ggctagcctc gagaattcac gcgt atg ggg ccc tgg   1256
                                                 Met Gly Pro Trp
                                                  1 ggc tgg aaa ttg cgc tgg acc gtc gcc ttg ctc ctc gcg gcg ggg         1304
Gly Trp Lys Leu Arg Trp Thr Val Ala Leu Leu Leu Ala Ala Ala Gly
 5              10                  15                  20 act gca gtg ggc gac aga tgt gaa aga aac gag ttc cag tgc caa gac     1352
Thr Ala Val Gly Asp Arg Cys Glu Arg Asn Glu Phe Gln Cys Gln Asp
                25                  30                  35 ggg aaa tgc atc tcc tac aag tgg gtc tgc gat ggc agc gct gag tgc     1400
Gly Lys Cys Ile Ser Tyr Lys Trp Val Cys Asp Gly Ser Ala Glu Cys
            40                  45                  50 cag gat ggc tct gat gag tcc cag gag acg tgc ttg tct gtc acc tgc     1448
Gln Asp Gly Ser Asp Glu Ser Gln Glu Thr Cys Leu Ser Val Thr Cys
        55                  60                  65 aaa tcc ggg gac ttc agc tgt ggg ggc cgt gtc aac cgc tgc att cct     1496
Lys Ser Gly Asp Phe Ser Cys Gly Gly Arg Val Asn Arg Cys Ile Pro
    70                  75                  80 cag ttc tgg agg tgc gat ggc caa gtg gac tgc gac aac ggc tca gac     1544
Gln Phe Trp Arg Cys Asp Gly Gln Val Asp Cys Asp Asn Gly Ser Asp
85                  90                  95                 100 gag caa ggc tgt ccc ccc aag acg tgc tcc cag gac gag ttt cgc tgc     1592
Glu Gln Gly Cys Pro Pro Lys Thr Cys Ser Gln Asp Glu Phe Arg Cys
                105                 110                 115 cac gat ggg aag tgc atc tct cgg cag ttc gtc tgt gac tca gac cgg     1640
His Asp Gly Lys Cys Ile Ser Arg Gln Phe Val Cys Asp Ser Asp Arg
            120                 125                 130 gac tgc ttg gac ggc tca gac gag gcc tcc tgc ccg gtg ctc acc tgt     1688
Asp Cys Leu Asp Gly Ser Asp Glu Ala Ser Cys Pro Val Leu Thr Cys
        135                 140                 145 ggt ccc gcc agc ttc cag tgc aac agc tcc acc tgc atc ccc cag ctg     1736
Gly Pro Ala Ser Phe Gln Cys Asn Ser Ser Thr Cys Ile Pro Gln Leu
    150                 155                 160 tgg gcc tgc gac aac gac ccc gac tgc gaa gat ggc tcg gat gag tgg     1784
Trp Ala Cys Asp Asn Asp Pro Asp Cys Glu Asp Gly Ser Asp Glu Trp
165                 170                 175                 180 ccg cag cgc tgt agg ggt ctt tac gtg ttc caa ggg gac agt agc ccc     1832
Pro Gln Arg Cys Arg Gly Leu Tyr Val Phe Gln Gly Asp Ser Ser Pro
                185                 190                 195 tgc tcg gcc ttc gag ttc cac tgc cta agt ggc gag tgc atc cac tcc     1880
Cys Ser Ala Phe Glu Phe His Cys Leu Ser Gly Glu Cys Ile His Ser
            200                 205                 210 agc tgg cgc tgt gat ggt ggc ccc gac tgc aag gac aaa tct gac gag     1928
Ser Trp Arg Cys Asp Gly Gly Pro Asp Cys Lys Asp Lys Ser Asp Glu
        215                 220                 225 gaa aac tgc gct gtg gcc acc tgt cgc cct gac gaa ttc cag tgc tct     1976
Glu Asn Cys Ala Val Ala Thr Cys Arg Pro Asp Glu Phe Gln Cys Ser
    230                 235                 240 gat gga aac tgc atc cat ggc agc cgg cag tgt gac cgg gaa tat gac     2024
Asp Gly Asn Cys Ile His Gly Ser Arg Gln Cys Asp Arg Glu Tyr Asp
```

```
                245                 250                 255                 260
tgc aag gac atg agc gat gaa gtt ggc tgc gtt aat gtg aca ctc tgc    2072
Cys Lys Asp Met Ser Asp Glu Val Gly Cys Val Asn Val Thr Leu Cys
                    265                 270                 275 gag gga ccc aac aag ttc aag tgt cac agc ggc gaa tgc atc acc ctg    2120
Glu Gly Pro Asn Lys Phe Lys Cys His Ser Gly Glu Cys Ile Thr Leu
            280                 285                 290 gac aaa gtc tgc aac atg gct aga gac tgc cgg gac tgg tca gat gaa    2168
Asp Lys Val Cys Asn Met Ala Arg Asp Cys Arg Asp Trp Ser Asp Glu
        295                 300                 305 ccc atc aaa gag tgc ggg acc aac gaa tgc ttg gac aac aac ggc ggc    2216
Pro Ile Lys Glu Cys Gly Thr Asn Glu Cys Leu Asp Asn Asn Gly Gly
    310                 315                 320 tgt tcc cac gtc tgc aat gac ctt aag atc ggc tac gag tgc gac tgc    2264
Cys Ser His Val Cys Asn Asp Leu Lys Ile Gly Tyr Glu Cys Asp Cys
325                 330                 335                 340 ccc gac ggc ttc cag ctg gtg gcc cag cga aga tgc gaa gat atc gat    2312
Pro Asp Gly Phe Gln Leu Val Ala Gln Arg Arg Cys Glu Asp Ile Asp
                345                 350                 355 gag tgt cag gat ccc gac acc tgc agc cag ctc tgc gtg aac ctg gag    2360
Glu Cys Gln Asp Pro Asp Thr Cys Ser Gln Leu Cys Val Asn Leu Glu
            360                 365                 370 ggt ggc tac aag tgc cag tgt gag gaa ggc ttc cag ctg gac ccc cac    2408
Gly Gly Tyr Lys Cys Gln Cys Glu Glu Gly Phe Gln Leu Asp Pro His
        375                 380                 385 acg aag gcc tgc aag gct gtg ggc tcc atc gcc tac ctc ttc ttc acc    2456
Thr Lys Ala Cys Lys Ala Val Gly Ser Ile Ala Tyr Leu Phe Phe Thr
    390                 395                 400 aac cgg cac gag gtc agg aag atg acg ctg gac cgg agc gag tac acc    2504
Asn Arg His Glu Val Arg Lys Met Thr Leu Asp Arg Ser Glu Tyr Thr
405                 410                 415                 420 agc ctc atc ccc aac ctg agg aac gtg gtc gct ctg gac acg gag gtg    2552
Ser Leu Ile Pro Asn Leu Arg Asn Val Val Ala Leu Asp Thr Glu Val
                425                 430                 435 gcc agc aat aga atc tac tgg tct gac ctg tcc cag aga atg atc tgc    2600
Ala Ser Asn Arg Ile Tyr Trp Ser Asp Leu Ser Gln Arg Met Ile Cys
            440                 445                 450 agc acc cag ctt gac aga gcc cac ggc gtc tct tcc tat gac acc gtc    2648
Ser Thr Gln Leu Asp Arg Ala His Gly Val Ser Ser Tyr Asp Thr Val
        455                 460                 465 atc agc agg gac atc cag gcc ccc gac ggg ctg gct gtg gac tgg atc    2696
Ile Ser Arg Asp Ile Gln Ala Pro Asp Gly Leu Ala Val Asp Trp Ile
    470                 475                 480 cac agc aac atc tac tgg acc gac tct gtc ctg ggc act gtc tct gtt    2744
His Ser Asn Ile Tyr Trp Thr Asp Ser Val Leu Gly Thr Val Ser Val
485                 490                 495                 500 gcg gat acc aag ggc gtg aag agg aaa acg tta ttc agg gag aac ggc    2792
Ala Asp Thr Lys Gly Val Lys Arg Lys Thr Leu Phe Arg Glu Asn Gly
                505                 510                 515 tcc aag cca agg gcc atc gtg gtg gat cct gtt cat ggc ttc atg tac    2840
Ser Lys Pro Arg Ala Ile Val Val Asp Pro Val His Gly Phe Met Tyr
            520                 525                 530 tgg act gac tgg gga act ccc gcc aag atc aag aaa ggg ggc ctg aat    2888
Trp Thr Asp Trp Gly Thr Pro Ala Lys Ile Lys Lys Gly Gly Leu Asn
        535                 540                 545 ggt gtg gac atc tac tcg ctg gtg act gaa aac att cag tgg ccc aat    2936
Gly Val Asp Ile Tyr Ser Leu Val Thr Glu Asn Ile Gln Trp Pro Asn
    550                 555                 560 ggc atc acc cta gat ctc ctc agt ggc cgc ctc tac tgg gtt gac tcc    2984
```

```
                                                                -continued

Gly Ile Thr Leu Asp Leu Leu Ser Gly Arg Leu Tyr Trp Val Asp Ser
565                 570                 575                 580 aaa ctt cac tcc atc tca agc atc gat gtc aat ggg ggc aac cgg aag         3032
Lys Leu His Ser Ile Ser Ser Ile Asp Val Asn Gly Gly Asn Arg Lys
                585                 590                 595 acc atc ttg gag gat gaa aag agg ctg gcc cac ccc ttc tcc ttg gcc         3080
Thr Ile Leu Glu Asp Glu Lys Arg Leu Ala His Pro Phe Ser Leu Ala
            600                 605                 610 gtc ttt gag gac aaa gta ttt tgg aca gat atc atc aac gaa gcc att         3128
Val Phe Glu Asp Lys Val Phe Trp Thr Asp Ile Ile Asn Glu Ala Ile
        615                 620                 625 ttc agt gcc aac cgc ctc aca ggt tcc gat gtc aac ttg ttg gct gaa         3176
Phe Ser Ala Asn Arg Leu Thr Gly Ser Asp Val Asn Leu Leu Ala Glu
    630                 635                 640 aac cta ctg tcc cca gag gat atg gtc ctc ttc cac aac ctc acc cag         3224
Asn Leu Leu Ser Pro Glu Asp Met Val Leu Phe His Asn Leu Thr Gln
645                 650                 655                 660 cca aga gga gtg aac tgg tgt gag agg acc acc ctg agc aat ggc ggc         3272
Pro Arg Gly Val Asn Trp Cys Glu Arg Thr Thr Leu Ser Asn Gly Gly
                665                 670                 675 tgc cag tat ctg tgc ctc cct gcc ccg cag atc aac ccc cac tcg ccc         3320
Cys Gln Tyr Leu Cys Leu Pro Ala Pro Gln Ile Asn Pro His Ser Pro
            680                 685                 690 aag ttt acc tgc gcc tgc ccg gac ggc atg ctg ctg gcc agg gac atg         3368
Lys Phe Thr Cys Ala Cys Pro Asp Gly Met Leu Leu Ala Arg Asp Met
        695                 700                 705 agg agc tgc ctc aca gag gct gag gct gca gtg gcc acc cag gag aca         3416
Arg Ser Cys Leu Thr Glu Ala Glu Ala Ala Val Ala Thr Gln Glu Thr
    710                 715                 720 tcc acc gtc agg cta aag gtc agc tcc aca gcc gta agg aca cag cac         3464
Ser Thr Val Arg Leu Lys Val Ser Ser Thr Ala Val Arg Thr Gln His
725                 730                 735                 740 aca acc acc cgg cct gtt ccc gac acc tcc cgg ctg cct ggg gcc acc         3512
Thr Thr Thr Arg Pro Val Pro Asp Thr Ser Arg Leu Pro Gly Ala Thr
                745                 750                 755 cct ggg ctc acc acg gtg gag ata gtg aca atg tct cac caa gct ctg         3560
Pro Gly Leu Thr Thr Val Glu Ile Val Thr Met Ser His Gln Ala Leu
            760                 765                 770 ggc gac gtt gct ggc aga gga aat gag aag aag ccc agt agc gtg agg         3608
Gly Asp Val Ala Gly Arg Gly Asn Glu Lys Lys Pro Ser Ser Val Arg
        775                 780                 785 gct ctg tcc att gtc ctc ccc atc gtg ctc ctc gtc ttc ctt tgc ctg         3656
Ala Leu Ser Ile Val Leu Pro Ile Val Leu Leu Val Phe Leu Cys Leu
    790                 795                 800 ggg gtc ttc ctt cta tgg aag aac tgg cgg ctt aag aac atc aac agc         3704
Gly Val Phe Leu Leu Trp Lys Asn Trp Arg Leu Lys Asn Ile Asn Ser
805                 810                 815                 820 atc aac ttt gac aac ccc gtc tat cag agg acc aca gag gat gag gtc         3752
Ile Asn Phe Asp Asn Pro Val Tyr Gln Arg Thr Thr Glu Asp Glu Val
                825                 830                 835 cac att gcc cac aac cag gac ggc tac agc tac ccc tcg aga cag atg         3800
His Ile Ala His Asn Gln Asp Gly Tyr Ser Tyr Pro Ser Arg Gln Met
            840                 845                 850 gtc agt ctg gag gat gac gtg gcg tga acgcgtggta cctctagagt               3847
Val Ser Leu Glu Asp Asp Val Ala
        855                 860 cgacccgggc ggcctcgagg acggggtgaa ctacgcctga ggatccgatc tttttccctc       3907
tgccaaaaat tatggggaca tcatgaagcc ccttgagcat ctgacttctg gctaataaag       3967
```

```
gaaatttatt ttcattgcaa tagtgtgttg gaattttttg tgtctctcac tcggaagcaa    4027
ttcgttgatc tgaatttcga ccacccataa tacccattac cctggtagat aagtagcatg    4087
gcgggttaat cattaactac aaggaacccc tagtgatgga gttggccact ccctctctgc    4147
gcgctcgctc gctcactgag gccgggcgac caaaggtcgc ccgacgcccg ggctttgccc    4207
gggcggcctc agtgagcgag cgagcgcgca gccttaatta acctaattca ctggccgtcg    4267
ttttacaacg tcgtgactgg gaaaaccctg gcgttaccca acttaatcgc cttgcagcac    4327
atccccgttt cgccagctgg cgtaatagcg aagaggcccg caccgatcgc ccttcccaac    4387
agttgcgcag cctgaatggc gaatgggacg cgccctgtag cggcgcatta gcgcggcgg    4447 gtgtggtggt tacgcgcagc gtgaccgcta cacttgccag cgccctagcg cccgctcctt    4507
tcgctttctt cccttccttt ctcgccacgt tcgccggctt tccccgtcaa gctctaaatc    4567
gggggctccc tttagggttc cgatttagtg ctttacggca cctcgacccc aaaaaacttg    4627
attagggtga tggttcacgt agtgggccat cgccctgata acggttttt cgcccttga    4687 cgttggagtc cacgttcttt aatagtggac tcttgttcca aactggaaca cactcaacc    4747 ctatctcggt ctattctttt gatttataag ggattttgcc gatttcggcc tattggttaa    4807
aaaatgagct gatttaacaa aaatttaacg cgaattttaa caaatatta acgcttacaa    4867 tttaggtggc acttttcggg gaaatgtgcg cggaaccccct atttgtttat ttttctaaat    4927
acattcaaat atgtatccgc tcatgagaca ataaccctga taaatgcttc aataatattg    4987
aaaaaggaag agtatgagta ttcaacattt ccgtgtcgcc cttattccct ttttttgcggc    5047 attttgcctt cctgttttg ctcacccaga aacgctggtg aaagtaaaag atgctgaaga    5107
tcagttgggt gcacgagtgg gttacatcga actggatctc aacagcggta agatccttga    5167
gagttttcgc cccgaagaac gttttccaat gatgagcact tttaaagttc tgctatgtgg    5227
cgcggtatta tcccgtattg acgccgggca agagcaactc ggtcgccgca tacactattc    5287
tcagaatgac ttggttgagt actcaccagt cacagaaaag catcttacgg atggcatgac    5347
agtaagagaa ttatgcagtg ctgccataac catgagtgat aacactgcgg ccaacttact    5407
tctgacaacg atcggaggac cgaaggagct aaccgctttt ttgcacaaca tggggggatca    5467 tgtaactcgc cttgatcgtt gggaaccgga gctgaatgaa gccataccaa acgacgagcg    5527
tgacaccacg atgcctgtag caatggcaac aacgttgcgc aaactattaa ctggcgaact    5587
acttactcta gcttcccggc aacaattaat agactggatg gaggcggata agttgcagg    5647 accacttctg cgctcggccc ttccggctgg ctggtttatt gctgataaat ctggagccgg    5707
tgagcgtggg tctcgcggta tcattgcagc actggggcca gatggtaagc cctcccgtat    5767
cgtagttatc tacacgacgg ggagtcaggc aactatggat gaacgaaata gacagatcgc    5827
tgagataggt gcctcactga ttaagcattg gtaactgtca gaccaagttt actcatatat    5887
actttagatt gatttaaaac ttcatttta atttaaaagg atctaggtga agatcctttt    5947
tgataatctc atgaccaaaa tcccttaacg tgagttttcg ttccactgag cgtcagaccc    6007
cgtagaaaag atcaaaggat cttcttgaga tcctttttt ctgcgcgtaa tctgctgctt    6067
gcaaacaaaa aaaccaccgc taccagcggt ggtttgtttg ccggatcaag agctaccaac    6127 tcttttccg aaggtaactg gcttcagcag agcgcagata ccaaatactg ttcttctagt    6187
gtagccgtag ttaggccacc acttcaagaa ctctgtagca ccgcctacat acctcgctct    6247
gctaatcctg ttaccagtgg ctgctgccag tggcgataag tcgtgtctta ccgggttgga    6307
ctcaagacga tagttaccgg ataaggcgca gcggtcgggc tgaacggggg gttcgtgcac    6367
```

```
acagcccagc ttggagcgaa cgacctacac cgaactgaga tacctacagc gtgagctatg    6427
agaaagcgcc acgcttcccg aagggagaaa ggcggacagg tatccggtaa gcggcagggt    6487
cggaacagga gagcgcacga gggagcttcc aggggaaac gcctggtatc tttatagtcc     6547
tgtcgggttt cgccacctct gacttgagcg tcgattttg tgatgctcgt caggggggcg     6607
gagcctatgg aaaaacgcca gcaacgcggc cttttacgg ttcctggcct tttgctggcc     6667
ttttgctcac atgttctttc ctgcgttatc ccctgattct gtggataacc gtattaccgc    6727
ctttgagtga gctgataccg ctcgccgcag ccgaacgacc gagcgcagcg agtcagtgag    6787
cgaggaagcg gaagagcgcc caatacgcaa accgcctctc cccgcgcgtt ggccgattca    6847
ttaatgcagc tggcacgaca ggtttcccga ctggaaagcg ggcagtgagc gcaacgcaat    6907
taatgtgagt tagctcactc attaggcacc ccaggcttta cactttatgc ttccggctcg    6967
tatgttgtgt ggaattgtga gcggataaca atttcacaca ggaaacagct atgaccatga    7027
ttacgccaga tttaattaag gccttaatta gg                                   7059
```

<210> SEQ ID NO 13
<211> LENGTH: 860
<212> TYPE: PRT
<213> ORGANISM: Artificial Sequence
<220> FEATURE:
<223> OTHER INFORMATION: Synthetic Construct

<400> SEQUENCE: 13

```
Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240
```

```
Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Asp Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655
```

```
Asn Leu Thr Gln Pro Arg Gly Val Asn Trp Cys Glu Arg Thr Thr Leu
                660                 665                 670

Ser Asn Gly Gly Cys Gln Tyr Leu Cys Leu Pro Ala Pro Gln Ile Asn
            675                 680                 685

Pro His Ser Pro Lys Phe Thr Cys Ala Cys Pro Asp Gly Met Leu Leu
        690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Thr Ala Val
                725                 730                 735

Arg Thr Gln His Thr Thr Thr Arg Pro Val Pro Asp Thr Ser Arg Leu
                740                 745                 750

Pro Gly Ala Thr Pro Gly Leu Thr Thr Val Glu Ile Val Thr Met Ser
            755                 760                 765

His Gln Ala Leu Gly Asp Val Ala Gly Arg Gly Asn Glu Lys Lys Pro
        770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Arg Thr Thr
            820                 825                 830

Glu Asp Glu Val His Ile Ala His Asn Gln Asp Gly Tyr Ser Tyr Pro
        835                 840                 845

Ser Arg Gln Met Val Ser Leu Glu Asp Asp Val Ala
    850                 855                 860

<210> SEQ ID NO 14
<211> LENGTH: 7059
<212> TYPE: DNA
<213> ORGANISM: Artificial Sequence
<220> FEATURE:
<223> OTHER INFORMATION: Synthetic plasmid with hLDLR (K25K,
      C29A).PGT(P2701)Q
<220> FEATURE:
<221> NAME/KEY: repeat_region
<222> LOCATION: (1)..(130)
<223> OTHER INFORMATION: 5' ITR
<220> FEATURE:
<221> NAME/KEY: enhancer
<222> LOCATION: (221)..(320)
<223> OTHER INFORMATION: alpha mic/bik
<220> FEATURE:
<221> NAME/KEY: enhancer
<222> LOCATION: (327)..(426)
<223> OTHER INFORMATION: alpha mic/bik
<220> FEATURE:
<221> NAME/KEY: promoter
<222> LOCATION: (442)..(901)
<223> OTHER INFORMATION: TBG promoter
<220> FEATURE:
<221> NAME/KEY: TATA_signal
<222> LOCATION: (885)..(888)
<220> FEATURE:
<221> NAME/KEY: Intron
<222> LOCATION: (1027)..(1159)
<223> OTHER INFORMATION: Intron 1
<220> FEATURE:
<221> NAME/KEY: CDS
<222> LOCATION: (1245)..(3827)
<223> OTHER INFORMATION: hLDLR with K25R-C29A variants
<220> FEATURE:
<221> NAME/KEY: misc_feature
<222> LOCATION: (2259)..(2261)
<223> OTHER INFORMATION: site of L318D mutatoin affecctign PCSK9 binding
<220> FEATURE:
```

```
<221> NAME/KEY: misc_feature
<222> LOCATION: (3673)..(3710)
<223> OTHER INFORMATION: K6 ®£rimter
<220> FEATURE:
<221> NAME/KEY: misc_feature
<222> LOCATION: (3675)..(3773)
<223> OTHER INFORMATION: IDOL mutations
<220> FEATURE:
<221> NAME/KEY: misc_feature
<222> LOCATION: (3690)..(3692)
<223> OTHER INFORMATION: K796 (K6) mutation
<220> FEATURE:
<221> NAME/KEY: misc_feature
<222> LOCATION: (3716)..(3749)
<223> OTHER INFORMATION: K20 R Primer
<220> FEATURE:
<221> NAME/KEY: misc_feature
<222> LOCATION: (3732)..(3732)
<223> OTHER INFORMATION: K20 mutation
<220> FEATURE:
<221> NAME/KEY: misc_feature
<222> LOCATION: (3744)..(3776)
<223> OTHER INFORMATION: C29 A primer
<220> FEATURE:
<221> NAME/KEY: misc_feature
<222> LOCATION: (3761)..(3761)
<223> OTHER INFORMATION: C29 mutation
<220> FEATURE:
<221> NAME/KEY: polyA_signal
<222> LOCATION: (3894)..(4020)
<223> OTHER INFORMATION: rabbit globulin polyA
<220> FEATURE:
<221> NAME/KEY: repeat_region
<222> LOCATION: (4109)..(4238)
<223> OTHER INFORMATION: 3' ITR (complement)
<220> FEATURE:
<221> NAME/KEY: rep_origin
<222> LOCATION: (4415)..(4870)
<223> OTHER INFORMATION: complement f1 ori
<220> FEATURE:
<221> NAME/KEY: misc_feature
<222> LOCATION: (5001)..(5858)
<223> OTHER INFORMATION: AP(R) marker
<220> FEATURE:
<221> NAME/KEY: rep_origin
<222> LOCATION: (6032)..(6620)
<223> OTHER INFORMATION: origin of replication

<400> SEQUENCE: 14
ctgcgcgctc gctcgctcac tgaggccgcc cgggcaaagc ccgggcgtcg ggcgaccttt    60
ggtcgcccgg cctcagtgag cgagcgagcg cgcagagagg gagtggccaa ctccatcact   120
aggggttcct tgtagttaat gattaacccg ccatgctact tatctaccag ggtaatgggg   180
atcctctaga actatagcta gaattcgccc ttaagctagc aggttaattt ttaaaaagca   240
gtcaaaagtc caagtggccc ttggcagcat ttactctctc tgtttgctct ggttaataat   300
ctcaggagca caacattcc agatccaggt taattttaa aaagcagtca aaagtccaag   360
tggcccttgg cagcatttac tctctctgtt tgctctggtt aataatctca ggagcacaaa   420
cattccagat ccggcgcgcc agggctggaa gctacctttg acatcatttc ctctgcgaat   480
gcatgtataa tttctacaga acctattaga aaggatcacc cagcctctgc ttttgtacaa   540
ctttccctta aaaaactgcc aattccactg ctgtttggcc caatagtgag aacttttcc   600 tgctgcctct tggtgctttt gcctatggcc cctattctgc ctgctgaaga cactcttgcc   660
agcatggact taaacccctc cagctctgac aatcctcttt ctcttttgtt ttacatgaag   720
ggtctggcag ccaaagcaat cactcaaagt tcaaaccta tcattttttg ctttgttcct   780
cttggccttg gttttgtaca tcagctttga aaataccatc ccagggttaa tgctggggtt   840
aatttataac taagagtgct ctagttttgc aatacaggac atgctataaa aatggaaaga   900
```

```
tgttgctttc tgagagacag ctttattgcg gtagtttatc acagttaaat tgctaacgca      960
gtcagtgctt ctgacacaac agtctcgaac ttaagctgca gaagttggtc gtgaggcact     1020
gggcaggtaa gtatcaaggt tacaagacag gtttaaggag accaatagaa actgggcttg     1080
tcgagacaga gaagactctt gcgtttctga taggcaccta ttggtcttac tgacatccac     1140
tttgcctttc tctccacagg tgtccactcc cagttcaatt acagctctta aggctagagt     1200
acttaatacg actcactata ggctagcctc gagaattcac gcgt atg ggg ccc tgg     1256
                                                 Met Gly Pro Trp
                                                  1 ggc tgg aaa ttg cgc tgg acc gtc gcc ttg ctc ctc gcc gcg gcg ggg      1304
Gly Trp Lys Leu Arg Trp Thr Val Ala Leu Leu Leu Ala Ala Ala Gly
 5              10                  15                  20 act gca gtg ggc gac aga tgt gaa aga aac gag ttc cag tgc caa gac      1352
Thr Ala Val Gly Asp Arg Cys Glu Arg Asn Glu Phe Gln Cys Gln Asp
                25                  30                  35 ggg aaa tgc atc tcc tac aag tgg gtc tgc gat ggc agc gct gag tgc      1400
Gly Lys Cys Ile Ser Tyr Lys Trp Val Cys Asp Gly Ser Ala Glu Cys
            40                  45                  50 cag gat ggc tct gat gag tcc cag gag acg tgc ttg tct gtc acc tgc      1448
Gln Asp Gly Ser Asp Glu Ser Gln Glu Thr Cys Leu Ser Val Thr Cys
        55                  60                  65 aaa tcc ggg gac ttc agc tgt ggg ggc cgt gtc aac cgc tgc att cct      1496
Lys Ser Gly Asp Phe Ser Cys Gly Gly Arg Val Asn Arg Cys Ile Pro
    70                  75                  80 cag ttc tgg agg tgc gat ggc caa gtg gac tgc gac aac ggc tca gac      1544
Gln Phe Trp Arg Cys Asp Gly Gln Val Asp Cys Asp Asn Gly Ser Asp
85                  90                  95                 100 gag caa ggc tgt ccc ccc aag acg tgc tcc cag gac gag ttt cgc tgc      1592
Glu Gln Gly Cys Pro Pro Lys Thr Cys Ser Gln Asp Glu Phe Arg Cys
                105                 110                 115 cac gat ggg aag tgc atc tct cgg cag ttc gtc tgt gac tca gac cgg      1640
His Asp Gly Lys Cys Ile Ser Arg Gln Phe Val Cys Asp Ser Asp Arg
            120                 125                 130 gac tgc ttg gac ggc tca gac gag gcc tcc tgc ccg gtg ctc acc tgt      1688
Asp Cys Leu Asp Gly Ser Asp Glu Ala Ser Cys Pro Val Leu Thr Cys
        135                 140                 145 ggt ccc gcc agc ttc cag tgc aac agc tcc acc tgc atc ccc cag ctg      1736
Gly Pro Ala Ser Phe Gln Cys Asn Ser Ser Thr Cys Ile Pro Gln Leu
    150                 155                 160 tgg gcc tgc gac aac gac ccc gac tgc gaa gat ggc tcg gat gag tgg      1784
Trp Ala Cys Asp Asn Asp Pro Asp Cys Glu Asp Gly Ser Asp Glu Trp
165                 170                 175                 180 ccg cag cgc tgt agg ggt ctt tac gtg ttc caa ggg gac agt agc ccc      1832
Pro Gln Arg Cys Arg Gly Leu Tyr Val Phe Gln Gly Asp Ser Ser Pro
                185                 190                 195 tgc tcg gcc ttc gag ttc cac tgc cta agt ggc gag tgc atc cac tcc      1880
Cys Ser Ala Phe Glu Phe His Cys Leu Ser Gly Glu Cys Ile His Ser
            200                 205                 210 agc tgg cgc tgt gat ggt ggc ccc gac tgc aag gac aaa tct gac gag      1928
Ser Trp Arg Cys Asp Gly Gly Pro Asp Cys Lys Asp Lys Ser Asp Glu
        215                 220                 225 gaa aac tgc gct gtg gcc acc tgt cgc cct gac gaa ttc cag tgc tct      1976
Glu Asn Cys Ala Val Ala Thr Cys Arg Pro Asp Glu Phe Gln Cys Ser
    230                 235                 240 gat gga aac tgc atc cat ggc agc cgg cag tgt gac cgg gaa tat gac      2024
Asp Gly Asn Cys Ile His Gly Ser Arg Gln Cys Asp Arg Glu Tyr Asp
245                 250                 255                 260
```

-continued

| | |
|---|---|
| tgc aag gac atg agc gat gaa gtt ggc tgc gtt aat gtg aca ctc tgc<br>Cys Lys Asp Met Ser Asp Glu Val Gly Cys Val Asn Val Thr Leu Cys<br>265 270 275 | 2072 |
| gag gga ccc aac aag ttc aag tgt cac agc ggc gaa tgc atc acc ctg<br>Glu Gly Pro Asn Lys Phe Lys Cys His Ser Gly Glu Cys Ile Thr Leu<br>280 285 290 | 2120 |
| gac aaa gtc tgc aac atg gct aga gac tgc cgg gac tgg tca gat gaa<br>Asp Lys Val Cys Asn Met Ala Arg Asp Cys Arg Asp Trp Ser Asp Glu<br>295 300 305 | 2168 |
| ccc atc aaa gag tgc ggg acc aac gaa tgc ttg gac aac aac ggc ggc<br>Pro Ile Lys Glu Cys Gly Thr Asn Glu Cys Leu Asp Asn Asn Gly Gly<br>310 315 320 | 2216 |
| tgt tcc cac gtc tgc aat gac ctt aag atc ggc tac gag tgc ctg tgc<br>Cys Ser His Val Cys Asn Asp Leu Lys Ile Gly Tyr Glu Cys Leu Cys<br>325 330 335 340 | 2264 |
| ccc gac ggc ttc cag ctg gtg gcc cag cga aga tgc gaa gat atc gat<br>Pro Asp Gly Phe Gln Leu Val Ala Gln Arg Arg Cys Glu Asp Ile Asp<br>345 350 355 | 2312 |
| gag tgt cag gat ccc gac acc tgc agc cag ctc tgc gtg aac ctg gag<br>Glu Cys Gln Asp Pro Asp Thr Cys Ser Gln Leu Cys Val Asn Leu Glu<br>360 365 370 | 2360 |
| ggt ggc tac aag tgc cag tgt gag gaa ggc ttc cag ctg gac ccc cac<br>Gly Gly Tyr Lys Cys Gln Cys Glu Glu Gly Phe Gln Leu Asp Pro His<br>375 380 385 | 2408 |
| acg aag gcc tgc aag gct gtg ggc tcc atc gcc tac ctc ttc ttc acc<br>Thr Lys Ala Cys Lys Ala Val Gly Ser Ile Ala Tyr Leu Phe Phe Thr<br>390 395 400 | 2456 |
| aac cgg cac gag gtc agg aag atg acg ctg gac cgg agc gag tac acc<br>Asn Arg His Glu Val Arg Lys Met Thr Leu Asp Arg Ser Glu Tyr Thr<br>405 410 415 420 | 2504 |
| agc ctc atc ccc aac ctg agg aac gtg gtc gct ctg gac acg gag gtg<br>Ser Leu Ile Pro Asn Leu Arg Asn Val Val Ala Leu Asp Thr Glu Val<br>425 430 435 | 2552 |
| gcc agc aat aga atc tac tgg tct gac ctg tcc cag aga atg atc tgc<br>Ala Ser Asn Arg Ile Tyr Trp Ser Asp Leu Ser Gln Arg Met Ile Cys<br>440 445 450 | 2600 |
| agc acc cag ctt gac aga gcc cac ggc gtc tct tcc tat gac acc gtc<br>Ser Thr Gln Leu Asp Arg Ala His Gly Val Ser Ser Tyr Asp Thr Val<br>455 460 465 | 2648 |
| atc agc agg gac atc cag gcc ccc gac ggg ctg gct gtg gac tgg atc<br>Ile Ser Arg Asp Ile Gln Ala Pro Asp Gly Leu Ala Val Asp Trp Ile<br>470 475 480 | 2696 |
| cac agc aac atc tac tgg acc gac tct gtc ctg ggc act gtc tct gtt<br>His Ser Asn Ile Tyr Trp Thr Asp Ser Val Leu Gly Thr Val Ser Val<br>485 490 495 500 | 2744 |
| gcg gat acc aag ggc gtg aag agg aaa acg tta ttc agg gag aac ggc<br>Ala Asp Thr Lys Gly Val Lys Arg Lys Thr Leu Phe Arg Glu Asn Gly<br>505 510 515 | 2792 |
| tcc aag cca agg gcc atc gtg gtg gat cct gtt cat ggc ttc atg tac<br>Ser Lys Pro Arg Ala Ile Val Val Asp Pro Val His Gly Phe Met Tyr<br>520 525 530 | 2840 |
| tgg act gac tgg gga act ccc gcc aag atc aag aaa ggg ggc ctg aat<br>Trp Thr Asp Trp Gly Thr Pro Ala Lys Ile Lys Lys Gly Gly Leu Asn<br>535 540 545 | 2888 |
| ggt gtg gac atc tac tcg ctg gtg act gaa aac att cag tgg ccc aat<br>Gly Val Asp Ile Tyr Ser Leu Val Thr Glu Asn Ile Gln Trp Pro Asn<br>550 555 560 | 2936 |
| ggc atc acc cta gat ctc ctc agt ggc cgc ctc tac tgg gtt gac tcc<br>Gly Ile Thr Leu Asp Leu Leu Ser Gly Arg Leu Tyr Trp Val Asp Ser<br>565 570 575 580 | 2984 |

|   |   |   |   |   |   |   |   |   |   |   |   |   |   |   |   |      |
|---|---|---|---|---|---|---|---|---|---|---|---|---|---|---|---|------|
| aaa | ctt | cac | tcc | atc | tca | agc | atc | gat | gtc | aat | ggg | ggc | aac | cgg | aag | 3032 |
| Lys | Leu | His | Ser | Ile | Ser | Ser | Ile | Asp | Val | Asn | Gly | Gly | Asn | Arg | Lys |      |
|     |     |     | 585 |     |     |     |     | 590 |     |     |     |     | 595 |     |     |      |

| acc | atc | ttg | gag | gat | gaa | aag | agg | ctg | gcc | cac | ccc | ttc | tcc | ttg | gcc | 3080 |
|-----|-----|-----|-----|-----|-----|-----|-----|-----|-----|-----|-----|-----|-----|-----|-----|------|
| Thr | Ile | Leu | Glu | Asp | Glu | Lys | Arg | Leu | Ala | His | Pro | Phe | Ser | Leu | Ala |      |
|     |     |     | 600 |     |     |     |     | 605 |     |     |     |     | 610 |     |     |      |

| gtc | ttt | gag | gac | aaa | gta | ttt | tgg | aca | gat | atc | atc | aac | gaa | gcc | att | 3128 |
|-----|-----|-----|-----|-----|-----|-----|-----|-----|-----|-----|-----|-----|-----|-----|-----|------|
| Val | Phe | Glu | Asp | Lys | Val | Phe | Trp | Thr | Asp | Ile | Ile | Asn | Glu | Ala | Ile |      |
|     |     |     | 615 |     |     |     |     | 620 |     |     |     |     | 625 |     |     |      |

| ttc | agt | gcc | aac | cgc | ctc | aca | ggt | tcc | gat | gtc | aac | ttg | ttg | gct | gaa | 3176 |
|-----|-----|-----|-----|-----|-----|-----|-----|-----|-----|-----|-----|-----|-----|-----|-----|------|
| Phe | Ser | Ala | Asn | Arg | Leu | Thr | Gly | Ser | Asp | Val | Asn | Leu | Leu | Ala | Glu |      |
|     |     | 630 |     |     |     |     | 635 |     |     |     |     | 640 |     |     |     |      |

| aac | cta | ctg | tcc | cca | gag | gat | atg | gtc | ctc | ttc | cac | aac | ctc | acc | cag | 3224 |
|-----|-----|-----|-----|-----|-----|-----|-----|-----|-----|-----|-----|-----|-----|-----|-----|------|
| Asn | Leu | Leu | Ser | Pro | Glu | Asp | Met | Val | Leu | Phe | His | Asn | Leu | Thr | Gln |      |
| 645 |     |     |     |     | 650 |     |     |     |     | 655 |     |     |     |     | 660 |      |

| cca | aga | gga | gtg | aac | tgg | tgt | gag | agg | acc | acc | ctg | agc | aat | ggc | ggc | 3272 |
|-----|-----|-----|-----|-----|-----|-----|-----|-----|-----|-----|-----|-----|-----|-----|-----|------|
| Pro | Arg | Gly | Val | Asn | Trp | Cys | Glu | Arg | Thr | Thr | Leu | Ser | Asn | Gly | Gly |      |
|     |     |     |     | 665 |     |     |     |     | 670 |     |     |     |     | 675 |     |      |

| tgc | cag | tat | ctg | tgc | ctc | cct | gcc | ccg | cag | atc | aac | ccc | cac | tcg | ccc | 3320 |
|-----|-----|-----|-----|-----|-----|-----|-----|-----|-----|-----|-----|-----|-----|-----|-----|------|
| Cys | Gln | Tyr | Leu | Cys | Leu | Pro | Ala | Pro | Gln | Ile | Asn | Pro | His | Ser | Pro |      |
|     |     |     | 680 |     |     |     |     | 685 |     |     |     |     | 690 |     |     |      |

| aag | ttt | acc | tgc | gcc | tgc | ccg | gac | ggc | atg | ctg | ctg | gcc | agg | gac | atg | 3368 |
|-----|-----|-----|-----|-----|-----|-----|-----|-----|-----|-----|-----|-----|-----|-----|-----|------|
| Lys | Phe | Thr | Cys | Ala | Cys | Pro | Asp | Gly | Met | Leu | Leu | Ala | Arg | Asp | Met |      |
|     |     | 695 |     |     |     |     | 700 |     |     |     |     | 705 |     |     |     |      |

| agg | agc | tgc | ctc | aca | gag | gct | gag | gct | gca | gtg | gcc | acc | cag | gag | aca | 3416 |
|-----|-----|-----|-----|-----|-----|-----|-----|-----|-----|-----|-----|-----|-----|-----|-----|------|
| Arg | Ser | Cys | Leu | Thr | Glu | Ala | Glu | Ala | Ala | Val | Ala | Thr | Gln | Glu | Thr |      |
|     | 710 |     |     |     |     | 715 |     |     |     |     | 720 |     |     |     |     |      |

| tcc | acc | gtc | agg | cta | aag | gtc | agc | tcc | aca | gcc | gta | agg | aca | cag | cac | 3464 |
|-----|-----|-----|-----|-----|-----|-----|-----|-----|-----|-----|-----|-----|-----|-----|-----|------|
| Ser | Thr | Val | Arg | Leu | Lys | Val | Ser | Ser | Thr | Ala | Val | Arg | Thr | Gln | His |      |
| 725 |     |     |     |     | 730 |     |     |     |     | 735 |     |     |     |     | 740 |      |

| aca | acc | acc | cgg | cct | gtt | ccc | gac | acc | tcc | cgg | ctg | cct | ggg | gcc | acc | 3512 |
|-----|-----|-----|-----|-----|-----|-----|-----|-----|-----|-----|-----|-----|-----|-----|-----|------|
| Thr | Thr | Thr | Arg | Pro | Val | Pro | Asp | Thr | Ser | Arg | Leu | Pro | Gly | Ala | Thr |      |
|     |     |     | 745 |     |     |     |     | 750 |     |     |     |     | 755 |     |     |      |

| cct | ggg | ctc | acc | acg | gtg | gag | ata | gtg | aca | atg | tct | cac | caa | gct | ctg | 3560 |
|-----|-----|-----|-----|-----|-----|-----|-----|-----|-----|-----|-----|-----|-----|-----|-----|------|
| Pro | Gly | Leu | Thr | Thr | Val | Glu | Ile | Val | Thr | Met | Ser | His | Gln | Ala | Leu |      |
|     |     |     | 760 |     |     |     |     | 765 |     |     |     |     | 770 |     |     |      |

| ggc | gac | gtt | gct | ggc | aga | gga | aat | gag | aag | aag | ccc | agt | agc | gtg | agg | 3608 |
|-----|-----|-----|-----|-----|-----|-----|-----|-----|-----|-----|-----|-----|-----|-----|-----|------|
| Gly | Asp | Val | Ala | Gly | Arg | Gly | Asn | Glu | Lys | Lys | Pro | Ser | Ser | Val | Arg |      |
|     |     |     | 775 |     |     |     |     | 780 |     |     |     |     | 785 |     |     |      |

| gct | ctg | tcc | att | gtc | ctc | ccc | atc | gtg | ctc | ctc | gtc | ttc | ctt | tgc | ctg | 3656 |
|-----|-----|-----|-----|-----|-----|-----|-----|-----|-----|-----|-----|-----|-----|-----|-----|------|
| Ala | Leu | Ser | Ile | Val | Leu | Pro | Ile | Val | Leu | Leu | Val | Phe | Leu | Cys | Leu |      |
|     |     | 790 |     |     |     |     | 795 |     |     |     |     | 800 |     |     |     |      |

| ggg | gtc | ttc | ctt | cta | tgg | aag | aac | tgg | cgg | ctt | aag | aac | atc | aac | agc | 3704 |
|-----|-----|-----|-----|-----|-----|-----|-----|-----|-----|-----|-----|-----|-----|-----|-----|------|
| Gly | Val | Phe | Leu | Leu | Trp | Lys | Asn | Trp | Arg | Leu | Lys | Asn | Ile | Asn | Ser |      |
| 805 |     |     |     |     | 810 |     |     |     |     | 815 |     |     |     |     | 820 |      |

| atc | aac | ttt | gac | aac | ccc | gtc | tat | cag | agg | acc | aca | gag | gat | gag | gtc | 3752 |
|-----|-----|-----|-----|-----|-----|-----|-----|-----|-----|-----|-----|-----|-----|-----|-----|------|
| Ile | Asn | Phe | Asp | Asn | Pro | Val | Tyr | Gln | Arg | Thr | Thr | Glu | Asp | Glu | Val |      |
|     |     |     |     | 825 |     |     |     |     | 830 |     |     |     |     | 835 |     |      |

| cac | att | gcc | cac | aac | cag | gac | ggc | tac | agc | tac | ccc | tcg | aga | cag | atg | 3800 |
|-----|-----|-----|-----|-----|-----|-----|-----|-----|-----|-----|-----|-----|-----|-----|-----|------|
| His | Ile | Ala | His | Asn | Gln | Asp | Gly | Tyr | Ser | Tyr | Pro | Ser | Arg | Gln | Met |      |
|     |     |     | 840 |     |     |     |     | 845 |     |     |     |     | 850 |     |     |      |

| gtc | agt | ctg | gag | gat | gac | gtg | gcg | tga | acgcgtggta | cctctagagt |   |   |   |   |   | 3847 |
|-----|-----|-----|-----|-----|-----|-----|-----|-----|------------|------------|---|---|---|---|---|------|
| Val | Ser | Leu | Glu | Asp | Asp | Val | Ala |     |            |            |   |   |   |   |   |      |
|     |     | 855 |     |     |     |     | 860 |     |            |            |   |   |   |   |   |      |

| cgaccccgggc ggcctcgagg acggggtgaa ctacgcctga ggatccgatc tttttccctc | 3907 |
|---|---|
| tgccaaaaat tatggggaca tcatgaagcc ccttgagcat ctgacttctg gctaataaag | 3967 |
| gaaatttatt ttcattgcaa tagtgtgttg gaatttttg tgtctctcac tcggaagcaa | 4027 |

```
ttcgttgatc tgaatttcga ccacccataa tacccattac cctggtagat aagtagcatg   4087
gcgggttaat cattaactac aaggaacccc tagtgatgga gttggccact ccctctctgc   4147
gcgctcgctc gctcactgag gccgggcgac caaaggtcgc ccgacgcccg ggctttgccc   4207
gggcggcctc agtgagcgag cgagcgcgca gccttaatta acctaattca ctggccgtcg   4267
ttttacaacg tcgtgactgg gaaaaccctg gcgttaccca acttaatcgc cttgcagcac   4327
atcccccttt cgccagctgg cgtaatagcg aagaggcccg caccgatcgc ccttcccaac   4387
agttgcgcag cctgaatggc gaatgggacg cgccctgtag cggcgcatta agcgcggcgg   4447
gtgtggtggt tacgcgcagc gtgaccgcta cacttgccag cgccctagcg cccgctcctt   4507
tcgctttctt cccttccttt ctcgccacgt tcgccggctt tccccgtcaa gctctaaatc   4567
gggggctccc tttagggttc cgatttagtg ctttacggca cctcgacccc aaaaaacttg   4627
attagggtga tggttcacgt agtgggccat cgccctgata cacggttttt cgccctttga   4687
cgttggagtc cacgttcttt aatagtggac tcttgttcca aactggaaca cactcaacc   4747 ctatctcggt ctattctttt gatttataag ggattttgcc gatttcggcc tattggttaa   4807
aaaatgagct gatttaacaa aaatttaacg cgaattttaa caaaatatta acgcttacaa   4867
tttaggtggc acttttcggg gaaatgtgcg cggaacccct atttgtttat ttttctaaat   4927
acattcaaat atgtatccgc tcatgagaca ataaccctga taaatgcttc aataatattg   4987
aaaaaggaag agtatgagta ttcaacattt ccgtgtcgcc cttattccct ttttgcggc   5047 attttgcctt cctgtttttg ctcacccaga aacgctggtg aaagtaaaag atgctgaaga   5107
tcagttgggt gcacgagtgg gttacatcga actggatctc aacagcggta agatccttga   5167
gagttttcgc cccgaagaac gttttccaat gatgagcact tttaaagttc tgctatgtgg   5227
cgcggtatta tcccgtattg acgccgggca agagcaactc ggtcgccgca tacactattc   5287
tcagaatgac ttggttgagt actcaccagt cacagaaaag catcttacgg atggcatgac   5347
agtaagagaa ttatgcagtg ctgccataac catgagtgat aacactgcgg ccaacttact   5407
tctgacaacg atcggaggac cgaaggagct aaccgctttt ttgcacaaca tgggggatca   5467
tgtaactcgc cttgatcgtt gggaaccgga gctgaatgaa gccataccaa acgacgagcg   5527
tgacaccacg atgcctgtag caatggcaac aacgttgcgc aaactattaa ctggcgaact   5587
acttactcta gcttcccggc aacaattaat agactggatg gaggcggata agttgcagg   5647 accacttctg cgctcggccc ttccggctgg ctggtttatt gctgataaat ctggagccgg   5707
tgagcgtggg tctcgcggta tcattgcagc actggggcca gatggtaagc cctcccgtat   5767
cgtagttatc tacacgacgg ggagtcaggc aactatggat gaacgaaata cacagatcgc   5827
tgagataggt gcctcactga ttaagcattg gtaactgtca gaccaagttt actcatatat   5887
actttagatt gatttaaaac ttcatttta atttaaaagg atctaggtga agatccttt   5947 tgataatctc atgaccaaaa tcccttaacg tgagttttcg ttccactgag cgtcagaccc   6007
cgtagaaaag atcaaaggat cttcttgaga tcctttttt ctgcgcgtaa tctgctgctt   6067
gcaaacaaaa aaaccaccgc taccagcggt ggtttgtttg ccggatcaag agctaccaac   6127 tcttttccg aaggtaactg gcttcagcag agcgcagata ccaaatactg ttcttctagt   6187
gtagccgtag ttaggccacc acttcaagaa ctctgtagca ccgcctacat acctcgctct   6247
gctaatcctg ttaccagtgg ctgctgccag tggcgataag tcgtgtctta ccgggttgga   6307
ctcaagacga tagttaccgg ataaggcgca gcggtcgggc tgaacggggg gttcgtgcac   6367
acagcccagc ttggagcgaa cgacctacac cgaactgaga tacctacagc gtgagctatg   6427
```

```
agaaagcgcc acgcttcccg aagggagaaa ggcggacagg tatccggtaa gcggcagggt    6487
cggaacagga gagcgcacga gggagcttcc agggggaaac gcctggtatc tttatagtcc    6547
tgtcgggttt cgccacctct gacttgagcg tcgattttg tgatgctcgt caggggggcg     6607
gagcctatgg aaaaacgcca gcaacgcggc cttttttacgg ttcctggcct tttgctggcc   6667
ttttgctcac atgttctttc ctgcgttatc ccctgattct gtggataacc gtattaccgc    6727
ctttgagtga gctgataccg ctcgccgcag ccgaacgacc gagcgcagcg agtcagtgag    6787
cgaggaagcg gaagagcgcc caatacgcaa accgcctctc cccgcgcgtt ggccgattca    6847
ttaatgcagc tggcacgaca ggtttcccga ctggaaagcg ggcagtgagc gcaacgcaat    6907
taatgtgagt tagctcactc attaggcacc ccaggcttta cactttatgc ttccggctcg    6967
tatgttgtgt ggaattgtga gcggataaca atttcacaca ggaaacagct atgaccatga    7027
ttacgccaga tttaattaag gccttaatta gg                                   7059
```

<210> SEQ ID NO 15
<211> LENGTH: 860
<212> TYPE: PRT
<213> ORGANISM: Artificial Sequence
<220> FEATURE:
<223> OTHER INFORMATION: Synthetic Construct

<400> SEQUENCE: 15

```
Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
```

-continued

```
                245                 250                 255
Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670
```

```
Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
        690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
                740                 745                 750

Pro Gly Ala Thr Pro Gly Leu Thr Thr Val Glu Ile Val Thr Met Ser
            755                 760                 765

His Gln Ala Leu Gly Asp Val Ala Gly Arg Gly Asn Glu Lys Lys Pro
        770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Arg Thr Thr
                820                 825                 830

Glu Asp Glu Val His Ile Ala His Asn Gln Asp Gly Tyr Ser Tyr Pro
                835                 840                 845

Ser Arg Gln Met Val Ser Leu Glu Asp Asp Val Ala
        850                 855                 860

<210> SEQ ID NO 16
<211> LENGTH: 2583
<212> TYPE: DNA
<213> ORGANISM: Artificial Sequence
<220> FEATURE:
<223> OTHER INFORMATION: hLDLR varient D299N with leader
<220> FEATURE:
<221> NAME/KEY: CDS
<222> LOCATION: (1)..(2583)

<400> SEQUENCE: 16 atg ggg ccc tgg ggc tgg aaa ttg cgc tgg acc gtc gcc ttg ctc ctc      48
Met Gly Pro Trp Gly Trp Lys Leu Arg Trp Thr Val Ala Leu Leu Leu
1               5                   10                  15 gcc gcg gcg ggg act gca gtg ggc gac aga tgt gaa aga aac gag ttc      96
Ala Ala Ala Gly Thr Ala Val Gly Asp Arg Cys Glu Arg Asn Glu Phe
            20                  25                  30 cag tgc caa gac ggg aaa tgc atc tcc tac aag tgg gtc tgc gat ggc     144
Gln Cys Gln Asp Gly Lys Cys Ile Ser Tyr Lys Trp Val Cys Asp Gly
        35                  40                  45 agc gct gag tgc cag gat ggc tct gat gag tcc cag gag acg tgc ttg     192
Ser Ala Glu Cys Gln Asp Gly Ser Asp Glu Ser Gln Glu Thr Cys Leu
    50                  55                  60 tct gtc acc tgc aaa tcc ggg gac ttc agc tgt ggg ggc cgt gtc aac     240
Ser Val Thr Cys Lys Ser Gly Asp Phe Ser Cys Gly Gly Arg Val Asn
65                  70                  75                  80 cgc tgc att cct cag ttc tgg agg tgc gat ggc caa gtg gac tgc gac     288
Arg Cys Ile Pro Gln Phe Trp Arg Cys Asp Gly Gln Val Asp Cys Asp
                85                  90                  95 aac ggc tca gac gag caa ggc tgt ccc ccc aag acg tgc tcc cag gac     336
Asn Gly Ser Asp Glu Gln Gly Cys Pro Pro Lys Thr Cys Ser Gln Asp
            100                 105                 110 gag ttt cgc tgc cac gat ggg aag tgc atc tct cgg cag ttc gtc tgt     384
```

-continued

|  |  |
|---|---|
| Glu Phe Arg Cys His Asp Gly Lys Cys Ile Ser Arg Gln Phe Val Cys<br>                115                 120                 125 |  |
| gac tca gac cgg gac tgc ttg gac ggc tca gac gag gcc tcc tgc ccg<br>Asp Ser Asp Arg Asp Cys Leu Asp Gly Ser Asp Glu Ala Ser Cys Pro<br>130                 135                 140 | 432 |
| gtg ctc acc tgt ggt ccc gcc agc ttc cag tgc aac agc tcc acc tgc<br>Val Leu Thr Cys Gly Pro Ala Ser Phe Gln Cys Asn Ser Ser Thr Cys<br>145                 150                 155                 160 | 480 |
| atc ccc cag ctg tgg gcc tgc gac aac gac ccc gac tgc gaa gat ggc<br>Ile Pro Gln Leu Trp Ala Cys Asp Asn Asp Pro Asp Cys Glu Asp Gly<br>                165                 170                 175 | 528 |
| tcg gat gag tgg ccg cag cgc tgt agg ggt ctt tac gtg ttc caa ggg<br>Ser Asp Glu Trp Pro Gln Arg Cys Arg Gly Leu Tyr Val Phe Gln Gly<br>                180                 185                 190 | 576 |
| gac agt agc ccc tgc tcg gcc ttc gag ttc cac tgc cta agt ggc gag<br>Asp Ser Ser Pro Cys Ser Ala Phe Glu Phe His Cys Leu Ser Gly Glu<br>                195                 200                 205 | 624 |
| tgc atc cac tcc agc tgg cgc tgt gat ggt ggc ccc gac tgc aag gac<br>Cys Ile His Ser Ser Trp Arg Cys Asp Gly Gly Pro Asp Cys Lys Asp<br>210                 215                 220 | 672 |
| aaa tct gac gag gaa aac tgc gct gtg gcc acc tgt cgc cct gac gaa<br>Lys Ser Asp Glu Glu Asn Cys Ala Val Ala Thr Cys Arg Pro Asp Glu<br>225                 230                 235                 240 | 720 |
| ttc cag tgc tct gat gga aac tgc atc cat ggc agc cgg cag tgt gac<br>Phe Gln Cys Ser Asp Gly Asn Cys Ile His Gly Ser Arg Gln Cys Asp<br>                245                 250                 255 | 768 |
| cgg gaa tat gac tgc aag gac atg agc gat gaa gtt ggc tgc gtt aat<br>Arg Glu Tyr Asp Cys Lys Asp Met Ser Asp Glu Val Gly Cys Val Asn<br>                260                 265                 270 | 816 |
| gtg aca ctc tgc gag gga ccc aac aag ttc aag tgt cac agc ggc gaa<br>Val Thr Leu Cys Glu Gly Pro Asn Lys Phe Lys Cys His Ser Gly Glu<br>                275                 280                 285 | 864 |
| tgc atc acc ctg gac aaa gtc tgc aac atg gct aga gac tgc cgg gac<br>Cys Ile Thr Leu Asp Lys Val Cys Asn Met Ala Arg Asp Cys Arg Asp<br>290                 295                 300 | 912 |
| tgg tca gat gaa ccc atc aaa gag tgc ggg acc aac gaa tgc ttg aac<br>Trp Ser Asp Glu Pro Ile Lys Glu Cys Gly Thr Asn Glu Cys Leu Asn<br>305                 310                 315                 320 | 960 |
| aac aac ggc ggc tgt tcc cac gtc tgc aat gac ctt aag atc ggc tac<br>Asn Asn Gly Gly Cys Ser His Val Cys Asn Asp Leu Lys Ile Gly Tyr<br>                325                 330                 335 | 1008 |
| gag tgc ctg tgc ccc gac ggc ttc cag ctg gtg gcc cag cga aga tgc<br>Glu Cys Leu Cys Pro Asp Gly Phe Gln Leu Val Ala Gln Arg Arg Cys<br>                340                 345                 350 | 1056 |
| gaa gat atc gat gag tgt cag gat ccc gac acc tgc agc cag ctc tgc<br>Glu Asp Ile Asp Glu Cys Gln Asp Pro Asp Thr Cys Ser Gln Leu Cys<br>                355                 360                 365 | 1104 |
| gtg aac ctg gag ggt ggc tac aag tgc cag tgt gag gaa ggc ttc cag<br>Val Asn Leu Glu Gly Gly Tyr Lys Cys Gln Cys Glu Glu Gly Phe Gln<br>370                 375                 380 | 1152 |
| ctg gac ccc cac acg aag gcc tgc aag gct gtg ggc tcc atc gcc tac<br>Leu Asp Pro His Thr Lys Ala Cys Lys Ala Val Gly Ser Ile Ala Tyr<br>385                 390                 395                 400 | 1200 |
| ctc ttc ttc acc aac cgg cac gag gtc agg aag atg acg ctg gac cgg<br>Leu Phe Phe Thr Asn Arg His Glu Val Arg Lys Met Thr Leu Asp Arg<br>                405                 410                 415 | 1248 |
| agc gag tac acc agc ctc atc ccc aac ctg agg aac gtg gtc gct ctg<br>Ser Glu Tyr Thr Ser Leu Ile Pro Asn Leu Arg Asn Val Val Ala Leu<br>                420                 425                 430 | 1296 |

```
gac acg gag gtg gcc agc aat aga atc tac tgg tct gac ctg tcc cag    1344
Asp Thr Glu Val Ala Ser Asn Arg Ile Tyr Trp Ser Asp Leu Ser Gln
            435                 440                 445 aga atg atc tgc agc acc cag ctt gac aga gcc cac ggc gtc tct tcc    1392
Arg Met Ile Cys Ser Thr Gln Leu Asp Arg Ala His Gly Val Ser Ser
450                 455                 460 tat gac acc gtc atc agc agg gac atc cag gcc ccc gac ggg ctg gct    1440
Tyr Asp Thr Val Ile Ser Arg Asp Ile Gln Ala Pro Asp Gly Leu Ala
465                 470                 475                 480 gtg gac tgg atc cac agc aac atc tac tgg acc gac tct gtc ctg ggc    1488
Val Asp Trp Ile His Ser Asn Ile Tyr Trp Thr Asp Ser Val Leu Gly
                485                 490                 495 act gtc tct gtt gcg gat acc aag ggc gtg aag agg aaa acg tta ttc    1536
Thr Val Ser Val Ala Asp Thr Lys Gly Val Lys Arg Lys Thr Leu Phe
            500                 505                 510 agg gag aac ggc tcc aag cca agg gcc atc gtg gtg gat cct gtt cat    1584
Arg Glu Asn Gly Ser Lys Pro Arg Ala Ile Val Val Asp Pro Val His
        515                 520                 525 ggc ttc atg tac tgg act gac tgg gga act ccc gcc aag atc aag aaa    1632
Gly Phe Met Tyr Trp Thr Asp Trp Gly Thr Pro Ala Lys Ile Lys Lys
    530                 535                 540 ggg ggc ctg aat ggt gtg gac atc tac tcg ctg gtg act gaa aac att    1680
Gly Gly Leu Asn Gly Val Asp Ile Tyr Ser Leu Val Thr Glu Asn Ile
545                 550                 555                 560 cag tgg ccc aat ggc atc acc cta gat ctc ctc agt ggc cgc ctc tac    1728
Gln Trp Pro Asn Gly Ile Thr Leu Asp Leu Leu Ser Gly Arg Leu Tyr
                565                 570                 575 tgg gtt gac tcc aaa ctt cac tcc atc tca agc atc gat gtc aat ggg    1776
Trp Val Asp Ser Lys Leu His Ser Ile Ser Ser Ile Asp Val Asn Gly
            580                 585                 590 ggc aac cgg aag acc atc ttg gag gat gaa aag agg ctg gcc cac ccc    1824
Gly Asn Arg Lys Thr Ile Leu Glu Asp Glu Lys Arg Leu Ala His Pro
        595                 600                 605 ttc tcc ttg gcc gtc ttt gag gac aaa gta ttt tgg aca gat atc atc    1872
Phe Ser Leu Ala Val Phe Glu Asp Lys Val Phe Trp Thr Asp Ile Ile
    610                 615                 620 aac gaa gcc att ttc agt gcc aac cgc ctc aca ggt tcc gat gtc aac    1920
Asn Glu Ala Ile Phe Ser Ala Asn Arg Leu Thr Gly Ser Asp Val Asn
625                 630                 635                 640 ttg ttg gct gaa aac cta ctg tcc cca gag gat atg gtc ctc ttc cac    1968
Leu Leu Ala Glu Asn Leu Leu Ser Pro Glu Asp Met Val Leu Phe His
                645                 650                 655 aac ctc acc cag cca aga gga gtg aac tgg tgt gag agg acc acc ctg    2016
Asn Leu Thr Gln Pro Arg Gly Val Asn Trp Cys Glu Arg Thr Thr Leu
            660                 665                 670 agc aat ggc ggc tgc cag tat ctg tgc ctc cct gcc ccg cag atc aac    2064
Ser Asn Gly Gly Cys Gln Tyr Leu Cys Leu Pro Ala Pro Gln Ile Asn
        675                 680                 685 ccc cac tcg ccc aag ttt acc tgc gcc tgc ccg gac ggc atg ctg ctg    2112
Pro His Ser Pro Lys Phe Thr Cys Ala Cys Pro Asp Gly Met Leu Leu
    690                 695                 700 gcc agg gac atg agg agc tgc ctc aca gag gct gag gct gca gtg gcc    2160
Ala Arg Asp Met Arg Ser Cys Leu Thr Glu Ala Glu Ala Ala Val Ala
705                 710                 715                 720 acc cag gag aca tcc acc gtc agg cta aag gtc agc tcc aca gcc gta    2208
Thr Gln Glu Thr Ser Thr Val Arg Leu Lys Val Ser Ser Thr Ala Val
                725                 730                 735 agg aca cag cac aca acc acc cgg cct gtt ccc gac acc tcc cgg ctg    2256
Arg Thr Gln His Thr Thr Thr Arg Pro Val Pro Asp Thr Ser Arg Leu
            740                 745                 750
```

```
cct ggg gcc acc cct ggg ctc acc acg gtg gag ata gtg aca atg tct    2304
Pro Gly Ala Thr Pro Gly Leu Thr Thr Val Glu Ile Val Thr Met Ser
            755                 760                 765 cac caa gct ctg ggc gac gtt gct ggc aga gga aat gag aag aag ccc    2352
His Gln Ala Leu Gly Asp Val Ala Gly Arg Gly Asn Glu Lys Lys Pro
    770                 775                 780 agt agc gtg agg gct ctg tcc att gtc ctc ccc atc gtg ctc ctc gtc    2400
Ser Ser Val Arg Ala Leu Ser Ile Val Leu Pro Ile Val Leu Leu Val
785                 790                 795                 800 ttc ctt tgc ctg ggg gtc ttc ctt cta tgg aag aac tgg cgg ctt aag    2448
Phe Leu Cys Leu Gly Val Phe Leu Leu Trp Lys Asn Trp Arg Leu Lys
                805                 810                 815 aac atc aac agc atc aac ttt gac aac ccc gtc tat cag aag acc aca    2496
Asn Ile Asn Ser Ile Asn Phe Asp Asn Pro Val Tyr Gln Lys Thr Thr
            820                 825                 830 gag gat gag gtc cac att tgc cac aac cag gac ggc tac agc tac ccc    2544
Glu Asp Glu Val His Ile Cys His Asn Gln Asp Gly Tyr Ser Tyr Pro
835                 840                 845 tcg aga cag atg gtc agt ctg gag gat gac gtg gcg tga                2583
Ser Arg Gln Met Val Ser Leu Glu Asp Asp Val Ala
    850                 855                 860

<210> SEQ ID NO 17
<211> LENGTH: 860
<212> TYPE: PRT
<213> ORGANISM: Artificial Sequence
<220> FEATURE:
<223> OTHER INFORMATION: Synthetic Construct

<400> SEQUENCE: 17

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
```

-continued

```
            210                 215                 220
Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                    245                 250                 255

Arg Glu Tyr Asp Cys Lys Asp Met Ser Asp Glu Val Gly Cys Val Asn
                260                 265                 270

Val Thr Leu Cys Glu Gly Pro Asn Lys Phe Lys Cys His Ser Gly Glu
            275                 280                 285

Cys Ile Thr Leu Asp Lys Val Cys Asn Met Ala Arg Asp Cys Arg Asp
        290                 295                 300

Trp Ser Asp Glu Pro Ile Lys Glu Cys Gly Thr Asn Glu Cys Leu Asn
305                 310                 315                 320

Asn Asn Gly Gly Cys Ser His Val Cys Asn Asp Leu Lys Ile Gly Tyr
                    325                 330                 335

Glu Cys Leu Cys Pro Asp Gly Phe Gln Leu Val Ala Gln Arg Arg Cys
                340                 345                 350

Glu Asp Ile Asp Glu Cys Gln Asp Pro Asp Thr Cys Ser Gln Leu Cys
            355                 360                 365

Val Asn Leu Glu Gly Gly Tyr Lys Cys Gln Cys Glu Glu Gly Phe Gln
        370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
                420                 425                 430

Asp Thr Glu Val Ala Ser Asn Arg Ile Tyr Trp Ser Asp Leu Ser Gln
            435                 440                 445

Arg Met Ile Cys Ser Thr Gln Leu Asp Arg Ala His Gly Val Ser Ser
        450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
        530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
        610                 615                 620

Asn Glu Ala Ile Phe Ser Ala Asn Arg Leu Thr Gly Ser Asp Val Asn
625                 630                 635                 640
```

```
Leu Leu Ala Glu Asn Leu Leu Ser Pro Glu Asp Met Val Leu Phe His
            645                 650                 655

Asn Leu Thr Gln Pro Arg Gly Val Asn Trp Cys Glu Arg Thr Thr Leu
        660                 665                 670

Ser Asn Gly Gly Cys Gln Tyr Leu Cys Leu Pro Ala Pro Gln Ile Asn
    675                 680                 685

Pro His Ser Pro Lys Phe Thr Cys Ala Cys Pro Asp Gly Met Leu Leu
690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860

<210> SEQ ID NO 18
<211> LENGTH: 2583
<212> TYPE: DNA
<213> ORGANISM: Artificial Sequence
<220> FEATURE:
<223> OTHER INFORMATION: hLDLR variant D310N with leader
<220> FEATURE:
<221> NAME/KEY: CDS
<222> LOCATION: (1)..(2583)

<400> SEQUENCE: 18 atg ggg ccc tgg ggc tgg aaa ttg cgc tgg acc gtc gcc ttg ctc ctc    48
Met Gly Pro Trp Gly Trp Lys Leu Arg Trp Thr Val Ala Leu Leu Leu
1               5                   10                  15 gcc gcg gcg ggg act gca gtg ggc gac aga tgt gaa aga aac gag ttc    96
Ala Ala Ala Gly Thr Ala Val Gly Asp Arg Cys Glu Arg Asn Glu Phe
            20                  25                  30 cag tgc caa gac ggg aaa tgc atc tcc tac aag tgg gtc tgc gat ggc   144
Gln Cys Gln Asp Gly Lys Cys Ile Ser Tyr Lys Trp Val Cys Asp Gly
        35                  40                  45 agc gct gag tgc cag gat ggc tct gat gag tcc cag gag acg tgc ttg   192
Ser Ala Glu Cys Gln Asp Gly Ser Asp Glu Ser Gln Glu Thr Cys Leu
    50                  55                  60 tct gtc acc tgc aaa tcc ggg gac ttc agc tgt ggg ggc cgt gtc aac   240
Ser Val Thr Cys Lys Ser Gly Asp Phe Ser Cys Gly Gly Arg Val Asn
65                  70                  75                  80 cgc tgc att cct cag ttc tgg agg tgc gat ggc caa gtg gac tgc gac   288
Arg Cys Ile Pro Gln Phe Trp Arg Cys Asp Gly Gln Val Asp Cys Asp
                85                  90                  95
```

```
aac ggc tca gac gag caa ggc tgt ccc ccc aag acg tgc tcc cag gac      336
Asn Gly Ser Asp Glu Gln Gly Cys Pro Pro Lys Thr Cys Ser Gln Asp
            100                 105                 110 gag ttt cgc tgc cac gat ggg aag tgc atc tct cgg cag ttc gtc tgt      384
Glu Phe Arg Cys His Asp Gly Lys Cys Ile Ser Arg Gln Phe Val Cys
        115                 120                 125 gac tca gac cgg gac tgc ttg gac ggc tca gac gag gcc tcc tgc ccg      432
Asp Ser Asp Arg Asp Cys Leu Asp Gly Ser Asp Glu Ala Ser Cys Pro
130                 135                 140 gtg ctc acc tgt ggt ccc gcc agc ttc cag tgc aac agc tcc acc tgc      480
Val Leu Thr Cys Gly Pro Ala Ser Phe Gln Cys Asn Ser Ser Thr Cys
145                 150                 155                 160 atc ccc cag ctg tgg gcc tgc gac aac gac ccc gac tgc gaa gat ggc      528
Ile Pro Gln Leu Trp Ala Cys Asp Asn Asp Pro Asp Cys Glu Asp Gly
                165                 170                 175 tcg gat gag tgg ccg cag cgc tgt agg ggt ctt tac gtg ttc caa ggg      576
Ser Asp Glu Trp Pro Gln Arg Cys Arg Gly Leu Tyr Val Phe Gln Gly
            180                 185                 190 gac agt agc ccc tgc tcg gcc ttc gag ttc cac tgc cta agt ggc gag      624
Asp Ser Ser Pro Cys Ser Ala Phe Glu Phe His Cys Leu Ser Gly Glu
        195                 200                 205 tgc atc cac tcc agc tgg cgc tgt gat ggt ggc ccc gac tgc aag gac      672
Cys Ile His Ser Ser Trp Arg Cys Asp Gly Gly Pro Asp Cys Lys Asp
210                 215                 220 aaa tct gac gag gaa aac tgc gct gtg gcc acc tgt cgc cct gac gaa      720
Lys Ser Asp Glu Glu Asn Cys Ala Val Ala Thr Cys Arg Pro Asp Glu
225                 230                 235                 240 ttc cag tgc tct gat gga aac tgc atc cat ggc agc cgg cag tgt gac      768
Phe Gln Cys Ser Asp Gly Asn Cys Ile His Gly Ser Arg Gln Cys Asp
                245                 250                 255 cgg gaa tat gac tgc aag gac atg agc gat gaa gtt ggc tgc gtt aat      816
Arg Glu Tyr Asp Cys Lys Asp Met Ser Asp Glu Val Gly Cys Val Asn
            260                 265                 270 gtg aca ctc tgc gag gga ccc aac aag ttc aag tgt cac agc ggc gaa      864
Val Thr Leu Cys Glu Gly Pro Asn Lys Phe Lys Cys His Ser Gly Glu
        275                 280                 285 tgc atc acc ctg gac aaa gtc tgc aac atg gct aga gac tgc cgg gac      912
Cys Ile Thr Leu Asp Lys Val Cys Asn Met Ala Arg Asp Cys Arg Asp
290                 295                 300 tgg tca gat gaa ccc atc aaa gag tgc ggg acc aac gaa tgc ttg gac      960
Trp Ser Asp Glu Pro Ile Lys Glu Cys Gly Thr Asn Glu Cys Leu Asp
305                 310                 315                 320 aac aac ggc ggt tgt tcc cac gtc tgc aat aac ctt aag atc ggc tac     1008
Asn Asn Gly Gly Cys Ser His Val Cys Asn Asn Leu Lys Ile Gly Tyr
                325                 330                 335 gag tgc ctg tgc ccc gac ggc ttc cag ctg gtg gcc cag cga aga tgc     1056
Glu Cys Leu Cys Pro Asp Gly Phe Gln Leu Val Ala Gln Arg Arg Cys
            340                 345                 350 gaa gat atc gat gag tgt cag gat ccc gac acc tgc agc cag ctc tgc     1104
Glu Asp Ile Asp Glu Cys Gln Asp Pro Asp Thr Cys Ser Gln Leu Cys
        355                 360                 365 gtg aac ctg gag ggt ggc tac aag tgc cag tgt gag gaa ggc ttc cag     1152
Val Asn Leu Glu Gly Gly Tyr Lys Cys Gln Cys Glu Glu Gly Phe Gln
370                 375                 380 ctg gac ccc cac acg aag gcc tgc aag gct gtg ggc tcc atc gcc tac     1200
Leu Asp Pro His Thr Lys Ala Cys Lys Ala Val Gly Ser Ile Ala Tyr
385                 390                 395                 400 ctc ttc ttc acc aac cgg cac gag gtc agg aag atg acg ctg gac cgg     1248
Leu Phe Phe Thr Asn Arg His Glu Val Arg Lys Met Thr Leu Asp Arg
```

|  |  |  |  |  |  |  |  |  |  |  |  |  |  |  |  |
|---|---|---|---|---|---|---|---|---|---|---|---|---|---|---|---|
| | | | 405 | | | | 410 | | | | 415 | | | | |

```
agc gag tac acc agc ctc atc ccc aac ctg agg aac gtg gtc gct ctg      1296
Ser Glu Tyr Thr Ser Leu Ile Pro Asn Leu Arg Asn Val Val Ala Leu
                420                 425                 430 gac acg gag gtg gcc agc aat aga atc tac tgg tct gac ctg tcc cag      1344
Asp Thr Glu Val Ala Ser Asn Arg Ile Tyr Trp Ser Asp Leu Ser Gln
            435                 440                 445 aga atg atc tgc agc acc cag ctt gac aga gcc cac ggc gtc tct tcc      1392
Arg Met Ile Cys Ser Thr Gln Leu Asp Arg Ala His Gly Val Ser Ser
        450                 455                 460 tat gac acc gtc atc agc agg gac atc cag gcc ccc gac ggg ctg gct      1440
Tyr Asp Thr Val Ile Ser Arg Asp Ile Gln Ala Pro Asp Gly Leu Ala
465                 470                 475                 480 gtg gac tgg atc cac agc aac atc tac tgg acc gac tct gtc ctg ggc      1488
Val Asp Trp Ile His Ser Asn Ile Tyr Trp Thr Asp Ser Val Leu Gly
                485                 490                 495 act gtc tct gtt gcg gat acc aag ggc gtg aag agg aaa acg tta ttc      1536
Thr Val Ser Val Ala Asp Thr Lys Gly Val Lys Arg Lys Thr Leu Phe
            500                 505                 510 agg gag aac ggc tcc aag cca agg gcc atc gtg gtg gat cct gtt cat      1584
Arg Glu Asn Gly Ser Lys Pro Arg Ala Ile Val Val Asp Pro Val His
        515                 520                 525 ggc ttc atg tac tgg act gac tgg gga act ccc gcc aag atc aag aaa      1632
Gly Phe Met Tyr Trp Thr Asp Trp Gly Thr Pro Ala Lys Ile Lys Lys
    530                 535                 540 ggg ggc ctg aat ggt gtg gac atc tac tcg ctg gtg act gaa aac att      1680
Gly Gly Leu Asn Gly Val Asp Ile Tyr Ser Leu Val Thr Glu Asn Ile
545                 550                 555                 560 cag tgg ccc aat ggc atc acc cta gat ctc ctc agt ggc cgc ctc tac      1728
Gln Trp Pro Asn Gly Ile Thr Leu Asp Leu Leu Ser Gly Arg Leu Tyr
                565                 570                 575 tgg gtt gac tcc aaa ctt cac tcc atc tca agc atc gat gtc aat ggg      1776
Trp Val Asp Ser Lys Leu His Ser Ile Ser Ser Ile Asp Val Asn Gly
            580                 585                 590 ggc aac cgg aag acc atc ttg gag gat gaa aag agg ctg gcc cac ccc      1824
Gly Asn Arg Lys Thr Ile Leu Glu Asp Glu Lys Arg Leu Ala His Pro
        595                 600                 605 ttc tcc ttg gcc gtc ttt gag gac aaa gta ttt tgg aca gat atc atc      1872
Phe Ser Leu Ala Val Phe Glu Asp Lys Val Phe Trp Thr Asp Ile Ile
    610                 615                 620 aac gaa gcc att ttc agt gcc aac cgc ctc aca ggt tcc gat gtc aac      1920
Asn Glu Ala Ile Phe Ser Ala Asn Arg Leu Thr Gly Ser Asp Val Asn
625                 630                 635                 640 ttg ttg gct gaa aac cta ctg tcc cca gag gat atg gtc ctc ttc cac      1968
Leu Leu Ala Glu Asn Leu Leu Ser Pro Glu Asp Met Val Leu Phe His
                645                 650                 655 aac ctc acc cag cca aga gga gtg aac tgg tgt gag agg acc acc ctg      2016
Asn Leu Thr Gln Pro Arg Gly Val Asn Trp Cys Glu Arg Thr Thr Leu
            660                 665                 670 agc aat ggc ggc tgc cag tat ctg tgc ctc cct gcc ccg cag atc aac      2064
Ser Asn Gly Gly Cys Gln Tyr Leu Cys Leu Pro Ala Pro Gln Ile Asn
        675                 680                 685 ccc cac tcg ccc aag ttt acc tgc gcc tgc ccg gac ggc atg ctg ctg      2112
Pro His Ser Pro Lys Phe Thr Cys Ala Cys Pro Asp Gly Met Leu Leu
    690                 695                 700 gcc agg gac atg agg agc tgc ctc aca gag gct gag gct gca gtg gcc      2160
Ala Arg Asp Met Arg Ser Cys Leu Thr Glu Ala Glu Ala Ala Val Ala
705                 710                 715                 720 acc cag gag aca tcc acc gtc agg cta aag gtc agc tcc aca gcc gta      2208
```

```
Thr Gln Glu Thr Ser Thr Val Arg Leu Lys Val Ser Ser Thr Ala Val
                725                 730                 735 agg aca cag cac aca acc acc cgg cct gtt ccc gac acc tcc cgg ctg      2256
Arg Thr Gln His Thr Thr Thr Arg Pro Val Pro Asp Thr Ser Arg Leu
            740                 745                 750 cct ggg gcc acc cct ggg ctc acc acg gtg gag ata gtg aca atg tct      2304
Pro Gly Ala Thr Pro Gly Leu Thr Thr Val Glu Ile Val Thr Met Ser
        755                 760                 765 cac caa gct ctg ggc gac gtt gct ggc aga gga aat gag aag aag ccc      2352
His Gln Ala Leu Gly Asp Val Ala Gly Arg Gly Asn Glu Lys Lys Pro
    770                 775                 780 agt agc gtg agg gct ctg tcc att gtc ctc ccc atc gtg ctc ctc gtc      2400
Ser Ser Val Arg Ala Leu Ser Ile Val Leu Pro Ile Val Leu Leu Val
785                 790                 795                 800 ttc ctt tgc ctg ggg gtc ttc ctt cta tgg aag aac tgg cgg ctt aag      2448
Phe Leu Cys Leu Gly Val Phe Leu Leu Trp Lys Asn Trp Arg Leu Lys
                805                 810                 815 aac atc aac agc atc aac ttt gac aac ccc gtc tat cag aag acc aca      2496
Asn Ile Asn Ser Ile Asn Phe Asp Asn Pro Val Tyr Gln Lys Thr Thr
            820                 825                 830 gag gat gag gtc cac att tgc cac aac cag gac ggc tac agc tac ccc      2544
Glu Asp Glu Val His Ile Cys His Asn Gln Asp Gly Tyr Ser Tyr Pro
        835                 840                 845 tcg aga cag atg gtc agt ctg gag gat gac gtg gcg tga                  2583
Ser Arg Gln Met Val Ser Leu Glu Asp Asp Val Ala
    850                 855                 860

<210> SEQ ID NO 19
<211> LENGTH: 860
<212> TYPE: PRT
<213> ORGANISM: Artificial Sequence
<220> FEATURE:
<223> OTHER INFORMATION: Synthetic Construct

<400> SEQUENCE: 19

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
```

```
            180                 185                 190
Asp Ser Ser Pro Cys Ser Ala Phe Glu Phe His Cys Leu Ser Gly Glu
        195                 200                 205
Cys Ile His Ser Ser Trp Arg Cys Asp Gly Pro Asp Cys Lys Asp
    210                 215                 220
Lys Ser Asp Glu Glu Asn Cys Ala Val Ala Thr Cys Arg Pro Asp Glu
225                 230                 235                 240
Phe Gln Cys Ser Asp Gly Asn Cys Ile His Gly Ser Arg Gln Cys Asp
            245                 250                 255
Arg Glu Tyr Asp Cys Lys Asp Met Ser Asp Glu Val Gly Cys Val Asn
                260                 265                 270
Val Thr Leu Cys Glu Gly Pro Asn Lys Phe Lys Cys His Ser Gly Glu
            275                 280                 285
Cys Ile Thr Leu Asp Lys Val Cys Asn Met Ala Arg Asp Cys Arg Asp
        290                 295                 300
Trp Ser Asp Glu Pro Ile Lys Glu Cys Gly Thr Asn Glu Cys Leu Asp
305                 310                 315                 320
Asn Asn Gly Gly Cys Ser His Val Cys Asn Asn Leu Lys Ile Gly Tyr
                325                 330                 335
Glu Cys Leu Cys Pro Asp Gly Phe Gln Leu Val Ala Gln Arg Arg Cys
            340                 345                 350
Glu Asp Ile Asp Glu Cys Gln Asp Pro Asp Thr Cys Ser Gln Leu Cys
        355                 360                 365
Val Asn Leu Glu Gly Gly Tyr Lys Cys Gln Cys Glu Glu Gly Phe Gln
    370                 375                 380
Leu Asp Pro His Thr Lys Ala Cys Lys Ala Val Gly Ser Ile Ala Tyr
385                 390                 395                 400
Leu Phe Phe Thr Asn Arg His Glu Val Arg Lys Met Thr Leu Asp Arg
                405                 410                 415
Ser Glu Tyr Thr Ser Leu Ile Pro Asn Leu Arg Asn Val Val Ala Leu
            420                 425                 430
Asp Thr Glu Val Ala Ser Asn Arg Ile Tyr Trp Ser Asp Leu Ser Gln
        435                 440                 445
Arg Met Ile Cys Ser Thr Gln Leu Asp Arg Ala His Gly Val Ser Ser
    450                 455                 460
Tyr Asp Thr Val Ile Ser Arg Asp Ile Gln Ala Pro Asp Gly Leu Ala
465                 470                 475                 480
Val Asp Trp Ile His Ser Asn Ile Tyr Trp Thr Asp Ser Val Leu Gly
                485                 490                 495
Thr Val Ser Val Ala Asp Thr Lys Gly Val Lys Arg Lys Thr Leu Phe
            500                 505                 510
Arg Glu Asn Gly Ser Lys Pro Arg Ala Ile Val Val Asp Pro Val His
        515                 520                 525
Gly Phe Met Tyr Trp Thr Asp Trp Gly Thr Pro Ala Lys Ile Lys Lys
    530                 535                 540
Gly Gly Leu Asn Gly Val Asp Ile Tyr Ser Leu Val Thr Glu Asn Ile
545                 550                 555                 560
Gln Trp Pro Asn Gly Ile Thr Leu Asp Leu Leu Ser Gly Arg Leu Tyr
                565                 570                 575
Trp Val Asp Ser Lys Leu His Ser Ile Ser Ser Ile Asp Val Asn Gly
            580                 585                 590
Gly Asn Arg Lys Thr Ile Leu Glu Asp Glu Lys Arg Leu Ala His Pro
        595                 600                 605
```

-continued

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860

<210> SEQ ID NO 20
<211> LENGTH: 2583
<212> TYPE: DNA
<213> ORGANISM: Artificial Sequence
<220> FEATURE:
<223> OTHER INFORMATION: hLDLR variant H306G with leader
<220> FEATURE:
<221> NAME/KEY: CDS
<222> LOCATION: (1)..(2583)

<400> SEQUENCE: 20 atg ggg ccc tgg ggc tgg aaa ttg cgc tgg acc gtc gcc ttg ctc ctc        48
Met Gly Pro Trp Gly Trp Lys Leu Arg Trp Thr Val Ala Leu Leu Leu
1               5                   10                  15 gcc gcg gcg ggg act gca gtg ggc gac aga tgt gaa aga aac gag ttc        96
Ala Ala Ala Gly Thr Ala Val Gly Asp Arg Cys Glu Arg Asn Glu Phe
            20                  25                  30 cag tgc caa gac ggg aaa tgc atc tcc tac aag tgg gtc tgc gat ggc       144
Gln Cys Gln Asp Gly Lys Cys Ile Ser Tyr Lys Trp Val Cys Asp Gly
        35                  40                  45 agc gct gag tgc cag gat ggc tct gat gag tcc cag gag acg tgc ttg       192
Ser Ala Glu Cys Gln Asp Gly Ser Asp Glu Ser Gln Glu Thr Cys Leu
    50                  55                  60 tct gtc acc tgc aaa tcc ggg gac ttc agc tgt ggg ggc cgt gtc aac       240

```
Ser Val Thr Cys Lys Ser Gly Asp Phe Ser Cys Gly Gly Arg Val Asn
 65                  70                  75                  80 cgc tgc att cct cag ttc tgg agg tgc gat ggc caa gtg gac tgc gac        288
Arg Cys Ile Pro Gln Phe Trp Arg Cys Asp Gly Gln Val Asp Cys Asp
                 85                  90                  95 aac ggc tca gac gag caa ggc tgt ccc ccc aag acg tgc tcc cag gac        336
Asn Gly Ser Asp Glu Gln Gly Cys Pro Pro Lys Thr Cys Ser Gln Asp
            100                 105                 110 gag ttt cgc tgc cac gat ggg aag tgc atc tct cgg cag ttc gtc tgt        384
Glu Phe Arg Cys His Asp Gly Lys Cys Ile Ser Arg Gln Phe Val Cys
            115                 120                 125 gac tca gac cgg gac tgc ttg gac ggc tca gac gag gcc tcc tgc ccg        432
Asp Ser Asp Arg Asp Cys Leu Asp Gly Ser Asp Glu Ala Ser Cys Pro
130                 135                 140 gtg ctc acc tgt ggt ccc gcc agc ttc cag tgc aac agc tcc acc tgc        480
Val Leu Thr Cys Gly Pro Ala Ser Phe Gln Cys Asn Ser Ser Thr Cys
145                 150                 155                 160 atc ccc cag ctg tgg gcc tgt gac aac gac ccc gac tgc gaa gat ggc        528
Ile Pro Gln Leu Trp Ala Cys Asp Asn Asp Pro Asp Cys Glu Asp Gly
                165                 170                 175 tcg gat gag tgg ccg cag cgc tgt agg ggt ctt tac gtg ttc caa ggg        576
Ser Asp Glu Trp Pro Gln Arg Cys Arg Gly Leu Tyr Val Phe Gln Gly
            180                 185                 190 gac agt agc ccc tgc tcg gcc ttc gag ttc cac tgc cta agt ggc gag        624
Asp Ser Ser Pro Cys Ser Ala Phe Glu Phe His Cys Leu Ser Gly Glu
            195                 200                 205 tgc atc cac tcc agc tgg cgc tgt gat ggt ggc ccc gac tgc aag gac        672
Cys Ile His Ser Ser Trp Arg Cys Asp Gly Gly Pro Asp Cys Lys Asp
            210                 215                 220 aaa tct gac gag gaa aac tgc gct gtg gcc acc tgt cgc cct gac gaa        720
Lys Ser Asp Glu Glu Asn Cys Ala Val Ala Thr Cys Arg Pro Asp Glu
225                 230                 235                 240 ttc cag tgc tct gat gga aac tgc atc cat ggc agc cgg cag tgt gac        768
Phe Gln Cys Ser Asp Gly Asn Cys Ile His Gly Ser Arg Gln Cys Asp
                245                 250                 255 cgg gaa tat gac tgc aag gac atg agc gat gaa gtt ggc tgc gtt aat        816
Arg Glu Tyr Asp Cys Lys Asp Met Ser Asp Glu Val Gly Cys Val Asn
            260                 265                 270 gtg aca ctc tgc gag gga ccc aac aag ttc aag tgt cac agc ggc gaa        864
Val Thr Leu Cys Glu Gly Pro Asn Lys Phe Lys Cys His Ser Gly Glu
            275                 280                 285 tgc atc acc ctg gac aaa gtc tgc aac atg gct aga gac tgc cgg gac        912
Cys Ile Thr Leu Asp Lys Val Cys Asn Met Ala Arg Asp Cys Arg Asp
            290                 295                 300 tgg tca gat gaa ccc atc aaa gag tgc ggg acc aac gaa tgc ttg gac        960
Trp Ser Asp Glu Pro Ile Lys Glu Cys Gly Thr Asn Glu Cys Leu Asp
305                 310                 315                 320 aac aac ggc ggc tgt tcc ggc gtc tgc aat gac ctt aag atc ggc tac       1008
Asn Asn Gly Gly Cys Ser Gly Val Cys Asn Asp Leu Lys Ile Gly Tyr
                325                 330                 335 gag tgc ctg tgc ccc gac ggc ttc cag ctg gtg gcc cag cga aga tgc       1056
Glu Cys Leu Cys Pro Asp Gly Phe Gln Leu Val Ala Gln Arg Arg Cys
            340                 345                 350 gaa gat atc gat gag tgt cag gat ccc gac acc tgc agc cag ctc tgc       1104
Glu Asp Ile Asp Glu Cys Gln Asp Pro Asp Thr Cys Ser Gln Leu Cys
            355                 360                 365 gtg aac ctg gag ggt ggc tac aag tgc cag tgt gag gaa ggc ttc cag       1152
Val Asn Leu Glu Gly Gly Tyr Lys Cys Gln Cys Glu Glu Gly Phe Gln
            370                 375                 380
```

-continued

| | | |
|---|---|---|
| ctg gac ccc cac acg aag gcc tgc aag gct gtg ggc tcc atc gcc tac<br>Leu Asp Pro His Thr Lys Ala Cys Lys Ala Val Gly Ser Ile Ala Tyr<br>385                           390                       395                 400 | 1200 | ctc ttc ttc acc aac cgg cac gag gtc agg aag atg acg ctg gac cgg     1248
Leu Phe Phe Thr Asn Arg His Glu Val Arg Lys Met Thr Leu Asp Arg
                        405                 410                 415 agc gag tac acc agc ctc atc ccc aac ctg agg aac gtg gtc gct ctg     1296
Ser Glu Tyr Thr Ser Leu Ile Pro Asn Leu Arg Asn Val Val Ala Leu
                420                 425                 430 gac acg gag gtg gcc agc aat aga atc tac tgg tct gac ctg tcc cag     1344
Asp Thr Glu Val Ala Ser Asn Arg Ile Tyr Trp Ser Asp Leu Ser Gln
            435                 440                 445 aga atg atc tgc agc acc cag ctt gac aga gcc cac ggc gtc tct tcc     1392
Arg Met Ile Cys Ser Thr Gln Leu Asp Arg Ala His Gly Val Ser Ser
        450                 455                 460 tat gac acc gtc atc agc agg gac atc cag gcc ccc gac ggg ctg gct     1440
Tyr Asp Thr Val Ile Ser Arg Asp Ile Gln Ala Pro Asp Gly Leu Ala
465                 470                 475                 480 gtg gac tgg atc cac agc aac atc tac tgg acc gac tct gtc ctg ggc     1488
Val Asp Trp Ile His Ser Asn Ile Tyr Trp Thr Asp Ser Val Leu Gly
                        485                 490                 495 act gtc tct gtt gcg gat acc aag ggc gtg aag agg aaa acg tta ttc     1536
Thr Val Ser Val Ala Asp Thr Lys Gly Val Lys Arg Lys Thr Leu Phe
                500                 505                 510 agg gag aac ggc tcc aag cca agg gcc atc gtg gtg gat cct gtt cat     1584
Arg Glu Asn Gly Ser Lys Pro Arg Ala Ile Val Val Asp Pro Val His
            515                 520                 525 ggc ttc atg tac tgg act gac tgg gga act ccc gcc aag atc aag aaa     1632
Gly Phe Met Tyr Trp Thr Asp Trp Gly Thr Pro Ala Lys Ile Lys Lys
        530                 535                 540 ggg ggc ctg aat ggt gtg gac atc tac tcg ctg gtg act gaa aac att     1680
Gly Gly Leu Asn Gly Val Asp Ile Tyr Ser Leu Val Thr Glu Asn Ile
545                 550                 555                 560 cag tgg ccc aat ggc atc acc cta gat ctc ctc agt ggc cgc ctc tac     1728
Gln Trp Pro Asn Gly Ile Thr Leu Asp Leu Leu Ser Gly Arg Leu Tyr
                        565                 570                 575 tgg gtt gac tcc aaa ctt cac tcc atc tca agc atc gat gtc aat ggg     1776
Trp Val Asp Ser Lys Leu His Ser Ile Ser Ser Ile Asp Val Asn Gly
                580                 585                 590 ggc aac cgg aag acc atc ttg gag gat gaa aag agg ctg gcc cac ccc     1824
Gly Asn Arg Lys Thr Ile Leu Glu Asp Glu Lys Arg Leu Ala His Pro
            595                 600                 605 ttc tcc ttg gcc gtc ttt gag gac aaa gta ttt tgg aca gat atc atc     1872
Phe Ser Leu Ala Val Phe Glu Asp Lys Val Phe Trp Thr Asp Ile Ile
        610                 615                 620 aac gaa gcc att ttc agt gcc aac cgc ctc aca ggt tcc gat gtc aac     1920
Asn Glu Ala Ile Phe Ser Ala Asn Arg Leu Thr Gly Ser Asp Val Asn
625                 630                 635                 640 ttg ttg gct gaa aac cta ctg tcc cca gag gat atg gtc ctc ttc cac     1968
Leu Leu Ala Glu Asn Leu Leu Ser Pro Glu Asp Met Val Leu Phe His
                        645                 650                 655 aac ctc acc cag cca aga gga gtg aac tgg tgt gag agg acc acc ctg     2016
Asn Leu Thr Gln Pro Arg Gly Val Asn Trp Cys Glu Arg Thr Thr Leu
                660                 665                 670 agc aat ggc ggc tgc cag tat ctg tgc ctc cct gcc ccg cag atc aac     2064
Ser Asn Gly Gly Cys Gln Tyr Leu Cys Leu Pro Ala Pro Gln Ile Asn
            675                 680                 685 ccc cac tcg ccc aag ttt acc tgc gcc tgc ccg gac ggc atg ctg ctg     2112
Pro His Ser Pro Lys Phe Thr Cys Ala Cys Pro Asp Gly Met Leu Leu
        690                 695                 700

-continued

```
gcc agg gac atg agg agc tgc ctc aca gag gct gag gct gca gtg gcc      2160
Ala Arg Asp Met Arg Ser Cys Leu Thr Glu Ala Glu Ala Ala Val Ala
705                 710                 715                 720 acc cag gag aca tcc acc gtc agg cta aag gtc agc tcc aca gcc gta      2208
Thr Gln Glu Thr Ser Thr Val Arg Leu Lys Val Ser Ser Thr Ala Val
                725                 730                 735 agg aca cag cac aca acc acc cgg cct gtt ccc gac acc tcc cgg ctg      2256
Arg Thr Gln His Thr Thr Thr Arg Pro Val Pro Asp Thr Ser Arg Leu
            740                 745                 750 cct ggg gcc acc cct ggg ctc acc acg gtg gag ata gtg aca atg tct      2304
Pro Gly Ala Thr Pro Gly Leu Thr Thr Val Glu Ile Val Thr Met Ser
        755                 760                 765 cac caa gct ctg ggc gac gtt gct ggc aga gga aat gag aag aag ccc      2352
His Gln Ala Leu Gly Asp Val Ala Gly Arg Gly Asn Glu Lys Lys Pro
    770                 775                 780 agt agc gtg agg gct ctg tcc att gtc ctc ccc atc gtg ctc ctc gtc      2400
Ser Ser Val Arg Ala Leu Ser Ile Val Leu Pro Ile Val Leu Leu Val
785                 790                 795                 800 ttc ctt tgc ctg ggg gtc ttc ctt cta tgg aag aac tgg cgg ctt aag      2448
Phe Leu Cys Leu Gly Val Phe Leu Leu Trp Lys Asn Trp Arg Leu Lys
                805                 810                 815 aac atc aac agc atc aac ttt gac aac ccc gtc tat cag aag acc aca      2496
Asn Ile Asn Ser Ile Asn Phe Asp Asn Pro Val Tyr Gln Lys Thr Thr
            820                 825                 830 gag gat gag gtc cac att tgc cac aac cag gac ggc tac agc tac ccc      2544
Glu Asp Glu Val His Ile Cys His Asn Gln Asp Gly Tyr Ser Tyr Pro
        835                 840                 845 tcg aga cag atg gtc agt ctg gag gat gac gtg gcg tga                  2583
Ser Arg Gln Met Val Ser Leu Glu Asp Asp Val Ala
    850                 855                 860

<210> SEQ ID NO 21
<211> LENGTH: 860
<212> TYPE: PRT
<213> ORGANISM: Artificial Sequence
<220> FEATURE:
<223> OTHER INFORMATION: Synthetic Construct

<400> SEQUENCE: 21

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
                20                  25                  30

Gln Cys Gln Asp Gly Lys Cys Ile Ser Tyr Lys Trp Val Cys Asp Gly
            35                  40                  45

Ser Ala Glu Cys Gln Asp Gly Ser Asp Glu Ser Gln Glu Thr Cys Leu
        50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
```

```
            145                 150                 155                 160
        Ile Pro Gln Leu Trp Ala Cys Asp Asn Asp Pro Asp Cys Glu Asp Gly
                        165                 170                 175

Ser Asp Glu Trp Pro Gln Arg Cys Arg Gly Leu Tyr Val Phe Gln Gly
                        180                 185                 190

Asp Ser Ser Pro Cys Ser Ala Phe Glu Phe His Cys Leu Ser Gly Glu
                        195                 200                 205

Cys Ile His Ser Ser Trp Arg Cys Asp Gly Pro Asp Cys Lys Asp
            210                 215                 220

Lys Ser Asp Glu Glu Asn Cys Ala Val Ala Thr Cys Arg Pro Asp Glu
        225                 230                 235                 240

Phe Gln Cys Ser Asp Gly Asn Cys Ile His Gly Ser Arg Gln Cys Asp
                        245                 250                 255

Arg Glu Tyr Asp Cys Lys Asp Met Ser Asp Glu Val Gly Cys Val Asn
                        260                 265                 270

Val Thr Leu Cys Glu Gly Pro Asn Lys Phe Lys Cys His Ser Gly Glu
                        275                 280                 285

Cys Ile Thr Leu Asp Lys Val Cys Asn Met Ala Arg Asp Cys Arg Asp
                        290                 295                 300

Trp Ser Asp Glu Pro Ile Lys Glu Cys Gly Thr Asn Glu Cys Leu Asp
        305                 310                 315                 320

Asn Asn Gly Gly Cys Ser Gly Val Cys Asn Asp Leu Lys Ile Gly Tyr
                        325                 330                 335

Glu Cys Leu Cys Pro Asp Gly Phe Gln Leu Val Ala Gln Arg Arg Cys
                        340                 345                 350

Glu Asp Ile Asp Glu Cys Gln Asp Pro Asp Thr Cys Ser Gln Leu Cys
                        355                 360                 365

Val Asn Leu Glu Gly Gly Tyr Lys Cys Gln Cys Glu Glu Gly Phe Gln
                        370                 375                 380

Leu Asp Pro His Thr Lys Ala Cys Lys Ala Val Gly Ser Ile Ala Tyr
        385                 390                 395                 400

Leu Phe Phe Thr Asn Arg His Glu Val Arg Lys Met Thr Leu Asp Arg
                        405                 410                 415

Ser Glu Tyr Thr Ser Leu Ile Pro Asn Leu Arg Asn Val Val Ala Leu
                        420                 425                 430

Asp Thr Glu Val Ala Ser Asn Arg Ile Tyr Trp Ser Asp Leu Ser Gln
                        435                 440                 445

Arg Met Ile Cys Ser Thr Gln Leu Asp Arg Ala His Gly Val Ser Ser
        450                 455                 460

Tyr Asp Thr Val Ile Ser Arg Asp Ile Gln Ala Pro Asp Gly Leu Ala
        465                 470                 475                 480

Val Asp Trp Ile His Ser Asn Ile Tyr Trp Thr Asp Ser Val Leu Gly
                        485                 490                 495

Thr Val Ser Val Ala Asp Thr Lys Gly Val Lys Arg Lys Thr Leu Phe
                        500                 505                 510

Arg Glu Asn Gly Ser Lys Pro Arg Ala Ile Val Val Asp Pro Val His
                        515                 520                 525

Gly Phe Met Tyr Trp Thr Asp Trp Gly Thr Pro Ala Lys Ile Lys Lys
                        530                 535                 540

Gly Gly Leu Asn Gly Val Asp Ile Tyr Ser Leu Val Thr Glu Asn Ile
        545                 550                 555                 560

Gln Trp Pro Asn Gly Ile Thr Leu Asp Leu Leu Ser Gly Arg Leu Tyr
                        565                 570                 575
```

```
Trp Val Asp Ser Lys Leu His Ser Ile Ser Ile Asp Val Asn Gly
        580                 585                 590

Gly Asn Arg Lys Thr Ile Leu Glu Asp Glu Lys Arg Leu Ala His Pro
    595                 600                 605

Phe Ser Leu Ala Val Phe Glu Asp Lys Val Phe Trp Thr Asp Ile Ile
610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860

<210> SEQ ID NO 22
<211> LENGTH: 2583
<212> TYPE: DNA
<213> ORGANISM: Artificial Sequence
<220> FEATURE:
<223> OTHER INFORMATION: hLDLR variant L311T with leader
<220> FEATURE:
<221> NAME/KEY: CDS
<222> LOCATION: (1)..(2583)

<400> SEQUENCE: 22 atg ggg ccc tgg ggc tgg aaa ttg cgc tgg acc gtc gcc ttg ctc ctc     48
Met Gly Pro Trp Gly Trp Lys Leu Arg Trp Thr Val Ala Leu Leu Leu
1               5                   10                  15 gcc gcg gcg ggg act gca gtg ggc gac aga tgt gaa aga aac gag ttc     96
Ala Ala Ala Gly Thr Ala Val Gly Asp Arg Cys Glu Arg Asn Glu Phe
            20                  25                  30 cag tgc caa gac ggg aaa tgc atc tcc tac aag tgg gtc tgc gat ggc    144
Gln Cys Gln Asp Gly Lys Cys Ile Ser Tyr Lys Trp Val Cys Asp Gly
        35                  40                  45
```

```
agc gct gag tgc cag gat ggc tct gat gag tcc cag gag acg tgc ttg        192
Ser Ala Glu Cys Gln Asp Gly Ser Asp Glu Ser Gln Glu Thr Cys Leu
    50              55                  60 tct gtc acc tgc aaa tcc ggg gac ttc agc tgt ggg ggc cgt gtc aac        240
Ser Val Thr Cys Lys Ser Gly Asp Phe Ser Cys Gly Gly Arg Val Asn
65              70                  75                  80 cgc tgc att cct cag ttc tgg agg tgc gat ggc caa gtg gac tgc gac        288
Arg Cys Ile Pro Gln Phe Trp Arg Cys Asp Gly Gln Val Asp Cys Asp
                85                  90                  95 aac ggc tca gac gag caa ggc tgt ccc ccc aag acg tgc tcc cag gac        336
Asn Gly Ser Asp Glu Gln Gly Cys Pro Pro Lys Thr Cys Ser Gln Asp
            100                 105                 110 gag ttt cgc tgc cac gat ggg aag tgc atc tct cgg cag ttc gtc tgt        384
Glu Phe Arg Cys His Asp Gly Lys Cys Ile Ser Arg Gln Phe Val Cys
        115                 120                 125 gac tca gac cgg gac tgc ttg gac ggc tca gac gag gcc tcc tgc ccg        432
Asp Ser Asp Arg Asp Cys Leu Asp Gly Ser Asp Glu Ala Ser Cys Pro
130                 135                 140 gtg ctc acc tgt ggt ccc gcc agc ttc cag tgc aac agc tcc acc tgc        480
Val Leu Thr Cys Gly Pro Ala Ser Phe Gln Cys Asn Ser Ser Thr Cys
145                 150                 155                 160 atc ccc cag ctg tgg gcc tgc gac aac gac ccc gac tgc gaa gat ggc        528
Ile Pro Gln Leu Trp Ala Cys Asp Asn Asp Pro Asp Cys Glu Asp Gly
                165                 170                 175 tcg gat gag tgg ccg cag cgc tgt agg ggt ctt tac gtg ttc caa ggg        576
Ser Asp Glu Trp Pro Gln Arg Cys Arg Gly Leu Tyr Val Phe Gln Gly
            180                 185                 190 gac agt agc ccc tgc tcg gcc ttc gag ttc cac tgc cta agt ggc gag        624
Asp Ser Ser Pro Cys Ser Ala Phe Glu Phe His Cys Leu Ser Gly Glu
        195                 200                 205 tgc atc cac tcc agc tgg cgc tgt gat ggt ggc ccc gac tgc aag gac        672
Cys Ile His Ser Ser Trp Arg Cys Asp Gly Gly Pro Asp Cys Lys Asp
210                 215                 220 aaa tct gac gag gaa aac tgc gct gtg gcc acc tgt cgc cct gac gaa        720
Lys Ser Asp Glu Glu Asn Cys Ala Val Ala Thr Cys Arg Pro Asp Glu
225                 230                 235                 240 ttc cag tgc tct gat gga aac tgc atc cat ggc agc cgg cag tgt gac        768
Phe Gln Cys Ser Asp Gly Asn Cys Ile His Gly Ser Arg Gln Cys Asp
                245                 250                 255 cgg gaa tat gac tgc aag gac atg agc gat gaa gtt ggc tgc gtt aat        816
Arg Glu Tyr Asp Cys Lys Asp Met Ser Asp Glu Val Gly Cys Val Asn
            260                 265                 270 gtg aca ctc tgc gag gga ccc aac aag ttc aag tgt cac agc ggc gaa        864
Val Thr Leu Cys Glu Gly Pro Asn Lys Phe Lys Cys His Ser Gly Glu
        275                 280                 285 tgc atc acc ctg gac aaa gtc tgc aac atg gct aga gac tgc cgg gac        912
Cys Ile Thr Leu Asp Lys Val Cys Asn Met Ala Arg Asp Cys Arg Asp
290                 295                 300 tgg tca gat gaa ccc atc aaa gag tgc ggg acc aac gaa tgc ttg gac        960
Trp Ser Asp Glu Pro Ile Lys Glu Cys Gly Thr Asn Glu Cys Leu Asp
305                 310                 315                 320 aac aac ggc ggc tgt tcc cac gtc tgc aat gac act aag atc ggc tac       1008
Asn Asn Gly Gly Cys Ser His Val Cys Asn Asp Thr Lys Ile Gly Tyr
                325                 330                 335 gag tgc ctg tgc ccc gac ggc ttc cag ctg gtg gcc cag cga aga tgc       1056
Glu Cys Leu Cys Pro Asp Gly Phe Gln Leu Val Ala Gln Arg Arg Cys
            340                 345                 350 gaa gat atc gat gag tgt cag gat ccc gac acc tgc agc cag ctc tgc       1104
Glu Asp Ile Asp Glu Cys Gln Asp Pro Asp Thr Cys Ser Gln Leu Cys
```

|  |  |  |  |  |  |  |  |  |  |  |  |  |  |  |  |
|---|---|---|---|---|---|---|---|---|---|---|---|---|---|---|---|
|  | 355 |  |  |  | 360 |  |  |  | 365 |  |  |  |  |  |  |
| gtg<br>Val<br>370 | aac<br>Asn | ctg<br>Leu | gag<br>Glu | ggt<br>Gly | ggc<br>Gly<br>375 | tac<br>Tyr | aag<br>Lys | tgc<br>Cys | cag<br>Gln | tgt<br>Cys<br>380 | gag<br>Glu | gaa<br>Glu | ggc<br>Gly | ttc<br>Phe | cag<br>Gln | 1152 |
| ctg<br>Leu<br>385 | gac<br>Asp | ccc<br>Pro | cac<br>His | acg<br>Thr | aag<br>Lys<br>390 | gcc<br>Ala | tgc<br>Cys | aag<br>Lys | gct<br>Ala | gtg<br>Val<br>395 | ggc<br>Gly | tcc<br>Ser | atc<br>Ile | gcc<br>Ala | tac<br>Tyr<br>400 | 1200 |
| ctc<br>Leu | ttc<br>Phe | ttc<br>Phe | acc<br>Thr | aac<br>Asn<br>405 | cgg<br>Arg | cac<br>His | gag<br>Glu | gtc<br>Val | agg<br>Arg<br>410 | aag<br>Lys | atg<br>Met | acg<br>Thr | ctg<br>Leu | gac<br>Asp<br>415 | cgg<br>Arg | 1248 |
| agc<br>Ser | gag<br>Glu | tac<br>Tyr | acc<br>Thr<br>420 | agc<br>Ser | ctc<br>Leu | atc<br>Ile | ccc<br>Pro | aac<br>Asn<br>425 | ctg<br>Leu | agg<br>Arg | aac<br>Asn | gtc<br>Val | gtc<br>Val<br>430 | gct<br>Ala | ctg<br>Leu | 1296 |
| gac<br>Asp | acg<br>Thr | gag<br>Glu<br>435 | gtg<br>Val | gcc<br>Ala | agc<br>Ser | aat<br>Asn | aga<br>Arg<br>440 | atc<br>Ile | tac<br>Tyr | tgg<br>Trp | tct<br>Ser | gac<br>Asp<br>445 | ctg<br>Leu | tcc<br>Ser | cag<br>Gln | 1344 |
| aga<br>Arg | atg<br>Met<br>450 | atc<br>Ile | tgc<br>Cys | agc<br>Ser | acc<br>Thr | cag<br>Gln<br>455 | ctt<br>Leu | gac<br>Asp | aga<br>Arg | gcc<br>Ala | cac<br>His<br>460 | ggc<br>Gly | gtc<br>Val | tct<br>Ser | tcc<br>Ser | 1392 |
| tat<br>Tyr<br>465 | gac<br>Asp | acc<br>Thr | gtc<br>Val | atc<br>Ile | agc<br>Ser<br>470 | agg<br>Arg | gac<br>Asp | atc<br>Ile | cag<br>Gln | gcc<br>Ala<br>475 | ccc<br>Pro | gac<br>Asp | ggg<br>Gly | ctg<br>Leu | gct<br>Ala<br>480 | 1440 |
| gtg<br>Val | gac<br>Asp | tgg<br>Trp | atc<br>Ile | cac<br>His<br>485 | agc<br>Ser | aac<br>Asn | atc<br>Ile | tac<br>Tyr | tgg<br>Trp<br>490 | acc<br>Thr | gac<br>Asp | tct<br>Ser | gtc<br>Val | ctg<br>Leu<br>495 | ggc<br>Gly | 1488 |
| act<br>Thr | gtc<br>Val | tct<br>Ser | gtt<br>Val<br>500 | gcg<br>Ala | gat<br>Asp | acc<br>Thr | aag<br>Lys | ggc<br>Gly<br>505 | gtg<br>Val | aag<br>Lys | agg<br>Arg | aaa<br>Lys | acg<br>Thr<br>510 | tta<br>Leu | ttc<br>Phe | 1536 |
| agg<br>Arg | gag<br>Glu | aac<br>Asn<br>515 | ggc<br>Gly | tcc<br>Ser | aag<br>Lys | cca<br>Pro | agg<br>Arg<br>520 | gcc<br>Ala | atc<br>Ile | gtg<br>Val | gtg<br>Val | gat<br>Asp<br>525 | cct<br>Pro | gtt<br>Val | cat<br>His | 1584 |
| ggc<br>Gly | ttc<br>Phe | atg<br>Met | tac<br>Tyr | tgg<br>Trp | act<br>Thr<br>535 | gac<br>Asp | tgg<br>Trp | gga<br>Gly | act<br>Thr | ccc<br>Pro<br>540 | gcc<br>Ala | aag<br>Lys | atc<br>Ile | aag<br>Lys | aaa<br>Lys | 1632 |
|  | 530 |  |  |  |  |  |  |  |  |  |  |  |  |  |  |  |
| ggg<br>Gly<br>545 | ggc<br>Gly | ctg<br>Leu | aat<br>Asn | ggt<br>Gly | gtg<br>Val<br>550 | gac<br>Asp | atc<br>Ile | tac<br>Tyr | tcg<br>Ser | ctg<br>Leu<br>555 | gtg<br>Val | act<br>Thr | gaa<br>Glu | aac<br>Asn | att<br>Ile<br>560 | 1680 |
| cag<br>Gln | tgg<br>Trp | ccc<br>Pro | aat<br>Asn | ggc<br>Gly<br>565 | atc<br>Ile | acc<br>Thr | cta<br>Leu | gat<br>Asp | ctc<br>Leu<br>570 | ctc<br>Leu | agt<br>Ser | ggc<br>Gly | cgc<br>Arg | ctc<br>Leu<br>575 | tac<br>Tyr | 1728 |
| tgg<br>Trp | gtt<br>Val | gac<br>Asp | tcc<br>Ser<br>580 | aaa<br>Lys | ctt<br>Leu | cac<br>His | tcc<br>Ser | atc<br>Ile<br>585 | tca<br>Ser | agc<br>Ser | atc<br>Ile | gat<br>Asp | gtc<br>Val<br>590 | aat<br>Asn | ggg<br>Gly | 1776 |
| ggc<br>Gly | aac<br>Asn | cgg<br>Arg<br>595 | aag<br>Lys | acc<br>Thr | atc<br>Ile | ttg<br>Leu | gag<br>Glu<br>600 | gat<br>Asp | gaa<br>Glu | aag<br>Lys | agg<br>Arg | ctg<br>Leu<br>605 | gcc<br>Ala | cac<br>His | ccc<br>Pro | 1824 |
| ttc<br>Phe<br>610 | tcc<br>Ser | ttg<br>Leu | gcc<br>Ala | gtc<br>Val | ttt<br>Phe<br>615 | gag<br>Glu | gac<br>Asp | aaa<br>Lys | gta<br>Val | ttt<br>Phe<br>620 | tgg<br>Trp | aca<br>Thr | gat<br>Asp | atc<br>Ile | atc<br>Ile | 1872 |
| aac<br>Asn<br>625 | gaa<br>Glu | gcc<br>Ala | att<br>Ile | ttc<br>Phe | agt<br>Ser<br>630 | gcc<br>Ala | aac<br>Asn | cgc<br>Arg | ctc<br>Leu | aca<br>Thr<br>635 | ggt<br>Gly | tcc<br>Ser | gat<br>Asp | gtc<br>Val | aac<br>Asn<br>640 | 1920 |
| ttg<br>Leu | ttg<br>Leu | gct<br>Ala | gaa<br>Glu | aac<br>Asn<br>645 | cta<br>Leu | ctg<br>Leu | tcc<br>Ser | cca<br>Pro | gag<br>Glu<br>650 | gat<br>Asp | atg<br>Met | gtc<br>Val | ctc<br>Leu | ttc<br>Phe<br>655 | cac<br>His | 1968 |
| aac<br>Asn | ctc<br>Leu | acc<br>Thr | cag<br>Gln<br>660 | cca<br>Pro | aga<br>Arg | gga<br>Gly | gtg<br>Val | aac<br>Asn<br>665 | tgg<br>Trp | tgt<br>Cys | gag<br>Glu | agg<br>Arg | acc<br>Thr<br>670 | acc<br>Thr | ctg<br>Leu | 2016 |
| agc<br>Ser | aat<br>Asn | ggc<br>Gly | ggc<br>Gly | tgc<br>Cys | cag<br>Gln | tat<br>Tyr | ctg<br>Leu | tgc<br>Cys | ctc<br>Leu | cct<br>Pro | gcc<br>Ala | ccg<br>Pro | cag<br>Gln | atc<br>Ile | aac<br>Asn | 2064 |

```
                                                           -continued

Ser Asn Gly Gly Cys Gln Tyr Leu Cys Leu Pro Ala Pro Gln Ile Asn
        675                 680                 685 ccc cac tcg ccc aag ttt acc tgc gcc tgc ccg gac ggc atg ctg ctg      2112
Pro His Ser Pro Lys Phe Thr Cys Ala Cys Pro Asp Gly Met Leu Leu
    690                 695                 700 gcc agg gac atg agg agc tgc ctc aca gag gct gag gct gca gtg gcc      2160
Ala Arg Asp Met Arg Ser Cys Leu Thr Glu Ala Glu Ala Ala Val Ala
705                 710                 715                 720 acc cag gag aca tcc acc gtc agg cta aag gtc agc tcc aca gcc gta      2208
Thr Gln Glu Thr Ser Thr Val Arg Leu Lys Val Ser Ser Thr Ala Val
                725                 730                 735 agg aca cag cac aca acc acc cgg cct gtt ccc gac acc tcc cgg ctg      2256
Arg Thr Gln His Thr Thr Thr Arg Pro Val Pro Asp Thr Ser Arg Leu
            740                 745                 750 cct ggg gcc acc cct ggg ctc acc acg gtg gag ata gtg aca atg tct      2304
Pro Gly Ala Thr Pro Gly Leu Thr Thr Val Glu Ile Val Thr Met Ser
        755                 760                 765 cac caa gct ctg ggc gac gtt gct ggc aga gga aat gag aag aag ccc      2352
His Gln Ala Leu Gly Asp Val Ala Gly Arg Gly Asn Glu Lys Lys Pro
    770                 775                 780 agt agc gtg agg gct ctg tcc att gtc ctc ccc atc gtg ctc ctc gtc      2400
Ser Ser Val Arg Ala Leu Ser Ile Val Leu Pro Ile Val Leu Leu Val
785                 790                 795                 800 ttc ctt tgc ctg ggg gtc ttc ctt cta tgg aag aac tgg cgg ctt aag      2448
Phe Leu Cys Leu Gly Val Phe Leu Leu Trp Lys Asn Trp Arg Leu Lys
                805                 810                 815 aac atc aac agc atc aac ttt gac aac ccc gtc tat cag aag acc aca      2496
Asn Ile Asn Ser Ile Asn Phe Asp Asn Pro Val Tyr Gln Lys Thr Thr
            820                 825                 830 gag gat gag gtc cac att tgc cac aac cag gac ggc tac agc tac ccc      2544
Glu Asp Glu Val His Ile Cys His Asn Gln Asp Gly Tyr Ser Tyr Pro
        835                 840                 845 tcg aga cag atg gtc agt ctg gag gat gac gtg gcg tga                  2583
Ser Arg Gln Met Val Ser Leu Glu Asp Asp Val Ala
    850                 855                 860

<210> SEQ ID NO 23
<211> LENGTH: 860
<212> TYPE: PRT
<213> ORGANISM: Artificial Sequence
<220> FEATURE:
<223> OTHER INFORMATION: Synthetic Construct

<400> SEQUENCE: 23

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
```

```
            115                 120                 125
Asp Ser Asp Arg Asp Cys Leu Asp Gly Ser Asp Glu Ala Ser Cys Pro
            130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
                180                 185                 190

Asp Ser Ser Pro Cys Ser Ala Phe Glu Phe His Cys Leu Ser Gly Glu
                195                 200                 205

Cys Ile His Ser Ser Trp Arg Cys Asp Gly Gly Pro Asp Cys Lys Asp
            210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
                260                 265                 270

Val Thr Leu Cys Glu Gly Pro Asn Lys Phe Lys Cys His Ser Gly Glu
                275                 280                 285

Cys Ile Thr Leu Asp Lys Val Cys Asn Met Ala Arg Asp Cys Arg Asp
            290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Thr Lys Ile Gly Tyr
                325                 330                 335

Glu Cys Leu Cys Pro Asp Gly Phe Gln Leu Val Ala Gln Arg Arg Cys
                340                 345                 350

Glu Asp Ile Asp Glu Cys Gln Asp Pro Asp Thr Cys Ser Gln Leu Cys
            355                 360                 365

Val Asn Leu Glu Gly Gly Tyr Lys Cys Gln Cys Glu Glu Gly Phe Gln
370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
                420                 425                 430

Asp Thr Glu Val Ala Ser Asn Arg Ile Tyr Trp Ser Asp Leu Ser Gln
            435                 440                 445

Arg Met Ile Cys Ser Thr Gln Leu Asp Arg Ala His Gly Val Ser Ser
            450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
                500                 505                 510

Arg Glu Asn Gly Ser Lys Pro Arg Ala Ile Val Val Asp Pro Val His
            515                 520                 525

Gly Phe Met Tyr Trp Thr Asp Trp Gly Thr Pro Ala Lys Ile Lys Lys
            530                 535                 540
```

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
            565                 570                 575

Trp Val Asp Ser Lys Leu His Ser Ile Ser Ser Ile Asp Val Asn Gly
        580                 585                 590

Gly Asn Arg Lys Thr Ile Leu Glu Asp Glu Lys Arg Leu Ala His Pro
    595                 600                 605

Phe Ser Leu Ala Val Phe Glu Asp Lys Val Phe Trp Thr Asp Ile Ile
610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860

<210> SEQ ID NO 24
<211> LENGTH: 2583
<212> TYPE: DNA
<213> ORGANISM: Artificial Sequence
<220> FEATURE:
<223> OTHER INFORMATION: hLDLR variant L318D with leader
<220> FEATURE:
<221> NAME/KEY: CDS
<222> LOCATION: (1)..(2583)

<400> SEQUENCE: 24

```
atg ggg ccc tgg ggc tgg aaa ttg cgc tgg acc gtc gcc ttg ctc ctc    48
Met Gly Pro Trp Gly Trp Lys Leu Arg Trp Thr Val Ala Leu Leu Leu
1               5                   10                  15 gcc gcg gcg ggg act gca gtg ggc gac aga tgt gaa aga aac gag ttc    96
```

|     |     |     |     |     |     |     |     |     |     |     |     |     |
|---|---|---|---|---|---|---|---|---|---|---|---|---|
| Ala | Ala | Ala | Gly | Thr | Ala | Val | Gly | Asp | Arg | Cys | Glu | Arg | Asn | Glu | Phe |
|     |     |     | 20  |     |     |     | 25  |     |     |     | 30  |

```
cag tgc caa gac ggg aaa tgc atc tcc tac aag tgg gtc tgc gat ggc      144
Gln Cys Gln Asp Gly Lys Cys Ile Ser Tyr Lys Trp Val Cys Asp Gly
         35                  40                  45 agc gct gag tgc cag gat ggc tct gat gag tcc cag gag acg tgc ttg      192
Ser Ala Glu Cys Gln Asp Gly Ser Asp Glu Ser Gln Glu Thr Cys Leu
 50                  55                  60 tct gtc acc tgc aaa tcc ggg gac ttc agc tgt ggg ggc cgt gtc aac      240
Ser Val Thr Cys Lys Ser Gly Asp Phe Ser Cys Gly Gly Arg Val Asn
 65                  70                  75                  80 cgc tgc att cct cag ttc tgg agg tgc gat ggc caa gtg gac tgc gac      288
Arg Cys Ile Pro Gln Phe Trp Arg Cys Asp Gly Gln Val Asp Cys Asp
             85                  90                  95 aac ggc tca gac gag caa ggc tgt ccc ccc aag acg tgc tcc cag gac      336
Asn Gly Ser Asp Glu Gln Gly Cys Pro Pro Lys Thr Cys Ser Gln Asp
            100                 105                 110 gag ttt cgc tgc cac gat ggg aag tgc atc tct cgg cag ttc gtc tgt      384
Glu Phe Arg Cys His Asp Gly Lys Cys Ile Ser Arg Gln Phe Val Cys
            115                 120                 125 gac tca gac cgg gac tgc ttg gac ggc tca gac gag gcc tcc tgc ccg      432
Asp Ser Asp Arg Asp Cys Leu Asp Gly Ser Asp Glu Ala Ser Cys Pro
130                 135                 140 gtg ctc acc tgt ggt ccc gcc agc ttc cag tgc aac agc tcc acc tgc      480
Val Leu Thr Cys Gly Pro Ala Ser Phe Gln Cys Asn Ser Ser Thr Cys
145                 150                 155                 160 atc ccc cag ctg tgg gcc tgc gac aac gac ccc gac tgc gaa gat ggc      528
Ile Pro Gln Leu Trp Ala Cys Asp Asn Asp Pro Asp Cys Glu Asp Gly
                165                 170                 175 tcg gat gag tgg ccg cag cgc tgt agg ggt ctt tac gtg ttc caa ggg      576
Ser Asp Glu Trp Pro Gln Arg Cys Arg Gly Leu Tyr Val Phe Gln Gly
            180                 185                 190 gac agt agc ccc tgc tcg gcc ttc gag ttc cac tgc cta agt ggc gag      624
Asp Ser Ser Pro Cys Ser Ala Phe Glu Phe His Cys Leu Ser Gly Glu
            195                 200                 205 tgc atc cac tcc agc tgg cgc tgt gat ggt ggc ccc gac tgc aag gac      672
Cys Ile His Ser Ser Trp Arg Cys Asp Gly Gly Pro Asp Cys Lys Asp
210                 215                 220 aaa tct gac gag gaa aac tgc gct gtg gcc acc tgt cgc cct gac gaa      720
Lys Ser Asp Glu Glu Asn Cys Ala Val Ala Thr Cys Arg Pro Asp Glu
225                 230                 235                 240 ttc cag tgc tct gat gga aac tgc atc cat ggc agc cgg cag tgt gac      768
Phe Gln Cys Ser Asp Gly Asn Cys Ile His Gly Ser Arg Gln Cys Asp
                245                 250                 255 cgg gaa tat gac tgc aag gac atg agc gat gaa gtt ggc tgc gtt aat      816
Arg Glu Tyr Asp Cys Lys Asp Met Ser Asp Glu Val Gly Cys Val Asn
            260                 265                 270 gtg aca ctc tgc gag gga ccc aac aag ttc aag tgt cac agc ggc gaa      864
Val Thr Leu Cys Glu Gly Pro Asn Lys Phe Lys Cys His Ser Gly Glu
            275                 280                 285 tgc atc acc ctg gac aaa gtc tgc aac atg gct aga gac tgc cgg gac      912
Cys Ile Thr Leu Asp Lys Val Cys Asn Met Ala Arg Asp Cys Arg Asp
            290                 295                 300 tgg tca gat gaa ccc atc aaa gag tgc ggg acc aac gaa tgc ttg gac      960
Trp Ser Asp Glu Pro Ile Lys Glu Cys Gly Thr Asn Glu Cys Leu Asp
305                 310                 315                 320 aac aac ggc ggt tgt tcc cac gtc tgc aat gac ctt aag atc ggc tac     1008
Asn Asn Gly Gly Cys Ser His Val Cys Asn Asp Leu Lys Ile Gly Tyr
                325                 330                 335
```

```
gag tgc gac tgc ccc gac ggc ttc cag ctg gtg gcc cag cga aga tgc    1056
Glu Cys Asp Cys Pro Asp Gly Phe Gln Leu Val Ala Gln Arg Arg Cys
            340                 345                 350 gaa gat atc gat gag tgt cag gat ccc gac acc tgc agc cag ctc tgc    1104
Glu Asp Ile Asp Glu Cys Gln Asp Pro Asp Thr Cys Ser Gln Leu Cys
        355                 360                 365 gtg aac ctg gag ggt ggc tac aag tgc cag tgt gag gaa ggc ttc cag    1152
Val Asn Leu Glu Gly Gly Tyr Lys Cys Gln Cys Glu Glu Gly Phe Gln
    370                 375                 380 ctg gac ccc cac acg aag gcc tgc aag gct gtg ggc tcc atc gcc tac    1200
Leu Asp Pro His Thr Lys Ala Cys Lys Ala Val Gly Ser Ile Ala Tyr
385                 390                 395                 400 ctc ttc ttc acc aac cgg cac gag gtc agg aag atg acg ctg gac cgg    1248
Leu Phe Phe Thr Asn Arg His Glu Val Arg Lys Met Thr Leu Asp Arg
                405                 410                 415 agc gag tac acc agc ctc atc ccc aac ctg agg aac gtg gtc gct ctg    1296
Ser Glu Tyr Thr Ser Leu Ile Pro Asn Leu Arg Asn Val Val Ala Leu
            420                 425                 430 gac acg gag gtg gcc agc aat aga atc tac tgg tct gac ctg tcc cag    1344
Asp Thr Glu Val Ala Ser Asn Arg Ile Tyr Trp Ser Asp Leu Ser Gln
        435                 440                 445 aga atg atc tgc agc acc cag ctt gac aga gcc cac ggc gtc tct tcc    1392
Arg Met Ile Cys Ser Thr Gln Leu Asp Arg Ala His Gly Val Ser Ser
    450                 455                 460 tat gac acc gtc atc agc agg gac atc cag gcc ccc gac ggg ctg gct    1440
Tyr Asp Thr Val Ile Ser Arg Asp Ile Gln Ala Pro Asp Gly Leu Ala
465                 470                 475                 480 gtg gac tgg atc cac agc aac atc tac tgg acc gac tct gtc ctg ggc    1488
Val Asp Trp Ile His Ser Asn Ile Tyr Trp Thr Asp Ser Val Leu Gly
                485                 490                 495 act gtc tct gtt gcg gat acc aag ggc gtg aag agg aaa acg tta ttc    1536
Thr Val Ser Val Ala Asp Thr Lys Gly Val Lys Arg Lys Thr Leu Phe
            500                 505                 510 agg gag aac ggc tcc aag cca agg gcc atc gtg gtg gat cct gtt cat    1584
Arg Glu Asn Gly Ser Lys Pro Arg Ala Ile Val Val Asp Pro Val His
        515                 520                 525 ggc ttc atg tac tgg act gac tgg gga act ccc gcc aag atc aag aaa    1632
Gly Phe Met Tyr Trp Thr Asp Trp Gly Thr Pro Ala Lys Ile Lys Lys
    530                 535                 540 ggg ggc ctg aat ggt gtg gac atc tac tcg ctg gtg act gaa aac att    1680
Gly Gly Leu Asn Gly Val Asp Ile Tyr Ser Leu Val Thr Glu Asn Ile
545                 550                 555                 560 cag tgg ccc aat ggc atc acc cta gat ctc ctc agt ggc cgc ctc tac    1728
Gln Trp Pro Asn Gly Ile Thr Leu Asp Leu Leu Ser Gly Arg Leu Tyr
                565                 570                 575 tgg gtt gac tcc aaa ctt cac tcc atc tca agc atc gat gtc aat ggg    1776
Trp Val Asp Ser Lys Leu His Ser Ile Ser Ser Ile Asp Val Asn Gly
            580                 585                 590 ggc aac cgg aag acc atc ttg gag gat gaa aag agg ctg gcc cac ccc    1824
Gly Asn Arg Lys Thr Ile Leu Glu Asp Glu Lys Arg Leu Ala His Pro
        595                 600                 605 ttc tcc ttg gcc gtc ttt gag gac aaa gta ttt tgg aca gat atc atc    1872
Phe Ser Leu Ala Val Phe Glu Asp Lys Val Phe Trp Thr Asp Ile Ile
    610                 615                 620 aac gaa gcc att ttc agt gcc aac cgc ctc aca ggt tcc gat gtc aac    1920
Asn Glu Ala Ile Phe Ser Ala Asn Arg Leu Thr Gly Ser Asp Val Asn
625                 630                 635                 640 ttg ttg gct gaa aac cta ctg tcc cca gag gat atg gtc ctc ttc cac    1968
Leu Leu Ala Glu Asn Leu Leu Ser Pro Glu Asp Met Val Leu Phe His
                645                 650                 655
```

```
aac ctc acc cag cca aga gga gtg aac tgg tgt gag agg acc acc ctg    2016
Asn Leu Thr Gln Pro Arg Gly Val Asn Trp Cys Glu Arg Thr Thr Leu
            660                 665                 670 agc aat ggc ggc tgc cag tat ctg tgc ctc cct gcc ccg cag atc aac    2064
Ser Asn Gly Gly Cys Gln Tyr Leu Cys Leu Pro Ala Pro Gln Ile Asn
        675                 680                 685 ccc cac tcg ccc aag ttt acc tgc gcc tgc ccg gac ggc atg ctg ctg    2112
Pro His Ser Pro Lys Phe Thr Cys Ala Cys Pro Asp Gly Met Leu Leu
    690                 695                 700 gcc agg gac atg agg agc tgc ctc aca gag gct gag gct gca gtg gcc    2160
Ala Arg Asp Met Arg Ser Cys Leu Thr Glu Ala Glu Ala Ala Val Ala
705                 710                 715                 720 acc cag gag aca tcc acc gtc agg cta aag gtc agc tcc aca gcc gta    2208
Thr Gln Glu Thr Ser Thr Val Arg Leu Lys Val Ser Ser Thr Ala Val
                725                 730                 735 agg aca cag cac aca acc acc cgg cct gtt ccc gac acc tcc cgg ctg    2256
Arg Thr Gln His Thr Thr Thr Arg Pro Val Pro Asp Thr Ser Arg Leu
            740                 745                 750 cct ggg gcc acc cct ggg ctc acc acg gtg gag ata gtg aca atg tct    2304
Pro Gly Ala Thr Pro Gly Leu Thr Thr Val Glu Ile Val Thr Met Ser
        755                 760                 765 cac caa gct ctg ggc gac gtt gct ggc aga gga aat gag aag aag ccc    2352
His Gln Ala Leu Gly Asp Val Ala Gly Arg Gly Asn Glu Lys Lys Pro
    770                 775                 780 agt agc gtg agg gct ctg tcc att gtc ctc ccc atc gtg ctc ctc gtc    2400
Ser Ser Val Arg Ala Leu Ser Ile Val Leu Pro Ile Val Leu Leu Val
785                 790                 795                 800 ttc ctt tgc ctg ggg gtc ttc ctt cta tgg aag aac tgg cgg ctt aag    2448
Phe Leu Cys Leu Gly Val Phe Leu Leu Trp Lys Asn Trp Arg Leu Lys
                805                 810                 815 aac atc aac agc atc aac ttt gac aac ccc gtc tat cag aag acc aca    2496
Asn Ile Asn Ser Ile Asn Phe Asp Asn Pro Val Tyr Gln Lys Thr Thr
            820                 825                 830 gag gat gag gtc cac att tgc cac aac cag gac ggc tac agc tac ccc    2544
Glu Asp Glu Val His Ile Cys His Asn Gln Asp Gly Tyr Ser Tyr Pro
        835                 840                 845 tcg aga cag atg gtc agt ctg gag gat gac gtg gcg tga                2583
Ser Arg Gln Met Val Ser Leu Glu Asp Asp Val Ala
    850                 855                 860

<210> SEQ ID NO 25
<211> LENGTH: 860
<212> TYPE: PRT
<213> ORGANISM: Artificial Sequence
<220> FEATURE:
<223> OTHER INFORMATION: Synthetic Construct

<400> SEQUENCE: 25

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
```

```
                        85                  90                  95
Asn Gly Ser Asp Glu Gln Gly Cys Pro Pro Lys Thr Cys Ser Gln Asp
            100                 105                 110
Glu Phe Arg Cys His Asp Gly Lys Cys Ile Ser Arg Gln Phe Val Cys
            115                 120                 125
Asp Ser Asp Arg Asp Cys Leu Asp Gly Ser Asp Glu Ala Ser Cys Pro
    130                 135                 140
Val Leu Thr Cys Gly Pro Ala Ser Phe Gln Cys Asn Ser Ser Thr Cys
145                 150                 155                 160
Ile Pro Gln Leu Trp Ala Cys Asp Asn Asp Pro Asp Cys Glu Asp Gly
                165                 170                 175
Ser Asp Glu Trp Pro Gln Arg Cys Arg Gly Leu Tyr Val Phe Gln Gly
            180                 185                 190
Asp Ser Ser Pro Cys Ser Ala Phe Glu Phe His Cys Leu Ser Gly Glu
            195                 200                 205
Cys Ile His Ser Ser Trp Arg Cys Asp Gly Gly Pro Asp Cys Lys Asp
    210                 215                 220
Lys Ser Asp Glu Glu Asn Cys Ala Val Ala Thr Cys Arg Pro Asp Glu
225                 230                 235                 240
Phe Gln Cys Ser Asp Gly Asn Cys Ile His Gly Ser Arg Gln Cys Asp
                245                 250                 255
Arg Glu Tyr Asp Cys Lys Asp Met Ser Asp Glu Val Gly Cys Val Asn
            260                 265                 270
Val Thr Leu Cys Glu Gly Pro Asn Lys Phe Lys Cys His Ser Gly Glu
            275                 280                 285
Cys Ile Thr Leu Asp Lys Val Cys Asn Met Ala Arg Asp Cys Arg Asp
    290                 295                 300
Trp Ser Asp Glu Pro Ile Lys Glu Cys Gly Thr Asn Glu Cys Leu Asp
305                 310                 315                 320
Asn Asn Gly Gly Cys Ser His Val Cys Asn Asp Leu Lys Ile Gly Tyr
                325                 330                 335
Glu Cys Asp Cys Pro Asp Gly Phe Gln Leu Val Ala Gln Arg Arg Cys
            340                 345                 350
Glu Asp Ile Asp Glu Cys Gln Asp Pro Asp Thr Cys Ser Gln Leu Cys
            355                 360                 365
Val Asn Leu Glu Gly Gly Tyr Lys Cys Gln Cys Glu Glu Gly Phe Gln
    370                 375                 380
Leu Asp Pro His Thr Lys Ala Cys Lys Ala Val Gly Ser Ile Ala Tyr
385                 390                 395                 400
Leu Phe Phe Thr Asn Arg His Glu Val Arg Lys Met Thr Leu Asp Arg
                405                 410                 415
Ser Glu Tyr Thr Ser Leu Ile Pro Asn Leu Arg Asn Val Val Ala Leu
            420                 425                 430
Asp Thr Glu Val Ala Ser Asn Arg Ile Tyr Trp Ser Asp Leu Ser Gln
            435                 440                 445
Arg Met Ile Cys Ser Thr Gln Leu Asp Arg Ala His Gly Val Ser Ser
    450                 455                 460
Tyr Asp Thr Val Ile Ser Arg Asp Ile Gln Ala Pro Asp Gly Leu Ala
465                 470                 475                 480
Val Asp Trp Ile His Ser Asn Ile Tyr Trp Thr Asp Ser Val Leu Gly
                485                 490                 495
Thr Val Ser Val Ala Asp Thr Lys Gly Val Lys Arg Lys Thr Leu Phe
            500                 505                 510
```

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ile Asp Val Asn Gly
        580                 585                 590

Gly Asn Arg Lys Thr Ile Leu Glu Asp Glu Lys Arg Leu Ala His Pro
    595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860

<210> SEQ ID NO 26
<211> LENGTH: 2583
<212> TYPE: DNA
<213> ORGANISM: Artificial Sequence
<220> FEATURE:
<223> OTHER INFORMATION: hLDLR varient L318H with leader
<220> FEATURE:
<221> NAME/KEY: CDS
<222> LOCATION: (1)..(2583)

<400> SEQUENCE: 26

```
atg ggg ccc tgg ggc tgg aaa ttg cgc tgg acc gtc gcc ttg ctc ctc        48
Met Gly Pro Trp Gly Trp Lys Leu Arg Trp Thr Val Ala Leu Leu Leu
1               5                   10                  15 gcc gcg gcg ggg act gca gtg ggc gac aga tgt gaa aga aac gag ttc        96
Ala Ala Ala Gly Thr Ala Val Gly Asp Arg Cys Glu Arg Asn Glu Phe
                20                  25                  30 cag tgc caa gac ggg aaa tgc atc tcc tac aag tgg gtc tgc gat ggc       144
Gln Cys Gln Asp Gly Lys Cys Ile Ser Tyr Lys Trp Val Cys Asp Gly
        35                  40                  45 agc gct gag tgc cag gat ggc tct gat gag tcc cag gag acg tgc ttg       192
Ser Ala Glu Cys Gln Asp Gly Ser Asp Glu Ser Gln Glu Thr Cys Leu
    50                  55                  60 tct gtc acc tgc aaa tcc ggg gac ttc agc tgt ggg ggc cgt gtc aac       240
Ser Val Thr Cys Lys Ser Gly Asp Phe Ser Cys Gly Gly Arg Val Asn
65                  70                  75                  80 cgc tgc att cct cag ttc tgg agg tgc gat ggc caa gtg gac tgc gac       288
Arg Cys Ile Pro Gln Phe Trp Arg Cys Asp Gly Gln Val Asp Cys Asp
                85                  90                  95 aac ggc tca gac gag caa ggc tgt ccc ccc aag acg tgc tcc cag gac       336
Asn Gly Ser Asp Glu Gln Gly Cys Pro Pro Lys Thr Cys Ser Gln Asp
                100                 105                 110 gag ttt cgc tgc cac gat ggg aag tgc atc tct cgg cag ttc gtc tgt       384
Glu Phe Arg Cys His Asp Gly Lys Cys Ile Ser Arg Gln Phe Val Cys
        115                 120                 125 gac tca gac cgg gac tgc ttg gac ggc tca gac gag gcc tcc tgc ccg       432
Asp Ser Asp Arg Asp Cys Leu Asp Gly Ser Asp Glu Ala Ser Cys Pro
    130                 135                 140 gtg ctc acc tgt ggt ccc gcc agc ttc cag tgc aac agc tcc acc tgc       480
Val Leu Thr Cys Gly Pro Ala Ser Phe Gln Cys Asn Ser Ser Thr Cys
145                 150                 155                 160 atc ccc cag ctg tgg gcc tgc gac aac gac ccc gac tgc gaa gat ggc       528
Ile Pro Gln Leu Trp Ala Cys Asp Asn Asp Pro Asp Cys Glu Asp Gly
                165                 170                 175 tcg gat gag tgg ccg cag cgc tgt agg ggt ctt tac gtg ttc caa ggg       576
Ser Asp Glu Trp Pro Gln Arg Cys Arg Gly Leu Tyr Val Phe Gln Gly
                180                 185                 190 gac agt agc ccc tgc tcg gcc ttc gag ttc cac tgc cta agt ggc gag       624
Asp Ser Ser Pro Cys Ser Ala Phe Glu Phe His Cys Leu Ser Gly Glu
        195                 200                 205 tgc atc cac tcc agc tgg cgc tgt gat ggt ggc ccc gac tgc aag gac       672
Cys Ile His Ser Ser Trp Arg Cys Asp Gly Gly Pro Asp Cys Lys Asp
    210                 215                 220 aaa tct gac gag gaa aac tgc gct gtg gcc acc tgt cgc cct gac gaa       720
Lys Ser Asp Glu Glu Asn Cys Ala Val Ala Thr Cys Arg Pro Asp Glu
225                 230                 235                 240 ttc cag tgc tct gat gga aac tgc atc cat ggc agc cgg cag tgt gac       768
Phe Gln Cys Ser Asp Gly Asn Cys Ile His Gly Ser Arg Gln Cys Asp
                245                 250                 255 cgg gaa tat gac tgc aag gac atg agc gat gaa gtt ggc tgc gtt aat       816
Arg Glu Tyr Asp Cys Lys Asp Met Ser Asp Glu Val Gly Cys Val Asn
                260                 265                 270 gtg aca ctc tgc gag gga ccc aac aag ttc aag tgt cac agc ggc gaa       864
Val Thr Leu Cys Glu Gly Pro Asn Lys Phe Lys Cys His Ser Gly Glu
        275                 280                 285 tgc atc acc ctg gac aaa gtc tgc aac atg gct aga gac tgc cgg gac       912
Cys Ile Thr Leu Asp Lys Val Cys Asn Met Ala Arg Asp Cys Arg Asp
    290                 295                 300 tgg tca gat gaa ccc atc aaa gag tgc ggg acc aac gaa tgc ttg gac       960
Trp Ser Asp Glu Pro Ile Lys Glu Cys Gly Thr Asn Glu Cys Leu Asp
```

-continued

| | | | | |
|---|---|---|---|---|
| | 305 | 310 | 315 | 320 |
| aac aac ggc ggc tgt tcc cac gtc tgc aat gac ctt aag atc ggc tac<br>Asn Asn Gly Gly Cys Ser His Val Cys Asn Asp Leu Lys Ile Gly Tyr<br>325 330 335 | | | | 1008 |
| gag tgc gac tgc ccc gac ggc ttc cag ctg gtg gcc cag cga aga tgc<br>Glu Cys Asp Cys Pro Asp Gly Phe Gln Leu Val Ala Gln Arg Arg Cys<br>340 345 350 | | | | 1056 |
| gaa gat atc gat gag tgt cag gat ccc gac acc tgc agc cag ctc tgc<br>Glu Asp Ile Asp Glu Cys Gln Asp Pro Asp Thr Cys Ser Gln Leu Cys<br>355 360 365 | | | | 1104 |
| gtg aac ctg gag ggt ggc tac aag tgc cag tgt gag gaa ggc ttc cag<br>Val Asn Leu Glu Gly Gly Tyr Lys Cys Gln Cys Glu Glu Gly Phe Gln<br>370 375 380 | | | | 1152 |
| ctg gac ccc cac acg aag gcc tgc aag gct gtg ggc tcc atc gcc tac<br>Leu Asp Pro His Thr Lys Ala Cys Lys Ala Val Gly Ser Ile Ala Tyr<br>385 390 395 400 | | | | 1200 |
| ctc ttc ttc acc aac cgg cac gag gtc agg aag atg acg ctg gac cgg<br>Leu Phe Phe Thr Asn Arg His Glu Val Arg Lys Met Thr Leu Asp Arg<br>405 410 415 | | | | 1248 |
| agc gag tac acc agc ctc atc ccc aac ctg agg aac gtg gtc gct ctg<br>Ser Glu Tyr Thr Ser Leu Ile Pro Asn Leu Arg Asn Val Val Ala Leu<br>420 425 430 | | | | 1296 |
| gac acg gag gtg gcc agc aat aga atc tac tgg tct gac ctg tcc cag<br>Asp Thr Glu Val Ala Ser Asn Arg Ile Tyr Trp Ser Asp Leu Ser Gln<br>435 440 445 | | | | 1344 |
| aga atg atc tgc agc acc cag ctt gac aga gcc cac ggc gtc tct tcc<br>Arg Met Ile Cys Ser Thr Gln Leu Asp Arg Ala His Gly Val Ser Ser<br>450 455 460 | | | | 1392 |
| tat gac acc gtc atc agc agg gac atc cag gcc ccc gac ggg ctg gct<br>Tyr Asp Thr Val Ile Ser Arg Asp Ile Gln Ala Pro Asp Gly Leu Ala<br>465 470 475 480 | | | | 1440 |
| gtg gac tgg atc cac agc aac atc tac tgg acc gac tct gtc ctg ggc<br>Val Asp Trp Ile His Ser Asn Ile Tyr Trp Thr Asp Ser Val Leu Gly<br>485 490 495 | | | | 1488 |
| act gtc tct gtt gcg gat acc aag ggc gtg aag agg aaa acg tta ttc<br>Thr Val Ser Val Ala Asp Thr Lys Gly Val Lys Arg Lys Thr Leu Phe<br>500 505 510 | | | | 1536 |
| agg gag aac ggc tcc aag cca agg gcc atc gtg gtg gat cct gtt cat<br>Arg Glu Asn Gly Ser Lys Pro Arg Ala Ile Val Val Asp Pro Val His<br>515 520 525 | | | | 1584 |
| ggc ttc atg tac tgg act gac tgg gga act ccc gcc aag atc aag aaa<br>Gly Phe Met Tyr Trp Thr Asp Trp Gly Thr Pro Ala Lys Ile Lys Lys<br>530 535 540 | | | | 1632 |
| ggg ggc ctg aat ggt gtg gac atc tac tcg ctg gtg act gaa aac att<br>Gly Gly Leu Asn Gly Val Asp Ile Tyr Ser Leu Val Thr Glu Asn Ile<br>545 550 555 560 | | | | 1680 |
| cag tgg ccc aat ggc atc acc cta gat ctc ctc agt ggc cgc ctc tac<br>Gln Trp Pro Asn Gly Ile Thr Leu Asp Leu Leu Ser Gly Arg Leu Tyr<br>565 570 575 | | | | 1728 |
| tgg gtt gac tcc aaa ctt cac tcc atc tca agc atc gat gtc aat ggg<br>Trp Val Asp Ser Lys Leu His Ser Ile Ser Ser Ile Asp Val Asn Gly<br>580 585 590 | | | | 1776 |
| ggc aac cgg aag acc atc ttg gag gat gaa aag agg ctg gcc cac ccc<br>Gly Asn Arg Lys Thr Ile Leu Glu Asp Glu Lys Arg Leu Ala His Pro<br>595 600 605 | | | | 1824 |
| ttc tcc ttg gcc gtc ttt gag gac aaa gta ttt tgg aca gat atc atc<br>Phe Ser Leu Ala Val Phe Glu Asp Lys Val Phe Trp Thr Asp Ile Ile<br>610 615 620 | | | | 1872 |
| aac gaa gcc att ttc agt gcc aac cgc ctc aca ggt tcc gat gtc aac | | | | 1920 |

```
Asn Glu Ala Ile Phe Ser Ala Asn Arg Leu Thr Gly Ser Asp Val Asn
625                 630                 635                 640 ttg ttg gct gaa aac cta ctg tcc cca gag gat atg gtc ctc ttc cac      1968
Leu Leu Ala Glu Asn Leu Leu Ser Pro Glu Asp Met Val Leu Phe His
                    645                 650                 655 aac ctc acc cag cca aga gga gtg aac tgg tgt gag agg acc acc ctg      2016
Asn Leu Thr Gln Pro Arg Gly Val Asn Trp Cys Glu Arg Thr Thr Leu
                660                 665                 670 agc aat ggc ggc tgc cag tat ctg tgc ctc cct gcc ccg cag atc aac      2064
Ser Asn Gly Gly Cys Gln Tyr Leu Cys Leu Pro Ala Pro Gln Ile Asn
            675                 680                 685 ccc cac tcg ccc aag ttt acc tgc gcc tgc ccg gac ggc atg ctg ctg      2112
Pro His Ser Pro Lys Phe Thr Cys Ala Cys Pro Asp Gly Met Leu Leu
        690                 695                 700 gcc agg gac atg agg agc tgc ctc aca gag gct gag gct gca gtg gcc      2160
Ala Arg Asp Met Arg Ser Cys Leu Thr Glu Ala Glu Ala Ala Val Ala
705                 710                 715                 720 acc cag gag aca tcc acc gtc agg cta aag gtc agc tcc aca gcc gta      2208
Thr Gln Glu Thr Ser Thr Val Arg Leu Lys Val Ser Ser Thr Ala Val
                    725                 730                 735 agg aca cag cac aca acc acc cgg cct gtt ccc gac acc tcc cgg ctg      2256
Arg Thr Gln His Thr Thr Thr Arg Pro Val Pro Asp Thr Ser Arg Leu
                740                 745                 750 cct ggg gcc acc cct ggg ctc acc acg gtg gag ata gtg aca atg tct      2304
Pro Gly Ala Thr Pro Gly Leu Thr Thr Val Glu Ile Val Thr Met Ser
            755                 760                 765 cac caa gct ctg ggc gac gtt gct ggc aga gga aat gag aag aag ccc      2352
His Gln Ala Leu Gly Asp Val Ala Gly Arg Gly Asn Glu Lys Lys Pro
        770                 775                 780 agt agc gtg agg gct ctg tcc att gtc ctc ccc atc gtg ctc ctc gtc      2400
Ser Ser Val Arg Ala Leu Ser Ile Val Leu Pro Ile Val Leu Leu Val
785                 790                 795                 800 ttc ctt tgc ctg ggg gtc ttc ctt cta tgg aag aac tgg cgg ctt aag      2448
Phe Leu Cys Leu Gly Val Phe Leu Leu Trp Lys Asn Trp Arg Leu Lys
                    805                 810                 815 aac atc aac agc atc aac ttt gac aac ccc gtc tat cag aag acc aca      2496
Asn Ile Asn Ser Ile Asn Phe Asp Asn Pro Val Tyr Gln Lys Thr Thr
                820                 825                 830 gag gat gag gtc cac att tgc cac aac cag gac ggc tac agc tac ccc      2544
Glu Asp Glu Val His Ile Cys His Asn Gln Asp Gly Tyr Ser Tyr Pro
            835                 840                 845 tcg aga cag atg gtc agt ctg gag gat gac gtg gcg tga                  2583
Ser Arg Gln Met Val Ser Leu Glu Asp Asp Val Ala
        850                 855                 860

<210> SEQ ID NO 27
<211> LENGTH: 860
<212> TYPE: PRT
<213> ORGANISM: Artificial Sequence
<220> FEATURE:
<223> OTHER INFORMATION: Synthetic Construct

<400> SEQUENCE: 27

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
                20                  25                  30

Gln Cys Gln Asp Gly Lys Cys Ile Ser Tyr Lys Trp Val Cys Asp Gly
            35                  40                  45

Ser Ala Glu Cys Gln Asp Gly Ser Asp Glu Ser Gln Glu Thr Cys Leu
```

-continued

```
                50                  55                  60
Ser Val Thr Cys Lys Ser Gly Asp Phe Ser Cys Gly Arg Val Asn
65                  70                  75                  80
Arg Cys Ile Pro Gln Phe Trp Arg Cys Asp Gly Gln Val Asp Cys Asp
                85                  90                  95
Asn Gly Ser Asp Glu Gln Gly Cys Pro Pro Lys Thr Cys Ser Gln Asp
                100                 105                 110
Glu Phe Arg Cys His Asp Gly Lys Cys Ile Ser Arg Gln Phe Val Cys
                115                 120                 125
Asp Ser Asp Arg Asp Cys Leu Asp Gly Ser Asp Glu Ala Ser Cys Pro
                130                 135                 140
Val Leu Thr Cys Gly Pro Ala Ser Phe Gln Cys Asn Ser Ser Thr Cys
145                 150                 155                 160
Ile Pro Gln Leu Trp Ala Cys Asp Asn Asp Pro Asp Cys Glu Asp Gly
                165                 170                 175
Ser Asp Glu Trp Pro Gln Arg Cys Arg Gly Leu Tyr Val Phe Gln Gly
                180                 185                 190
Asp Ser Ser Pro Cys Ser Ala Phe Glu Phe His Cys Leu Ser Gly Glu
                195                 200                 205
Cys Ile His Ser Ser Trp Arg Cys Asp Gly Gly Pro Asp Cys Lys Asp
                210                 215                 220
Lys Ser Asp Glu Glu Asn Cys Ala Val Ala Thr Cys Arg Pro Asp Glu
225                 230                 235                 240
Phe Gln Cys Ser Asp Gly Asn Cys Ile His Gly Ser Arg Gln Cys Asp
                245                 250                 255
Arg Glu Tyr Asp Cys Lys Asp Met Ser Asp Glu Val Gly Cys Val Asn
                260                 265                 270
Val Thr Leu Cys Glu Gly Pro Asn Lys Phe Lys Cys His Ser Gly Glu
                275                 280                 285
Cys Ile Thr Leu Asp Lys Val Cys Asn Met Ala Arg Asp Cys Arg Asp
                290                 295                 300
Trp Ser Asp Glu Pro Ile Lys Glu Cys Gly Thr Asn Glu Cys Leu Asp
305                 310                 315                 320
Asn Asn Gly Gly Cys Ser His Val Cys Asn Asp Leu Lys Ile Gly Tyr
                325                 330                 335
Glu Cys Asp Cys Pro Asp Gly Phe Gln Leu Val Ala Gln Arg Arg Cys
                340                 345                 350
Glu Asp Ile Asp Glu Cys Gln Asp Pro Asp Thr Cys Ser Gln Leu Cys
                355                 360                 365
Val Asn Leu Glu Gly Gly Tyr Lys Cys Gln Cys Glu Glu Gly Phe Gln
                370                 375                 380
Leu Asp Pro His Thr Lys Ala Cys Lys Ala Val Gly Ser Ile Ala Tyr
385                 390                 395                 400
Leu Phe Phe Thr Asn Arg His Glu Val Arg Lys Met Thr Leu Asp Arg
                405                 410                 415
Ser Glu Tyr Thr Ser Leu Ile Pro Asn Leu Arg Asn Val Val Ala Leu
                420                 425                 430
Asp Thr Glu Val Ala Ser Asn Arg Ile Tyr Trp Ser Asp Leu Ser Gln
                435                 440                 445
Arg Met Ile Cys Ser Thr Gln Leu Asp Arg Ala His Gly Val Ser Ser
                450                 455                 460
Tyr Asp Thr Val Ile Ser Arg Asp Ile Gln Ala Pro Asp Gly Leu Ala
465                 470                 475                 480
```

Val Asp Trp Ile His Ser Asn Ile Tyr Trp Thr Asp Ser Val Leu Gly
            485                 490                 495

Thr Val Ser Val Ala Asp Thr Lys Gly Val Lys Arg Lys Thr Leu Phe
        500                 505                 510

Arg Glu Asn Gly Ser Lys Pro Arg Ala Ile Val Val Asp Pro Val His
    515                 520                 525

Gly Phe Met Tyr Trp Thr Asp Trp Gly Thr Pro Ala Lys Ile Lys Lys
530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
        595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830

Glu Asp Glu Val His Ile Cys His Asn Gln Asp Gly Tyr Ser Tyr Pro
        835                 840                 845

Ser Arg Gln Met Val Ser Leu Glu Asp Asp Val Ala
    850                 855                 860

<210> SEQ ID NO 28
<211> LENGTH: 2583
<212> TYPE: DNA
<213> ORGANISM: Artificial Sequence
<220> FEATURE:

<223> OTHER INFORMATION: hLDLR N295D with leader
<220> FEATURE:
<221> NAME/KEY: CDS
<222> LOCATION: (1)..(2583)

<400> SEQUENCE: 28

| | | | | | | | | | | | | | | | | |
|---|---|---|---|---|---|---|---|---|---|---|---|---|---|---|---|---|
| atg | ggg | ccc | tgg | ggc | tgg | aaa | ttg | cgc | tgg | acc | gtc | gcc | ttg | ctc | ctc | 48 |
| Met | Gly | Pro | Trp | Gly | Trp | Lys | Leu | Arg | Trp | Thr | Val | Ala | Leu | Leu | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcc | gcg | gcg | ggg | act | gca | gtg | ggc | gac | aga | tgt | gaa | aga | aac | gag | ttc | 96 |
| Ala | Ala | Ala | Gly | Thr | Ala | Val | Gly | Asp | Arg | Cys | Glu | Arg | Asn | Glu | Phe | |
| | | | 20 | | | | | 25 | | | | | 30 | | | |

| | | | | | | | | | | | | | | | | |
|---|---|---|---|---|---|---|---|---|---|---|---|---|---|---|---|---|
| cag | tgc | caa | gac | ggg | aaa | tgc | atc | tcc | tac | aag | tgg | gtc | tgc | gat | ggc | 144 |
| Gln | Cys | Gln | Asp | Gly | Lys | Cys | Ile | Ser | Tyr | Lys | Trp | Val | Cys | Asp | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| agc | gct | gag | tgc | cag | gat | ggc | tct | gat | gag | tcc | cag | gag | acg | tgc | ttg | 192 |
| Ser | Ala | Glu | Cys | Gln | Asp | Gly | Ser | Asp | Glu | Ser | Gln | Glu | Thr | Cys | Leu | |
| | 50 | | | | | 55 | | | | | 60 | | | | | |

| | | | | | | | | | | | | | | | | |
|---|---|---|---|---|---|---|---|---|---|---|---|---|---|---|---|---|
| tct | gtc | acc | tgc | aaa | tcc | ggg | gac | ttc | agc | tgt | ggg | ggc | cgt | gtc | aac | 240 |
| Ser | Val | Thr | Cys | Lys | Ser | Gly | Asp | Phe | Ser | Cys | Gly | Gly | Arg | Val | Asn | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cgc | tgc | att | cct | cag | ttc | tgg | agg | tgc | gat | ggc | caa | gtg | gac | tgc | gac | 288 |
| Arg | Cys | Ile | Pro | Gln | Phe | Trp | Arg | Cys | Asp | Gly | Gln | Val | Asp | Cys | Asp | |
| | | | | 85 | | | | | 90 | | | | | 95 | | |

| | | | | | | | | | | | | | | | | |
|---|---|---|---|---|---|---|---|---|---|---|---|---|---|---|---|---|
| aac | ggc | tca | gac | gag | caa | ggc | tgt | ccc | ccc | aag | acg | tgc | tcc | cag | gac | 336 |
| Asn | Gly | Ser | Asp | Glu | Gln | Gly | Cys | Pro | Pro | Lys | Thr | Cys | Ser | Gln | Asp | |
| | | | 100 | | | | | 105 | | | | | 110 | | | |

| | | | | | | | | | | | | | | | | |
|---|---|---|---|---|---|---|---|---|---|---|---|---|---|---|---|---|
| gag | ttt | cgc | tgc | cac | gat | ggg | aag | tgc | atc | tct | cgg | cag | ttc | gtc | tgt | 384 |
| Glu | Phe | Arg | Cys | His | Asp | Gly | Lys | Cys | Ile | Ser | Arg | Gln | Phe | Val | Cys | |
| | | 115 | | | | | 120 | | | | | 125 | | | | |

| | | | | | | | | | | | | | | | | |
|---|---|---|---|---|---|---|---|---|---|---|---|---|---|---|---|---|
| gac | tca | gac | cgg | gac | tgc | ttg | gac | ggc | tca | gac | gag | gcc | tcc | tgc | ccg | 432 |
| Asp | Ser | Asp | Arg | Asp | Cys | Leu | Asp | Gly | Ser | Asp | Glu | Ala | Ser | Cys | Pro | |
| | 130 | | | | | 135 | | | | | 140 | | | | | |

| | | | | | | | | | | | | | | | | |
|---|---|---|---|---|---|---|---|---|---|---|---|---|---|---|---|---|
| gtg | ctc | acc | tgt | ggt | ccc | gcc | agc | ttc | cag | tgc | aac | agc | tcc | acc | tgc | 480 |
| Val | Leu | Thr | Cys | Gly | Pro | Ala | Ser | Phe | Gln | Cys | Asn | Ser | Ser | Thr | Cys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| atc | ccc | cag | ctg | tgg | gcc | tgc | gac | aac | gac | ccc | gac | tgc | gaa | gat | ggc | 528 |
| Ile | Pro | Gln | Leu | Trp | Ala | Cys | Asp | Asn | Asp | Pro | Asp | Cys | Glu | Asp | Gly | |
| | | | | 165 | | | | | 170 | | | | | 175 | | |

| | | | | | | | | | | | | | | | | |
|---|---|---|---|---|---|---|---|---|---|---|---|---|---|---|---|---|
| tcg | gat | gag | tgg | ccg | cag | cgc | tgt | agg | ggt | ctt | tac | gtg | ttc | caa | ggg | 576 |
| Ser | Asp | Glu | Trp | Pro | Gln | Arg | Cys | Arg | Gly | Leu | Tyr | Val | Phe | Gln | Gly | |
| | | | 180 | | | | | 185 | | | | | 190 | | | |

| | | | | | | | | | | | | | | | | |
|---|---|---|---|---|---|---|---|---|---|---|---|---|---|---|---|---|
| gac | agt | agc | ccc | tgc | tcg | gcc | ttc | gag | ttc | cac | tgc | cta | agt | ggc | gag | 624 |
| Asp | Ser | Ser | Pro | Cys | Ser | Ala | Phe | Glu | Phe | His | Cys | Leu | Ser | Gly | Glu | |
| | | 195 | | | | | 200 | | | | | 205 | | | | |

| | | | | | | | | | | | | | | | | |
|---|---|---|---|---|---|---|---|---|---|---|---|---|---|---|---|---|
| tgc | atc | cac | tcc | agc | tgg | cgc | tgt | gat | ggt | ggc | ccc | gac | tgc | aag | gac | 672 |
| Cys | Ile | His | Ser | Ser | Trp | Arg | Cys | Asp | Gly | Gly | Pro | Asp | Cys | Lys | Asp | |
| | 210 | | | | | 215 | | | | | 220 | | | | | |

| | | | | | | | | | | | | | | | | |
|---|---|---|---|---|---|---|---|---|---|---|---|---|---|---|---|---|
| aaa | tct | gac | gag | gaa | aac | tgc | gct | gtg | gcc | acc | tgt | cgc | cct | gac | gaa | 720 |
| Lys | Ser | Asp | Glu | Glu | Asn | Cys | Ala | Val | Ala | Thr | Cys | Arg | Pro | Asp | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ttc | cag | tgc | tct | gat | gga | aac | tgc | atc | cat | ggc | agc | cgg | cag | tgt | gac | 768 |
| Phe | Gln | Cys | Ser | Asp | Gly | Asn | Cys | Ile | His | Gly | Ser | Arg | Gln | Cys | Asp | |
| | | | | 245 | | | | | 250 | | | | | 255 | | |

| | | | | | | | | | | | | | | | | |
|---|---|---|---|---|---|---|---|---|---|---|---|---|---|---|---|---|
| cgg | gaa | tat | gac | tgc | aag | gac | atg | agc | gat | gaa | gtt | ggc | tgc | gtt | aat | 816 |
| Arg | Glu | Tyr | Asp | Cys | Lys | Asp | Met | Ser | Asp | Glu | Val | Gly | Cys | Val | Asn | |
| | | | 260 | | | | | 265 | | | | | 270 | | | |

| | | | | | | | | | | | | | | | | |
|---|---|---|---|---|---|---|---|---|---|---|---|---|---|---|---|---|
| gtg | aca | ctc | tgc | gag | gga | ccc | aac | aag | ttc | aag | tgt | cac | agc | ggc | gaa | 864 |
| Val | Thr | Leu | Cys | Glu | Gly | Pro | Asn | Lys | Phe | Lys | Cys | His | Ser | Gly | Glu | |
| | | 275 | | | | | 280 | | | | | 285 | | | | |

-continued

| | |
|---|---|
| tgc atc acc ctg gac aaa gtc tgc aac atg gct aga gac tgc cgg gac<br>Cys Ile Thr Leu Asp Lys Val Cys Asn Met Ala Arg Asp Cys Arg Asp<br>290                     295                   300 | 912 |
| tgg tca gat gaa ccc atc aaa gag tgc ggg acc gac gaa tgc ttg gac<br>Trp Ser Asp Glu Pro Ile Lys Glu Cys Gly Thr Asp Glu Cys Leu Asp<br>305                     310                   315               320 | 960 |
| aac aac ggc ggc tgt tcc cac gtc tgc aat gac ctt aag atc ggc tac<br>Asn Asn Gly Gly Cys Ser His Val Cys Asn Asp Leu Lys Ile Gly Tyr<br>                 325                   330                   335 | 1008 |
| gag tgc ctg tgc ccc gac ggc ttc cag ctg gtg gcc cag cga aga tgc<br>Glu Cys Leu Cys Pro Asp Gly Phe Gln Leu Val Ala Gln Arg Arg Cys<br>           340                   345                   350 | 1056 |
| gaa gat atc gat gag tgt cag gat ccc gac acc tgc agc cag ctc tgc<br>Glu Asp Ile Asp Glu Cys Gln Asp Pro Asp Thr Cys Ser Gln Leu Cys<br>355                     360                   365 | 1104 |
| gtg aac ctg gag ggt ggc tac aag tgc cag tgt gag gaa ggc ttc cag<br>Val Asn Leu Glu Gly Gly Tyr Lys Cys Gln Cys Glu Glu Gly Phe Gln<br>     370                   375                   380 | 1152 |
| ctg gac ccc cac acg aag gcc tgc aag gct gtg ggc tcc atc gcc tac<br>Leu Asp Pro His Thr Lys Ala Cys Lys Ala Val Gly Ser Ile Ala Tyr<br>385                     390                   395               400 | 1200 |
| ctc ttc ttc acc aac cgg cac gag gtc agg aag atg acg ctg gac cgg<br>Leu Phe Phe Thr Asn Arg His Glu Val Arg Lys Met Thr Leu Asp Arg<br>                 405                   410                   415 | 1248 |
| agc gag tac acc agc ctc atc ccc aac ctg agg aac gtg gtc gct ctg<br>Ser Glu Tyr Thr Ser Leu Ile Pro Asn Leu Arg Asn Val Val Ala Leu<br>           420                   425                   430 | 1296 |
| gac acg gag gtg gcc agc aat aga atc tac tgg tct gac ctg tcc cag<br>Asp Thr Glu Val Ala Ser Asn Arg Ile Tyr Trp Ser Asp Leu Ser Gln<br>       435                   440                   445 | 1344 |
| aga atg atc tgc agc acc cag ctt gac aga gcc cac ggc gtc tct tcc<br>Arg Met Ile Cys Ser Thr Gln Leu Asp Arg Ala His Gly Val Ser Ser<br>450                     455                   460 | 1392 |
| tat gac acc gtc atc agc agg gac atc cag gcc ccc gac ggg ctg gct<br>Tyr Asp Thr Val Ile Ser Arg Asp Ile Gln Ala Pro Asp Gly Leu Ala<br>465                     470                   475               480 | 1440 |
| gtg gac tgg atc cac agc aac atc tac tgg acc gac tct gtc ctg ggc<br>Val Asp Trp Ile His Ser Asn Ile Tyr Trp Thr Asp Ser Val Leu Gly<br>                 485                   490                   495 | 1488 |
| act gtc tct gtt gcg gat acc aag ggc gtg aag agg aaa acg tta ttc<br>Thr Val Ser Val Ala Asp Thr Lys Gly Val Lys Arg Lys Thr Leu Phe<br>           500                   505                   510 | 1536 |
| agg gag aac ggc tcc aag cca agg gcc atc gtg gtg gat cct gtt cat<br>Arg Glu Asn Gly Ser Lys Pro Arg Ala Ile Val Val Asp Pro Val His<br>       515                   520                   525 | 1584 |
| ggc ttc atg tac tgg act gac tgg gga act ccc gcc aag atc aag aaa<br>Gly Phe Met Tyr Trp Thr Asp Trp Gly Thr Pro Ala Lys Ile Lys Lys<br>530                     535                   540 | 1632 |
| ggg ggc ctg aat ggt gtg gac atc tac tcg ctg gtg act gaa aac att<br>Gly Gly Leu Asn Gly Val Asp Ile Tyr Ser Leu Val Thr Glu Asn Ile<br>545                     550                   555               560 | 1680 |
| cag tgg ccc aat ggc atc acc cta gat ctc ctc agt ggc cgc ctc tac<br>Gln Trp Pro Asn Gly Ile Thr Leu Asp Leu Leu Ser Gly Arg Leu Tyr<br>                 565                   570                   575 | 1728 |
| tgg gtt gac tcc aaa ctt cac tcc atc tca agc atc gat gtc aat ggg<br>Trp Val Asp Ser Lys Leu His Ser Ile Ser Ser Ile Asp Val Asn Gly<br>           580                   585                   590 | 1776 |
| ggc aac cgg aag acc atc ttg gag gat gaa aag agg ctg gcc cac ccc<br>Gly Asn Arg Lys Thr Ile Leu Glu Asp Glu Lys Arg Leu Ala His Pro<br>       595                   600                   605 | 1824 |

-continued

```
ttc tcc ttg gcc gtc ttt gag gac aaa gta ttt tgg aca gat atc atc       1872
Phe Ser Leu Ala Val Phe Glu Asp Lys Val Phe Trp Thr Asp Ile Ile
610                 615                 620 aac gaa gcc att ttc agt gcc aac cgc ctc aca ggt tcc gat gtc aac       1920
Asn Glu Ala Ile Phe Ser Ala Asn Arg Leu Thr Gly Ser Asp Val Asn
625                 630                 635                 640 ttg ttg gct gaa aac cta ctg tcc cca gag gat atg gtc ctc ttc cac       1968
Leu Leu Ala Glu Asn Leu Leu Ser Pro Glu Asp Met Val Leu Phe His
            645                 650                 655 aac ctc acc cag cca aga gga gtg aac tgg tgt gag agg acc acc ctg       2016
Asn Leu Thr Gln Pro Arg Gly Val Asn Trp Cys Glu Arg Thr Thr Leu
        660                 665                 670 agc aat ggc ggc tgc cag tat ctg tgc ctc cct gcc ccg cag atc aac       2064
Ser Asn Gly Gly Cys Gln Tyr Leu Cys Leu Pro Ala Pro Gln Ile Asn
    675                 680                 685 ccc cac tcg ccc aag ttt acc tgc gcc tgc ccg gac ggc atg ctg ctg       2112
Pro His Ser Pro Lys Phe Thr Cys Ala Cys Pro Asp Gly Met Leu Leu
690                 695                 700 gcc agg gac atg agg agc tgc ctc aca gag gct gag gct gca gtg gcc       2160
Ala Arg Asp Met Arg Ser Cys Leu Thr Glu Ala Glu Ala Ala Val Ala
705                 710                 715                 720 acc cag gag aca tcc acc gtc agg cta aag gtc agc tcc aca gcc gta       2208
Thr Gln Glu Thr Ser Thr Val Arg Leu Lys Val Ser Ser Thr Ala Val
                725                 730                 735 agg aca cag cac aca acc acc cgg cct gtt ccc gac acc tcc cgg ctg       2256
Arg Thr Gln His Thr Thr Thr Arg Pro Val Pro Asp Thr Ser Arg Leu
            740                 745                 750 cct ggg gcc acc cct ggg ctc acc acg gtg gag ata gtg aca atg tct       2304
Pro Gly Ala Thr Pro Gly Leu Thr Thr Val Glu Ile Val Thr Met Ser
        755                 760                 765 cac caa gct ctg ggc gac gtt gct ggc aga gga aat gag aag aag ccc       2352
His Gln Ala Leu Gly Asp Val Ala Gly Arg Gly Asn Glu Lys Lys Pro
    770                 775                 780 agt agc gtg agg gct ctg tcc att gtc ctc ccc atc gtg ctc ctc gtc       2400
Ser Ser Val Arg Ala Leu Ser Ile Val Leu Pro Ile Val Leu Leu Val
785                 790                 795                 800 ttc ctt tgc ctg ggg gtc ttc ctt cta tgg aag aac tgg cgg ctt aag       2448
Phe Leu Cys Leu Gly Val Phe Leu Leu Trp Lys Asn Trp Arg Leu Lys
                805                 810                 815 aac atc aac agc atc aac ttt gac aac ccc gtc tat cag aag acc aca       2496
Asn Ile Asn Ser Ile Asn Phe Asp Asn Pro Val Tyr Gln Lys Thr Thr
            820                 825                 830 gag gat gag gtc cac att tgc cac aac cag gac ggc tac agc tac ccc       2544
Glu Asp Glu Val His Ile Cys His Asn Gln Asp Gly Tyr Ser Tyr Pro
        835                 840                 845 tcg aga cag atg gtc agt ctg gag gat gac gtg gcg tga               2583
Ser Arg Gln Met Val Ser Leu Glu Asp Asp Val Ala
    850                 855                 860

<210> SEQ ID NO 29
<211> LENGTH: 860
<212> TYPE: PRT
<213> ORGANISM: Artificial Sequence
<220> FEATURE:
<223> OTHER INFORMATION: Synthetic Construct

<400> SEQUENCE: 29

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
```

```
                   20                  25                  30
Gln Cys Gln Asp Gly Lys Cys Ile Ser Tyr Lys Trp Val Cys Asp Gly
                35                  40                  45
Ser Ala Glu Cys Gln Asp Gly Ser Asp Glu Ser Gln Glu Thr Cys Leu
50                  55                  60
Ser Val Thr Cys Lys Ser Gly Asp Phe Ser Cys Gly Gly Arg Val Asn
65                  70                  75                  80
Arg Cys Ile Pro Gln Phe Trp Arg Cys Asp Gly Gln Val Asp Cys Asp
                85                  90                  95
Asn Gly Ser Asp Glu Gln Gly Cys Pro Pro Lys Thr Cys Ser Gln Asp
                100                 105                 110
Glu Phe Arg Cys His Asp Gly Lys Cys Ile Ser Arg Gln Phe Val Cys
                115                 120                 125
Asp Ser Asp Arg Asp Cys Leu Asp Gly Ser Asp Glu Ala Ser Cys Pro
                130                 135                 140
Val Leu Thr Cys Gly Pro Ala Ser Phe Gln Cys Asn Ser Ser Thr Cys
145                 150                 155                 160
Ile Pro Gln Leu Trp Ala Cys Asp Asn Asp Pro Asp Cys Glu Asp Gly
                165                 170                 175
Ser Asp Glu Trp Pro Gln Arg Cys Arg Gly Leu Tyr Val Phe Gln Gly
                180                 185                 190
Asp Ser Ser Pro Cys Ser Ala Phe Glu Phe His Cys Leu Ser Gly Glu
                195                 200                 205
Cys Ile His Ser Ser Trp Arg Cys Asp Gly Gly Pro Asp Cys Lys Asp
                210                 215                 220
Lys Ser Asp Glu Glu Asn Cys Ala Val Ala Thr Cys Arg Pro Asp Glu
225                 230                 235                 240
Phe Gln Cys Ser Asp Gly Asn Cys Ile His Gly Ser Arg Gln Cys Asp
                245                 250                 255
Arg Glu Tyr Asp Cys Lys Asp Met Ser Asp Glu Val Gly Cys Val Asn
                260                 265                 270
Val Thr Leu Cys Glu Gly Pro Asn Lys Phe Lys Cys His Ser Gly Glu
                275                 280                 285
Cys Ile Thr Leu Asp Lys Val Cys Asn Met Ala Arg Asp Cys Arg Asp
                290                 295                 300
Trp Ser Asp Glu Pro Ile Lys Glu Cys Gly Thr Asp Glu Cys Leu Asp
305                 310                 315                 320
Asn Asn Gly Gly Cys Ser His Val Cys Asn Asp Leu Lys Ile Gly Tyr
                325                 330                 335
Glu Cys Leu Cys Pro Asp Gly Phe Gln Leu Val Ala Gln Arg Arg Cys
                340                 345                 350
Glu Asp Ile Asp Glu Cys Gln Asp Pro Asp Thr Cys Ser Gln Leu Cys
                355                 360                 365
Val Asn Leu Glu Gly Gly Tyr Lys Cys Gln Cys Glu Glu Gly Phe Gln
                370                 375                 380
Leu Asp Pro His Thr Lys Ala Cys Lys Ala Val Gly Ser Ile Ala Tyr
385                 390                 395                 400
Leu Phe Phe Thr Asn Arg His Glu Val Arg Lys Met Thr Leu Asp Arg
                405                 410                 415
Ser Glu Tyr Thr Ser Leu Ile Pro Asn Leu Arg Asn Val Val Ala Leu
                420                 425                 430
Asp Thr Glu Val Ala Ser Asn Arg Ile Tyr Trp Ser Asp Leu Ser Gln
                435                 440                 445
```

```
Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
                580                 585                 590

Gly Asn Arg Lys Thr Ile Leu Glu Asp Glu Lys Arg Leu Ala His Pro
            595                 600                 605

Phe Ser Leu Ala Val Phe Glu Asp Lys Val Phe Trp Thr Asp Ile Ile
610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
                660                 665                 670

Ser Asn Gly Gly Cys Gln Tyr Leu Cys Leu Pro Ala Pro Gln Ile Asn
            675                 680                 685

Pro His Ser Pro Lys Phe Thr Cys Ala Cys Pro Asp Gly Met Leu Leu
690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
                820                 825                 830

Glu Asp Glu Val His Ile Cys His Asn Gln Asp Gly Tyr Ser Tyr Pro
            835                 840                 845

Ser Arg Gln Met Val Ser Leu Glu Asp Asp Val Ala
850                 855                 860
```

<210> SEQ ID NO 30
<211> LENGTH: 2583
<212> TYPE: DNA
<213> ORGANISM: Artificial Sequence
<220> FEATURE:
<223> OTHER INFORMATION: synthetic hLDLR variant N309A with leader
<220> FEATURE:
<221> NAME/KEY: CDS
<222> LOCATION: (1)..(2583)

<400> SEQUENCE: 30

```
atg ggg ccc tgg ggc tgg aaa ttg cgc tgg acc gtc gcc ttg ctc ctc      48
Met Gly Pro Trp Gly Trp Lys Leu Arg Trp Thr Val Ala Leu Leu Leu
1               5                   10                  15 gcc gcg gcg ggg act gca gtg ggc gac aga tgt gaa aga aac gag ttc      96
Ala Ala Ala Gly Thr Ala Val Gly Asp Arg Cys Glu Arg Asn Glu Phe
            20                  25                  30 cag tgc caa gac ggg aaa tgc atc tcc tac aag tgg gtc tgc gat ggc     144
Gln Cys Gln Asp Gly Lys Cys Ile Ser Tyr Lys Trp Val Cys Asp Gly
        35                  40                  45 agc gct gag tgc cag gat ggc tct gat gag tcc cag gag acg tgc ttg     192
Ser Ala Glu Cys Gln Asp Gly Ser Asp Glu Ser Gln Glu Thr Cys Leu
    50                  55                  60 tct gtc acc tgc aaa tcc ggg gac ttc agc tgt ggg ggc cgt gtc aac     240
Ser Val Thr Cys Lys Ser Gly Asp Phe Ser Cys Gly Gly Arg Val Asn
65                  70                  75                  80 cgc tgc att cct cag ttc tgg agg tgc gat ggc caa gtg gac tgc gac     288
Arg Cys Ile Pro Gln Phe Trp Arg Cys Asp Gly Gln Val Asp Cys Asp
                85                  90                  95 aac ggc tca gac gag caa ggc tgt ccc ccc aag acg tgc tcc cag gac     336
Asn Gly Ser Asp Glu Gln Gly Cys Pro Pro Lys Thr Cys Ser Gln Asp
            100                 105                 110 gag ttt cgc tgc cac gat ggg aag tgc atc tct cgg cag ttc gtc tgt     384
Glu Phe Arg Cys His Asp Gly Lys Cys Ile Ser Arg Gln Phe Val Cys
        115                 120                 125 gac tca gac cgg gac tgc ttg gac ggc tca gac gag gcc tcc tgc ccg     432
Asp Ser Asp Arg Asp Cys Leu Asp Gly Ser Asp Glu Ala Ser Cys Pro
    130                 135                 140 gtg ctc acc tgt ggt ccc gcc agc ttc cag tgc aac agc tcc acc tgc     480
Val Leu Thr Cys Gly Pro Ala Ser Phe Gln Cys Asn Ser Ser Thr Cys
145                 150                 155                 160 atc ccc cag ctg tgg gcc tgc gac aac gac ccc gac tgc gaa gat ggc     528
Ile Pro Gln Leu Trp Ala Cys Asp Asn Asp Pro Asp Cys Glu Asp Gly
                165                 170                 175 tcg gat gag tgg ccg cag cgc tgt agg ggt ctt tac gtg ttc caa ggg     576
Ser Asp Glu Trp Pro Gln Arg Cys Arg Gly Leu Tyr Val Phe Gln Gly
            180                 185                 190 gac agt agc ccc tgc tcg gcc ttc gag ttc cac tgc cta agt ggc gag     624
Asp Ser Ser Pro Cys Ser Ala Phe Glu Phe His Cys Leu Ser Gly Glu
        195                 200                 205 tgc atc cac tcc agc tgg cgc tgt gat ggt ggc ccc gac tgc aag gac     672
Cys Ile His Ser Ser Trp Arg Cys Asp Gly Gly Pro Asp Cys Lys Asp
    210                 215                 220 aaa tct gac gag gaa aac tgc gct gtg gcc acc tgt cgc cct gac gaa     720
Lys Ser Asp Glu Glu Asn Cys Ala Val Ala Thr Cys Arg Pro Asp Glu
225                 230                 235                 240 ttc cag tgc tct gat gga aac tgc atc cat ggc agc cgg cag tgt gac     768
Phe Gln Cys Ser Asp Gly Asn Cys Ile His Gly Ser Arg Gln Cys Asp
                245                 250                 255 cgg gaa tat gac tgc aag gac atg agc gat gaa gtt ggc tgc gtt aat     816
Arg Glu Tyr Asp Cys Lys Asp Met Ser Asp Glu Val Gly Cys Val Asn
```

```
                260                 265                 270
gtg aca ctc tgc gag gga ccc aac aag ttc aag tgt cac agc ggc gaa     864
Val Thr Leu Cys Glu Gly Pro Asn Lys Phe Lys Cys His Ser Gly Glu
        275                 280                 285 tgc atc acc ctg gac aaa gtc tgc aac atg gct aga gac tgc cgg gac     912
Cys Ile Thr Leu Asp Lys Val Cys Asn Met Ala Arg Asp Cys Arg Asp
        290                 295                 300 tgg tca gat gaa ccc atc aaa gag tgc ggg acc aac gaa tgc ttg gac     960
Trp Ser Asp Glu Pro Ile Lys Glu Cys Gly Thr Asn Glu Cys Leu Asp
305                 310                 315                 320 aac aac ggc ggc tgt tcc cac gtc tgc gct gac ctt aag atc ggc tac    1008
Asn Asn Gly Gly Cys Ser His Val Cys Ala Asp Leu Lys Ile Gly Tyr
                325                 330                 335 gag tgc ctg tgc ccc gac ggc ttc cag ctg gtg gcc cag cga aga tgc    1056
Glu Cys Leu Cys Pro Asp Gly Phe Gln Leu Val Ala Gln Arg Arg Cys
            340                 345                 350 gaa gat atc gat gag tgt cag gat ccc gac acc tgc agc cag ctc tgc    1104
Glu Asp Ile Asp Glu Cys Gln Asp Pro Asp Thr Cys Ser Gln Leu Cys
        355                 360                 365 gtg aac ctg gag ggt ggc tac aag tgc cag tgt gag gaa ggc ttc cag    1152
Val Asn Leu Glu Gly Gly Tyr Lys Cys Gln Cys Glu Glu Gly Phe Gln
370                 375                 380 ctg gac ccc cac acg aag gcc tgc aag gct gtg ggc tcc atc gcc tac    1200
Leu Asp Pro His Thr Lys Ala Cys Lys Ala Val Gly Ser Ile Ala Tyr
385                 390                 395                 400 ctc ttc ttc acc aac cgg cac gag gtc agg aag atg acg ctg gac cgg    1248
Leu Phe Phe Thr Asn Arg His Glu Val Arg Lys Met Thr Leu Asp Arg
                405                 410                 415 agc gag tac acc agc ctc atc ccc aac ctg agg aac gtg gtc gct ctg    1296
Ser Glu Tyr Thr Ser Leu Ile Pro Asn Leu Arg Asn Val Val Ala Leu
            420                 425                 430 gac acg gag gtg gcc agc aat aga atc tac tgg tct gac ctg tcc cag    1344
Asp Thr Glu Val Ala Ser Asn Arg Ile Tyr Trp Ser Asp Leu Ser Gln
        435                 440                 445 aga atg atc tgc agc acc cag ctt gac aga gcc cac ggc gtc tct tcc    1392
Arg Met Ile Cys Ser Thr Gln Leu Asp Arg Ala His Gly Val Ser Ser
450                 455                 460 tat gac acc gtc atc agc agg gac atc cag gcc ccc gac ggg ctg gct    1440
Tyr Asp Thr Val Ile Ser Arg Asp Ile Gln Ala Pro Asp Gly Leu Ala
465                 470                 475                 480 gtg gac tgg atc cac agc aac atc tac tgg acc gac tct gtc ctg ggc    1488
Val Asp Trp Ile His Ser Asn Ile Tyr Trp Thr Asp Ser Val Leu Gly
                485                 490                 495 act gtc tct gtt gcg gat acc aag ggc gtg aag agg aaa acg tta ttc    1536
Thr Val Ser Val Ala Asp Thr Lys Gly Val Lys Arg Lys Thr Leu Phe
            500                 505                 510 agg gag aac ggc tcc aag cca agg gcc atc gtg gtg gat cct gtt cat    1584
Arg Glu Asn Gly Ser Lys Pro Arg Ala Ile Val Val Asp Pro Val His
        515                 520                 525 ggc ttc atg tac tgg act gac tgg gga act ccc gcc aag atc aag aaa    1632
Gly Phe Met Tyr Trp Thr Asp Trp Gly Thr Pro Ala Lys Ile Lys Lys
530                 535                 540 ggg ggc ctg aat ggt gtg gac atc tac tcg ctg gtg act gaa aac att    1680
Gly Gly Leu Asn Gly Val Asp Ile Tyr Ser Leu Val Thr Glu Asn Ile
545                 550                 555                 560 cag tgg ccc aat ggc atc acc cta gat ctc ctc agt ggc cgc ctc tac    1728
Gln Trp Pro Asn Gly Ile Thr Leu Asp Leu Leu Ser Gly Arg Leu Tyr
                565                 570                 575 tgg gtt gac tcc aaa ctt cac tcc atc tca agc atc gat gtc aat ggg    1776
```

```
Trp Val Asp Ser Lys Leu His Ser Ile Ser Ser Ile Asp Val Asn Gly
            580                 585                 590 ggc aac cgg aag acc atc ttg gag gat gaa aag agg ctg gcc cac ccc     1824
Gly Asn Arg Lys Thr Ile Leu Glu Asp Glu Lys Arg Leu Ala His Pro
        595                 600                 605 ttc tcc ttg gcc gtc ttt gag gac aaa gta ttt tgg aca gat atc atc     1872
Phe Ser Leu Ala Val Phe Glu Asp Lys Val Phe Trp Thr Asp Ile Ile
610                 615                 620 aac gaa gcc att ttc agt gcc aac cgc ctc aca ggt tcc gat gtc aac     1920
Asn Glu Ala Ile Phe Ser Ala Asn Arg Leu Thr Gly Ser Asp Val Asn
625                 630                 635                 640 ttg ttg gct gaa aac cta ctg tcc cca gag gat atg gtc ctc ttc cac     1968
Leu Leu Ala Glu Asn Leu Leu Ser Pro Glu Asp Met Val Leu Phe His
                645                 650                 655 aac ctc acc cag cca aga gga gtg aac tgg tgt gag agg acc acc ctg     2016
Asn Leu Thr Gln Pro Arg Gly Val Asn Trp Cys Glu Arg Thr Thr Leu
            660                 665                 670 agc aat ggc ggc tgc cag tat ctg tgc ctc cct gcc ccg cag atc aac     2064
Ser Asn Gly Gly Cys Gln Tyr Leu Cys Leu Pro Ala Pro Gln Ile Asn
        675                 680                 685 ccc cac tcg ccc aag ttt acc tgc gcc tgc ccg gac ggc atg ctg ctg     2112
Pro His Ser Pro Lys Phe Thr Cys Ala Cys Pro Asp Gly Met Leu Leu
690                 695                 700 gcc agg gac atg agg agc tgc ctc aca gag gct gag gct gca gtg gcc     2160
Ala Arg Asp Met Arg Ser Cys Leu Thr Glu Ala Glu Ala Ala Val Ala
705                 710                 715                 720 acc cag gag aca tcc acc gtc agg cta aag gtc agc tcc aca gcc gta     2208
Thr Gln Glu Thr Ser Thr Val Arg Leu Lys Val Ser Ser Thr Ala Val
                725                 730                 735 agg aca cag cac aca acc acc cgg cct gtt ccc gac acc tcc cgg ctg     2256
Arg Thr Gln His Thr Thr Thr Arg Pro Val Pro Asp Thr Ser Arg Leu
            740                 745                 750 cct ggg gcc acc cct ggg ctc acc acg gtg gag ata gtg aca atg tct     2304
Pro Gly Ala Thr Pro Gly Leu Thr Thr Val Glu Ile Val Thr Met Ser
        755                 760                 765 cac caa gct ctg ggc gac gtt gct ggc aga gga aat gag aag aag ccc     2352
His Gln Ala Leu Gly Asp Val Ala Gly Arg Gly Asn Glu Lys Lys Pro
770                 775                 780 agt agc gtg agg gct ctg tcc att gtc ctc ccc atc gtg ctc ctc gtc     2400
Ser Ser Val Arg Ala Leu Ser Ile Val Leu Pro Ile Val Leu Leu Val
785                 790                 795                 800 ttc ctt tgc ctg ggg gtc ttc ctt cta tgg aag aac tgg cgg ctt aag     2448
Phe Leu Cys Leu Gly Val Phe Leu Leu Trp Lys Asn Trp Arg Leu Lys
                805                 810                 815 aac atc aac agc atc aac ttt gac aac ccc gtc tat cag aag acc aca     2496
Asn Ile Asn Ser Ile Asn Phe Asp Asn Pro Val Tyr Gln Lys Thr Thr
            820                 825                 830 gag gat gag gtc cac att tgc cac aac cag gac ggc tac agc tac ccc     2544
Glu Asp Glu Val His Ile Cys His Asn Gln Asp Gly Tyr Ser Tyr Pro
        835                 840                 845 tcg aga cag atg gtc agt ctg gag gat gac gtg gcg tga                 2583
Ser Arg Gln Met Val Ser Leu Glu Asp Asp Val Ala
850                 855                 860

<210> SEQ ID NO 31
<211> LENGTH: 860
<212> TYPE: PRT
<213> ORGANISM: Artificial Sequence
<220> FEATURE:
<223> OTHER INFORMATION: Synthetic Construct
```

```
<400> SEQUENCE: 31

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Ala Asp Leu Lys Ile Gly Tyr
                325                 330                 335

Glu Cys Leu Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415
```

```
Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
            435                 440                 445

Arg Met Ile Cys Ser Thr Gln Leu Asp Arg Ala His Gly Val Ser Ser
            450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
            515                 520                 525

Gly Phe Met Tyr Trp Thr Asp Trp Gly Thr Pro Ala Lys Ile Lys Lys
            530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro
            595                 600                 605

Phe Ser Leu Ala Val Phe Glu Asp Lys Val Phe Trp Thr Asp Ile Ile
            610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
            675                 680                 685

Pro His Ser Pro Lys Phe Thr Cys Ala Cys Pro Asp Gly Met Leu Leu
            690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
            755                 760                 765

His Gln Ala Leu Gly Asp Val Ala Gly Arg Gly Asn Glu Lys Lys Pro
            770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Lys Thr Thr
            820                 825                 830
```

Glu Asp Glu Val His Ile Cys His Asn Gln Asp Gly Tyr Ser Tyr Pro
835                 840                 845

Ser Arg Gln Met Val Ser Leu Glu Asp Asp Val Ala
    850                 855                 860

<210> SEQ ID NO 32
<211> LENGTH: 2583
<212> TYPE: DNA
<213> ORGANISM: Artificial Sequence
<220> FEATURE:
<223> OTHER INFORMATION: synthetic hLDLR V307D with leader

<400> SEQUENCE: 32

| | | | | |
|---|---|---|---|---|
| atgggcccct | ggggctggaa | attgcgctgg | accgtcgcct | tgctcctcgc cgcggcgggg | 60 |
| actgcagtgg | cgacagatg | tgaaagaaac | gagttccagt | gccaagacgg gaaatgcatc | 120 |
| tcctacaagt | gggtctgcga | tggcagcgct | gagtgccagg | atggctctga tgagtcccag | 180 |
| gagacgtgct | tgtctgtcac | ctgcaaatcc | ggggacttca | gctgtggggg ccgtgtcaac | 240 |
| cgctgcattc | tcagttctg | gaggtgcgat | ggccaagtgg | actgcgacaa cggctcagac | 300 |
| gagcaaggct | gtccccccaa | gacgtgctcc | caggacgagt | tcgctgcca cgatgggaag | 360 |
| tgcatctctc | ggcagttcgt | ctgtgactca | gaccgggact | gcttgacgg ctcagacgag | 420 |
| gcctcctgcc | cggtgctcac | ctgtggtccc | gccagcttcc | agtgcaacag ctccacctgc | 480 |
| atccccagc | tgtgggcctg | cgacaacgac | cccgactgcg | aagatggctc ggatgagtgg | 540 |
| ccgcagcgct | gtagggtct | ttacgtgttc | caaggggaca | gtagccctg ctcggccttc | 600 |
| gagttccact | gcctaagtgg | cgagtgcatc | cactccagct | ggcgctgtga tggtggcccc | 660 |
| gactgcaagg | acaaatctga | cgaggaaaac | tgcgctgtgg | ccacctgtcg ccctgacgaa | 720 |
| ttccagtgct | ctgatggaaa | ctgcatccat | ggcagccggc | agtgtgaccg ggaatatgac | 780 |
| tgcaaggaca | tgagcgatga | agttggctgc | gttaatgtga | cactctgcga gggacccaac | 840 |
| aagttcaagt | gtcacagcgg | cgaatgcatc | accctggaca | aagtctgcaa catggctaga | 900 |
| gactgccggg | actggtcaga | tgaacccatc | aaagagtgcg | ggaccaacga atgcttggac | 960 |
| aacaacggcg | gctgttccca | cgactgcaat | gaccttaaga | tcggctacga gtgcctgtgc | 1020 |
| cccgacggct | tccagctggt | ggcccagcga | agatgcgaag | atatcgatga gtgtcaggat | 1080 |
| cccgacacct | gcagccagct | ctgcgtgaac | ctggagggtg | gctacaagtg ccagtgtgag | 1140 |
| gaaggcttcc | agctggaccc | ccacacgaag | gcctgcaagg | ctgtgggctc catcgcctac | 1200 |
| ctcttcttca | ccaaccggca | cgaggtcagg | aagatgacgc | tggaccggag cgagtacacc | 1260 |
| agcctcatcc | ccaacctgag | gaacgtggtc | gctctggaca | cggaggtggc cagcaataga | 1320 |
| atctactggt | ctgacctgtc | ccagagaatg | atctgcagca | cccagcttga cagagcccac | 1380 |
| ggcgtctctt | cctatgacac | cgtcatcagc | agggacatcc | aggcccccga cgggctggct | 1440 |
| gtggactgga | tccacagcaa | catctactgg | accgactctg | tcctgggcac tgtctctgtt | 1500 |
| gcggatacca | agggcgtgaa | gaggaaaacg | ttattcaggg | agaacggctc caagccaagg | 1560 |
| gccatcgtgg | tggatcctgt | tcatggcttc | atgtactgga | ctgactgggg aactcccgcc | 1620 |
| aagatcaaga | aagggggcct | gaatggtgtg | gacatctact | cgctggtgac tgaaaacatt | 1680 |
| cagtggccca | atggcatcac | cctagatctc | ctcagtggcc | gcctctactg ggttgactcc | 1740 |
| aaacttcact | ccatctcaag | catcgatgtc | aatgggggca | accggaagac catcttggag | 1800 |
| gatgaaaaga | ggctggccca | ccccttctcc | ttggccgtct | tgaggacaa agtatttggg | 1860 |
| acagatatca | tcaacgaagc | catttcagt | gccaaccgcc | tcacaggttc cgatgtcaac | 1920 |

-continued

```
ttgttggctg aaaacctact gtccccagag gatatggtcc tcttccacaa cctcacccag    1980
ccaagaggag tgaactggtg tgagaggacc accctgagca atggcggctg ccagtatctg    2040
tgcctccctg ccccgcagat caaccccac tcgcccaagt ttacctgcgc ctgcccggac     2100
ggcatgctgc tggccaggga catgaggagc tgcctcacag aggctgaggc tgcagtggcc    2160
acccaggaga catccaccgt caggctaaag gtcagctcca cagccgtaag gacacagcac    2220
acaaccaccc ggcctgttcc cgacacctcc cggctgcctg ggccaccccc tgggctcacc    2280
acggtggaga tagtgacaat gtctcaccaa gctctgggcg acgttgctgg cagaggaaat    2340
gagaagaagc ccagtagcgt gagggctctg tccattgtcc tccccatcgt gctcctcgtc    2400
ttcctttgcc tgggggtctt ccttctatgg aagaactggc ggcttaagaa catcaacagc    2460
atcaactttg acaaccccgt ctatcagaag accacagagg atgaggtcca catttgccac    2520
aaccaggacg gctacagcta cccctcgaga cagatggtca gtctggagga tgacgtggcg    2580
tga                                                                 2583
```

<210> SEQ ID NO 33
<211> LENGTH: 2583
<212> TYPE: DNA
<213> ORGANISM: Artificial Sequence
<220> FEATURE:
<223> OTHER INFORMATION: synthetic hLDLR-IDOL-K796R, K809R, C818A with leader
<220> FEATURE:
<221> NAME/KEY: CDS
<222> LOCATION: (1)..(2583)

<400> SEQUENCE: 33

```
atg ggg ccc tgg ggc tgg aaa ttg cgc tgg acc gtc gcc ttg ctc ctc      48
Met Gly Pro Trp Gly Trp Lys Leu Arg Trp Thr Val Ala Leu Leu Leu
1               5                   10                  15 gcc gcg gcg ggg act gca gtg ggc gac aga tgt gaa aga aac gag ttc      96
Ala Ala Ala Gly Thr Ala Val Gly Asp Arg Cys Glu Arg Asn Glu Phe
            20                  25                  30 cag tgc caa gac ggg aaa tgc atc tcc tac aag tgg gtc tgc gat ggc     144
Gln Cys Gln Asp Gly Lys Cys Ile Ser Tyr Lys Trp Val Cys Asp Gly
        35                  40                  45 agc gct gag tgc cag gat ggc tct gat gag tcc cag gag acg tgc ttg     192
Ser Ala Glu Cys Gln Asp Gly Ser Asp Glu Ser Gln Glu Thr Cys Leu
    50                  55                  60 tct gtc acc tgc aaa tcc ggg gac ttc agc tgt ggg ggc cgt gtc aac     240
Ser Val Thr Cys Lys Ser Gly Asp Phe Ser Cys Gly Gly Arg Val Asn
65                  70                  75                  80 cgc tgc att cct cag ttc tgg agg tgc gat ggc caa gtg gac tgc gac     288
Arg Cys Ile Pro Gln Phe Trp Arg Cys Asp Gly Gln Val Asp Cys Asp
                85                  90                  95 aac ggc tca gac gag caa ggc tgt ccc ccc aag acg tgc tcc cag gac     336
Asn Gly Ser Asp Glu Gln Gly Cys Pro Pro Lys Thr Cys Ser Gln Asp
            100                 105                 110 gag ttt cgc tgc cac gat ggg aag tgc atc tct cgg cag ttc gtc tgt     384
Glu Phe Arg Cys His Asp Gly Lys Cys Ile Ser Arg Gln Phe Val Cys
        115                 120                 125 gac tca gac cgg gac tgc ttg gac ggc tca gac gag gcc tcc tgc ccg     432
Asp Ser Asp Arg Asp Cys Leu Asp Gly Ser Asp Glu Ala Ser Cys Pro
    130                 135                 140 gtg ctc acc tgt ggt ccc gcc agc ttc cag tgc aac agc tcc acc tgc     480
Val Leu Thr Cys Gly Pro Ala Ser Phe Gln Cys Asn Ser Ser Thr Cys
145                 150                 155                 160
```

```
atc ccc cag ctg tgg gcc tgc gac aac gac ccc gac tgc gaa gat ggc      528
Ile Pro Gln Leu Trp Ala Cys Asp Asn Asp Pro Asp Cys Glu Asp Gly
            165                 170                 175 tcg gat gag tgg ccg cag cgc tgt agg ggt ctt tac gtg ttc caa ggg      576
Ser Asp Glu Trp Pro Gln Arg Cys Arg Gly Leu Tyr Val Phe Gln Gly
            180                 185                 190 gac agt agc ccc tgc tcg gcc ttc gag ttc cac tgc cta agt ggc gag      624
Asp Ser Ser Pro Cys Ser Ala Phe Glu Phe His Cys Leu Ser Gly Glu
            195                 200                 205 tgc atc cac tcc agc tgg cgc tgt gat ggt ggc ccc gac tgc aag gac      672
Cys Ile His Ser Ser Trp Arg Cys Asp Gly Gly Pro Asp Cys Lys Asp
            210                 215                 220 aaa tct gac gag gaa aac tgc gct gtg gcc acc tgt cgc cct gac gaa      720
Lys Ser Asp Glu Glu Asn Cys Ala Val Ala Thr Cys Arg Pro Asp Glu
225                 230                 235                 240 ttc cag tgc tct gat gga aac tgc atc cat ggc agc cgg cag tgt gac      768
Phe Gln Cys Ser Asp Gly Asn Cys Ile His Gly Ser Arg Gln Cys Asp
            245                 250                 255 cgg gaa tat gac tgc aag gac atg agc gat gaa gtt ggc tgc gtt aat      816
Arg Glu Tyr Asp Cys Lys Asp Met Ser Asp Glu Val Gly Cys Val Asn
            260                 265                 270 gtg aca ctc tgc gag gga ccc aac aag ttc aag tgt cac agc ggc gaa      864
Val Thr Leu Cys Glu Gly Pro Asn Lys Phe Lys Cys His Ser Gly Glu
            275                 280                 285 tgc atc acc ctg gac aaa gtc tgc aac atg gct aga gac tgc cgg gac      912
Cys Ile Thr Leu Asp Lys Val Cys Asn Met Ala Arg Asp Cys Arg Asp
            290                 295                 300 tgg tca gat gaa ccc atc aaa gag tgc ggg acc aac gaa tgc ttg gac      960
Trp Ser Asp Glu Pro Ile Lys Glu Cys Gly Thr Asn Glu Cys Leu Asp
305                 310                 315                 320 aac aac ggc ggt tgt tcc cac gtc tgc aat gac ctt aag atc ggc tac     1008
Asn Asn Gly Gly Cys Ser His Val Cys Asn Asp Leu Lys Ile Gly Tyr
            325                 330                 335 gag tgc ctg tgc ccc gac ggc ttc cag ctg gtg gcc cag cga aga tgc     1056
Glu Cys Leu Cys Pro Asp Gly Phe Gln Leu Val Ala Gln Arg Arg Cys
            340                 345                 350 gaa gat atc gat gag tgt cag gat ccc gac acc tgc agc cag ctc tgc     1104
Glu Asp Ile Asp Glu Cys Gln Asp Pro Asp Thr Cys Ser Gln Leu Cys
            355                 360                 365 gtg aac ctg gag ggt ggc tac aag tgc cag tgt gag gaa ggc ttc cag     1152
Val Asn Leu Glu Gly Gly Tyr Lys Cys Gln Cys Glu Glu Gly Phe Gln
            370                 375                 380 ctg gac ccc cac acg aag gcc tgc aag gct gtg ggc tcc atc gcc tac     1200
Leu Asp Pro His Thr Lys Ala Cys Lys Ala Val Gly Ser Ile Ala Tyr
385                 390                 395                 400 ctc ttc ttc acc aac cgg cac gag gtc agg aag atg acg ctg gac cgg     1248
Leu Phe Phe Thr Asn Arg His Glu Val Arg Lys Met Thr Leu Asp Arg
            405                 410                 415 agc gag tac acc agc ctc atc ccc aac ctg agg aac gtg gtc gct ctg     1296
Ser Glu Tyr Thr Ser Leu Ile Pro Asn Leu Arg Asn Val Val Ala Leu
            420                 425                 430 gac acg gag gtg gcc agc aat aga atc tac tgg tct gac ctg tcc cag     1344
Asp Thr Glu Val Ala Ser Asn Arg Ile Tyr Trp Ser Asp Leu Ser Gln
            435                 440                 445 aga atg atc tgc agc acc cag ctt gac aga gcc cac ggc gtc tct tcc     1392
Arg Met Ile Cys Ser Thr Gln Leu Asp Arg Ala His Gly Val Ser Ser
            450                 455                 460 tat gac acc gtc atc agc agg gac atc cag gcc ccc gac ggg ctg gct     1440
Tyr Asp Thr Val Ile Ser Arg Asp Ile Gln Ala Pro Asp Gly Leu Ala
465                 470                 475                 480
```

```
gtg gac tgg atc cac agc aac atc tac tgg acc gac tct gtc ctg ggc      1488
Val Asp Trp Ile His Ser Asn Ile Tyr Trp Thr Asp Ser Val Leu Gly
                485                 490                 495 act gtc tct gtt gcg gat acc aag ggc gtg aag agg aaa acg tta ttc      1536
Thr Val Ser Val Ala Asp Thr Lys Gly Val Lys Arg Lys Thr Leu Phe
                500                 505                 510 agg gag aac ggc tcc aag cca agg gcc atc gtg gtg gat cct gtt cat      1584
Arg Glu Asn Gly Ser Lys Pro Arg Ala Ile Val Val Asp Pro Val His
                515                 520                 525 ggc ttc atg tac tgg act gac tgg gga act ccc gcc aag atc aag aaa      1632
Gly Phe Met Tyr Trp Thr Asp Trp Gly Thr Pro Ala Lys Ile Lys Lys
            530                 535                 540 ggg ggc ctg aat ggt gtg gac atc tac tcg ctg gtg act gaa aac att      1680
Gly Gly Leu Asn Gly Val Asp Ile Tyr Ser Leu Val Thr Glu Asn Ile
545                 550                 555                 560 cag tgg ccc aat ggc atc acc cta gat ctc ctc agt ggc cgc ctc tac      1728
Gln Trp Pro Asn Gly Ile Thr Leu Asp Leu Leu Ser Gly Arg Leu Tyr
                565                 570                 575 tgg gtt gac tcc aaa ctt cac tcc atc tca agc atc gat gtc aat ggg      1776
Trp Val Asp Ser Lys Leu His Ser Ile Ser Ser Ile Asp Val Asn Gly
                580                 585                 590 ggc aac cgg aag acc atc ttg gag gat gaa aag agg ctg gcc cac ccc      1824
Gly Asn Arg Lys Thr Ile Leu Glu Asp Glu Lys Arg Leu Ala His Pro
                595                 600                 605 ttc tcc ttg gcc gtc ttt gag gac aaa gta ttt tgg aca gat atc atc      1872
Phe Ser Leu Ala Val Phe Glu Asp Lys Val Phe Trp Thr Asp Ile Ile
                610                 615                 620 aac gaa gcc att ttc agt gcc aac cgc ctc aca ggt tcc gat gtc aac      1920
Asn Glu Ala Ile Phe Ser Ala Asn Arg Leu Thr Gly Ser Asp Val Asn
625                 630                 635                 640 ttg ttg gct gaa aac cta ctg tcc cca gag gat atg gtc ctc ttc cac      1968
Leu Leu Ala Glu Asn Leu Leu Ser Pro Glu Asp Met Val Leu Phe His
                645                 650                 655 aac ctc acc cag cca aga gga gtg aac tgg tgt gag agg acc acc ctg      2016
Asn Leu Thr Gln Pro Arg Gly Val Asn Trp Cys Glu Arg Thr Thr Leu
                660                 665                 670 agc aat ggc ggc tgc cag tat ctg tgc ctc cct gcc ccg cag atc aac      2064
Ser Asn Gly Gly Cys Gln Tyr Leu Cys Leu Pro Ala Pro Gln Ile Asn
                675                 680                 685 ccc cac tcg ccc aag ttt acc tgc gcc tgc ccg gac ggc atg ctg ctg      2112
Pro His Ser Pro Lys Phe Thr Cys Ala Cys Pro Asp Gly Met Leu Leu
                690                 695                 700 gcc agg gac atg agg agc tgc ctc aca gag gct gag gct gca gtg gcc      2160
Ala Arg Asp Met Arg Ser Cys Leu Thr Glu Ala Glu Ala Ala Val Ala
705                 710                 715                 720 acc cag gag aca tcc acc gtc agg cta aag gtc agc tcc aca gcc gta      2208
Thr Gln Glu Thr Ser Thr Val Arg Leu Lys Val Ser Ser Thr Ala Val
                725                 730                 735 agg aca cag cac aca acc acc cgg cct gtt ccc gac acc tcc cgg ctg      2256
Arg Thr Gln His Thr Thr Thr Arg Pro Val Pro Asp Thr Ser Arg Leu
                740                 745                 750 cct ggg gcc acc cct ggg ctc acc acg gtg gag ata gtg aca atg tct      2304
Pro Gly Ala Thr Pro Gly Leu Thr Thr Val Glu Ile Val Thr Met Ser
                755                 760                 765 cac caa gct ctg ggc gac gtt gct ggc aga gga aat gag aag aag ccc      2352
His Gln Ala Leu Gly Asp Val Ala Gly Arg Gly Asn Glu Lys Lys Pro
                770                 775                 780 agt agc gtg agg gct ctg tcc att gtc ctc ccc atc gtg ctc ctc gtc      2400
Ser Ser Val Arg Ala Leu Ser Ile Val Leu Pro Ile Val Leu Leu Val
```

```
                  785                 790                 795                 800
ttc ctt tgc ctg ggg gtc ttc ctt cta tgg aag aac tgg cgg ctt agg      2448
Phe Leu Cys Leu Gly Val Phe Leu Leu Trp Lys Asn Trp Arg Leu Arg
                805                 810                 815 aac atc aac agc atc aac ttt gac aac ccc gtc tat cag agg acc aca      2496
Asn Ile Asn Ser Ile Asn Phe Asp Asn Pro Val Tyr Gln Arg Thr Thr
            820                 825                 830 gag gat gag gtc cac att gcc cac aac cag gac ggc tac agc tac ccc      2544
Glu Asp Glu Val His Ile Ala His Asn Gln Asp Gly Tyr Ser Tyr Pro
835                 840                 845 tcg aga cag atg gtc agt ctg gag gat gac gtg gcg tga                  2583
Ser Arg Gln Met Val Ser Leu Glu Asp Asp Val Ala
    850                 855                 860
```

<210> SEQ ID NO 34
<211> LENGTH: 860
<212> TYPE: PRT
<213> ORGANISM: Artificial Sequence
<220> FEATURE:
<223> OTHER INFORMATION: Synthetic Construct

<400> SEQUENCE: 34

```
Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270
```

-continued

```
Val Thr Leu Cys Glu Gly Pro Asn Lys Phe Lys Cys His Ser Gly Glu
            275                 280                 285
Cys Ile Thr Leu Asp Lys Val Cys Asn Met Ala Arg Asp Cys Arg Asp
    290                 295                 300
Trp Ser Asp Glu Pro Ile Lys Glu Cys Gly Thr Asn Glu Cys Leu Asp
305                 310                 315                 320
Asn Asn Gly Gly Cys Ser His Val Cys Asn Asp Leu Lys Ile Gly Tyr
                325                 330                 335
Glu Cys Leu Cys Pro Asp Gly Phe Gln Leu Val Ala Gln Arg Arg Cys
            340                 345                 350
Glu Asp Ile Asp Glu Cys Gln Asp Pro Asp Thr Cys Ser Gln Leu Cys
        355                 360                 365
Val Asn Leu Glu Gly Gly Tyr Lys Cys Gln Cys Glu Glu Gly Phe Gln
    370                 375                 380
Leu Asp Pro His Thr Lys Ala Cys Lys Ala Val Gly Ser Ile Ala Tyr
385                 390                 395                 400
Leu Phe Phe Thr Asn Arg His Glu Val Arg Lys Met Thr Leu Asp Arg
                405                 410                 415
Ser Glu Tyr Thr Ser Leu Ile Pro Asn Leu Arg Asn Val Val Ala Leu
            420                 425                 430
Asp Thr Glu Val Ala Ser Asn Arg Ile Tyr Trp Ser Asp Leu Ser Gln
        435                 440                 445
Arg Met Ile Cys Ser Thr Gln Leu Asp Arg Ala His Gly Val Ser Ser
    450                 455                 460
Tyr Asp Thr Val Ile Ser Arg Asp Ile Gln Ala Pro Asp Gly Leu Ala
465                 470                 475                 480
Val Asp Trp Ile His Ser Asn Ile Tyr Trp Thr Asp Ser Val Leu Gly
                485                 490                 495
Thr Val Ser Val Ala Asp Thr Lys Gly Val Lys Arg Lys Thr Leu Phe
            500                 505                 510
Arg Glu Asn Gly Ser Lys Pro Arg Ala Ile Val Val Asp Pro Val His
        515                 520                 525
Gly Phe Met Tyr Trp Thr Asp Trp Gly Thr Pro Ala Lys Ile Lys Lys
    530                 535                 540
Gly Gly Leu Asn Gly Val Asp Ile Tyr Ser Leu Val Thr Glu Asn Ile
545                 550                 555                 560
Gln Trp Pro Asn Gly Ile Thr Leu Asp Leu Leu Ser Gly Arg Leu Tyr
                565                 570                 575
Trp Val Asp Ser Lys Leu His Ser Ile Ser Ser Ile Asp Val Asn Gly
            580                 585                 590
Gly Asn Arg Lys Thr Ile Leu Glu Asp Glu Lys Arg Leu Ala His Pro
        595                 600                 605
Phe Ser Leu Ala Val Phe Glu Asp Lys Val Phe Trp Thr Asp Ile Ile
    610                 615                 620
Asn Glu Ala Ile Phe Ser Ala Asn Arg Leu Thr Gly Ser Asp Val Asn
625                 630                 635                 640
Leu Leu Ala Glu Asn Leu Leu Ser Pro Glu Asp Met Val Leu Phe His
                645                 650                 655
Asn Leu Thr Gln Pro Arg Gly Val Asn Trp Cys Glu Arg Thr Thr Leu
            660                 665                 670
Ser Asn Gly Gly Cys Gln Tyr Leu Cys Leu Pro Ala Pro Gln Ile Asn
        675                 680                 685
Pro His Ser Pro Lys Phe Thr Cys Ala Cys Pro Asp Gly Met Leu Leu
```

```
                       690                 695                 700
Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                    725                 730                 735

Arg Thr Gln His Thr Thr Thr Arg Pro Val Pro Asp Thr Ser Arg Leu
                740                 745                 750

Pro Gly Ala Thr Pro Gly Leu Thr Thr Val Glu Ile Val Thr Met Ser
            755                 760                 765

His Gln Ala Leu Gly Asp Val Ala Gly Arg Gly Asn Glu Lys Lys Pro
        770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Arg
                    805                 810                 815

Asn Ile Asn Ser Ile Asn Phe Asp Asn Pro Val Tyr Gln Arg Thr Thr
                820                 825                 830

Glu Asp Glu Val His Ile Ala His Asn Gln Asp Gly Tyr Ser Tyr Pro
            835                 840                 845

Ser Arg Gln Met Val Ser Leu Glu Asp Asp Val Ala
        850                 855                 860

<210> SEQ ID NO 35
<211> LENGTH: 2583
<212> TYPE: DNA
<213> ORGANISM: Artificial Sequence
<220> FEATURE:
<223> OTHER INFORMATION: synthetic hLDLR.K809R-818A with leader
<220> FEATURE:
<221> NAME/KEY: CDS
<222> LOCATION: (1)..(2583)

<400> SEQUENCE: 35 atg ggg ccc tgg ggc tgg aaa ttg cgc tgg acc gtc gcc ttg ctc ctc      48
Met Gly Pro Trp Gly Trp Lys Leu Arg Trp Thr Val Ala Leu Leu Leu
1               5                   10                  15 gcc gcg gcg ggg act gca gtg ggc gac aga tgt gaa aga aac gag ttc      96
Ala Ala Ala Gly Thr Ala Val Gly Asp Arg Cys Glu Arg Asn Glu Phe
            20                  25                  30 cag tgc caa gac ggg aaa tgc atc tcc tac aag tgg gtc tgc gat ggc     144
Gln Cys Gln Asp Gly Lys Cys Ile Ser Tyr Lys Trp Val Cys Asp Gly
        35                  40                  45 agc gct gag tgc cag gat ggc tct gat gag tcc cag gag acg tgc ttg     192
Ser Ala Glu Cys Gln Asp Gly Ser Asp Glu Ser Gln Glu Thr Cys Leu
    50                  55                  60 tct gtc acc tgc aaa tcc ggg gac ttc agc tgt ggg ggc cgt gtc aac     240
Ser Val Thr Cys Lys Ser Gly Asp Phe Ser Cys Gly Gly Arg Val Asn
65                  70                  75                  80 cgc tgc att cct cag ttc tgg agg tgc gat ggc caa gtg gac tgc gac     288
Arg Cys Ile Pro Gln Phe Trp Arg Cys Asp Gly Gln Val Asp Cys Asp
                85                  90                  95 aac ggc tca gac gag caa ggc tgt ccc ccc aag acg tgc tcc cag gac     336
Asn Gly Ser Asp Glu Gln Gly Cys Pro Pro Lys Thr Cys Ser Gln Asp
            100                 105                 110 gag ttt cgc tgc cac gat ggg aag tgc atc tct cgg cag ttc gtc tgt     384
Glu Phe Arg Cys His Asp Gly Lys Cys Ile Ser Arg Gln Phe Val Cys
        115                 120                 125 gac tca gac cgg gac tgc ttg gac ggc tca gac gag gcc tcc tgc ccg     432
Asp Ser Asp Arg Asp Cys Leu Asp Gly Ser Asp Glu Ala Ser Cys Pro
```

```
              130                 135                 140
gtg ctc acc tgt ggt ccc gcc agc ttc cag tgc aac agc tcc acc tgc       480
Val Leu Thr Cys Gly Pro Ala Ser Phe Gln Cys Asn Ser Ser Thr Cys
145                 150                 155                 160 atc ccc cag ctg tgg gcc tgc gac aac gac ccc gac tgc gaa gat ggc       528
Ile Pro Gln Leu Trp Ala Cys Asp Asn Asp Pro Asp Cys Glu Asp Gly
                165                 170                 175 tcg gat gag tgg ccg cag cgc tgt agg ggt ctt tac gtg ttc caa ggg       576
Ser Asp Glu Trp Pro Gln Arg Cys Arg Gly Leu Tyr Val Phe Gln Gly
            180                 185                 190 gac agt agc ccc tgc tcg gcc ttc gag ttc cac tgc cta agt ggc gag       624
Asp Ser Ser Pro Cys Ser Ala Phe Glu Phe His Cys Leu Ser Gly Glu
        195                 200                 205 tgc atc cac tcc agc tgg cgc tgt gat ggt ggc ccc gac tgc aag gac       672
Cys Ile His Ser Ser Trp Arg Cys Asp Gly Gly Pro Asp Cys Lys Asp
    210                 215                 220 aaa tct gac gag gaa aac tgc gct gtg gcc acc tgt cgc cct gac gaa       720
Lys Ser Asp Glu Glu Asn Cys Ala Val Ala Thr Cys Arg Pro Asp Glu
225                 230                 235                 240 ttc cag tgc tct gat gga aac tgc atc cat ggc agc cgg cag tgt gac       768
Phe Gln Cys Ser Asp Gly Asn Cys Ile His Gly Ser Arg Gln Cys Asp
                245                 250                 255 cgg gaa tat gac tgc aag gac atg agc gat gaa gtt ggc tgc gtt aat       816
Arg Glu Tyr Asp Cys Lys Asp Met Ser Asp Glu Val Gly Cys Val Asn
            260                 265                 270 gtg aca ctc tgc gag gga ccc aac aag ttc aag tgt cac agc ggc gaa       864
Val Thr Leu Cys Glu Gly Pro Asn Lys Phe Lys Cys His Ser Gly Glu
        275                 280                 285 tgc atc acc ctg gac aaa gtc tgc aac atg gct aga gac tgc cgg gac       912
Cys Ile Thr Leu Asp Lys Val Cys Asn Met Ala Arg Asp Cys Arg Asp
    290                 295                 300 tgg tca gat gaa ccc atc aaa gag tgc ggg acc aac gaa tgc ttg gac       960
Trp Ser Asp Glu Pro Ile Lys Glu Cys Gly Thr Asn Glu Cys Leu Asp
305                 310                 315                 320 aac aac ggc ggc tgt tcc cac gtc tgc aat gac ctt aag atc ggc tac      1008
Asn Asn Gly Gly Cys Ser His Val Cys Asn Asp Leu Lys Ile Gly Tyr
                325                 330                 335 gag tgc ctg tgc ccc gac ggc ttc cag ctg gtg gcc cag cga aga tgc      1056
Glu Cys Leu Cys Pro Asp Gly Phe Gln Leu Val Ala Gln Arg Arg Cys
            340                 345                 350 gaa gat atc gat gag tgt cag gat ccc gac acc tgc agc cag ctc tgc      1104
Glu Asp Ile Asp Glu Cys Gln Asp Pro Asp Thr Cys Ser Gln Leu Cys
        355                 360                 365 gtg aac ctg gag ggt ggc tac aag tgc cag tgt gag gaa ggc ttc cag      1152
Val Asn Leu Glu Gly Gly Tyr Lys Cys Gln Cys Glu Glu Gly Phe Gln
    370                 375                 380 ctg gac ccc cac acg aag gcc tgc aag gct gtg ggc tcc atc gcc tac      1200
Leu Asp Pro His Thr Lys Ala Cys Lys Ala Val Gly Ser Ile Ala Tyr
385                 390                 395                 400 ctc ttc ttc acc aac cgg cac gag gtc agg aag atg acg ctg gac cgg      1248
Leu Phe Phe Thr Asn Arg His Glu Val Arg Lys Met Thr Leu Asp Arg
                405                 410                 415 agc gag tac acc agc ctc atc ccc aac ctg agg aac gtg gtc gct ctg      1296
Ser Glu Tyr Thr Ser Leu Ile Pro Asn Leu Arg Asn Val Val Ala Leu
            420                 425                 430 gac acg gag gtg gcc agc aat aga atc tac tgg tct gac ctg tcc cag      1344
Asp Thr Glu Val Ala Ser Asn Arg Ile Tyr Trp Ser Asp Leu Ser Gln
        435                 440                 445 aga atg atc tgc agc acc cag ctt gac aga gcc cac ggc gtc tct tcc      1392
```

|     |     |     |     |     |     |     |     |     |     |     |     |     |     |     |      |
| --- | --- | --- | --- | --- | --- | --- | --- | --- | --- | --- | --- | --- | --- | --- | ---- |
|     | Arg | Met | Ile | Cys | Ser | Thr | Gln | Leu | Asp | Arg | Ala | His | Gly | Val | Ser Ser |
|     | 450 |     |     |     | 455 |     |     |     | 460 |     |     |     |     |     |      |

```
tat gac acc gtc atc agc agg gac atc cag gcc ccc gac ggg ctg gct      1440
Tyr Asp Thr Val Ile Ser Arg Asp Ile Gln Ala Pro Asp Gly Leu Ala
465                 470                 475                 480 gtg gac tgg atc cac agc aac atc tac tgg acc gac tct gtc ctg ggc      1488
Val Asp Trp Ile His Ser Asn Ile Tyr Trp Thr Asp Ser Val Leu Gly
                485                 490                 495 act gtc tct gtt gcg gat acc aag ggc gtg aag agg aaa acg tta ttc      1536
Thr Val Ser Val Ala Asp Thr Lys Gly Val Lys Arg Lys Thr Leu Phe
            500                 505                 510 agg gag aac ggc tcc aag cca agg gcc atc gtg gtg gat cct gtt cat      1584
Arg Glu Asn Gly Ser Lys Pro Arg Ala Ile Val Val Asp Pro Val His
        515                 520                 525 ggc ttc atg tac tgg act gac tgg gga act ccc gcc aag atc aag aaa      1632
Gly Phe Met Tyr Trp Thr Asp Trp Gly Thr Pro Ala Lys Ile Lys Lys
    530                 535                 540 ggg ggc ctg aat ggt gtg gac atc tac tcg ctg gtg act gaa aac att      1680
Gly Gly Leu Asn Gly Val Asp Ile Tyr Ser Leu Val Thr Glu Asn Ile
545                 550                 555                 560 cag tgg ccc aat ggc atc acc cta gat ctc ctc agt ggc cgc ctc tac      1728
Gln Trp Pro Asn Gly Ile Thr Leu Asp Leu Leu Ser Gly Arg Leu Tyr
                565                 570                 575 tgg gtt gac tcc aaa ctt cac tcc atc tca agc atc gat gtc aat ggg      1776
Trp Val Asp Ser Lys Leu His Ser Ile Ser Ser Ile Asp Val Asn Gly
            580                 585                 590 ggc aac cgg aag acc atc ttg gag gat gaa aag agg ctg gcc cac ccc      1824
Gly Asn Arg Lys Thr Ile Leu Glu Asp Glu Lys Arg Leu Ala His Pro
        595                 600                 605 ttc tcc ttg gcc gtc ttt gag gac aaa gta ttt tgg aca gat atc atc      1872
Phe Ser Leu Ala Val Phe Glu Asp Lys Val Phe Trp Thr Asp Ile Ile
    610                 615                 620 aac gaa gcc att ttc agt gcc aac cgc ctc aca ggt tcc gat gtc aac      1920
Asn Glu Ala Ile Phe Ser Ala Asn Arg Leu Thr Gly Ser Asp Val Asn
625                 630                 635                 640 ttg ttg gct gaa aac cta ctg tcc cca gag gat atg gtc ctc ttc cac      1968
Leu Leu Ala Glu Asn Leu Leu Ser Pro Glu Asp Met Val Leu Phe His
                645                 650                 655 aac ctc acc cag cca aga gga gtg aac tgg tgt gag agg acc acc ctg      2016
Asn Leu Thr Gln Pro Arg Gly Val Asn Trp Cys Glu Arg Thr Thr Leu
            660                 665                 670 agc aat ggc ggc tgc cag tat ctg tgc ctc cct gcc ccg cag atc aac      2064
Ser Asn Gly Gly Cys Gln Tyr Leu Cys Leu Pro Ala Pro Gln Ile Asn
        675                 680                 685 ccc cac tcg ccc aag ttt acc tgc gcc tgc ccg gac ggc atg ctg ctg      2112
Pro His Ser Pro Lys Phe Thr Cys Ala Cys Pro Asp Gly Met Leu Leu
    690                 695                 700 gcc agg gac atg agg agc tgc ctc aca gag gct gag gct gca gtg gcc      2160
Ala Arg Asp Met Arg Ser Cys Leu Thr Glu Ala Glu Ala Ala Val Ala
705                 710                 715                 720 acc cag gag aca tcc acc gtc agg cta aag gtc agc tcc aca gcc gta      2208
Thr Gln Glu Thr Ser Thr Val Arg Leu Lys Val Ser Ser Thr Ala Val
                725                 730                 735 agg aca cag cac aca acc acc cgg cct gtt ccc gac acc tcc cgg ctg      2256
Arg Thr Gln His Thr Thr Thr Arg Pro Val Pro Asp Thr Ser Arg Leu
            740                 745                 750 cct ggg gcc acc cct ggg ctc acc acg gtg gag ata gtg aca atg tct      2304
Pro Gly Ala Thr Pro Gly Leu Thr Thr Val Glu Ile Val Thr Met Ser
        755                 760                 765
```

| | | |
|---|---|---|
| cac caa gct ctg ggc gac gtt gct ggc aga gga aat gag aag aag ccc<br>His Gln Ala Leu Gly Asp Val Ala Gly Arg Gly Asn Glu Lys Lys Pro<br>770                         775                       780 | | 2352 |
| agt agc gtg agg gct ctg tcc att gtc ctc ccc atc gtg ctc ctc gtc<br>Ser Ser Val Arg Ala Leu Ser Ile Val Leu Pro Ile Val Leu Leu Val<br>785                         790                     795                     800 | | 2400 |
| ttc ctt tgc ctg ggg gtc ttc ctt cta tgg aag aac tgg cgg ctt aag<br>Phe Leu Cys Leu Gly Val Phe Leu Leu Trp Lys Asn Trp Arg Leu Lys<br>                  805                     810                   815 | | 2448 |
| aac atc aac agc atc aac ttt gac aac ccc gtc tat cag agg acc aca<br>Asn Ile Asn Ser Ile Asn Phe Asp Asn Pro Val Tyr Gln Arg Thr Thr<br>                    820                     825                   830 | | 2496 |
| gag gat gag gtc cac att gcc cac aac cag gac ggc tac agc tac ccc<br>Glu Asp Glu Val His Ile Ala His Asn Gln Asp Gly Tyr Ser Tyr Pro<br>835                         840                     845 | | 2544 |
| tcg aga cag atg gtc agt ctg gag gat gac gtg gcg tga<br>Ser Arg Gln Met Val Ser Leu Glu Asp Asp Val Ala<br>850                         855                     860 | | 2583 |

<210> SEQ ID NO 36
<211> LENGTH: 860
<212> TYPE: PRT
<213> ORGANISM: Artificial Sequence
<220> FEATURE:
<223> OTHER INFORMATION: Synthetic Construct

<400> SEQUENCE: 36

Met Gly Pro Trp Gly Trp Lys Leu Arg Trp Thr Val Ala Leu Leu Leu
1                 5                    10                 15

Ala Ala Ala Gly Thr Ala Val Gly Asp Arg Cys Glu Arg Asn Glu Phe
                 20                    25                   30

Gln Cys Gln Asp Gly Lys Cys Ile Ser Tyr Lys Trp Val Cys Asp Gly
        35                    40                   45

Ser Ala Glu Cys Gln Asp Gly Ser Asp Glu Ser Gln Glu Thr Cys Leu
50                    55                    60

Ser Val Thr Cys Lys Ser Gly Asp Phe Ser Cys Gly Gly Arg Val Asn
65                 70                    75                   80

Arg Cys Ile Pro Gln Phe Trp Arg Cys Asp Gly Gln Val Asp Cys Asp
                 85                    90                   95

Asn Gly Ser Asp Glu Gln Gly Cys Pro Pro Lys Thr Cys Ser Gln Asp
               100                   105               110

Glu Phe Arg Cys His Asp Gly Lys Cys Ile Ser Arg Gln Phe Val Cys
       115                  120               125

Asp Ser Asp Arg Asp Cys Leu Asp Gly Ser Asp Glu Ala Ser Cys Pro
130                   135                   140

Val Leu Thr Cys Gly Pro Ala Ser Phe Gln Cys Asn Ser Ser Thr Cys
145                 150                 155               160

Ile Pro Gln Leu Trp Ala Cys Asp Asn Asp Pro Asp Cys Glu Asp Gly
               165                   170               175

Ser Asp Glu Trp Pro Gln Arg Cys Arg Gly Leu Tyr Val Phe Gln Gly
       180                  185               190

Asp Ser Ser Pro Cys Ser Ala Phe Glu Phe His Cys Leu Ser Gly Glu
       195                  200               205

Cys Ile His Ser Ser Trp Arg Cys Asp Gly Gly Pro Asp Cys Lys Asp
210                   215                   220

Lys Ser Asp Glu Glu Asn Cys Ala Val Ala Thr Cys Arg Pro Asp Glu
225                 230                 235               240

```
Phe Gln Cys Ser Asp Gly Asn Cys Ile His Gly Ser Arg Gln Cys Asp
                245                 250                 255
Arg Glu Tyr Asp Cys Lys Asp Met Ser Asp Glu Val Gly Cys Val Asn
            260                 265                 270
Val Thr Leu Cys Glu Gly Pro Asn Lys Phe Lys Cys His Ser Gly Glu
        275                 280                 285
Cys Ile Thr Leu Asp Lys Val Cys Asn Met Ala Arg Asp Cys Arg Asp
    290                 295                 300
Trp Ser Asp Glu Pro Ile Lys Glu Cys Gly Thr Asn Glu Cys Leu Asp
305                 310                 315                 320
Asn Asn Gly Gly Cys Ser His Val Cys Asn Asp Leu Lys Ile Gly Tyr
                325                 330                 335
Glu Cys Leu Cys Pro Asp Gly Phe Gln Leu Val Ala Gln Arg Arg Cys
            340                 345                 350
Glu Asp Ile Asp Glu Cys Gln Asp Pro Asp Thr Cys Ser Gln Leu Cys
        355                 360                 365
Val Asn Leu Glu Gly Gly Tyr Lys Cys Gln Cys Glu Glu Gly Phe Gln
    370                 375                 380
Leu Asp Pro His Thr Lys Ala Cys Lys Ala Val Gly Ser Ile Ala Tyr
385                 390                 395                 400
Leu Phe Phe Thr Asn Arg His Glu Val Arg Lys Met Thr Leu Asp Arg
                405                 410                 415
Ser Glu Tyr Thr Ser Leu Ile Pro Asn Leu Arg Asn Val Val Ala Leu
            420                 425                 430
Asp Thr Glu Val Ala Ser Asn Arg Ile Tyr Trp Ser Asp Leu Ser Gln
        435                 440                 445
Arg Met Ile Cys Ser Thr Gln Leu Asp Arg Ala His Gly Val Ser Ser
    450                 455                 460
Tyr Asp Thr Val Ile Ser Arg Asp Ile Gln Ala Pro Asp Gly Leu Ala
465                 470                 475                 480
Val Asp Trp Ile His Ser Asn Ile Tyr Trp Thr Asp Ser Val Leu Gly
                485                 490                 495
Thr Val Ser Val Ala Asp Thr Lys Gly Val Lys Arg Lys Thr Leu Phe
            500                 505                 510
Arg Glu Asn Gly Ser Lys Pro Arg Ala Ile Val Val Asp Pro Val His
        515                 520                 525
Gly Phe Met Tyr Trp Thr Asp Trp Gly Thr Pro Ala Lys Ile Lys Lys
    530                 535                 540
Gly Gly Leu Asn Gly Val Asp Ile Tyr Ser Leu Val Thr Glu Asn Ile
545                 550                 555                 560
Gln Trp Pro Asn Gly Ile Thr Leu Asp Leu Leu Ser Gly Arg Leu Tyr
                565                 570                 575
Trp Val Asp Ser Lys Leu His Ser Ile Ser Ser Ile Asp Val Asn Gly
            580                 585                 590
Gly Asn Arg Lys Thr Ile Leu Glu Asp Glu Lys Arg Leu Ala His Pro
        595                 600                 605
Phe Ser Leu Ala Val Phe Glu Asp Lys Val Phe Trp Thr Asp Ile Ile
    610                 615                 620
Asn Glu Ala Ile Phe Ser Ala Asn Arg Leu Thr Gly Ser Asp Val Asn
625                 630                 635                 640
Leu Leu Ala Glu Asn Leu Leu Ser Pro Glu Asp Met Val Leu Phe His
                645                 650                 655
Asn Leu Thr Gln Pro Arg Gly Val Asn Trp Cys Glu Arg Thr Thr Leu
```

```
                    660                 665                 670
Ser Asn Gly Gly Cys Gln Tyr Leu Cys Leu Pro Ala Pro Gln Ile Asn
            675                 680                 685

Pro His Ser Pro Lys Phe Thr Cys Ala Cys Pro Asp Gly Met Leu Leu
        690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Arg Thr Thr
            820                 825                 830

Glu Asp Glu Val His Ile Ala His Asn Gln Asp Gly Tyr Ser Tyr Pro
        835                 840                 845

Ser Arg Gln Met Val Ser Leu Glu Asp Asp Val Ala
    850                 855                 860

<210> SEQ ID NO 37
<211> LENGTH: 2583
<212> TYPE: DNA
<213> ORGANISM: Artificial Sequence
<220> FEATURE:
<223> OTHER INFORMATION: synthetic hLDLR (K25R, C29A, L318D) with leader
<220> FEATURE:
<221> NAME/KEY: CDS
<222> LOCATION: (1)..(2583)

<400> SEQUENCE: 37 atg ggg ccc tgg ggc tgg aaa ttg cgc tgg acc gtc gcc ttg ctc ctc        48
Met Gly Pro Trp Gly Trp Lys Leu Arg Trp Thr Val Ala Leu Leu Leu
1               5                   10                  15 gcc gcg gcg ggg act gca gtg ggc gac aga tgt gaa aga aac gag ttc        96
Ala Ala Ala Gly Thr Ala Val Gly Asp Arg Cys Glu Arg Asn Glu Phe
            20                  25                  30 cag tgc caa gac ggg aaa tgc atc tcc tac aag tgg gtc tgc gat ggc       144
Gln Cys Gln Asp Gly Lys Cys Ile Ser Tyr Lys Trp Val Cys Asp Gly
        35                  40                  45 agc gct gag tgc cag gat ggc tct gat gag tcc cag gag acg tgc ttg       192
Ser Ala Glu Cys Gln Asp Gly Ser Asp Glu Ser Gln Glu Thr Cys Leu
    50                  55                  60 tct gtc acc tgc aaa tcc ggg gac ttc agc tgt ggg ggc cgt gtc aac       240
Ser Val Thr Cys Lys Ser Gly Asp Phe Ser Cys Gly Gly Arg Val Asn
65                  70                  75                  80 cgc tgc att cct cag ttc tgg agg tgc gat ggc caa gtg gac tgc gac       288
Arg Cys Ile Pro Gln Phe Trp Arg Cys Asp Gly Gln Val Asp Cys Asp
                85                  90                  95 aac ggc tca gac gag caa ggc tgt ccc ccc aag acg tgc tcc cag gac       336
Asn Gly Ser Asp Glu Gln Gly Cys Pro Pro Lys Thr Cys Ser Gln Asp
            100                 105                 110
```

-continued

| | | |
|---|---|---|
| gag ttt cgc tgc cac gat ggg aag tgc atc tct cgg cag ttc gtc tgt<br>Glu Phe Arg Cys His Asp Gly Lys Cys Ile Ser Arg Gln Phe Val Cys<br>115 120 125 | 384 | |
| gac tca gac cgg gac tgc ttg gac ggc tca gac gag gcc tcc tgc ccg<br>Asp Ser Asp Arg Asp Cys Leu Asp Gly Ser Asp Glu Ala Ser Cys Pro<br>130 135 140 | 432 | |
| gtg ctc acc tgt ggt ccc gcc agc ttc cag tgc aac agc tcc acc tgc<br>Val Leu Thr Cys Gly Pro Ala Ser Phe Gln Cys Asn Ser Ser Thr Cys<br>145 150 155 160 | 480 | |
| atc ccc cag ctg tgg gcc tgc gac aac gac ccc gac tgc gaa gat ggc<br>Ile Pro Gln Leu Trp Ala Cys Asp Asn Asp Pro Asp Cys Glu Asp Gly<br>165 170 175 | 528 | |
| tcg gat gag tgg ccg cag cgc tgt agg ggt ctt tac gtg ttc caa ggg<br>Ser Asp Glu Trp Pro Gln Arg Cys Arg Gly Leu Tyr Val Phe Gln Gly<br>180 185 190 | 576 | |
| gac agt agc ccc tgc tcg gcc ttc gag ttc cac tgc cta agt ggc gag<br>Asp Ser Ser Pro Cys Ser Ala Phe Glu Phe His Cys Leu Ser Gly Glu<br>195 200 205 | 624 | |
| tgc atc cac tcc agc tgg cgc tgt gat ggt ggc ccc gac tgc aag gac<br>Cys Ile His Ser Ser Trp Arg Cys Asp Gly Gly Pro Asp Cys Lys Asp<br>210 215 220 | 672 | |
| aaa tct gac gag gaa aac tgc gct gtg gcc acc tgt cgc cct gac gaa<br>Lys Ser Asp Glu Glu Asn Cys Ala Val Ala Thr Cys Arg Pro Asp Glu<br>225 230 235 240 | 720 | |
| ttc cag tgc tct gat gga aac tgc atc cat ggc agc cgg cag tgt gac<br>Phe Gln Cys Ser Asp Gly Asn Cys Ile His Gly Ser Arg Gln Cys Asp<br>245 250 255 | 768 | |
| cgg gaa tat gac tgc aag gac atg agc gat gaa gtt ggc tgc gtt aat<br>Arg Glu Tyr Asp Cys Lys Asp Met Ser Asp Glu Val Gly Cys Val Asn<br>260 265 270 | 816 | |
| gtg aca ctc tgc gag gga ccc aac aag ttc aag tgt cac agc ggc gaa<br>Val Thr Leu Cys Glu Gly Pro Asn Lys Phe Lys Cys His Ser Gly Glu<br>275 280 285 | 864 | |
| tgc atc acc ctg gac aaa gtc tgc aac atg gct aga gac tgc cgg gac<br>Cys Ile Thr Leu Asp Lys Val Cys Asn Met Ala Arg Asp Cys Arg Asp<br>290 295 300 | 912 | |
| tgg tca gat gaa ccc atc aaa gag tgc ggg acc aac gaa tgc ttg gac<br>Trp Ser Asp Glu Pro Ile Lys Glu Cys Gly Thr Asn Glu Cys Leu Asp<br>305 310 315 320 | 960 | |
| aac aac ggc ggc tgt tcc cac gtc tgc aat gac ctt aag atc ggc tac<br>Asn Asn Gly Gly Cys Ser His Val Cys Asn Asp Leu Lys Ile Gly Tyr<br>325 330 335 | 1008 | |
| gag tgc gac tgc ccc gac ggc ttc cag ctg gtg gcc cag cga aga tgc<br>Glu Cys Asp Cys Pro Asp Gly Phe Gln Leu Val Ala Gln Arg Arg Cys<br>340 345 350 | 1056 | |
| gaa gat atc gat gag tgt cag gat ccc gac acc tgc agc cag ctc tgc<br>Glu Asp Ile Asp Glu Cys Gln Asp Pro Asp Thr Cys Ser Gln Leu Cys<br>355 360 365 | 1104 | |
| gtg aac ctg gag ggt ggc tac aag tgc cag tgt gag gaa ggc ttc cag<br>Val Asn Leu Glu Gly Gly Tyr Lys Cys Gln Cys Glu Glu Gly Phe Gln<br>370 375 380 | 1152 | |
| ctg gac ccc cac acg aag gcc tgc aag gct gtg ggc tcc atc gcc tac<br>Leu Asp Pro His Thr Lys Ala Cys Lys Ala Val Gly Ser Ile Ala Tyr<br>385 390 395 400 | 1200 | |
| ctc ttc ttc acc aac cgg cac gag gtc agg aag atg acg ctg gac cgg<br>Leu Phe Phe Thr Asn Arg His Glu Val Arg Lys Met Thr Leu Asp Arg<br>405 410 415 | 1248 | |
| agc gag tac acc agc ctc atc ccc aac ctg agg aac gtg gtc gct ctg<br>Ser Glu Tyr Thr Ser Leu Ile Pro Asn Leu Arg Asn Val Val Ala Leu<br>420 425 430 | 1296 | |

```
gac acg gag gtg gcc agc aat aga atc tac tgg tct gac ctg tcc cag    1344
Asp Thr Glu Val Ala Ser Asn Arg Ile Tyr Trp Ser Asp Leu Ser Gln
        435                 440                 445 aga atg atc tgc agc acc cag ctt gac aga gcc cac ggc gtc tct tcc    1392
Arg Met Ile Cys Ser Thr Gln Leu Asp Arg Ala His Gly Val Ser Ser
450                 455                 460 tat gac acc gtc atc agc agg gac atc cag gcc ccc gac ggg ctg gct    1440
Tyr Asp Thr Val Ile Ser Arg Asp Ile Gln Ala Pro Asp Gly Leu Ala
465                 470                 475                 480 gtg gac tgg atc cac agc aac atc tac tgg acc gac tct gtc ctg ggc    1488
Val Asp Trp Ile His Ser Asn Ile Tyr Trp Thr Asp Ser Val Leu Gly
                485                 490                 495 act gtc tct gtt gcg gat acc aag ggc gtg aag agg aaa acg tta ttc    1536
Thr Val Ser Val Ala Asp Thr Lys Gly Val Lys Arg Lys Thr Leu Phe
            500                 505                 510 agg gag aac ggc tcc aag cca agg gcc atc gtg gtg gat cct gtt cat    1584
Arg Glu Asn Gly Ser Lys Pro Arg Ala Ile Val Val Asp Pro Val His
        515                 520                 525 ggc ttc atg tac tgg act gac tgg gga act ccc gcc aag atc aag aaa    1632
Gly Phe Met Tyr Trp Thr Asp Trp Gly Thr Pro Ala Lys Ile Lys Lys
    530                 535                 540 ggg ggc ctg aat ggt gtg gac atc tac tcg ctg gtg act gaa aac att    1680
Gly Gly Leu Asn Gly Val Asp Ile Tyr Ser Leu Val Thr Glu Asn Ile
545                 550                 555                 560 cag tgg ccc aat ggc atc acc cta gat ctc ctc agt ggc cgc ctc tac    1728
Gln Trp Pro Asn Gly Ile Thr Leu Asp Leu Leu Ser Gly Arg Leu Tyr
                565                 570                 575 tgg gtt gac tcc aaa ctt cac tcc atc tca agc atc gat gtc aat ggg    1776
Trp Val Asp Ser Lys Leu His Ser Ile Ser Ser Ile Asp Val Asn Gly
            580                 585                 590 ggc aac cgg aag acc atc ttg gag gat gaa aag agg ctg gcc cac ccc    1824
Gly Asn Arg Lys Thr Ile Leu Glu Asp Glu Lys Arg Leu Ala His Pro
        595                 600                 605 ttc tcc ttg gcc gtc ttt gag gac aaa gta ttt tgg aca gat atc atc    1872
Phe Ser Leu Ala Val Phe Glu Asp Lys Val Phe Trp Thr Asp Ile Ile
    610                 615                 620 aac gaa gcc att ttc agt gcc aac cgc ctc aca ggt tcc gat gtc aac    1920
Asn Glu Ala Ile Phe Ser Ala Asn Arg Leu Thr Gly Ser Asp Val Asn
625                 630                 635                 640 ttg ttg gct gaa aac cta ctg tcc cca gag gat atg gtc ctc ttc cac    1968
Leu Leu Ala Glu Asn Leu Leu Ser Pro Glu Asp Met Val Leu Phe His
                645                 650                 655 aac ctc acc cag cca aga gga gtg aac tgg tgt gag agg acc acc ctg    2016
Asn Leu Thr Gln Pro Arg Gly Val Asn Trp Cys Glu Arg Thr Thr Leu
            660                 665                 670 agc aat ggc ggc tgc cag tat ctg tgc ctc cct gcc ccg cag atc aac    2064
Ser Asn Gly Gly Cys Gln Tyr Leu Cys Leu Pro Ala Pro Gln Ile Asn
        675                 680                 685 ccc cac tcg ccc aag ttt acc tgc gcc tgc ccg gac ggc atg ctg ctg    2112
Pro His Ser Pro Lys Phe Thr Cys Ala Cys Pro Asp Gly Met Leu Leu
    690                 695                 700 gcc agg gac atg agg agc tgc ctc aca gag gct gag gct gca gtg gcc    2160
Ala Arg Asp Met Arg Ser Cys Leu Thr Glu Ala Glu Ala Ala Val Ala
705                 710                 715                 720 acc cag gag aca tcc acc gtc agg cta aag gtc agc tcc aca gcc gta    2208
Thr Gln Glu Thr Ser Thr Val Arg Leu Lys Val Ser Ser Thr Ala Val
                725                 730                 735 agg aca cag cac aca acc acc cgg cct gtt ccc gac acc tcc cgg ctg    2256
Arg Thr Gln His Thr Thr Thr Arg Pro Val Pro Asp Thr Ser Arg Leu
```

|   |   |   |   |   |   |   |   |   |   |   |   |   |   |   |   |      |
|---|---|---|---|---|---|---|---|---|---|---|---|---|---|---|---|------|
|   |   |   | 740 |   |   |   | 745 |   |   |   | 750 |   |   |   |   |      |
| cct | ggg | gcc | acc | cct | ggg | ctc | acc | acg | gtg | gag | ata | gtg | aca | atg | tct | 2304 |
| Pro | Gly | Ala | Thr | Pro | Gly | Leu | Thr | Thr | Val | Glu | Ile | Val | Thr | Met | Ser |      |
|   |   | 755 |   |   |   |   | 760 |   |   |   |   | 765 |   |   |   |      |
| cac | caa | gct | ctg | ggc | gac | gtt | gct | ggc | aga | gga | aat | gag | aag | aag | ccc | 2352 |
| His | Gln | Ala | Leu | Gly | Asp | Val | Ala | Gly | Arg | Gly | Asn | Glu | Lys | Lys | Pro |      |
|   | 770 |   |   |   |   | 775 |   |   |   |   | 780 |   |   |   |   |      |
| agt | agc | gtg | agg | gct | ctg | tcc | att | gtc | ctc | ccc | atc | gtg | ctc | ctc | gtc | 2400 |
| Ser | Ser | Val | Arg | Ala | Leu | Ser | Ile | Val | Leu | Pro | Ile | Val | Leu | Leu | Val |      |
| 785 |   |   |   |   | 790 |   |   |   |   | 795 |   |   |   |   | 800 |      |
| ttc | ctt | tgc | ctg | ggg | gtc | ttc | ctt | cta | tgg | aag | aac | tgg | cgg | ctt | aag | 2448 |
| Phe | Leu | Cys | Leu | Gly | Val | Phe | Leu | Leu | Trp | Lys | Asn | Trp | Arg | Leu | Lys |      |
|   |   |   |   | 805 |   |   |   |   | 810 |   |   |   |   | 815 |   |      |
| aac | atc | aac | agc | atc | aac | ttt | gac | aac | ccc | gtc | tat | cag | agg | acc | aca | 2496 |
| Asn | Ile | Asn | Ser | Ile | Asn | Phe | Asp | Asn | Pro | Val | Tyr | Gln | Arg | Thr | Thr |      |
|   |   |   | 820 |   |   |   |   | 825 |   |   |   |   | 830 |   |   |      |
| gag | gat | gag | gtc | cac | att | gcc | cac | aac | cag | gac | ggc | tac | agc | tac | ccc | 2544 |
| Glu | Asp | Glu | Val | His | Ile | Ala | His | Asn | Gln | Asp | Gly | Tyr | Ser | Tyr | Pro |      |
|   | 835 |   |   |   |   | 840 |   |   |   |   | 845 |   |   |   |   |      |
| tcg | aga | cag | atg | gtc | agt | ctg | gag | gat | gac | gtg | gcg | tga |   |   |   | 2583 |
| Ser | Arg | Gln | Met | Val | Ser | Leu | Glu | Asp | Asp | Val | Ala |   |   |   |   |      |
| 850 |   |   |   |   | 855 |   |   |   |   | 860 |   |   |   |   |   |      |

<210> SEQ ID NO 38
<211> LENGTH: 860
<212> TYPE: PRT
<213> ORGANISM: Artificial Sequence
<220> FEATURE:
<223> OTHER INFORMATION: Synthetic Construct

<400> SEQUENCE: 38

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

-continued

Cys Ile His Ser Ser Trp Arg Cys Asp Gly Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
            245                 250                 255

Arg Glu Tyr Asp Cys Lys Asp Met Ser Asp Glu Val Gly Cys Val Asn
        260                 265                 270

Val Thr Leu Cys Glu Gly Pro Asn Lys Phe Lys Cys His Ser Gly Glu
    275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
            325                 330                 335

Glu Cys Asp Cys Pro Asp Gly Phe Gln Leu Val Ala Gln Arg Arg Cys
        340                 345                 350

Glu Asp Ile Asp Glu Cys Gln Asp Pro Asp Thr Cys Ser Gln Leu Cys
    355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
            405                 410                 415

Ser Glu Tyr Thr Ser Leu Ile Pro Asn Leu Arg Asn Val Val Ala Leu
        420                 425                 430

Asp Thr Glu Val Ala Ser Asn Arg Ile Tyr Trp Ser Asp Leu Ser Gln
    435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
            485                 490                 495

Thr Val Ser Val Ala Asp Thr Lys Gly Val Lys Arg Lys Thr Leu Phe
        500                 505                 510

Arg Glu Asn Gly Ser Lys Pro Arg Ala Ile Val Val Asp Pro Val His
    515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
            565                 570                 575

Trp Val Asp Ser Lys Leu His Ser Ile Ser Ser Ile Asp Val Asn Gly
        580                 585                 590

Gly Asn Arg Lys Thr Ile Leu Glu Asp Glu Lys Arg Leu Ala His Pro
    595                 600                 605

Phe Ser Leu Ala Val Phe Glu Asp Lys Val Phe Trp Thr Asp Ile Ile
    610                 615                 620

Asn Glu Ala Ile Phe Ser Ala Asn Arg Leu Thr Gly Ser Asp Val Asn

```
              625                 630                 635                 640
Leu Leu Ala Glu Asn Leu Leu Ser Pro Glu Asp Met Val Leu Phe His
                    645                 650                 655

Asn Leu Thr Gln Pro Arg Gly Val Asn Trp Cys Glu Arg Thr Thr Leu
                660                 665                 670

Ser Asn Gly Gly Cys Gln Tyr Leu Cys Leu Pro Ala Pro Gln Ile Asn
            675                 680                 685

Pro His Ser Pro Lys Phe Thr Cys Ala Cys Pro Asp Gly Met Leu Leu
        690                 695                 700

Ala Arg Asp Met Arg Ser Cys Leu Thr Glu Ala Glu Ala Val Ala
705                 710                 715                 720

Thr Gln Glu Thr Ser Thr Val Arg Leu Lys Val Ser Ser Thr Ala Val
                    725                 730                 735

Arg Thr Gln His Thr Thr Thr Arg Pro Val Pro Asp Thr Ser Arg Leu
                740                 745                 750

Pro Gly Ala Thr Pro Gly Leu Thr Thr Val Glu Ile Val Thr Met Ser
            755                 760                 765

His Gln Ala Leu Gly Asp Val Ala Gly Arg Gly Asn Glu Lys Lys Pro
        770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                    805                 810                 815

Asn Ile Asn Ser Ile Asn Phe Asp Asn Pro Val Tyr Gln Arg Thr Thr
                820                 825                 830

Glu Asp Glu Val His Ile Ala His Asn Gln Asp Gly Tyr Ser Tyr Pro
            835                 840                 845

Ser Arg Gln Met Val Ser Leu Glu Asp Asp Val Ala
        850                 855                 860

<210> SEQ ID NO 39
<211> LENGTH: 2583
<212> TYPE: DNA
<213> ORGANISM: Artificial Sequence
<220> FEATURE:
<223> OTHER INFORMATION: synthetic K809R, C818A, L318D with leader
<220> FEATURE:
<221> NAME/KEY: CDS
<222> LOCATION: (1)..(2583)

<400> SEQUENCE: 39 atg ggg ccc tgg ggc tgg aaa ttg cgc tgg acc gtc gcc ttg ctc ctc        48
Met Gly Pro Trp Gly Trp Lys Leu Arg Trp Thr Val Ala Leu Leu Leu
1               5                   10                  15 gcc gcg gcg ggg act gca gtg ggc gac aga tgt gaa aga aac gag ttc        96
Ala Ala Ala Gly Thr Ala Val Gly Asp Arg Cys Glu Arg Asn Glu Phe
            20                  25                  30 cag tgc caa gac ggg aaa tgc atc tcc tac aag tgg gtc tgc gat ggc       144
Gln Cys Gln Asp Gly Lys Cys Ile Ser Tyr Lys Trp Val Cys Asp Gly
        35                  40                  45 agc gct gag tgc cag gat ggc tct gat gag tcc cag gag acg tgc ttg       192
Ser Ala Glu Cys Gln Asp Gly Ser Asp Glu Ser Gln Glu Thr Cys Leu
    50                  55                  60 tct gtc acc tgc aaa tcc ggg gac ttc agc tgt ggg ggc cgt gtc aac       240
Ser Val Thr Cys Lys Ser Gly Asp Phe Ser Cys Gly Gly Arg Val Asn
65                  70                  75                  80 cgc tgc att cct cag ttc tgg agg tgc gat ggc caa gtg gac tgc gac       288
Arg Cys Ile Pro Gln Phe Trp Arg Cys Asp Gly Gln Val Asp Cys Asp
```

```
            85                  90                  95
aac ggc tca gac gag caa ggc tgt ccc ccc aag acg tgc tcc cag gac    336
Asn Gly Ser Asp Glu Gln Gly Cys Pro Pro Lys Thr Cys Ser Gln Asp
        100                 105                 110 gag ttt cgc tgc cac gat ggg aag tgc atc tct cgg cag ttc gtc tgt    384
Glu Phe Arg Cys His Asp Gly Lys Cys Ile Ser Arg Gln Phe Val Cys
            115                 120                 125 gac tca gac cgg gac tgc ttg gac ggc tca gac gag gcc tcc tgc ccg    432
Asp Ser Asp Arg Asp Cys Leu Asp Gly Ser Asp Glu Ala Ser Cys Pro
130                 135                 140 gtg ctc acc tgt ggt ccc gcc agc ttc cag tgc aac agc tcc acc tgc    480
Val Leu Thr Cys Gly Pro Ala Ser Phe Gln Cys Asn Ser Ser Thr Cys
145                 150                 155                 160 atc ccc cag ctg tgg gcc tgt gac aac gac ccc gac tgc gaa gat ggc    528
Ile Pro Gln Leu Trp Ala Cys Asp Asn Asp Pro Asp Cys Glu Asp Gly
            165                 170                 175 tcg gat gag tgg ccg cag cgc tgt agg ggt ctt tac gtg ttc caa ggg    576
Ser Asp Glu Trp Pro Gln Arg Cys Arg Gly Leu Tyr Val Phe Gln Gly
            180                 185                 190 gac agt agc ccc tgc tcg gcc ttc gag ttc cac tgc cta agt ggc gag    624
Asp Ser Ser Pro Cys Ser Ala Phe Glu Phe His Cys Leu Ser Gly Glu
            195                 200                 205 tgc atc cac tcc agc tgg cgc tgt gat ggt ggc ccc gac tgc aag gac    672
Cys Ile His Ser Ser Trp Arg Cys Asp Gly Gly Pro Asp Cys Lys Asp
            210                 215                 220 aaa tct gac gag gaa aac tgc gct gtg gcc acc tgt cgc cct gac gaa    720
Lys Ser Asp Glu Glu Asn Cys Ala Val Ala Thr Cys Arg Pro Asp Glu
225                 230                 235                 240 ttc cag tgc tct gat gga aac tgc atc cat ggc agc cgg cag tgt gac    768
Phe Gln Cys Ser Asp Gly Asn Cys Ile His Gly Ser Arg Gln Cys Asp
            245                 250                 255 cgg gaa tat gac tgc aag gac atg agc gat gaa gtt ggc tgc gtt aat    816
Arg Glu Tyr Asp Cys Lys Asp Met Ser Asp Glu Val Gly Cys Val Asn
            260                 265                 270 gtg aca ctc tgc gag gga ccc aac aag ttc aag tgt cac agc ggc gaa    864
Val Thr Leu Cys Glu Gly Pro Asn Lys Phe Lys Cys His Ser Gly Glu
            275                 280                 285 tgc atc acc ctg gac aaa gtc tgc aac atg gct aga gac tgc cgg gac    912
Cys Ile Thr Leu Asp Lys Val Cys Asn Met Ala Arg Asp Cys Arg Asp
            290                 295                 300 tgg tca gat gaa ccc atc aaa gag tgc ggg acc aac gaa tgc ttg gac    960
Trp Ser Asp Glu Pro Ile Lys Glu Cys Gly Thr Asn Glu Cys Leu Asp
305                 310                 315                 320 aac aac ggc ggc tgt tcc cac gtc tgc aat gac ctt aag atc ggc tac    1008
Asn Asn Gly Gly Cys Ser His Val Cys Asn Asp Leu Lys Ile Gly Tyr
            325                 330                 335 gag tgc gac tgc ccc gac ggc ttc cag ctg gtg gcc cag cga aga tgc    1056
Glu Cys Asp Cys Pro Asp Gly Phe Gln Leu Val Ala Gln Arg Arg Cys
            340                 345                 350 gaa gat atc gat gag tgt cag gat ccc gac acc tgc agc cag ctc tgc    1104
Glu Asp Ile Asp Glu Cys Gln Asp Pro Asp Thr Cys Ser Gln Leu Cys
            355                 360                 365 gtg aac ctg gag ggt ggc tac aag tgc cag tgt gag gaa ggc ttc cag    1152
Val Asn Leu Glu Gly Gly Tyr Lys Cys Gln Cys Glu Glu Gly Phe Gln
370                 375                 380 ctg gac ccc cac acg aag gcc tgc aag gct gtg ggc tcc atc gcc tac    1200
Leu Asp Pro His Thr Lys Ala Cys Lys Ala Val Gly Ser Ile Ala Tyr
385                 390                 395                 400 ctc ttc ttc acc aac cgg cac gag gtc agg aag atg acg ctg gac cgg    1248
```

```
            Leu Phe Phe Thr Asn Arg His Glu Val Arg Lys Met Thr Leu Asp Arg
                            405                 410                 415 agc gag tac acc agc ctc atc ccc aac ctg agg aac gtg gtc gct ctg        1296
Ser Glu Tyr Thr Ser Leu Ile Pro Asn Leu Arg Asn Val Val Ala Leu
            420                 425                 430 gac acg gag gtg gcc agc aat aga atc tac tgg tct gac ctg tcc cag        1344
Asp Thr Glu Val Ala Ser Asn Arg Ile Tyr Trp Ser Asp Leu Ser Gln
            435                 440                 445 aga atg atc tgc agc acc cag ctt gac aga gcc cac ggc gtc tct tcc        1392
Arg Met Ile Cys Ser Thr Gln Leu Asp Arg Ala His Gly Val Ser Ser
        450                 455                 460 tat gac acc gtc atc agc agg gac atc cag gcc ccc gac ggg ctg gct        1440
Tyr Asp Thr Val Ile Ser Arg Asp Ile Gln Ala Pro Asp Gly Leu Ala
465                 470                 475                 480 gtg gac tgg atc cac agc aac atc tac tgg acc gac tct gtc ctg ggc        1488
Val Asp Trp Ile His Ser Asn Ile Tyr Trp Thr Asp Ser Val Leu Gly
                485                 490                 495 act gtc tct gtt gcg gat acc aag ggc gtg aag agg aaa acg tta ttc        1536
Thr Val Ser Val Ala Asp Thr Lys Gly Val Lys Arg Lys Thr Leu Phe
            500                 505                 510 agg gag aac ggc tcc aag cca agg gcc atc gtg gtg gat cct gtt cat        1584
Arg Glu Asn Gly Ser Lys Pro Arg Ala Ile Val Val Asp Pro Val His
            515                 520                 525 ggc ttc atg tac tgg act gac tgg gga act ccc gcc aag atc aag aaa        1632
Gly Phe Met Tyr Trp Thr Asp Trp Gly Thr Pro Ala Lys Ile Lys Lys
        530                 535                 540 ggg ggc ctg aat ggt gtg gac atc tac tcg ctg gtg act gaa aac att        1680
Gly Gly Leu Asn Gly Val Asp Ile Tyr Ser Leu Val Thr Glu Asn Ile
545                 550                 555                 560 cag tgg ccc aat ggc atc acc cta gat ctc ctc agt ggc cgc ctc tac        1728
Gln Trp Pro Asn Gly Ile Thr Leu Asp Leu Leu Ser Gly Arg Leu Tyr
                565                 570                 575 tgg gtt gac tcc aaa ctt cac tcc atc tca agc atc gat gtc aat ggg        1776
Trp Val Asp Ser Lys Leu His Ser Ile Ser Ser Ile Asp Val Asn Gly
            580                 585                 590 ggc aac cgg aag acc atc ttg gag gat gaa aag agg ctg gcc cac ccc        1824
Gly Asn Arg Lys Thr Ile Leu Glu Asp Glu Lys Arg Leu Ala His Pro
            595                 600                 605 ttc tcc ttg gcc gtc ttt gag gac aaa gta ttt tgg aca gat atc atc        1872
Phe Ser Leu Ala Val Phe Glu Asp Lys Val Phe Trp Thr Asp Ile Ile
        610                 615                 620 aac gaa gcc att ttc agt gcc aac cgc ctc aca ggt tcc gat gtc aac        1920
Asn Glu Ala Ile Phe Ser Ala Asn Arg Leu Thr Gly Ser Asp Val Asn
625                 630                 635                 640 ttg ttg gct gaa aac cta ctg tcc cca gag gat atg gtc ctc ttc cac        1968
Leu Leu Ala Glu Asn Leu Leu Ser Pro Glu Asp Met Val Leu Phe His
                645                 650                 655 aac ctc acc cag cca aga gga gtg aac tgg tgt gag agg acc acc ctg        2016
Asn Leu Thr Gln Pro Arg Gly Val Asn Trp Cys Glu Arg Thr Thr Leu
            660                 665                 670 agc aat ggc ggc tgc cag tat ctg tgc ctc cct gcc ccg cag atc aac        2064
Ser Asn Gly Gly Cys Gln Tyr Leu Cys Leu Pro Ala Pro Gln Ile Asn
            675                 680                 685 ccc cac tcg ccc aag ttt acc tgc gcc tgc ccg gac ggc atg ctg ctg        2112
Pro His Ser Pro Lys Phe Thr Cys Ala Cys Pro Asp Gly Met Leu Leu
        690                 695                 700 gcc agg gac atg agg agc tgc ctc aca gag gct gag gct gca gtg gcc        2160
Ala Arg Asp Met Arg Ser Cys Leu Thr Glu Ala Glu Ala Ala Val Ala
705                 710                 715                 720
```

| | | |
|---|---|---|
| acc cag gag aca tcc acc gtc agg cta aag gtc agc tcc aca gcc gta<br>Thr Gln Glu Thr Ser Thr Val Arg Leu Lys Val Ser Ser Thr Ala Val<br>                        725                                730                        735 | 2208 |
| agg aca cag cac aca acc acc cgg cct gtt ccc gac acc tcc cgg ctg<br>Arg Thr Gln His Thr Thr Thr Arg Pro Val Pro Asp Thr Ser Arg Leu<br>                        740                                745                        750 | 2256 |
| cct ggg gcc acc cct ggg ctc acc acg gtg gag ata gtg aca atg tct<br>Pro Gly Ala Thr Pro Gly Leu Thr Thr Val Glu Ile Val Thr Met Ser<br>                 755                                760                        765 | 2304 |
| cac caa gct ctg ggc gac gtt gct ggc aga gga aat gag aag aag ccc<br>His Gln Ala Leu Gly Asp Val Ala Gly Arg Gly Asn Glu Lys Lys Pro<br>              770                                775                        780 | 2352 |
| agt agc gtg agg gct ctg tcc att gtc ctc ccc atc gtg ctc ctc gtc<br>Ser Ser Val Arg Ala Leu Ser Ile Val Leu Pro Ile Val Leu Leu Val<br>785                        790                                795                        800 | 2400 |
| ttc ctt tgc ctg ggg gtc ttc ctt cta tgg aag aac tgg cgg ctt aag<br>Phe Leu Cys Leu Gly Val Phe Leu Leu Trp Lys Asn Trp Arg Leu Lys<br>                        805                                810                        815 | 2448 |
| aac atc aac agc atc aac ttt gac aac ccc gtc tat cag agg acc aca<br>Asn Ile Asn Ser Ile Asn Phe Asp Asn Pro Val Tyr Gln Arg Thr Thr<br>                    820                                825                        830 | 2496 |
| gag gat gag gtc cac att gcc cac aac cag gac ggc tac agc tac ccc<br>Glu Asp Glu Val His Ile Ala His Asn Gln Asp Gly Tyr Ser Tyr Pro<br>                835                                840                        845 | 2544 |
| tcg aga cag atg gtc agt ctg gag gat gac gtg gcg tga<br>Ser Arg Gln Met Val Ser Leu Glu Asp Asp Val Ala<br>          850                        855                        860 | 2583 |

<210> SEQ ID NO 40
<211> LENGTH: 860
<212> TYPE: PRT
<213> ORGANISM: Artificial Sequence
<220> FEATURE:
<223> OTHER INFORMATION: Synthetic Construct

<400> SEQUENCE: 40

Met Gly Pro Trp Gly Trp Lys Leu Arg Trp Thr Val Ala Leu Leu Leu
1               5                   10                  15

Ala Ala Ala Gly Thr Ala Val Gly Asp Arg Cys Glu Arg Asn Glu Phe
            20                  25                  30

Gln Cys Gln Asp Gly Lys Cys Ile Ser Tyr Lys Trp Val Cys Asp Gly
        35                  40                  45

Ser Ala Glu Cys Gln Asp Gly Ser Asp Glu Ser Gln Glu Thr Cys Leu
    50                  55                  60

Ser Val Thr Cys Lys Ser Gly Asp Phe Ser Cys Gly Gly Arg Val Asn
65                  70                  75                  80

Arg Cys Ile Pro Gln Phe Trp Arg Cys Asp Gly Gln Val Asp Cys Asp
                85                  90                  95

Asn Gly Ser Asp Glu Gln Gly Cys Pro Pro Lys Thr Cys Ser Gln Asp
            100                 105                 110

Glu Phe Arg Cys His Asp Gly Lys Cys Ile Ser Arg Gln Phe Val Cys
        115                 120                 125

Asp Ser Asp Arg Asp Cys Leu Asp Gly Ser Asp Glu Ala Ser Cys Pro
    130                 135                 140

Val Leu Thr Cys Gly Pro Ala Ser Phe Gln Cys Asn Ser Ser Thr Cys
145                 150                 155                 160

Ile Pro Gln Leu Trp Ala Cys Asp Asn Asp Pro Asp Cys Glu Asp Gly
                165                 170                 175

-continued

Ser Asp Glu Trp Pro Gln Arg Cys Arg Gly Leu Tyr Val Phe Gln Gly
            180                 185                 190

Asp Ser Ser Pro Cys Ser Ala Phe Glu Phe His Cys Leu Ser Gly Glu
        195                 200                 205

Cys Ile His Ser Ser Trp Arg Cys Asp Gly Pro Asp Cys Lys Asp
    210                 215                 220

Lys Ser Asp Glu Glu Asn Cys Ala Val Ala Thr Cys Arg Pro Asp Glu
225                 230                 235                 240

Phe Gln Cys Ser Asp Gly Asn Cys Ile His Gly Ser Arg Gln Cys Asp
                245                 250                 255

Arg Glu Tyr Asp Cys Lys Asp Met Ser Asp Glu Val Gly Cys Val Asn
            260                 265                 270

Val Thr Leu Cys Glu Gly Pro Asn Lys Phe Lys Cys His Ser Gly Glu
        275                 280                 285

Cys Ile Thr Leu Asp Lys Val Cys Asn Met Ala Arg Asp Cys Arg Asp
    290                 295                 300

Trp Ser Asp Glu Pro Ile Lys Glu Cys Gly Thr Asn Glu Cys Leu Asp
305                 310                 315                 320

Asn Asn Gly Gly Cys Ser His Val Cys Asn Asp Leu Lys Ile Gly Tyr
                325                 330                 335

Glu Cys Asp Cys Pro Asp Gly Phe Gln Leu Val Ala Gln Arg Arg Cys
            340                 345                 350

Glu Asp Ile Asp Glu Cys Gln Asp Pro Asp Thr Cys Ser Gln Leu Cys
        355                 360                 365

Val Asn Leu Glu Gly Gly Tyr Lys Cys Gln Cys Glu Glu Gly Phe Gln
    370                 375                 380

Leu Asp Pro His Thr Lys Ala Cys Lys Ala Val Gly Ser Ile Ala Tyr
385                 390                 395                 400

Leu Phe Phe Thr Asn Arg His Glu Val Arg Lys Met Thr Leu Asp Arg
                405                 410                 415

Ser Glu Tyr Thr Ser Leu Ile Pro Asn Leu Arg Asn Val Val Ala Leu
            420                 425                 430

Asp Thr Glu Val Ala Ser Asn Arg Ile Tyr Trp Ser Asp Leu Ser Gln
        435                 440                 445

Arg Met Ile Cys Ser Thr Gln Leu Asp Arg Ala His Gly Val Ser Ser
    450                 455                 460

Tyr Asp Thr Val Ile Ser Arg Asp Ile Gln Ala Pro Asp Gly Leu Ala
465                 470                 475                 480

Val Asp Trp Ile His Ser Asn Ile Tyr Trp Thr Asp Ser Val Leu Gly
                485                 490                 495

Thr Val Ser Val Ala Asp Thr Lys Gly Val Lys Arg Lys Thr Leu Phe
            500                 505                 510

Arg Glu Asn Gly Ser Lys Pro Arg Ala Ile Val Val Asp Pro Val His
        515                 520                 525

Gly Phe Met Tyr Trp Thr Asp Trp Gly Thr Pro Ala Lys Ile Lys Lys
    530                 535                 540

Gly Gly Leu Asn Gly Val Asp Ile Tyr Ser Leu Val Thr Glu Asn Ile
545                 550                 555                 560

Gln Trp Pro Asn Gly Ile Thr Leu Asp Leu Leu Ser Gly Arg Leu Tyr
                565                 570                 575

Trp Val Asp Ser Lys Leu His Ser Ile Ser Ser Ile Asp Val Asn Gly
            580                 585                 590

Gly Asn Arg Lys Thr Ile Leu Glu Asp Glu Lys Arg Leu Ala His Pro

```
                    595                 600                 605
Phe Ser Leu Ala Val Phe Glu Asp Lys Val Phe Trp Thr Asp Ile Ile
        610                 615                 620

Asn Glu Ala Ile Phe Ser Ala Asn Arg Leu Thr Gly Ser Asp Val Asn
625                 630                 635                 640

Leu Leu Ala Glu Asn Leu Leu Ser Pro Glu Asp Met Val Leu Phe His
                645                 650                 655

Asn Leu Thr Gln Pro Arg Gly Val Asn Trp Cys Glu Arg Thr Thr Leu
            660                 665                 670

Ser Asn Gly Gly Cys Gln Tyr Leu Cys Leu Pro Ala Pro Gln Ile Asn
        675                 680                 685

Pro His Ser Pro Lys Phe Thr Cys Ala Cys Pro Asp Gly Met Leu Leu
    690                 695                 700

Ala Arg Asp Met Arg Ser Cys Leu Thr Glu Ala Glu Ala Ala Val Ala
705                 710                 715                 720

Thr Gln Glu Thr Ser Thr Val Arg Leu Lys Val Ser Ser Thr Ala Val
                725                 730                 735

Arg Thr Gln His Thr Thr Thr Arg Pro Val Pro Asp Thr Ser Arg Leu
            740                 745                 750

Pro Gly Ala Thr Pro Gly Leu Thr Thr Val Glu Ile Val Thr Met Ser
        755                 760                 765

His Gln Ala Leu Gly Asp Val Ala Gly Arg Gly Asn Glu Lys Lys Pro
    770                 775                 780

Ser Ser Val Arg Ala Leu Ser Ile Val Leu Pro Ile Val Leu Leu Val
785                 790                 795                 800

Phe Leu Cys Leu Gly Val Phe Leu Leu Trp Lys Asn Trp Arg Leu Lys
                805                 810                 815

Asn Ile Asn Ser Ile Asn Phe Asp Asn Pro Val Tyr Gln Arg Thr Thr
            820                 825                 830

Glu Asp Glu Val His Ile Ala His Asn Gln Asp Gly Tyr Ser Tyr Pro
        835                 840                 845

Ser Arg Gln Met Val Ser Leu Glu Asp Asp Val Ala
    850                 855                 860
```

US 11,555,059 B2

LDLR VARIANTS AND THEIR USE IN COMPOSITIONS FOR REDUCING CHOLESTEROL LEVELS

CROSS-REFERENCE TO RELATED APPLICATIONS

This is a 371 national stage of PCT/US2015/027572, filed Apr. 24, 2015, which claims the benefit under 35 USC 119(e) of U.S. Provisional Patent Application No. 61/984,620, filed Apr. 25, 2014, now expired, and U.S. Provisional Patent Application No. 62/022,627, filed Jul. 9, 2014, now expired.

STATEMENT REGARDING FEDERALLY SPONSORED RESEARCH OR DEVELOPMENT

This invention was made with government support under grant number HL059407 awarded by the National Institutes of Health. The government has certain rights in the invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled "14-7025PCTST25.txt".

BACKGROUND OF THE INVENTION

Familial Hypercholesterolemia (FH) is an autosomal co-dominant disorder characterized by absence of the receptor for low-density lipoproteins (LDLR); a single chain glycoprotein containing 839 amino acids in its mature form. Hussain M M, et al, Annu Rev Nutr. 1999; 19:141-172. Patients with one abnormal allele, heterozygous FH (heFH) have moderate elevations in plasma LDL and suffer from premature coronary artery disease (CAD), whereas homozygous FH patients (hoFH) have high serum cholesterol (LDL-C>24 mmol/L) that often results in the early onset of life-threatening cardio vascular disease (CVD). Marais A D, Clin Biochem Rev. 2004; 25:49-68. Current treatment options to reduce excess serum cholesterol include LDL apheresis [McGowan M P. J Clin Lipidol. 2013; 7:521-26] and treatment with cholesterol lowering drugs. Hovingh G K, et al, Eur Heart J. 2013; 34:962-971. Orthotopic liver transplantation can lead to long term correction [Raal F J, 2012; 223:262-268], although, it is associated with substantial treatment related morbidity and mortality.

Liver-directed gene therapy using adeno-associated viral vectors (AAV) has been demonstrated in preclinical models to stably correct several metabolic disorders and is currently being pursued in clinical trials for treatment of hemophilia A and B, ornithine transcarbamylase deficiency (OTC) and alpha1-antitrypsin (A1AT) deficiency. Wang L, et al, Mol Genet Metab. 2012; 105:203-211; Brantly M L, et al, Proc Natl Acad Sci USA. 2009; 106:16363-16368; Nathwani A C, et al., N Engl J Med. 2011; 365:2357-2365; Ward N J, et al, Blood. 2011; 117:798-807]. Recently, the effectiveness of AAV mediated gene therapy in correcting serum cholesterol levels in humanized mouse models of FH has been demonstrated. Kassim S H, et al, PLoS One. 2010; 5:e13424. In these mice, systemic administration of AAV8 expressing human LDLR (AAV8.hLDLR) led to a lowering of cholesterol to normal levels by day 7 which was sustained for over a year and led to regression of pre-existing atherosclerosis. However, AAV8.LDLR transduction was dose dependent and statistically significant correction was only achieved at a vector dose of $1.5 \times 10^{11}$ GC/kg or above. For clinical gene therapy, minimizing the vector dose is critical for many reasons, including vector injection volume, toxicity, immune response and manufacturing and cost of goods constraints.

Hepatic LDLR expression is modulated by multiple pathways within the cell: LDLR transcription is regulated by the sterol response element binding proteins (SREBPs), and HMGcoA reductase inhibitors (statins) activate SREBPs by inhibiting cholesterol synthesis within hepatocytes [Blumenthal R S, Am Heart J. 2000; 139:577-583].

A second pathway of LDLR regulation, involving proprotein convertase subtilisin kexin 9 (PCSK9), was discovered based on human genetics gain-of-function mutations that caused high LDL-C levels [Abifadel M, et al., Nat Genet. 2003; 34:154-156] and loss-of-function mutations that caused low LDL-C levels [Cohen J, et al., Nat Genet. 2005; 37:161-1653]. The loss of PCSK9 function was associated with an 88% reduction in cardiovascular disease and has led to the development of a new class of cholesterol lowering drugs based on the inhibition of PCSK9 [Fitzgerald K, et al, Lancet. 2014; 383:60-68; Giugliano R P, et al, Lancet. 2012; 380:2007-2017]. Patients with FH have significantly higher plasma levels of PCSK9 [Raal F, et al., J Am Heart Assoc. 2013; 2:e000028].

A third pathway of LDLR regulation was discovered by Zelcher et al, [Zelcher N, et al., Science. 2009; 325:100-104] who demonstrated the degradation of LDLR by IDOL (inducible degrader of LDLR). An E3 ubiquitin ligase, IDOL was induced following activation of liver X receptors (LXRs) and subsequently interacted with the cytoplasmic tail of LDLR in mediating receptor ubiquitination and degradation. Furthermore, screening of subjects with low LDL-C identified loss-of-function mutations in IDOL that prevented degradation of LDLR [Sorrentino V, et al., Eur Heart J. 2013; 34:1292-1297].

Compositions useful for effectively lowering cholesterol in subjects, particularly those having familial hypercholesterolemia, are needed.

SUMMARY OF THE INVENTION

Novel engineered human low density lipoprotein receptor (hLDLR) variants are provided herein, which have increased efficacy as compared to prior art "wild-type" LDLR, due to PCSK9 and/or IDOL resistance. These engineered variants of hLDLR are suitably characterized by a reduced affinity for PCSK9 and/or IDOL, an increased systemic half-life, and are useful for lowering cholesterol as compared to the native hLDLR. These variants can be delivered to subjects in need thereof via a number of routes, and particularly by expression in vivo mediated by a recombinant vector such as a recombinant adeno-associated virus (rAAV) vector.

In some embodiments, a synthetic or recombinant vector comprising a modified hLDLr gene is provided. In some embodiments, the modified hLDLR gene encodes a modified hLDLR that reduces cholesterol following expression. In some embodiments, the modified hLDLR comprises one or more amino acid substitutions that interfere with the wild-type hLDLR IDOL pathway and/or one or more amino acid substitutions which are resistant to degradation of hLDLR by interfering with the PCSK9 pathway.

In certain embodiments, the synthetic or recombinant vector encodes a modified hLDLR that comprises an amino acid substitution at amino acid position N295, H306, V307, N309, D310, L318, L796, K809 and/or C818. These amino acid positions are based on the numbering of SEQ ID NO:1 (the LDLR without the signal peptide). In a specific embodiment, the one or more amino acid substitutions are N295D, H306D, V307D, N309A, D310N, L318H, and/or L318D, which are examples of amino acid substitutions that interfere with the wild-type hLDLR IDOL pathway. In another specific embodiment, the one or more amino acid substitutions are L769R, K809R and/or C818A, which are examples of amino acid substitutions which are resistant to degradation of hLDLR by interfering with the PCSK9 pathway. In another specific embodiment, the recombinant vector encodes a modified hLDLR that comprises one or more of amino acid substitutions N295D, H306D, V307D, N309A, D310N, L318H, and/or L318D in combination with one or more of amino acid substitutions L7696R, K809R and/or C818A (numbering based on SEQ ID NO:1).

In some embodiments, the recombinant vectors provided herein have an expression cassette comprising the modified hLDLR. In some embodiments, the expression cassette comprises a promoter which specifically directs expression of the modified hLDLR in liver cells.

In some embodiments, the recombinant vector is a recombinant adeno-associated virus (rAAV) vector. In some embodiments, the rAAV has a capsid selected from AAV8, rh64R1, AAV9, or rh10. In a particular embodiment, an rAAV vector is provided that has an expression cassette comprising a modified hLDLR gene, wherein said hLDLR gene encodes a modified hLDLR comprising an L318D amino acid substitution. In a specific embodiment, the modified hLDLR further comprises a K809R and/or C818A amino acid substitution. In a specific embodiment, the rAAV vector comprises an expression cassette comprising a promoter which specifically directs expression of the modified hLDLr in liver cells.

In certain embodiments, the hLDLR gene encodes a modified hLDLr having three substitutions: L318D/K809R/C818A (numbering based on SEQ ID NO: 1). Other combinations of substitutions may be selected.

In some embodiments, a pharmaceutical composition comprising a pharmaceutically acceptable carrier and a recombinant vector as described herein is provided. Also provided are methods for reducing circulating cholesterol levels by administering to a subject in need thereof a recombinant vector described herein that has an expression cassette, wherein said expression cassette further comprises regulatory control sequences which direct expression of modified hLDLr in the subject.

In yet another embodiment, methods for increasing the circulating half-life of a hLDLR are provided, comprising modifying the hLDLR at one or more amino acid positions (position numbers based on SEQ ID NO: 1) selected from: N295, H306, V307, N309, D310, L318, L7696, K809 and/or C818. In a specific embodiment, the hLDLR is modified to comprise one or more amino acid substitutions selected from: N295D, H306D, V307D, N309A, D310N, L318H, and/or L318D. In another specific embodiment, the hLDLR is further modified to comprise a K769R, K809R and/or C818A amino acid substitution.

The recombinant vectors described above can be used in a regimen for treating familial hypercholesterolemia.

Other aspects and advantages of the invention will be readily apparent from the following detailed description of the invention.

BRIEF DESCRIPTION OF THE DRAWINGS

FIGS. 1A and 1B provide the results of in vitro evaluation of LDLR variants that escape hPCSK9 regulation. Plasmids expressing wild type hLDLR or one of the LDLR variants were co-transfected along with hPCSK9 into HEK293 cells. 24 hours (hr) after transfection, cells were pulsed with BODIPY™-LDL [Molecular Probes] for 2 hr and then evaluated by flow cytometry for fluorescent LDL positive cells. FIG. 1A is a bar chart showing the percentage of BODIPY™-LDL positive cells when co-transfected with hLDLR or hLDLR along with hPCSK9. The experiment was controlled by transfecting cells with an irrelevant plasmid (Mock). FIG. 1B is a bar chart showing the fold change in BODIPY-LDL positive cells in hLDLR plus hPCSK9 co-transfected cells relative to hLDLR only transfected cells. FIG. 1C is a bar chart showing in vivo results in a mouse model expressing mLDLR. The results indicate some level of interaction between hPCSK9 and mLDLR.

FIG. 2A is a bar chart showing the percent change in day 30 non-HDL serum cholesterol relative to baseline levels in animals that received hLDLR with or without hPCSK9. FIG. 2B is a line graph showing the time course of hPCSK9 expression in serum from mice that received hLDLR or hLDLR plus hPCSK9. hPCSK9 expression was evaluated using a sandwich ELISA. The reported reference average hPCSK9 levels in humans is also shown on the graph. FIG. 2C is an immunoblot of hLDLR expression in mice treated with hLDLR or hLDLR with hPCSK9. Total liver lysates from two representative animals per group were electrophoresed on a 4-12% gradient SDS gel and probed with a polyclonal anti-hLDLR goat polyclonal antibody. Mouse tubulin expression was used as a loading control. All values are expressed as mean±SEM. ***p<0.001.

FIG. 3A is a bar chart showing the percent change in day 30 non-HDL serum cholesterol levels relative to pre-vector administration in DKO mice co-administered with hLDLR or hLDLR-L318D, along with hPCSK9. FIG. 3B show total liver lysates from two animals per group which were electrophoresed on a 4-12% SDS PAGE gel and probed for hLDLR expression. Mouse tubulin expression was used as a loading control. All values are expressed as mean±SEM. ***p<0.001. ns p>0.05.

FIG. 4A is a bar chart showing the percent BODIPY™-LDL positive cells transfected with hLDLR or hLDLR-K809R\C818A along with hIDOL. FIG. 4B is a line graph showing data from LDLR$^{+/-}$, Apobec$^{-/-}$, Tg-hApoB100 (LAHB) heterozygous FH (heFH) mice (n=4) which were systemically administered with 1×10¹¹ GC of AAV9hPCSK9 vector. Time course of non-HDL cholesterol levels following vector administration. FIG. 4C is a bar chart showing homozygous FH (hoFH) DKO mice (n=4\group) systemically administered with 3×10⁹GC AAV8.hLDLR, or AAV8.hLDLR-K809R\C818A, along with AAV9.hIDOL 5×10¹⁰ GC. Serum from animals pre- and 30 days post vector administration was evaluated for total serum cholesterol. Percent change in serum non-HDL levels at 30 day relative to pre-administration baseline levels. All values are expressed as mean±SEM. ***p<0.0001.*p<0.05. ns p>0.05. FIG. 4D provides the total cell lysates of transfected cells (FIG. 4A) electrophoresed on a 4-12% SDS gel and probed using anti-hLDLR antibody. The location of mature (M) and processed (P) forms of LDLR along with the tubulin loading control is shown.

FIG. 5A illustrates the results in a study in which DKO mice (n=4) were intravenously administered with 3×10⁹ GC of hLDLR or hLDLR-L318D\K809R\C818A. Additional groups of mice also received a simultaneous administration of AAV9.hIDOL. Total serum cholesterol levels were evaluated before and 30 days after vector administration. Percent decrease in non-HDL cholesterol relative to baseline. Total liver lysates from 2 representative animals per group were electrophoresed on a SDS PAGE gel and probed using an anti-hLDLR antibody along with tubulin as a loading control. FIG. 5B illustrates the results following coadministration of AAV8.hLDLR (5×10¹⁰ GC) or hLDLR-L318D\K809R\C818A along with AAV9.hPCSK9 (5×10¹⁰ GC). Percent decrease in day 30 non-HDL cholesterol relative to baseline is shown along with an immunoblot of hLDLR expression in livers. n ***p<0.001.

DETAILED DESCRIPTION OF THE INVENTION

Figure 2A:
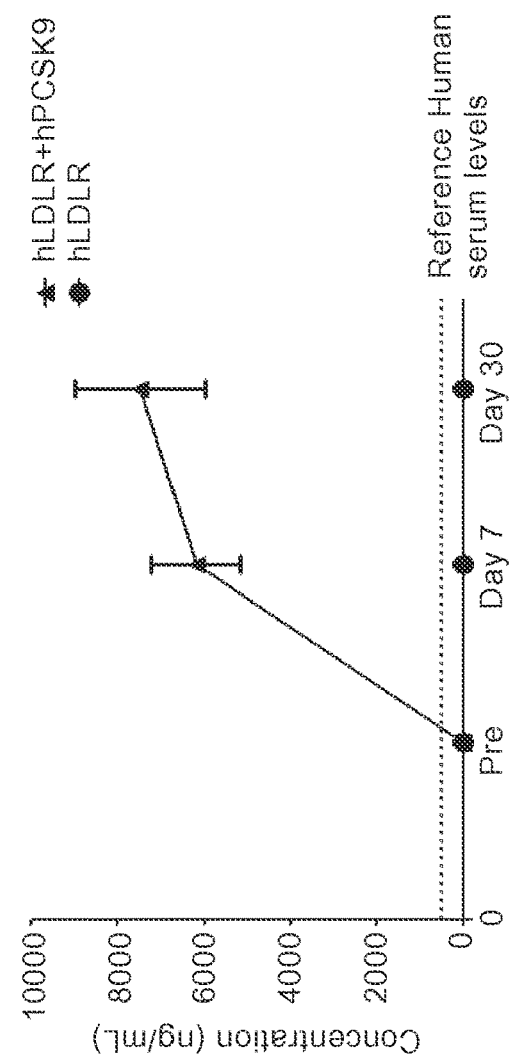
FIGS. 2A-2C provide results from a study showing in vivo overexpression of hPCSK9 leads to an increase in serum cholesterol in animals dosed with wild type hLDLR. LDLR$^{-/-}$, APOBEC-1$^{-/-}$ double knock-out (DKO) mice (n=4/group) were administered intravenously with a dose of $5 \times 10^{10}$ GC of AAV8.TBG.hLDLR or AAV8.TBG.hLDLR along with $5 \times 10^{10}$ GC of AAV9.hPCSK9 vector. Serum from animals before and 30 days after vector administration was analyzed for total serum cholesterol and HDL cholesterol. Non-HDL cholesterol levels were determined by subtracting the HDL component from total cholesterol.

The novel engineered human low density lipoprotein receptor (hLDLR) variants described herein are characterized by increased half-life and increased efficacy in decreasing cholesterol levels as compared to the native hLDLR due at least in part to their ability to substantially avoid degradation by pro-protein convertase subtilisin kexin 9 (PCSK9) and/or substantially avoid degradation by the inducible degrader of LDLR (IDOL).

Delivery of these variants to subjects in need thereof via a number of routes, and particularly by expression in vivo mediated by a recombinant vector such as a rAAV vector, are described. Also provided are methods of using these variants in regimens for lowering cholesterol levels in subject in need thereof, treating familial hypercholesterolemia, treating atherosclerosis, decreasing the risk of premature coronary artery disease and/or decreasing early onset of cardio vascular disease. Advantageously, compositions provided herein are useful for simultaneously targeting multiple pathways in these treatments and regimens.

As used herein, the term familial hypercholesterolemia (FH) refers to a genetic disorder of lipid metabolism. Unless otherwise specified herein, both homozygous FH (hoFH) subjects and heterozygous FH (heFH) subjects are encompassed within the term FH.

As used herein, the term "lowering cholesterol levels" may encompass decreasing serum cholesterol levels and/or decreasing low-density lipoprotein levels (e.g., in plasma). Treating atherosclerosis may include decreasing number and/or volume of plaques and/or preventing further accumulation of atherosclerotic plaques.

The amino acid sequence of the mature "wild-type" hLDLR (isoform 1) is reproduced herein as SEQ ID NO: 1 for convenience and provides a reference for the numbering of the amino acid variants provided herein. While the sequence numbering provided herein refers to the mature hLDLR protein (a single chain glycoprotein of 839 amino acids), it will be understood that wild-type hLDLR leader sequence (amino acids 1-21 of SEQ ID NO:2) may be used or a heterologous leader sequence may be selected for use in the constructs described herein. Additionally, or optionally, one or more of the other hLDLR isoforms 2, 3, 4, 5 and 6, the sequences of which are available, e.g., from the following web site: uniprot.org/uniport/P01130, and the amino acid substitutions described herein may be incorporated into these isoforms (see also, SEQ ID NO: 3-7 where the sequences of these isoforms are reproduced for convenience). In the following descriptions, substitutions may be written as (first amino acid identified by single letter code)-residue position #-(second amino acid identified by single letter code) whereby the first amino acid is the substituted amino acid and the second amino acid is the substituting amino acid at the specified position with reference to isoform 1; however, by conventional alignment steps, the corresponding amino acid residues identified herein with respect to the numbering of isoform 1 can be located in the other isoforms or hLDLR proteins identified herein.

The term "amino acid substitution" and its synonyms described above are intended to encompass modification of an amino acid sequence by replacement of an amino acid with another, substituting, amino acid. The substitution may be a conservative substitution. It may also be a non-conservative substitution. The term conservative, in referring to two amino acids, is intended to mean that the amino acids share a common property recognized by one of skill in the art. For example, amino acids having hydrophobic nonacidic side chains, amino acids having hydrophobic acidic side chains, amino acids having hydrophilic nonacidic side chains, amino acids having hydrophilic acidic side chains, and amino acids having hydrophilic basic side chains. Common properties may also be amino acids having hydrophobic side chains, amino acids having aliphatic hydrophobic side chains, amino acids having aromatic hydrophobic side chains, amino acids with polar neutral side chains, amino acids with electrically charged side chains, amino acids with electrically charged acidic side chains, and amino acids with electrically charged basic side chains. Both naturally occurring and non-naturally occurring amino acids are known in the art and may be used as substituting amino acids in embodiments. Methods for replacing an amino acid are well known to the skilled in the art and include, but are not limited to, mutations of the nucleotide sequence encoding the amino acid sequence. Reference to "one or more" herein is intended to encompass the individual embodiments of, for example, 1, 2, 3, 4, 5, 6, or more.

As described herein, the hLDLR variants provided herein are engineered to reduce the PCSK9 degradation characteristic of the wild-type LDLR. In one embodiment, the variant is a human LDLR having an amino acid substation at position 318, in which the native leucine (Leu) is modified. In one example, the L318 is modified to histidine (His, H). However, other substitutions (e.g., an L318D) may be made at this position. Alternatively or additionally, other hLDLR variants resistant to PCSK9 degradation may be selected from among those identified herein. These may include, e.g., substitutions of N295, H306, V307, N309, and/or D310 (position numbers based on SEQ ID NO:1). Methods of determining resistance to PCSK9 degradation and/or determining increased circulating half-life as compared to the wild-type hLDLR are known in the art, and at least one these assays is illustrated in the examples below.

Additionally, the PCSK9-resistant LDLR variants described herein may be further engineered to include resistance to degradation by IDOL. Suitable substitutions for conferring this characteristic include substitutions at position K796 (abbreviated K6 in sequence listing), K809 and C818. The substitutions illustrated herein are K809R and C818A. However, other IDOL-resistant substitutions may be selected. Methods of determining resistance to IDOL degradation and/or determining increased circulating half-life as compared to the wild-type hLDLR are known in the art, and at least one these assays is illustrated in the examples below.

Other modifications to the hLDLR isoform 1 amino acid sequence, which incorporate one or more of the above variants, are encompassed within the invention. For example, the corresponding modification to the amino acid sequence of any of isoforms 2 (SEQ ID NO:3), isoform 3 (SEQ ID NO: 4), isoform 4 (SEQ ID NO: 5), isoform 5 (SEQ ID NO: 6), and isoform 7 (SEQ ID NO: 7) may be utilized. These isoforms are reproduced in the Sequence Listing herein. In another example, the hLDLR variant described herein may be engineered to contain the hLDLR leader sequence. Alternatively, a heterologous leader sequence may be engineered to the N-terminus of the hLDLR variant. Alternatively, still other variations, which may include up to about 5% variation (about 95% identity to about 99.9% identity to the variant sequence, or about 97% to about 98% identity) to the hLDLR variants provided herein (excluding the leader sequence) may be selected which retain one or more of the therapeutic functions of the hLDLR variants described herein, and which are characterized by PCSK9-resistance and/or IDOL-resistance.

In the examples section of this description, while a number of constructs did escape PCSK9 regulation in initial in vitro screening, the studies focused on the L318D amino acid substitution. Among the variants provided herein, the L318D modification has been demonstrated to confer protection from PCSK9 both in vitro and in vivo. In the examples provided herein, L318D (position number based on SEQ ID NO:1, illustrative construct with leader sequence in SEQ ID NO: 26) conferred protection following hepatic expression in mice overexpressing PCSK9 and led to a significant decrease in serum cholesterol; whereas, wild-type LDLR was less efficient and more readily degraded by PCSK9.

As illustrated in the examples below, the K809R/C818A hLDLR double mutant (position numbers based on SEQ ID NO:1, illustrative construct with leader sequence in SEQ ID NO: 36] conferred protection following hepatic expression in mice expressing hIDOL and led to a significant decrease in serum cholesterol; whereas, wild-type LDLR was less efficient and more readily degraded by IDOL. These data thus establish that the amino acid modifications in the LDLR can also overcome in vivo IDOL mediated suppression. Factors that lead to LDLR degradation are expected to be higher in subjects lacking endogenous receptor expression due to lack of a substrate to remove the inhibitors. The usefulness of LDLR variants in overcoming negative cellular regulatory pathways, known to exist in FH subjects, is demonstrated herein. The findings presented here demonstrate for the first time the successful use of an AAV encoded 'gain-of-function' transgene in reducing cholesterol in humanized mouse models expressing high levels of inhibitory factors which is useful in gene therapy products for FH.

In addition to the hLDLR protein variants provided herein, nucleic acid sequences encoding these hLDLR protein variants are provided. The coding sequences for these variants may be generating using site-directed mutagenesis of the wild-type nucleic acid sequence. Alternatively or additionally, web-based or commercially available computer programs, as well as service based companies may be used to back translate the amino acids sequences to nucleic acid coding sequences, including both RNA and/or cDNA. See, e.g., backtranseq by EMBOSS, world wide web at ebi.ac.uk/Tools/st/; Gene Infinity (world wide web at geneinfinity.org/sms/sms_backtranslation.html); ExPasy (world wide web at expasy.org/tools/) In one embodiment, the RNA and/or cDNA coding sequences are designed for optimal expression in human cells.

Codon-optimized coding regions can be designed by various different methods. This optimization may be performed using methods which are available on-line, published methods, or a company which provides codon optimizing services. One codon optimizing method is described, e.g., in U.S. Patent Application No. 61/817,110, which is incorporated by reference herein. Briefly, the nucleic acid sequence encoding the product is modified with synonymous codon sequences. Suitably, the entire length of the open reading frame (ORF) for the product is modified. However, in some embodiments, only a fragment of the ORF may be altered. By using one of these methods, one can apply the frequencies to any given polypeptide sequence, and produce a nucleic acid fragment of a codon-optimized coding region which encodes the polypeptide.

The terms "percent (%) identity", "sequence identity", "percent sequence identity", or "percent identical" in the context of nucleic acid sequences refers to the bases in the two sequences which are the same when aligned for correspondence. The length of sequence identity comparison may be over the full-length of the genome, the full-length of a gene coding sequence, or a fragment of at least about 500 to 5000 nucleotides, or as desired. However, identity among smaller fragments, e.g. of at least about nine nucleotides, usually at least about 20 to 24 nucleotides, at least about 28 to 32 nucleotides, at least about 36 or more nucleotides, may also be desired. Multiple sequence alignment programs are also available for nucleic acid sequences. Examples of such programs include, "Clustal W", "CAP Sequence Assembly", "BLAST", "MAP", and "MEME", which are accessible through Web Servers on the internet. Other sources for such programs are known to those of skill in the art. Alternatively, Vector NTI utilities are also used. There are also a number of algorithms known in the art that can be used to measure nucleotide sequence identity, including those contained in the programs described above. As another example, polynucleotide sequences can be compared using Fasta™, a program in GCG Version 6.1. Fasta™ provides alignments and percent sequence identity of the regions of the best overlap between the query and search sequences. For instance, percent sequence identity between nucleic acid sequences can be determined using Fasta™ with its default parameters (a word size of 6 and the NOPAM factor for the scoring matrix) as provided in GCG Version 6.1, herein incorporated by reference.

The terms "percent (%) identity", "sequence identity", "percent sequence identity", or "percent identical" in the context of amino acid sequences refers to the residues in the two sequences which are the same when aligned for correspondence. Percent identity may be readily determined for amino acid sequences over the full-length of a protein, polypeptide, about 32 amino acids, about 330 amino acids, or a peptide fragment thereof or the corresponding nucleic acid sequence coding sequencers. A suitable amino acid fragment may be at least about 8 amino acids in length, and may be up to about 700 amino acids. Generally, when referring to "identity", "homology", or "similarity" between two different sequences, "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence. Alignments are performed using any of a variety of publicly or commercially available Multiple Sequence Alignment Programs. Sequence alignment programs are available for amino acid sequences, e.g., the "Clustal X", "MAP", "PIMA", "MSA", "BLOCKMAKER", "MEME", and "Match-Box" programs. Generally, any of these programs are used at default settings, although one of skill in the art can alter these settings as needed. Alternatively, one of skill in the art can utilize another algorithm or computer program which provides at least the level of identity or alignment as that provided by the referenced algorithms and programs. See, e.g., J. D. Thomson et al, Nucl. Acids. Res., "A comprehensive comparison of multiple sequence alignments", 27(13):2682-2690 (1999).

In one embodiment, the nucleic acid sequences encoding the hLDLR variants (e.g., LDLR variant gene) described herein are engineered into any suitable genetic element, e.g., naked DNA, phage, transposon, cosmid, RNA molecule (e.g., mRNA), episome, etc., which transfers the hLDLR sequences carried thereon to a host cell, e.g., for generating nanoparticles carrying DNA or RNA, viral vectors in a packaging host cell and/or for delivery to a host cells in subject. In one embodiment, the genetic element is a plasmid. The selected genetic element may be delivered by any suitable method, including transfection, electroporation, liposome delivery, membrane fusion techniques, high velocity DNA-coated pellets, viral infection and protoplast fusion. The methods used to make such constructs are known to those with skill in nucleic acid manipulation and include genetic engineering, recombinant engineering, and synthetic techniques. See, e.g., Green and Sambrook, Molecular Cloning: A Laboratory Manual, Cold Spring Harbor Press, Cold Spring Harbor, N.Y. (2012).

As used herein, an "expression cassette" refers to a nucleic acid molecule which comprises the hLDLR variant coding sequences, promoter, and may include other regulatory sequences therefor, which cassette may be engineered into a genetic element and/or packaged into the capsid of a viral vector (e.g., a viral particle). Typically, such an expression cassette for generating a viral vector contains the hLDLR sequences described herein flanked by packaging signals of the viral genome and other expression control sequences such as those described herein.

The expression cassette typically contains a promoter sequence as part of the expression control sequences. The illustrative plasmid and vector described herein uses the liver-specific promoter thyroxin binding globulin (TBG). Alternatively, other liver-specific promoters may be used [see, e.g., The Liver Specific Gene Promoter Database, Cold Spring Harbor, the world wide web at rulai.schl.edu/LSPD, alpha 1 anti-trypsin (A1AT); human albumin Miyatake et al., J. Virol., 71:5124 32 (1997), humAlb; and hepatitis B virus core promoter, Sandig et al., Gene Ther., 3:1002 9 (1996)]. TTR minimal enhancer/promoter, alpha-antitrypsin promoter, LSP (845 nt)25(requires intron-less scAAV). Although less desired, other promoters, such as viral promoters, constitutive promoters, regulatable promoters [see, e.g., WO 2011/126808 and WO 2013/04943], or a promoter responsive to physiologic cues may be used may be utilized in the vectors described herein.

In addition to a promoter, an expression cassette and/or a vector may contain other appropriate transcription initiation, termination, enhancer sequences, efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. Examples of suitable polyA sequences include, e.g., SV40, bovine growth hormone (bGH), and TK polyA. Examples of suitable enhancers include, e.g., the alpha fetoprotein enhancer, the TTR minimal promoter/enhancer, LSP (TH-binding globulin promoter/alpha1-microglobulin/bikunin enhancer), amongst others.

These control sequences are "operably linked" to the hLDLR gene sequences. As used herein, the term "operably linked" refers to both expression control sequences that are contiguous with the gene of interest and expression control sequences that act in trans or at a distance to control the gene of interest.

The expression cassette may be engineered onto a plasmid which is used for production of a viral vector. The minimal sequences required to package the expression cassette into an AAV viral particle are the AAV 5' and 3' ITRs, which may be of the same AAV origin as the capsid, or which of a different AAV origin (to produce an AAV pseudotype). In one embodiment, the ITR sequences from AAV2, or the deleted version thereof (ΔITR), are used for convenience and to accelerate regulatory approval. However, ITRs from other AAV sources may be selected. Where the source of the ITRs is from AAV2 and the AAV capsid is from another AAV source, the resulting vector may be termed pseudotyped. Typically, an expression cassette for an AAV vector comprises an AAV 5' ITR, the hLDLR coding sequences and any regulatory sequences, and an AAV 3' ITR. However, other configurations of these elements may be suitable. A shortened version of the 5' ITR, termed ΔITR, has been described in which the D-sequence and terminal resolution site (trs) are deleted. In other embodiments, the full-length AAV 5' and 3' ITRs are used.

The abbreviation "sc" refers to self-complementary. "Self-complementary AAV" refers a plasmid or vector having an expression cassette in which a coding region carried by a recombinant AAV nucleic acid sequence has been designed to form an intra-molecular double-stranded DNA template. Upon infection, rather than waiting for cell mediated synthesis of the second strand, the two complementary halves of scAAV will associate to form one double stranded DNA (dsDNA) unit that is ready for immediate replication and transcription. See, e.g., D M McCarty et al, "Self-complementary recombinant adeno-associated virus (scAAV) vectors promote efficient transduction independently of DNA synthesis", Gene Therapy, (August 2001), Vol 8, Number 16, Pages 1248-1254. Self-complementary AAVs are described in, e.g., U.S. Pat. Nos. 6,596,535; 7,125,717; and 7,456,683, each of which is incorporated herein by reference in its entirety.

An adeno-associated virus (AAV) viral vector is an AAV DNase-resistant particle having an AAV protein capsid into which is packaged nucleic acid sequences for delivery to target cells. An AAV capsid is composed of 60 capsid protein subunits, VP1, VP2, and VP3, that are arranged in an icosahedral symmetry in a ratio of approximately 1:1:10 to 1:1:20, depending upon the selected AAV. AAV serotypes may be selected as sources for capsids of AAV viral vectors (DNase resistant viral particles) including, e.g., AAV1, AAV2, AAV3, AAV4, AAV5, AAV6, AAV6.2, AAV7, AAV8, AAV9, rh10, AAVrh64R1, AAVrh64R2, rh8 [See, e.g., US Published Patent Application No. 2007-0036760-A1; US Published Patent Application No. 2009-0197338-A1; EP 1310571]. See also, WO 2003/042397 (AAV7 and other simian AAV), U.S. Pat. No. 7,790,449 and U.S. Pat. No. 7,282,199 (AAV8), WO 2005/033321 and U.S. Pat. No. 7,906,111 (AAV9), and WO 2006/110689], and rh10 [WO 2003/042397] or yet to be discovered, or a recombinant AAV based thereon, may be used as a source for the AAV capsid. These documents also describe other AAV which may be selected for generating AAV and are incorporated by reference. In some embodiments, an AAV cap for use in the viral vector can be generated by mutagenesis (i.e., by insertions, deletions, or substitutions) of one of the aforementioned AAV Caps or its encoding nucleic acid. In some embodiments, the AAV capsid is chimeric, comprising domains from two or three or four or more of the aforementioned AAV capsid proteins. In some embodiments, the AAV capsid is a mosaic of Vp1, Vp2, and Vp3 monomers from two or three different AAVs or recombinant AAVs. In some embodiments, an rAAV composition comprises more than one of the aforementioned Caps.

For packaging an expression cassette into virions, the ITRs are the only AAV components required in cis in the same construct as the gene. In one embodiment, the coding sequences for the replication (rep) and/or capsid (cap) are removed from the AAV genome and supplied in trans or by a packaging cell line in order to generate the AAV vector. For example, as described above, a pseudotyped AAV may contain ITRs from a source which differs from the source of the AAV capsid. Additionally or alternatively, a chimeric AAV capsid may be utilized. Still other AAV components may be selected. Sources of such AAV sequences are described herein and may also be isolated or obtained from academic, commercial, or public sources (e.g., the American Type Culture Collection, Manassas, Va.). Alternatively, the AAV sequences may be obtained through synthetic or other suitable means by reference to published sequences such as are available in the literature or in databases such as, e.g., GenBank®, PubMed®, or the like.

Methods for generating and isolating AAV viral vectors suitable for delivery to a subject are known in the art. See, e.g., U.S. Pat. No. 7,790,449; U.S. Pat. No. 7,282,199; WO 2003/042397; WO 2005/033321, WO 2006/110689; and U.S. Pat. No. 7,588,772 B2]. In a one system, a producer cell line is transiently transfected with a construct that encodes the transgene flanked by ITRs and a construct(s) that encodes rep and cap. In a second system, a packaging cell line that stably supplies rep and cap is transiently transfected with a construct encoding the transgene flanked by ITRs. In each of these systems, AAV virions are produced in response to infection with helper adenovirus or herpesvirus, requiring the separation of the rAAVs from contaminating virus. More recently, systems have been developed that do not require infection with helper virus to recover the AAV—the required helper functions (i.e., adenovirus E1, E2a, VA, and E4 or herpesvirus UL5, UL8, UL52, and UL29, and herpesvirus polymerase) are also supplied, in trans, by the system. In these newer systems, the helper functions can be supplied by transient transfection of the cells with constructs that encode the required helper functions, or the cells can be engineered to stably contain genes encoding the helper functions, the expression of which can be controlled at the transcriptional or posttranscriptional level. In yet another system, the transgene flanked by ITRs and rep/cap genes are introduced into insect cells by infection with baculovirus-based vectors. For reviews on these production systems, see generally, e.g., Zhang et al., 2009, "Adenovirus-adeno-associated virus hybrid for large-scale recombinant adeno-associated virus production," Human Gene Therapy 20:922-929, the contents of each of which is incorporated herein by reference in its entirety. Methods of making and using these and other AAV production systems are also described in the following U.S. patents, the contents of each of which is incorporated herein by reference in its entirety: U.S. Pat. Nos. 5,139,941; 5,741,683; 6,057,152; 6,204,059; 6,268,213; 6,491,907; 6,660,514; 6,951,753; 7,094,604; 7,172,893; 7,201,898; 7,229,823; and 7,439,065. See generally, e.g., Grieger & Samulski, 2005, "Adeno-associated virus as a gene therapy vector: Vector development, production and clinical applications," Adv. Biochem. Engin/Biotechnol. 99: 119-145; Buning et al., 2008, "Recent developments in adeno-associated virus vector technology," J. Gene Med. 10:717-733; and the references cited below, each of which is incorporated herein by reference in its entirety. The methods used to construct any embodiment of this invention are known to those with skill in nucleic acid manipulation and include genetic engineering, recombinant engineering, and synthetic techniques. See, e.g., Green and Sambrook et al, Molecular Cloning: A Laboratory Manual, Cold Spring Harbor Press, Cold Spring Harbor, N.Y. (2012). Similarly, methods of generating rAAV virions are well known and the selection of a suitable method is not a limitation on the present invention. See, e.g., K. Fisher et al, (1993) J. Virol., 70:520-532 and U.S. Pat. No. 5,478,745.

Optionally, the hLDLR genes described herein may be delivered via viral vectors other than rAAV. Such other viral vectors may include any virus suitable for gene therapy may be used, including but not limited to adenovirus; herpes virus; lentivirus; retrovirus; etc. Suitably, where one of these other vectors is generated, it is produced as a replication-defective viral vector.

A "replication-defective virus" or "viral vector" refers to a synthetic or artificial viral particle in which an expression cassette containing a gene of interest is packaged in a viral capsid or envelope, where any viral genomic sequences also packaged within the viral capsid or envelope are replication-deficient; i.e., they cannot generate progeny virions but retain the ability to infect target cells. In one embodiment, the genome of the viral vector does not include genes encoding the enzymes required to replicate (the genome can be engineered to be "gutless"—containing only the transgene of interest flanked by the signals required for amplification and packaging of the artificial genome), but these genes may be supplied during production. Therefore, it is deemed safe for use in gene therapy since replication and infection by progeny virions cannot occur except in the presence of the viral enzyme required for replication.

The pharmaceutical compositions described herein are designed for delivery to subjects in need thereof by any suitable route or a combination of different routes. Direct delivery to the liver (optionally via intravenous, via the hepatic artery, or by transplant), oral, inhalation, intranasal, intratracheal, intraarterial, intraocular, intravenous, intramuscular, subcutaneous, intradermal, and other parental routes of administration. The viral vectors described herein may be delivered in a single composition or multiple compositions. Optionally, two or more different AAV may be delivered, or multiple viruses [see, e.g., WO 2011/126808 and WO 2013/049493]. In another embodiment, multiple viruses may contain different replication-defective viruses (e.g., AAV and adenovirus).

The replication-defective viruses can be formulated with a physiologically acceptable carrier for use in gene transfer and gene therapy applications. In the case of AAV viral vectors, quantification of the genome copies ("GC") may be used as the measure of the dose contained in the formulation. Any method known in the art can be used to determine the genome copy (GC) number of the replication-defective virus compositions of the invention. One method for performing AAV GC number titration is as follows: Purified AAV vector samples are first treated with DNase to eliminate un-encapsidated AAV genome DNA or contaminating plasmid DNA from the production process. The DNase resistant particles are then subjected to heat treatment to release the genome from the capsid. The released genomes are then quantitated by real-time PCR using primer/probe sets targeting specific region of the viral genome (usually poly A signal).

Also, the replication-defective virus compositions can be formulated in dosage units to contain an amount of replication-defective virus that is in the range of about $1.0 \times 10^9$ GC to about $1.0 \times 10^{15}$ GC (to treat an average subject of 70 kg in body weight), and preferably $1.0 \times 10^{12}$ GC to $1.0 \times 10^{14}$ GC for a human patient. In another embodiment, the dose is less than about $1.5 \times 10^{11}$ GC/kg. For example, the dose of AAV virus may be about $1 \times 10^9$ GC, about $5 \times 10^9$ GC, about $1 \times 10^{10}$ GC, about $5 \times 10^{10}$ GC, or about $1 \times 10^{11}$ GC. In another example, the variants may be delivered in an amount of about 0.001 mg to about 10 mg/kg.

The above-described recombinant vectors may be delivered to host cells according to published methods. The rAAV, preferably suspended in a physiologically compatible carrier, may be administered to a human or non-human mammalian subject. Suitable carriers may be readily selected by one of skill in the art in view of the indication for which the transfer virus is directed. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the rAAV and/or variants and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

The viral vectors and other constructs described herein may be used in preparing a medicament for delivering a LDLR variant to a subject in need thereof, supplying LDLR variant having an increased half-life to a subject, and/or for treating elevated cholesterol levels, elevated high density lipoprotein (HDL), elevated triglycerides, familial hypercholesterolemia, atherosclerosis, coronary artery disease, cardiovascular disease, and/or another lipoprotein metabolic disorder.

A course of treatment may optionally involve repeat administration of the same viral vector (e.g., an AAV8 vector) or a different viral vector (e.g., an AAV8 and an AAVrh10). Still other combinations may be selected using the viral vectors described herein. Optionally, the composition described herein may be combined in a regimen involving other anti-lipid drugs (e.g., statins, monoclonal antibodies, etc), or protein-based therapies (including, e.g., delivery of a composition containing one or more LDLR variants as described herein).

It is to be noted that the term "a" or "an" refers to one or more. As such, the terms "a" (or "an"), "one or more," and "at least one" are used interchangeably herein.

The words "comprise", "comprises", and "comprising" are to be interpreted inclusively rather than exclusively. The words "consist", "consisting", and its variants, are to be interpreted exclusively, rather than inclusively. While various embodiments in the specification are presented using "comprising" language, under other circumstances, a related embodiment is also intended to be interpreted and described using "consisting of" or "consisting essentially of" language.

As used herein, the term "about" means a variability of 10% from the reference given, unless otherwise specified.

The term "regulation" or variations thereof as used herein refers to the ability of a composition to inhibit one or more components of a biological pathway.

A "subject" is a mammal, e.g., a human, mouse, rat, guinea pig, dog, cat, horse, cow, pig, or non-human primate, such as a monkey, chimpanzee, baboon or gorilla.

As used herein, "disease", "disorder" and "condition" are used interchangeably, to indicate an abnormal state in a subject.

Unless defined otherwise in this specification, technical and scientific terms used herein have the same meaning as commonly understood by one of ordinary skill in the art and by reference to published texts, which provide one skilled in the art with a general guide to many of the terms used in the present application.

The following examples are illustrative only and are not intended to limit the present invention.

EXAMPLES

Example 1—AAV Vectors Expressing LDLR Gain-of-Function Variants Demonstrate Increased Efficacy in Mouse Models of Familial Hypercholesterolemia A. Experimental Animals All animal studies were approved by the institutional review board (IRB) at the University of Pennsylvania.

LDLR$^{-/-}$, APOBEC-1$^{-/-}$ double knockout mice (DKO) and LDLR$^{-/-}$, APOBEC-1$^{-/-}$, human ApoB100 transgenic (LAHB) were maintained at the University of Pennsylvania. These mice overexpress hPCSK9. The absence of endogenous mouse LDLR expression in this animal model permits evaluation of hLDLR transgene expression without interference from mouse LDLR. Overexpression of hPCSK9 is achieved by coadministering an AAV vector expressing hPCSK9 (AAV9.TBG.hPCSK9), the preparation of which is described in Part C of this Example.

6-8 week old male mice were injected intravenously (tail vein) with vector diluted in phosphate buffered saline (PBS) in a total volume of 100 µL. Serum was collected pre and post vector administration by retro orbital bleeds. At the end of the study all animals were sacrificed and the livers harvested for analysis of vector genomes and transgene expression. Serum samples from animals were analyzed for total cholesterol (Tc), LDL, HDL and total triglycerides (Tg) using a MIRA analyzer (Roche). Non-HDL cholesterol was derived by subtracting the Tg from Tc. Livers from animals were harvested and homogenized using RIPA buffer. 25 µg of total liver lysate was electrophoresed on a 4-12% PAGE gel and probes with a polyclonal anti-hLDLR antibody.

B. LDLR Variants

Amino acid residues (position numbers based on SEQ ID NO:1) targeted for mutagenesis were as follows:

TABLE 1

| Amino acid substitutions and affected LDLR-PCSK9 interaction | |
|---|---|
| Amino acid substitution | Predicted LDLR-PCSK9 interaction |
| N295D | Prevent hydrogen bonding with PCSK9 Asp-238 |
| D299N | Affects salt bridge with PCSK9 Ser-153 |
| H306G | Affects salt bridge with PCSK9 Asp-374 |
| V307D | Prevents hydrophobic interaction with PCSK9 Val-380 |
| N309A | Prevent hydrogen bonding with PCSK9 Thr-377 |
| D310N | Affects salt bridge with PCSK9 Arg-194 |
| L311T | Prevent hydrogen bonding with PCSK9 Thr-377 |
| L318D | Hydrophobic interaction with PCSK9 Cys-378 |
| L318H | Hydrophobic interaction with PCSK9 Cys-378 |

In addition, amino acid substitutions, K809R and C818A, in the C-terminal cytoplasmic domain of LDLR that prevent IDOL mediated degradation were selected.

C. Vector

The AAV8 vector expressing wild type hLDLR cDNA from a liver-specific thyroxine binding globulin (TBG) promoter has been previously described and was obtained from the Vector Core at the University of Pennsylvania. Briefly, HEK293 cells were triple transfected using AAV cis- and trans-plasmid along with the Ad helper plasmids. AAV particles were purified from the culture supernatant and quantified using primers to the bGH polyadenylation sequence. Vector preparations were analyzed for DNA structure by restriction digests and endotoxin contamination (<20 EU/mL) before injection into animals. The wild type hLDLR cDNA was used as a template for site directed mutagenesis to introduce amino acid substitutions using the Quickchange XL kit (Stratagene) as per the manufacturers' recommendations.

The sequences of plasmids used for production of AAV vectors as described herein are provided in the appended sequence listing. The plasmid constructs having the TBG promoter were used in the animal (mice) studies; those with the CB promoter were used for in vitro screening.

The cDNA sequences encoding hPCSK9 and hIDOL were purchased (Origene, MD), cloned, and vectored to express from an AAV9 vector behind a TBG promoter and a bovine growth hormone (bGH) polyadenylation signal. An AAV9 vector expressing human alpha1-antitrypsin (A1AT) also expressed from a TBG promoter was used as a control in studies that required an irrelevant transgene.

TABLE 2

| Vectors |
|---|
| AAV8.hLDLR |
| AAV8.hLDLR-N295D |
| AAV8.hLDLR-D299N |
| AAV8.hLDLR-H306G |
| AAV8.hLDLR-V307D |
| AAV8.hLDLR-N309A |
| AAV8.hLDLR-D310N |
| AAV8.hLDLR-L311T |
| AAV8.hLDLR-L318D |
| AAV8.hLDLR-L318H |
| AAV8.hLDLR-K809R\C818A |
| AAV8.hLDLR-L318D\K809R\C818A |
| AAV9.hPCSK9 |
| AAV9.hIDOL |

D. In Vitro LDLR Assay

HEK 293 cells growing in 6 well plates were transfected overnight with plasmids expressing hLDLR along with hPCSK9 or hIDOL. All cDNAs were cloned behind a cytomegalovirus promoter (CMV) to obtain expression in HEK293 cells. Control cells were transfected with hLDLR plus a plasmid expressing an irrelevant transgene (A1AT). In studies where the dose of one vector was titrated lower an irrelevant plasmid was added to ensure that the total amount of plasmid did not vary from one experimental well to another. The following day cells were pulsed with BODIPY-LDL (Invitrogen) at a concentration of 4 µg/mL. Cells were removed after 2 hr and evaluated for fluorescent LDL uptake using a flow cytometer (FC500, Beckman Coulter).

E. Immunoblotting and Enzyme Linked Immune Assays

50 µg of total cell lysates prepared from cells or mouse livers expressing human LDLR were electrophoresed on a 4-12% gradient precast mini gel (Invitrogen) before transferring to PVDF membrane (Invitrogen). An anti-hLDLR goat polyclonal antibody (Invitrogen) was used to probe the membrane (1/1000 dilution) followed by a secondary anti-goat antibody conjugated to alkaline phosphatase (Invitrogen). Human PCSK9 expression levels in mouse serum were analyzed using an ELISA kit (R&D) as per the manufacturers' instructions.

F. Statistical Analysis

All experiments were analyzed using one-way Analysis of Variance models with pair-wise group differences in mean cholesterol level assessed using Tukey's post-hoc tests. However, for experiments evaluating the effect of PCSK9 in C57BL/6 mice, a linear mixed effects model was used to assess group differences in cholesterol level while taking into account correlation between repeated measurements on the same mouse. Similarly, analysis of PCSK9 on AAV transduced hLDLR relied on Analysis of Covariance modeling, with post-cholesterol level regressed on pre-cholesterol level and group. Statistical significance was taken at the 0.05 level for all experiments.

Results

G. Amino Acid Substitutions in hLDLR Confer PCSK9 Resistance

Nine LDLR variants with potentially decreased binding to PCSK9 (N295D, D299N, H306G, V307D, N309A, D310N, L311T, L318D and L318H see Table 1, position numbers based on numbering of SEQ ID NO:1) were initially screened in HEK293 cells using an in vitro assay for uptake of fluorescently labeled-LDL (BODPIY-LDL™), in the presence or absence of hPCSK9.

Studies in HEK293 cells that have low levels of endogenous expression of hLDLR and hPCSK9 were performed. As a source of exogenous hPCSK9, cells were co-transfected with a plasmid expressing hPCSK9 along with the hLDLR constructs. Mock transfected cells expressed low levels of LDLR based on immunoblotting which failed to detect LDLR protein (data not shown); moreover, mock transfected cells failed to demonstrate uptake of BODIPY™-LDL (FIG. 1A). In contrast, transient transfection of wild type hLDLR into HEK293 cells led to internalization of BODIPY™-LDL in 30% of cells which was reduced to 18% when co-transfected with hPCSK9 (FIG. 1A). Among the mutant constructs co-expressed with hPCSK9, only the D299N and L311T amino acid substitutions failed to afford any protection to PCSK9 mediated degradation in that BODIPY™-LDL uptake was reduced to a similar extent as wild type LDLR. All other amino acid substitutions afforded varying degrees of protection from PCSK9, although some constructs were less efficient in BODIPY™-LDL uptake in the absence of PCSK9 when compared to wild-type hLDLR. As an example, although the L318D and L318H substitutions were both resistant to hPCSK9 degradation, only L318D showed normal BODIPY™-LDL uptake in the absence of PCSK9 (FIG. 1B). In contrast, the L318H substitution led to reduced receptor activity and BODIPY™-LDL uptake was lower when compared to wild type hLDLR in the absence of hPCSK9 (30% vs 6%; hLDLR vs hLDLR-L318H). For this reason the hLDLR-L318D vector was selected for further in vivo evaluation in mice.

H. Overexpression of hPCSK9 in Mice Downregulates AAV Expressed hLDLR

Evaluating the activity of wildtype and L318D forms of hLDLR in mice was complicated because of potential diminished interactions between the exogenous hLDLR protein and the endogenous mouse PCSK9 protein. A fully humanized mouse model with the hoFH phenotype (lacking LDLR and APOBEC-1 by virtue of germ line interruption) and overexpressing hPCSK9 [following i.v. injection of an AAV9 vector expressing hPCSK9 via the liver specific promoter TBG (AAV9.hPCSK9)] was created (the LDLR−/−, ApoBec −/− double knock-out (DKO) mice described in Part A of this Example. Expression of AAV9.hPCSK9 vector was first evaluated in C57BL/6 mice who received increasing doses of hPCSK9. At high dose vector (i.e., $5 \times 10^{10}$ GC) serum non-HDL cholesterol increased approximately 2.5-fold (p=0.0015), indicating some level of interaction between hPCSK9 and mLDLR. See, FIG. 1C.

Figure 2B:
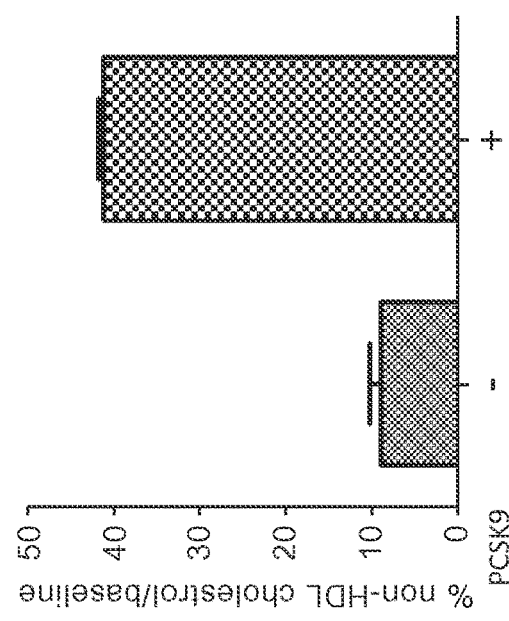
Figure 2C:
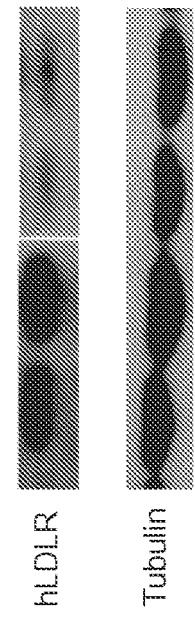

Prior to evaluating the effects of hPCSK9 on transgene derived hLDLR, the hoFH DKO mice were injected with AAV8.hLDLR alone. In these animals, baseline non-HDL levels on a chow diet were 417±23 mg/dl; which decreased by day 7 following administration of $5 \times 10^{10}$ GC of AAV8.hLDLR. Non-HDL levels stabilized and were only 37±7 mg/dl by day 30 which was 9% of baseline levels (p=0.037, FIG. 2A). Next, the performance of this vector in DKO mice expressing hPCSK9 were evaluated by co-administering (i.v.) an equal dose ($5 \times 10^{10}$ GC) of AAV9.hPCSK9 along with AAV8.hLDLR. Following vector administration, serum levels of hPCSK9 rose steadily and reached peak levels (7500±3000 ng/mL) by day 30 (FIG. 2B). Concomitantly, non-HDL levels in mice co-transduced with hPCSK9 were significantly higher (p=0.0008) when compared to animals that only received hLDLR (FIG. 2A). AAV8.hLDLR reduced non-HDL 10-fold in the absence of hPCSK9; however, this reduction was only 2.5-fold in the presence of hPCSK9. Immunoblotting of total liver lysates confirmed that co-transduction with PCSK9 resulted in reduced hLDLR protein in the liver (FIG. 2C); whereas, levels of hLDLR messenger RNA remained unchanged between the experimental groups (data not shown). These findings are consistent with the reported mode of action of PCSK9 to bind and sequester LDLR in an intracellular compartment that increases receptor degradation [Wang, et al, J Lipid Res, 2012; 53: 1932-1943]. No reduction in hLDLR expression was observed in animals co-transduced with an AAV9 vector expressing an irrelevant transgene.

Figures 3A, 3B:
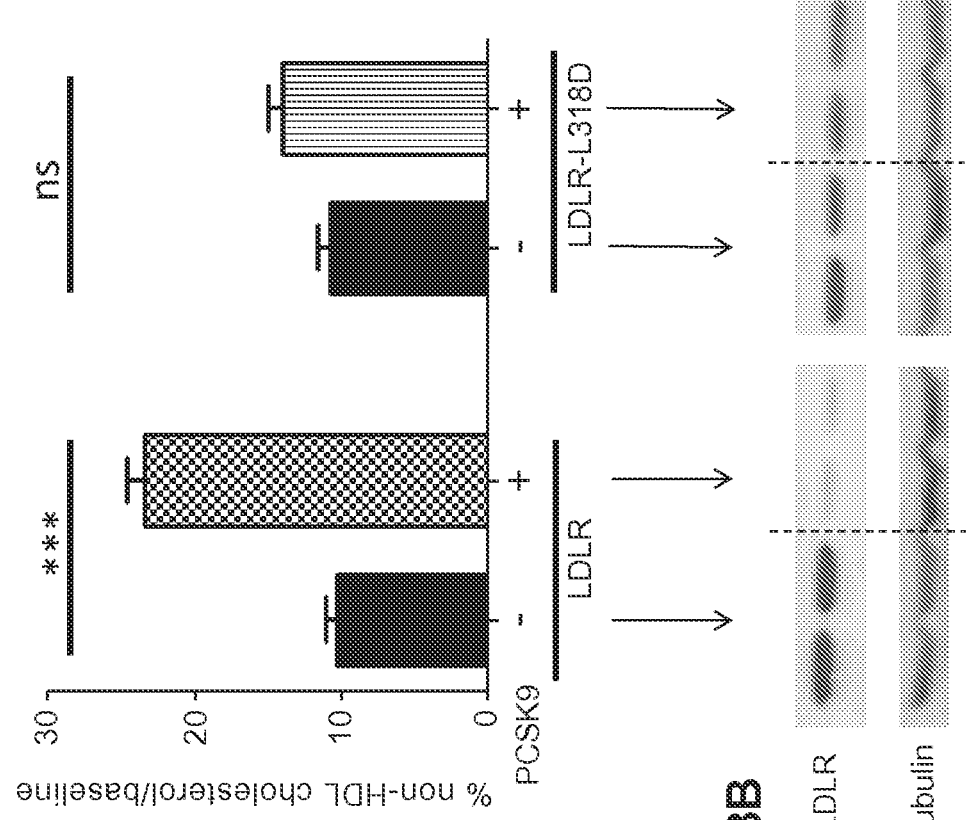
FIGS. 3A and 3B illustrate that mice transduced with hLDLR-L318D are resistant to hPCSK9 mediated regulation. DKO mice (n=4/group) were co-transduced with $5 \times 10^{10}$ GC of AAV8.hLDLR or hLDLR-L318D along with $5 \times 10^{10}$ GC of AA9.hPCSK9. Serum from animals pre and 30 days post vector administration was evaluated for total cholesterol and HDL cholesterol.

I. THE LDLR-L318D Amino Acid Substitution Confers Resistance to Human PCSK9 Mediated Degradation A similar strategy was used to evaluate the activity of hLDLR-L318D in DKO mice overexpressing hPCSK9 and compared the results to mice transduced with wild type hLDLR. As expected, transduction with hLDLR resulted in a dramatic lowering of serum cholesterol by day 30 (10% of baseline); while, co-transduction with hPCSK9 resulted in reduced hLDLR activity with non-HDL cholesterol levels only 23% of baseline (p<0.0001, FIG. 3A). In contrast, the L318D substitution apparently prevented receptor degradation in that differences in non-HDL levels between animals that received hLDLR-L318D or hLDLR-L318D along with hPCSK9 was not statistically significant (10% vs 14%; p=0.1337). Moreover, immunoblotting of livers collected at the end of the study (Day 30) revealed that hLDLR protein levels were significantly decreased only in animals that received wild-type hLDLR along with hPCSK9 but not in those that received hLDLR alone (FIG. 3B). However, liver levels of hLDLR-L318D were unaffected by co-expression with hPCSK9 and the same as observed with wild type hLDLR in the absence of hPCSK9 (FIG. 3B). To confirm that the observed differences did not arise from changes in mRNA expression, hLDLR transcripts were analyzed in livers using a quantitative PCR assay. These studies indicated only a modest decrease in wild type hLDLR treated mice that was substantially less than the decrease in hLDLR protein (FIG. 3B).

J. hLDLR-K809R\C81 8A Escapes h IDOL Regulation

Figure 4A:
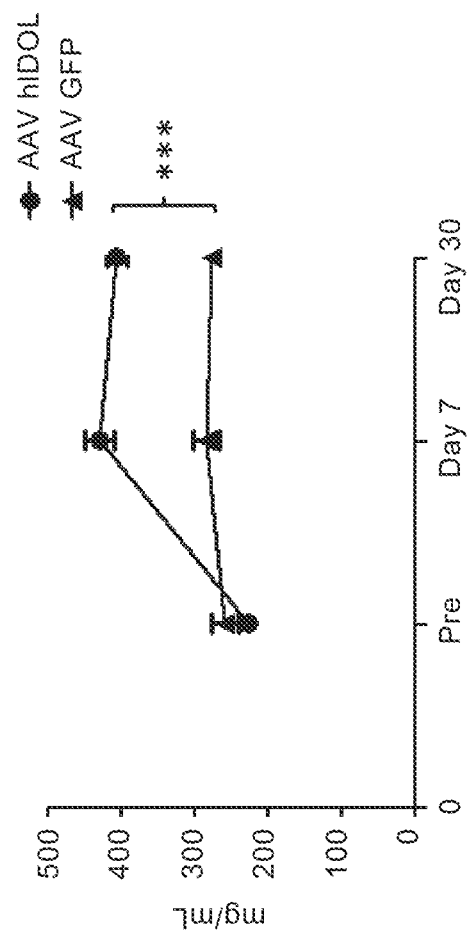
FIGS. 4A-4D illustrate AAV8.hLDLR-K809R\C818A escapes in vivo hIDOL mediated regulation. HEK293 cells were transiently transfected with plasmids expressing either hLDLR or hLDLR-K809R\C818A along with hIDOL. 24 hr later, cells were pulsed with BODIPY-LDL for 2 hr and then evaluated for fluorescent LDL uptake using a flow cytometer.

LDLR expression is also subject to regulation by IDOL; an E3 ubiquitin ligase transcriptionally upregulated by liver X receptors (LXRs) following an increase in intracellular concentrations of oxysterols. Activated IDOL interacts with the cytoplasmic tail region of LDLR leading to receptor degradation [Zhang L, et al, Arterioscler Thromb Vasc Biol. 2012; 32:2541-2546]. An AAV8 vector expressing hLDLR containing the K809R and C818A amino acid substitutions (AAV8.hLDLR-K808R\C818A) was constructed. This construct was first evaluated in HEK293 cells in the presence or absence of hIDOL; as a source of human IDOL, plasmids expressing hIDOL were co-expressed with hLDLR. As expected, transfection of wild type hLDLR resulted in LDL uptake in 28% of cells; however, co-transfection of hIDOL along with hLDLR dramatically reduced LDL positive cells to only 2% (FIG. 4A). The K808R\C818A amino acid substitutions did not impact receptor activity and the LDLR- K809R\C818A construct was as efficient as wild type hLDLR in internalizing LDL, in the absence of IDOL (LDLR vs LDLR-K809R\C818A, 28% vs 22%). However, differences between the two constructs did appear when co-transfected with hIDOL. The hLDLR-K809R\C818A construct was more resistant to the effects of hIDOL resulting in roughly 14% of cells taking up fluorescent LDL as opposed to 2% with wild type LDLR. Immunoblotting of whole cell lysates further confirmed that the observed differences in LDL uptake correlated with reduced levels of hLDLR protein, and not hLDLR-K809R\C818A, in the presence of hIDOL (FIG. 4A).

Figure 4B:
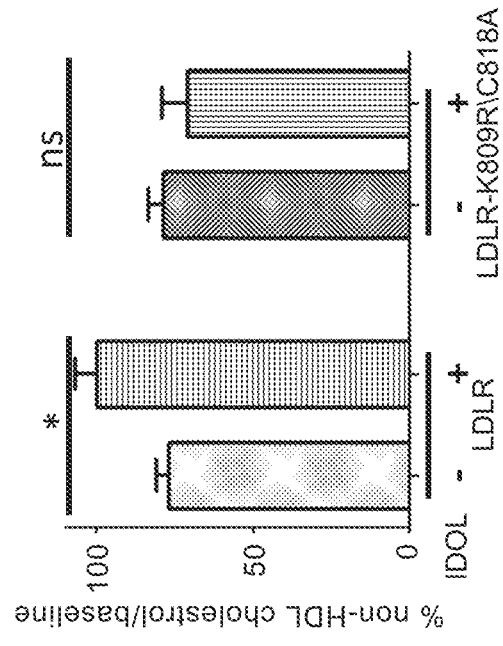
Figure 4D:
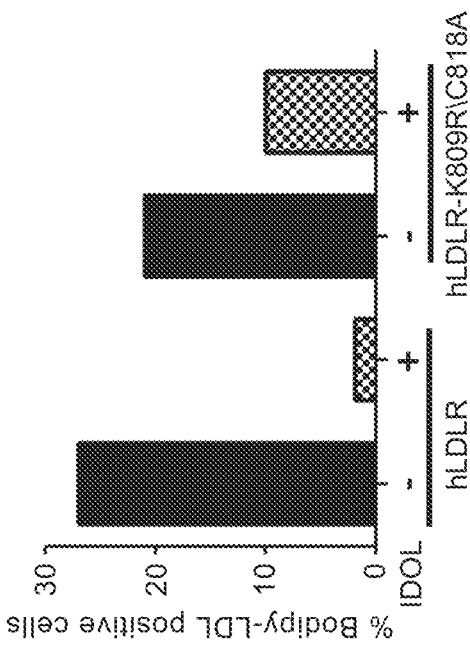
Figure 4C:
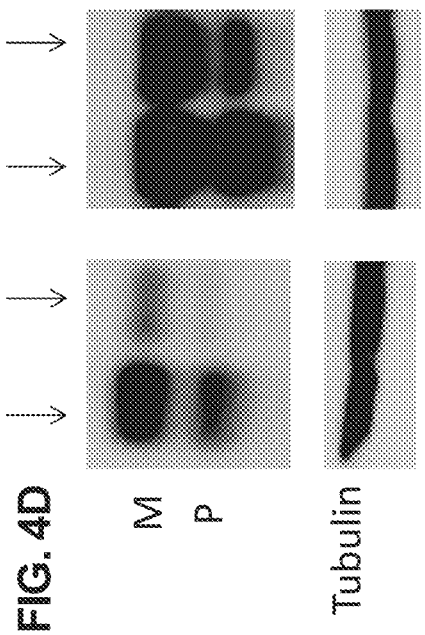

Next the activity of the hLDLR-K809R\C818A construct in DKO mice overexpressing human IDOL was evaluated. A phenotype of mice overexpressing human IDOL in liver was created by administering an AAV9 vector expressing human IDOL under control of a liver specific promoter. In pilot studies the efficacy of human IDOL in regulating endogenous LDLR expression was evaluated in mice by administering (i.v.) $5 \times 10^{10}$ GC of AAV9.hIDOL to FH mice heterozygous for LDLR expression (heFH). This strain of mice (LAHB mice) is deficient in APOBEC-1, heterozygous for mouse LDLR$^{+/-}$ and transgenic for human ApoB100 which leads to higher serum cholesterol. Following administration of AAV9.hIDOL, non-HDL levels increased by day 7 and reached stable levels by day 30 ($p<0.0001$, FIG. 4B). These results confirmed that AAV expressed hIDOL was active in mouse livers and can cause the loss of endogenous mLDLR. Next, the effect of hIDOL overexpression on vector encoded hLDLR was expressed in DKO mice. In pilot studies only low dose hLDLR vector administrations were significantly impacted by human IDOL; hence, mice were co-administered $3 \times 10^9$ GC of AAV8.hLDLR and $5 \times 10^{10}$ GC of AAV9.hIDOL. At this low dose, hLDLR and hLDLR-K809\C818A vectors were functionally similar ($p=0.9$) and induced a modest reduction (20% of baseline) in serum cholesterol in the absence of hIDOL (FIG. 4C). However, co-administration of hIDOL ablated wild type hLDLR activity and no correction was seen in non-HDL cholesterol levels which remained at pre-treatment baseline levels ($p=0.0248$, FIG. 4C). In contrast, non-HDL cholesterol levels in mice that received hLDLR-K809R\C818A in the presence or absence of hIDOL were similar ($p>0.05$) demonstrating the in vivo resistance of the modified constructs to hIDOL (FIG. 4C).

Example 2—hLDLR-L318D\K809R\C818A Avoids Regulation by Both PCSK9 and IDOL

Figure 5B:
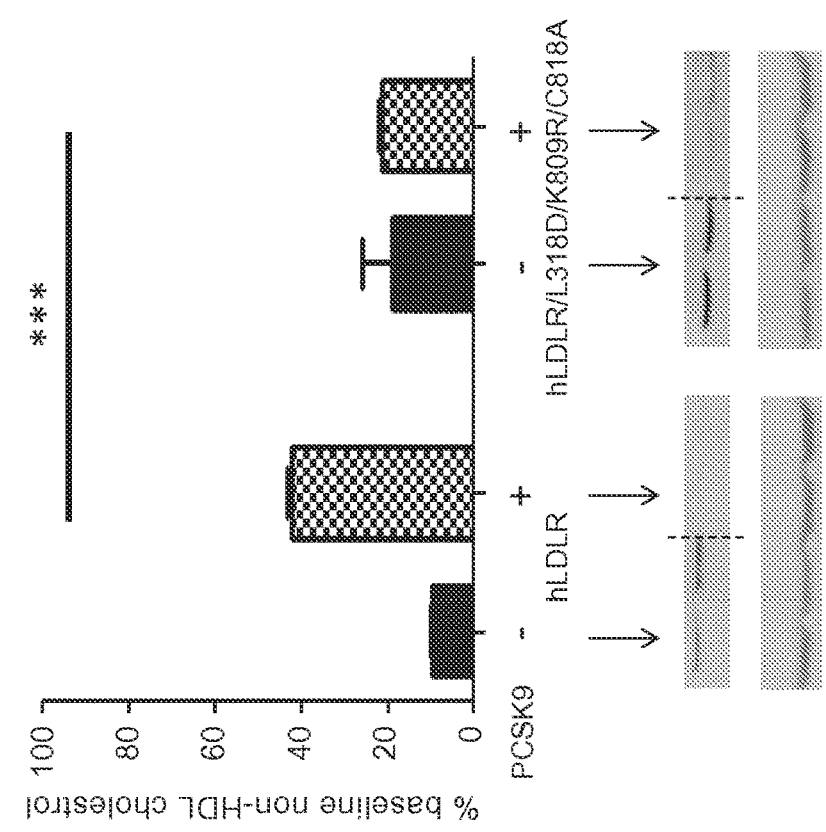
FIGS. 5A-5B illustrate the AAV8.hLDLR-L318D\K809R\C818A variant encoding three amino acid substitutions escapes both PCSK9 and IDOL mediated regulation.
Figure 5A:
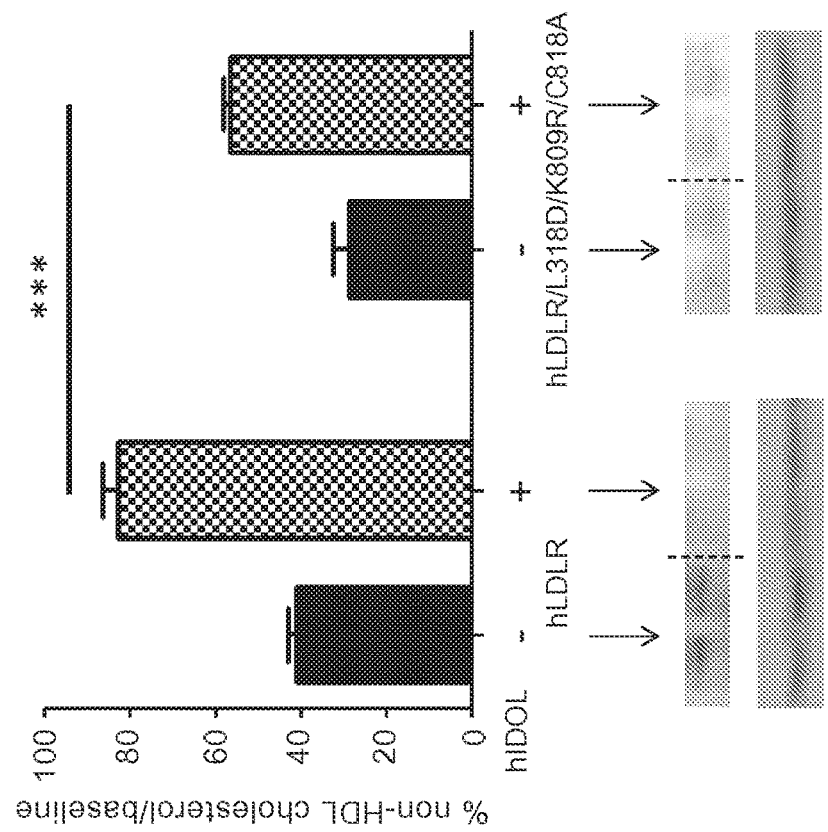

The L318D, K809R and C818A amino acid substitutions were cloned into a single vector to create a construct that would be resistant to regulation by both pathways. The vector was administered to DKO mice at a low dose ($3 \times 10^9$ GC), when evaluating the IDOL escape mutations; or at a higher dose ($5 \times 10^{10}$ GC), when evaluating the PCSK9 escape mutation. When administered at a low dose, hLDLR-L318D\K809R\C818A was comparable to wild type hLDLR ($p>0.05$) in that only a modest decrease in serum cholesterol was realized following either vector administration (FIG. 5A). However when administered in the presence of hIDOL, only the mutant vector showed any resistance to hIDOL in that serum cholesterol levels remained significantly lower than that seen in wild type hLDLR plus hIDOL ($p=0.0002$). Immunoblotting of liver samples confirmed that the mutant vector was more resistant to hIDOL mediated degradation (FIG. 5A). In the parallel study where vectors were administered at a higher dose along with hPCSK9, the variant protein performed significantly better in reducing serum cholesterol than the control wild type LDLR in mice overexpressing hPCSK9 ($p=0.0007$, FIG. 5B). Immunoblot analysis of livers demonstrated a nearly complete absence of wild type hLDLR in the presence of hPCSK9; in contrast, the mutant vector was protected and less degraded by hPCSK9.

Figure 6:
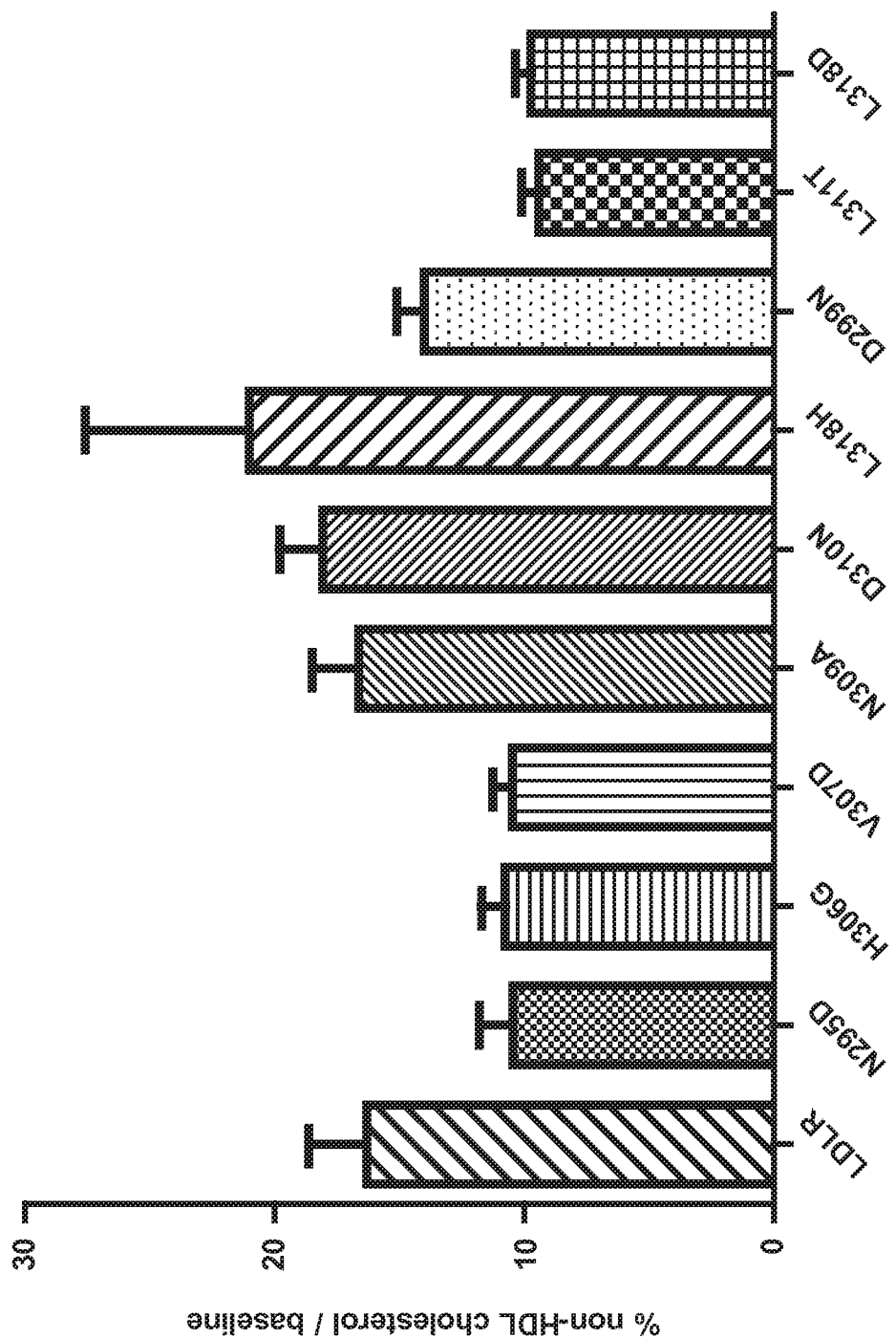
FIG. 6 is a bar chart illustrating the hLDLR activity of variants that escape PCSK9 regulation in DKO mice. DKO mice (n=4/group) were injected with 3×10¹⁰ GC of AAV8.TBG.hLDLR or AAV8 vectors expressing one of nine hPCSK9 escape variants. Serum from animals was analyzed before and 30 days after vector administration and percent reduction in non-HDL cholesterol at day 30 day compared to baseline is shown along with SD.

Example 3—Comparison of hLDLR Variants in a Mouse Model of Familial Hypercholesterolemia The panel of hLDLR carrying single amino acid substitutions that were expected to avoid PCSK9 regulation were screened by administering to LDLR-/-, APOBEC-/- double knockout mice (DKOs). Animals were injected intravenously (i.v. tail vein) with $3 \times 10^{10}$ GC of AAV8.TBG.hLDLR or one of the hLDLR variants that was expected to avoid hPCSK9 regulation. Reduction in serum levels of non-HDL cholesterol was used as a surrogate for comparing receptor activity from the different constructs. Serum was collected from animals by retro-orbital bleeds before and 30 days after vector administration and cholesterol levels analyzed using a MIRA analyzer (Roche). Non-HDL cholesterol levels were determined by subtracting the HDL component from total cholesterol. FIG. 6 shows percent decline in non-HDL levels over baseline in animals following vector administration.

Figure 8:
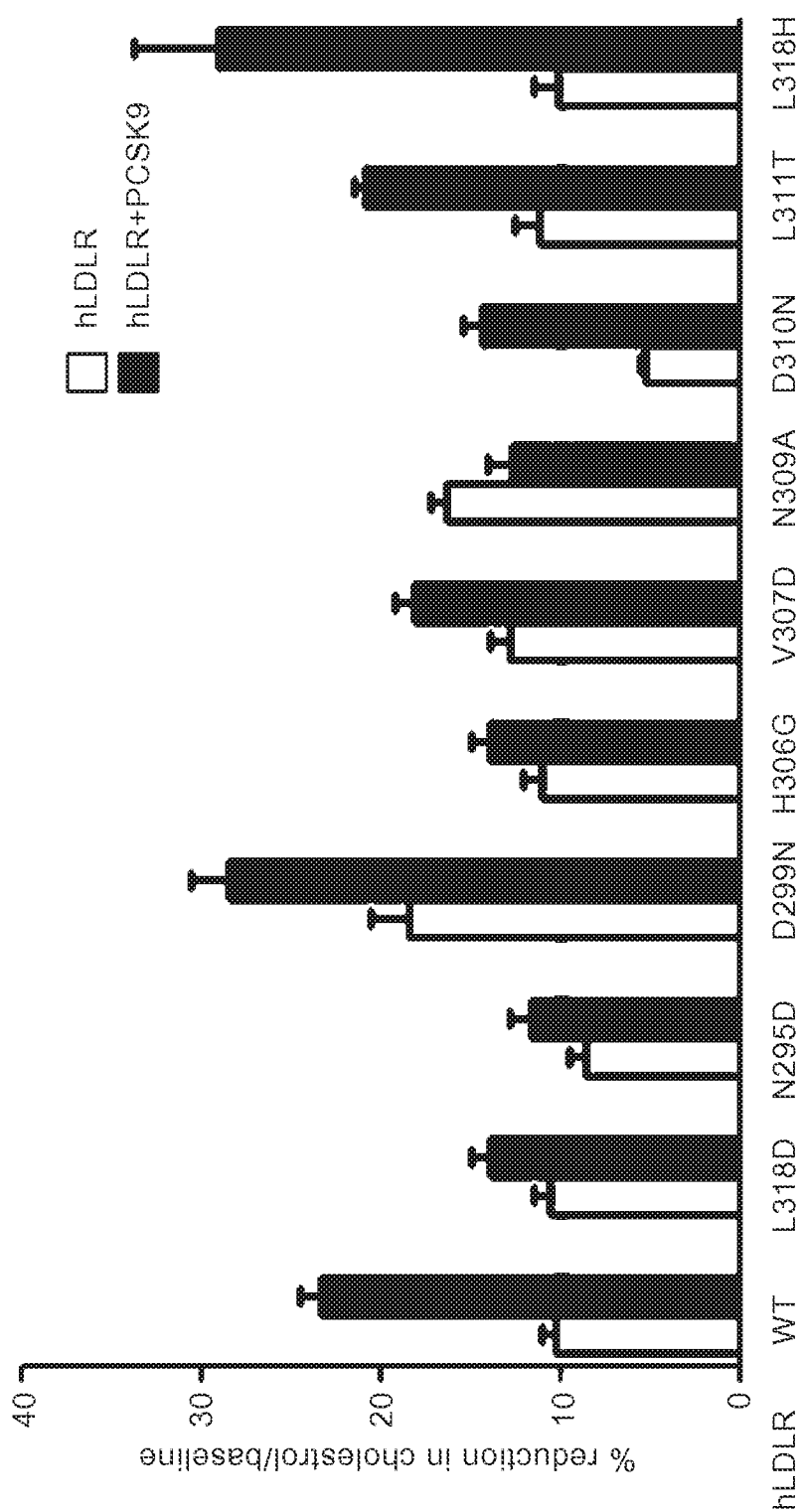
FIG. 8 is a bar chart illustrating the hLDLR activity of variants that escape PCSK9 regulation in a LDLR −/−, ApoBec −/−, double-knock out a mouse model. DKO mice (n=5/group) were injected (tail vein) with 5×10¹⁰ GC of AAV8.TBG.hLDLR or AAV8 vectors expressing one of nine hPCSK9 escape variants along with 5×10¹⁰ GC of AAV9.TBG.hPCSK9 vectors. Serum from animals was analyzed before and 30 days after vector administration. Percent reduction in non-HDL cholesterol at day 30 day compared to baseline is shown along with SD. Control mice received only the LDLR vector without co-administration of PCSK9 (bars to left in each pair).

This study was repeated under the same conditions, with the exception that vector administered at a higher dose, i.e., $5 \times 10^{10}$ GC of AAV8.TBGF.hLDLR for each of variants (L318D, N295D, H306G, V307D, N309A, D310N, L311T, L318H). Administration of $5 \times 10^{10}$ GC of wild type hLDLR by itself led to a 90% decrease in baseline non-HDL cholesterol levels (FIG. 8). With the exception of D299N, all other hLDLR variants also achieved similar reduction in non-HDL cholesterol. As expected, coadministration of hPCSK9 significantly reduced the efficacy of hLDLR vector. hPCSK9 overexpression had only a minimal effect on variants, L318D, N295D, H306G, V307D and N309A. Furthermore, immunoblotting of day 30 livers confirmed that with the exception of the H306G, these variants were significantly protected from degradation (not shown).

Figure 7:
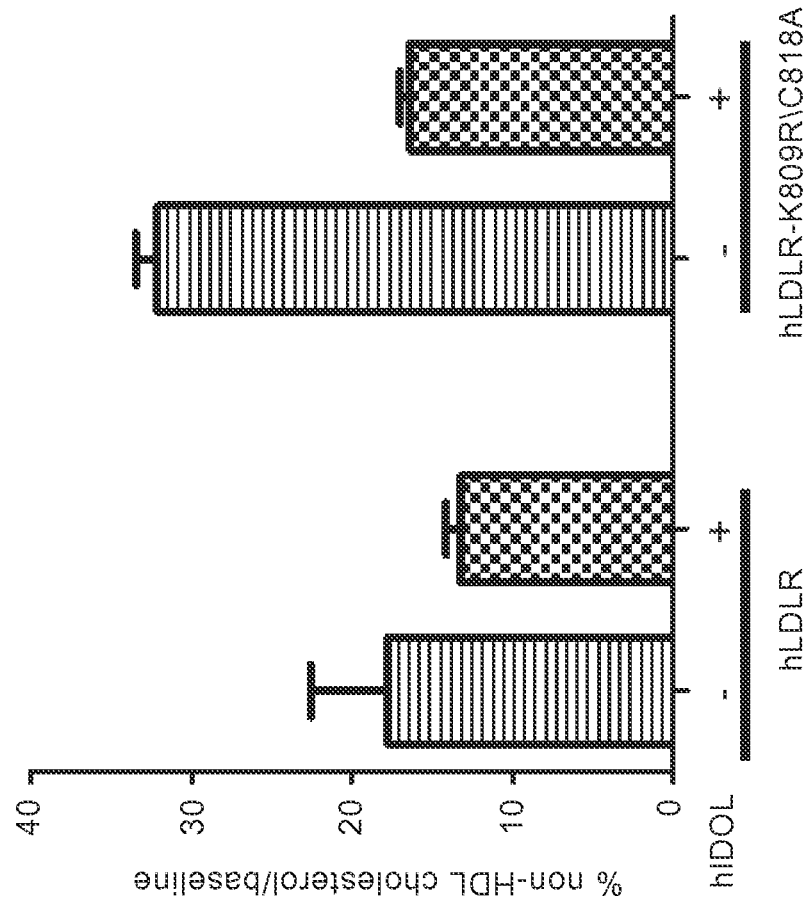
FIG. 7 is a bar chart illustrating that AAV.hLDLR overcome hIDOL mediated inhibition when administered at higher dose. DKO mice (n=4/group) were administered with of 5×10¹⁰ GC of AAV8.TBG.hLDLR or AAV8.TBG.hLDLR-K809R\C818A. Additional groups of mice received hLDLR along with of 5×10¹⁰ GC of AAV9.TBG.hIDOL. Percent non-HDL cholesterol levels on day 30 compared to baseline is shown along with SD.

Example 4—High Dose AAV.hLDLR Administration Circumvents In Vivo IDOL Inhibition LDLR-/-, APOBEC-/- double knockout mice (DKOs) were injected with AAV8.TBG.hLDLR or AAV8.TBG.K809R\C818A at a dose of $5 \times 10^{10}$ GC. In addition, some groups of mice were co-administered with an equal dose of an AAV9 vector expressing human IDOL (AAV9.TBG.hIDOL) to evaluate hLDLR activity in the presence of hIDOL. Non-HDL cholesterol levels were analyzed before and 30 days after vector administration. The percent non-HDL cholesterol at day 30 compared to baseline following vector administration is shown in FIG. 7.

All publications cited in this specification are incorporated herein by reference, as are US Provisional Patent Application Nos. 62/022,627, filed Jul. 9, 2014 and 61/984,620, filed Apr. 25, 2014. Similarly, the SEQ ID NOs which are referenced herein and which appear in the appended Sequence Listing are incorporated by reference. While the invention has been described with reference to particular embodiments, it will be appreciated that modifications can be made without departing from the spirit of the invention. Such modifications are intended to fall within the scope of the appended claims.

Sequence Listing Free Text

The following information is provided for sequences containing free text under numeric identifier <223>.

| SEQ ID NO: (containing free text) | Free text under <223> |
|---|---|
| 8 | <223> Synthetic pAAV-CB-hLDLR<br><220><br><221> CDS<br><222> (6) . . . (2588)<br><223> hLDLR<br><220><br><221> misc_feature<br><222> (2188) . . . (2207)<br><223> Y828F seq primer<br><220><br><221> misc_feature<br><222> (2434) . . . (2471)<br><223> K6 R primer<br><220><br><221> misc_feature<br><222> (2436) . . . (2534)<br><223> IDOL mutations<br><220><br><221> misc_feature<br><222> (2436) . . . (2588)<br><223> cytoplasmic tail<br><220><br><221> misc_feature<br><222> (2451) . . . (2453)<br><223> K5 mutation<br><220><br><221> misc_feature<br><222> (2477) . . . (2510)<br><223> K20 R primter<br><220><br><221> misc_feature<br><222> (2493) . . . (2495)<br><223> K20 mutation<br><220><br><221> misc_feature<br><222> (2505) . . . (2537)<br><223> C29 A primer<br><220><br><221> misc_feature<br><222> (2505) . . . (2537)<br><223> C29 A primer<br><220><br><221> misc_feature<br><222> (2520) . . . (2522)<br><223> C29 mutation<br><220><br><221> polyA_signal<br><222> (2655) . . . (2781)<br><223> rabbit globulin polyA<br><220><br><221> repeat_region<br><222> (2870) . . . (2999)<br><223> 3' ITR (complement)<br><220><br><221> rep_origin<br><222> (3176) . . . (3631)<br><223> complementary strand f1 ori<br><220><br><221> misc_feature<br><222> (3762) . . . (4619)<br><223> AP(R) marker<br><220><br><221> rep_origin<br><222> (4793) . . . (5381)<br><223> origin of replication<br><220> |

| SEQ ID NO: (containing free text) | Free text under <223> |
|---|---|
| | <221> repeat_region<br><222> (5821) . . . (5950)<br><223> 5' ITR<br><220><br><221> promoter<br><222> (6018) . . . (6399)<br><223> CMV IE promoter<br><220><br><221> promoter<br><222> (6402) . . . (6688)<br><223> CB promoter<br><220><br><221> Intron<br><222> (6778) . . . (7750)<br><223> chicken beta actin intron |
| 9 | <223> Synthetic Construct |
| 10 | <223> Synthetic CB7.hLDLR (K25R-C29A) - IDOL<br><220><br><221> polyA_signal<br><222> (66) . . . (192)<br><223> rabbit globulin polyA<br><220><br><221> repeat_region<br><222> (281) . . . (410)<br><223> 3' ITR, located on complement<br><220><br><221> rep_origin<br><222> (587) . . . (1042)<br><223> f1/ori, located on complement<br><220><br><221> misc_feature<br><222> (1173) . . . (2030)<br><223> maker AP(R)<br><220><br><221> rep_origin<br><222> (2204) . . . (2792)<br><223> origin of replication<br><220><br><221> repeat_region<br><222> (3232) . . . (3361)<br><223> 5' ITR<br><220><br><221> repeat_region<br><222> (3429) . . . (3810)<br><223> CMV IE promoter<br><220><br><221> CDS<br><222> (5173) . . . (7755)<br><223> hLDLR<br><220><br><221> misc_feature<br><222> (6187) . . . (6189)<br><223> site of L318D mutation affecting PCSK9 binding<br><220><br><221> misc_feature<br><222> (7601) . . . (7638)<br><223> K6\R\primer<br><220><br><221> misc_feature<br><222> (7603) . . . (7701)<br><223> IDOL mutations<br><220><br><221> misc_feature<br><222> (7618) . . . (7620)<br><223> K6-mutation<br><220><br><221> misc_feature<br><222> (7644) . . . (7677)<br><223> K20 R primer<br><220><br><221> misc_feature<br><222> (7660) . . . (7662)<br><223> K20 mutation |

| SEQ ID NO: (containing free text) | Free text under <223> |
|---|---|
| | <220><br><221> misc_structure<br><222> (7672) ... (7704)<br><223> C29 primer<br><220><br><221> misc_feature<br><222> (7689) ... (7689)<br><223> C29 mutation |
| 11 | <223> Synthetic Construct |
| 12 | <223> Synthetic pAAV.TBG.PI.hLDLR<br><220><br><221> repeat_region<br><222> (1) ... (130)<br><223> 5' ITR<br><220><br><221> enhancer<br><222> (221) ... (320)<br><223> alpha mic/bik<br><220><br><221> enhancer<br><222> (327) ... (426)<br><223> alpha mic/bik<br><220><br><221> promoter<br><222> (442) ... (901)<br><223> TBG<br><220><br><221> Intron<br><222> (1027) ... (1159)<br><223> intron 1<br><220><br><221> CDS<br><222> (1245) ... (3827)<br><223> hLDLR variant<br><220><br><221> misc_feature<br><222> (2256) ... (2258)<br><223> C before L318D<br><220><br><221> misc_feature<br><222> (2259) ... (2261)<br><223> L318D mutation<br><220><br><221> misc_feature<br><222> (3673) ... (3710)<br><223> K6 R primter<br><220><br><221> misc_feature<br><222> (3675) ... (3773)<br><223> IDOL mutations<br><220><br><221> misc_feature<br><222> (3690) ... (3692)<br><223> K6-mutation<br><220><br><221> misc_feature<br><222> (3716) ... (3749)<br><223> K20 R primter<br><220><br><221> misc_feature<br><222> (3732) ... (3734)<br><223> K20 mutations<br><220><br><221> misc_feature<br><222> (3744) ... (3776)<br><223> C29 A Primer<br><220><br><221> misc_feature<br><222> (3761) ... (3761)<br><223> C29 mutation<br><220><br><221> polyA_signal<br><222> (3894) ... (4020)<br><223> rabbit globulin polyA<br><220><br><221> repeat_region |

| SEQ ID NO: (containing free text) | Free text under <223> |
|---|---|
| | <222> (4109) ... (4238)<br><223> 3' ITR (complementary strand)<br><220><br><221> rep_origin<br><222> (4415) ... (4870)<br><223> (located on complementary strand) |
| 13 | <223> Synthetic Construct |
| 14 | <223> Synthetic plasmid with hLDLR (K25K, C29A).PGT(P2701)Q<br><220><br><221> repeat_region<br><222> (1) ... (130)<br><223> 5' ITR<br><220><br><221> enhancer<br><222> (221) ... (320)<br><223> alpha mic/bik<br><220><br><221> enhancer<br><222> (327) ... (426)<br><223> alpha mic/bik<br><220><br><221> promoter<br><222> (442) ... (901)<br><223> TBG promoter<br><220><br><221> Intron<br><222> (1027) ... (1159)<br><223> Intron 1<br><220><br><221> CDS<br><222> (1245) ... (3827)<br><223> hLDLR with K25R-C29A variants<br><220><br><221> misc_feature<br><222> (2259) ... (2261)<br><223> site of L318D mutatoin affecctign PCSK9 binding<br><220><br><221> misc_feature<br><222> (3673) ... (3710)<br><223> K6\R\Primer<br><220><br><221> misc_feature<br><222> (3675) ... (3773)<br><223> IDOL mutations<br><220><br><221> misc_feature<br><222> (3690) ... (3692)<br><223> K796 (K6) mutation<br><220><br><221> misc_feature<br><222> (3716) ... (3749)<br><223> K20 R Primer<br><220><br><221> misc_feature<br><222> (3732) ... (3732)<br><223> K20 mutation<br><220><br><221> misc_feature<br><222> (3744) ... (3776)<br><223> C29 A primer<br><220><br><221> misc_feature<br><222> (3761) ... (3761)<br><223> C29 mutation<br><220><br><221> polyA_signal<br><222> (3894) ... (4020)<br><223> rabbit globulin polyA<br><220><br><221> repeat_region<br><222> (4109) ... (4238) |

| SEQ ID NO: (containing free text) | Free text under <223> |
|---|---|
| | <223> 3' ITR (complement) |
| | <220> |
| | <221> rep_origin |
| | <222> (4415) . . . (4870) |
| | <223> complement f1 ori |
| | <220> |
| | <221> misc_feature |
| | <222> (5001) . . . (5858) |
| | <223> AP(R) marker |
| | <220> |
| | <221> rep_origin |
| | <222> (6032) . . . (6620) |
| | <223> origin of replication |
| 13 | <223> Synthetic Construct |
| 14 | Synthetic plasmid with hLDLR (K25K, C29A).PGT(P2701)Q |
| | <220> |
| | <221> repeat_region |
| | <222> (1) . . . (130) |
| | <223> 5' ITR |
| | <220> |
| | <221> enhancer |
| | <222> (221) . . . (320) |
| | <223> alpha mic/bik |
| | <220> |
| | <221> enhancer |
| | <222> (327) . . . (426) |
| | <223> alpha mic/bik |
| | <220> |
| | <221> promoter |
| | <222> (442) . . . (901) |
| | <223> TBG promoter |
| | <220> |
| | <221> TATA_signal |
| | <222> (885) . . . (888) |
| | <220> |
| | <221> Intron |
| | <222> (1027) . . . (1159) |
| | <223> Intron 1 |
| | <220> |
| | <221> CDS |
| | <222> (1245) . . . (3827) |
| | <223> hLDLR with K25R-C29A variants |
| | <220> |
| | <221> misc_feature |
| | <222> (2259) . . . (2261) |
| | <223> site of L318D mutatoin affecctign PCSK9 binding |
| | <220> |
| | <221> misc_feature |
| | <222> (3673) . . . (3710) |
| | <223> K6\R\Primter |
| | <220> |
| | <221> misc_feature |
| | <222> (3675) . . . (3773) |
| | <223> IDOL mutations |
| | <220> |
| | <221> misc_feature |
| | <222> (3690) . . . (3692) |
| | <223> K796 (K6) mutation |
| | <220> |
| | <221> misc_feature |
| | <222> (3716) . . . (3749) |
| | <223> K20 R Primer |
| | <220> |
| | <221> misc_feature |
| | <222> (3732) . . . (3732) |
| | <223> K20 mutation |
| | <220> |
| | <221> misc_feature |
| | <222> (3744) . . . (3776) |
| | <223> C29 A primer |
| | <220> |
| | <221> misc_feature |
| | <222> (3761) . . . (3761) |
| | <223> C29 mutation |
| | <220> |
| | <221> polyA_signal |
| | <222> (3894) . . . (4020) |
| | <223> rabbit globulin polyA |
| | <220> |
| | <221> repeat_region |
| | <222> (4109) . . . (4238) |
| | <223> 3' ITR (complement) |
| | <220> |
| | <221> rep_origin |
| | <222> (4415) . . . (4870) |
| | <223> complement f1 ori |
| | <220> |
| | <221> misc_feature |
| | <222> (5001) . . . (5858) |
| | <223> AP(R) marker |
| | <220> |
| | <221> rep_origin |
| | <222> (6032) . . . (6620) |
| | <223> origin of replication |
| 15 | <223> Synthetic Construct |
| 16 | <223> hLDLR varient D299N with leader |
| 17 | <223> Synthetic Construct |
| 18 | <223> hLDLR variant D310N with leader |
| 19 | <223> Synthetic Construct |
| 20 | <223> hLDLR variant H306G with leader |
| 21 | <223> Synthetic Construct |
| 22 | <223> hLDLR variant L311T with leader |
| 23 | <223> Synthetic Construct |
| 24 | <223> hLDLR variant L318D with leader |
| 25 | <223> Synthetic Construct |
| 26 | <223> hLDLR varient L318H with leader |
| 27 | <223> Synthetic Construct |
| 28 | <223> hLDLR N295D with leader |
| 29 | <223> Synthetic Construct |
| 30 | <223> synthetic hLDLR variant N309A with leader |
| 31 | <223> Synthetic Construct |
| 32 | <223> synthetic hLDLR V307D with leader |
| 33 | <223> synthetic hLDLR-IDOL-K796R, K809R, C818A with leader |
| 34 | <223> Synthetic Construct |
| 35 | <223> synthetic hLDLR.K809R-818A with leader |
| 36 | <223> Synthetic Construct |
| 37 | <223> synthetic hLDLR (K25R, C29A, L318D) with leader |
| 38 | <223> Synthetic Construct |
| 39 | <223> synthetic K809R, C818A, L318D with leader |
| 40 | <223> Synthetic Construct |

The invention claimed is:

1. A pharmaceutical composition useful for treating familial hypercholesterolemia comprising a recombinant AAV8 (rAAV8) having an AAV8 capsid and packaged therein an expression cassette comprising a modified human low density lipoprotein receptor (hLDLR) gene operably linked to expression control sequences which direct expression of the encoded modified hLDLR of SEQ ID NO: 40 in liver cells, wherein the expression control sequences comprise a liver specific promoter, enhancer sequences, and a polyadenylation signal sequence, and wherein said modified hLDLR gene comprises the nucleic acid sequence of SEQ ID NO: 39.

2. The pharmaceutical composition according to claim 1 which is a suspension and which further comprises a physiologically compatible saline solution.

3. The pharmaceutical composition according to claim 1, wherein the expression cassette comprises the liver-specific promoter which is a thyroxine binding globulin (TBG) promoter.

4. A recombinant adeno-associated virus (rAAV) having an AAV capsid and packaged therein an expression cassette comprising a modified human LDL receptor (hLDLR) gene operably linked to expression control sequences which direct expression of the encoded modified hLDLR of SEQ ID NO: 40 in liver cells, wherein said modified hLDLR gene comprises the nucleic acid sequence of SEQ ID NO: 39 and wherein the expression control sequences comprise a liver-specific promoter which is a thyroxine binding globulin (TBG) promoter and one or more enhancer sequences.

5. A pharmaceutical composition comprising a suspension of rAAV according to claim 4 and further comprising a physiologically compatible saline solution.

6. A method for reducing circulating cholesterol levels by administering a composition comprising at least about $5 \times 10^{10}$ genome copies (GC)/kg to $1.5 \times 10^{11}$ GC/kg of a rAAV according to claim 4 to a subject having familial hypercholesterolemia.

7. A method for treating familial hypercholesterolemia by administering to a subject in need thereof a composition comprising at least about $5 \times 10^{10}$ GC/kg to $1.5 \times 10^{11}$ GC/kg rAAV according to claim 4.

8. A method for reducing circulating cholesterol levels by administering to a subject in need thereof a pharmaceutical composition according to claim 1, wherein the pharmaceutical composition comprises at least about $5 \times 10^{10}$ GC/kg to $1.5 \times 10^{11}$ GC/kg rAAV8.

9. A method for treating familial hypercholesterolemia by administering to a subject in need thereof a pharmaceutical composition according to claim 1, wherein the pharmaceutical composition comprises at least about $5 \times 10^{10}$ GC/kg to $1.5 \times 10^{11}$ GC/kg rAAV8.

10. The rAAV of claim 4, wherein the AAV capsid is an rh10 capsid.

11. A pharmaceutical composition useful for treating familial hypercholesterolemia comprising a recombinant AAV8 (rAAV8) having an AAV8 capsid and packaged therein an expression cassette comprising a modified human low density lipoprotein receptor (hLDLR) gene operably linked to expression control sequences which direct expression of the encoded modified hLDLR in liver cells, wherein the expression control sequences comprise a liver specific thyroxine binding globulin (TBG) promoter, two alpha-l-microglobulin/bikunin (alpha mic/bik), enhancer sequences, an intron, and a rabbit globin (rBG) polyA signal sequence, and wherein the expression cassette comprises a nucleic acid sequence of nucleotides (nt) 221 to nt 4020 of SEQ ID NO: 12.

12. The pharmaceutical composition according to claim 11, which is a suspension and which further comprises a physiologically compatible saline solution.

13. A method for reducing circulating cholesterol levels by administering to a subject in need thereof a pharmaceutical composition according to claim 11, wherein the pharmaceutical composition comprises at least about $5 \times 10^{10}$ GC/kg to $1.5 \times 10^{11}$ GC/kg rAAV8.

* * * * *